United States Patent
Watterson

(10) Patent No.: US 9,850,258 B2
(45) Date of Patent: Dec. 26, 2017

(54) SUBSTITUTED TETRAHYDROCARBAZOLE AND CARBAZOLE CARBOXAMIDE COMPOUNDS

(71) Applicant: BRISTOL-MYERS SQUIBB COMPANY, Princeton, NJ (US)

(72) Inventor: Scott Hunter Watterson, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/625,417

(22) Filed: Jun. 16, 2017

(65) Prior Publication Data

US 2017/0283438 A1 Oct. 5, 2017

Related U.S. Application Data

(63) Continuation of application No. 15/067,915, filed on Mar. 11, 2016, which is a continuation of application No. 14/314,602, filed on Jun. 25, 2014, now Pat. No. 9,334,290.

(60) Provisional application No. 61/839,141, filed on Jun. 25, 2013.

(51) Int. Cl.
C07D 209/88 (2006.01)
C07D 513/04 (2006.01)
C07D 471/04 (2006.01)
C07D 403/10 (2006.01)
C07D 239/70 (2006.01)

(52) U.S. Cl.
CPC ......... *C07D 513/04* (2013.01); *C07D 209/88* (2013.01); *C07D 239/70* (2013.01); *C07D 403/10* (2013.01); *C07D 471/04* (2013.01)

(58) Field of Classification Search
CPC .................................................. C07D 209/88
See application file for complete search history.

(56) References Cited

U.S. PATENT DOCUMENTS

| 5,604,236 | A | 2/1997 | Jakubowski et al. |
| 8,084,620 | B2 | 12/2011 | Liu et al. |
| 8,362,065 | B2 | 1/2013 | Liu et al. |
| 2006/0084650 | A1 | 4/2006 | Dong et al. |
| 2008/0045536 | A1 | 2/2008 | Vaccaro et al. |

(Continued)

FOREIGN PATENT DOCUMENTS

| CN | 101475571 | 6/2011 |
| WO | WO 2005/005429 | 1/2005 |

(Continued)

OTHER PUBLICATIONS

Leplante, S.R.; "Assessing Atropisomer Axial Chirality in Drug Discovery and Development," J. Med. Chem., vol. 54(20), pp. 7005-7022 (2011).
Clayden, J., "The Challenge of Atropisomerism in Drug Discovery," Angew. Chem. Int. Ed., vol. 48, pp. 6398-6401, (2009).
Lou, Y., et al., "Bruton's Tyrosine Kinase Inhibitors: Approaches to Potent and Selective Inhibition, Preclinical and Clinical Evaluation for Inflammatory Diseases and B Cell Malignancies," Journal of Medicinal Chemistry, vol. 55, pp. 4539-4550 (2012).
International Search Report Application No. PCT/US2014/043978 dated Oct. 20, 2014.
Chinese Search Report dated January (English translation).

*Primary Examiner* — Susanna Moore
(74) *Attorney, Agent, or Firm* — Gary Greenblatt

(57) ABSTRACT

Disclosed are compounds of Formula (I)

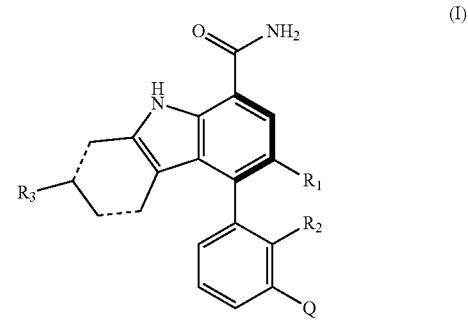

wherein: the two dotted lines represent either two single or two double bonds; Q is:

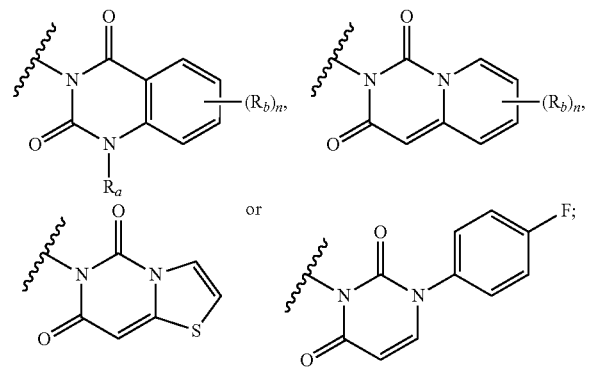

$R_1$ is F, Cl, —CN, or —CH$_3$; $R_2$ is Cl or —CH$_3$; $R_3$ is —C(CH$_3$)$_2$OH or —CH$_2$CH$_2$OH; $R_a$ is H or —CH$_3$; each $R_b$ is independently F, Cl, —CH$_3$, and/or —OCH$_3$; and n is zero, 1, or 2. Also disclosed are methods of using such compounds as inhibitors of Bruton's tyrosine kinase (Btk), and pharmaceutical compositions comprising such compounds. These compounds are useful in treating, preventing, or slowing the progression of diseases or disorders in a variety of therapeutic areas, such as autoimmune diseases and vascular disease.

3 Claims, 11 Drawing Sheets

(56) References Cited

U.S. PATENT DOCUMENTS

| | | |
|---|---|---|
| 2009/0281131 A1 | 11/2009 | Gopalan et al. |
| 2012/0136023 A1 | 5/2012 | Bell et al. |

FOREIGN PATENT DOCUMENTS

| | | |
|---|---|---|
| WO | WO 2005/014599 | 2/2005 |
| WO | WO 2005/047290 | 5/2005 |
| WO | WO 2006/053121 | 5/2006 |
| WO | WO 2006/064355 | 6/2006 |
| WO | WO 2006/099075 | 9/2006 |
| WO | WO 2007/035620 | 3/2007 |
| WO | WO 2007/038314 | 4/2007 |
| WO | WO 2007/061764 | 5/2007 |
| WO | WO 2008/032171 | 3/2008 |
| WO | WO 2008/033858 | 3/2008 |
| WO | WO 2009/024819 | 2/2009 |
| WO | WO 2909/075830 | 6/2009 |
| WO | WO 2009/102498 | 8/2009 |
| WO | WO 2009/141627 | 11/2009 |
| WO | WO 2010/015636 | 2/2010 |
| WO | WO 2011/159857 | 12/2011 |
| WO | WO 2012/059232 | 5/2012 |
| WO | WO 2012/156334 | 11/2012 |

SUBSTITUTED TETRAHYDROCARBAZOLE AND CARBAZOLE CARBOXAMIDE COMPOUNDS

CROSS-REFERENCE TO RELATED APPLICATIONS

This application is a continuation application, which claims priority to U.S. patent application Ser. No. 15/067,915, filed Mar. 11, 2016, which is continuation application claiming priority to U.S. patent application Ser. No. 14/314,602 filed Jun. 25, 2014, which claims priority to U.S. Provisional Application 61/839,141, filed Jun. 25, 2013, the contents of which are herein incorporated by reference in their entirety.

DESCRIPTION

The present invention generally relates to substituted tetrahydrocarbazole and carbazole carboxamide compounds useful as kinase inhibitors, including the modulation of Bruton's tyrosine kinase (Btk) and other Tec family kinases such as Itk. Provided herein are substituted tetrahydrocarbazole and carbazole carboxamide compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

Protein kinases, the largest family of human enzymes, encompass well over 500 proteins. Btk is a member of the Tec family of tyrosine kinases, and is a regulator of early B-cell development, as well as mature B-cell activation, signaling, and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis.

A large body of evidence supports the role of B-cells and the humoral immune system in the pathogenesis of autoimmune and/or inflammatory diseases. Protein-based therapeutics (such as RITUXAN®) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

U.S. Pat. No. 8,084,620 and WO 2011/159857 disclose tricyclic carboxamide compounds useful as kinase inhibitors, including the modulation of Btk and other Tec family kinases.

There still remains a need for compounds useful as Btk inhibitors and yet having selectivity over Jak2 tyrosine kinase. Further, there still remains a need for compounds useful as Btk inhibitors that have selectivity over Jak2 tyrosine kinase and also have improved potency in the whole blood BCR-stimulated CD69 expression assay.

Applicants have found potent compounds that have activity as Btk inhibitors. Further, applicants have found compounds that have activity as Btk inhibitors and are selective over Jak2 tyrosine kinase. Further still, applicants have found compounds that have activity as Btk inhibitors, are selective over Jak2 tyrosine kinase, and have improved potency in the whole blood BCR-stimulated CD69 expression assay. These compounds are provided to be useful as pharmaceuticals with desirable stability, bioavailability, therapeutic index, and toxicity values that are important to their drugability.

SUMMARY OF THE INVENTION

The present invention provides substituted tetrahydrocarbazole and carbazole compounds, which are useful as inhibitors of Btk, and are useful for the treatment of proliferative diseases, allergic diseases, autoimmune diseases and inflammatory diseases, including prodrugs thereof.

The present invention also provides pharmaceutical compositions comprising at least one compound of Formula (I) and a pharmaceutically acceptable carrier.

The present invention also provides a method of inhibiting Btk activity comprising administering to a mammal in need thereof at least one compound of Formula (I).

The present invention also provides a method for treating allergic disorders and/or autoimmune and/or inflammatory diseases, comprising administering to a mammal in need thereof at least one compound of Formula (I).

The present invention also provides a method for treating proliferative diseases, such as cancer, comprising administering to a mammal in need thereof at least one compound of Formula (I).

The present invention also provides a method of treating a disease or disorder associated with Btk activity, the method comprising administering to a mammal in need thereof, at least one compound of Formula (I).

The present invention also provides processes and intermediates for making the compounds of Formula (I).

The present invention also provides a compound of Formula (I) for use in therapy.

The present invention also provides the use of the compounds of Formula (I) for the manufacture of a medicament for the treatment or prophylaxis of Btk related conditions, such as proliferative diseases, allergic diseases, autoimmune diseases and inflammatory diseases.

The present invention also provides the use of the compounds of Formula (I) for the manufacture of a medicament for treatment of cancer.

The compounds of Formula (I) and compositions comprising the compounds of Formula (I) may be used in treating, preventing, or curing various Btk related conditions.

Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

BRIEF DESCRIPTION OF THE DRAWINGS

The invention is illustrated by reference to the accompanying drawings described below.

DETAILED DESCRIPTION

Figure 1:
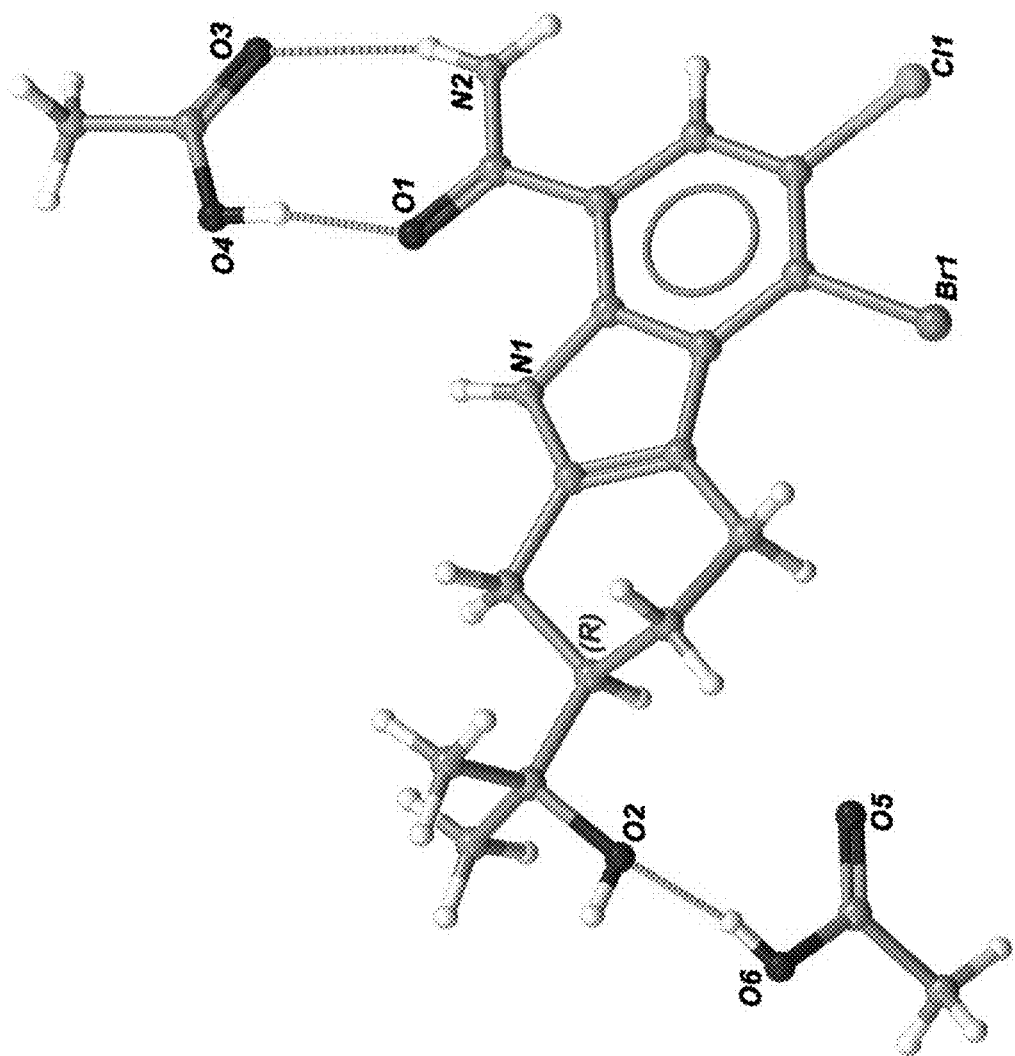
FIG. 1 shows the absolute stereochemistry of Intermediate 30 diacetic acid solvate.

The first aspect of the present invention provides at least one compound of Formula (I):

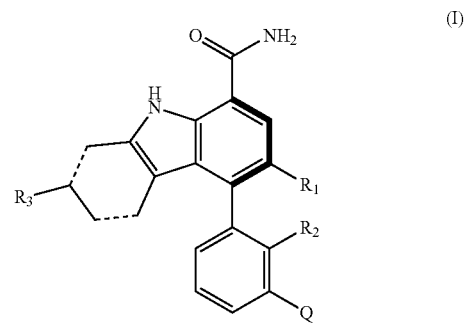

wherein:

the two dotted lines represent either two single or two double bonds;

Q is

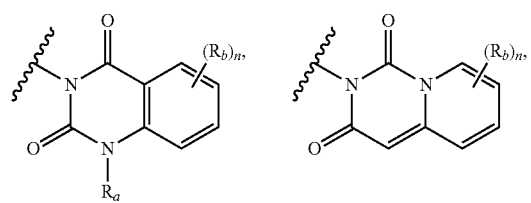

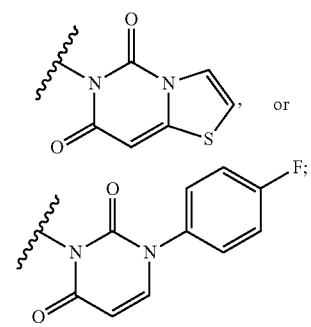

$R_1$ is F, Cl, —CN, or —CH$_3$;

$R_2$ is Cl or —CH$_3$;

$R_3$ is —C(CH$_3$)$_2$OH or —CH$_2$CH$_2$OH;

$R_a$ is H or —CH$_3$;

each $R_b$ is independently F, Cl, —CH$_3$, and/or —OCH$_3$; and n is zero, 1, or 2.

Atropisomers are stereoisomers resulting from hindered rotation about a single bond axis where the rotational barrier is high enough to allow for the isolation of the individual rotational isomers. (LaPlante et al., *J. Med. Chem.*, 54:7005-7022 (2011).) The compounds of Formula (A):

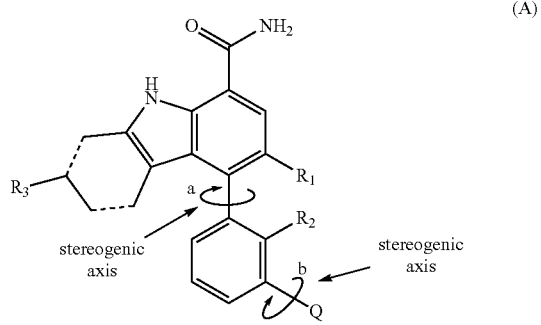

have two stereogenic axes: bond (a) between the tricyclic tetrahydrocarbazole/carbazole group and the phenyl group; and bond (b) between the asymmetric heterocyclic dione group Q and the phenyl group. Due to the non-symmetric nature of the substitutions on the rings connected by the single bonds labeled a and b, and due to limited rotation about these bonds caused by steric hindrance, the compounds of Formula (A) can form rotational isomers. If the rotational energy barriers are sufficiently high, hindered rotations about bond (a) and/or bond (b) occur at rates that are slow enough to allow isolation of the separated atropisomers as different compounds. Thus, the compounds of Formula (A) can form four rotational isomers, which under certain conditions, such as chromatography on a chiral stationary phase, can be separated into individual atropisomers. In solution, the compounds of Formula (A) can be provided as a mixture of four diastereomers, or mixtures of two pairs of diastereomers, or single atropisomers.

For the compounds of Formula (A), the pair of rotational isomers formed by hindered rotation about stereogenic axis (a) can be represented by the compounds of Formula (I) and Formula (B) having the structures:

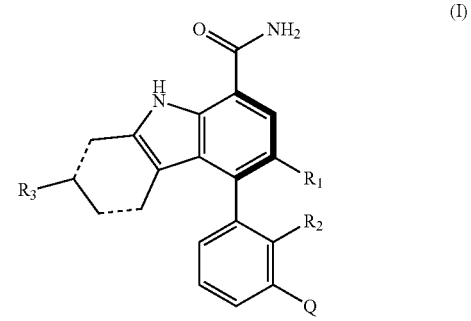

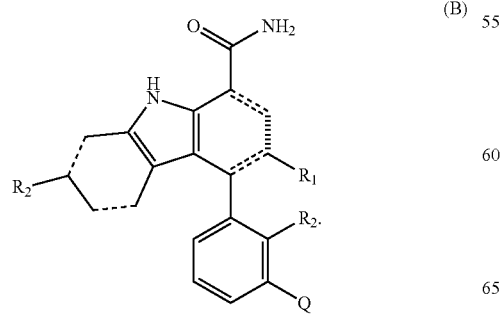

The compounds of Formula (I) and the compounds of Formula (B) were found to be separable and stable in solution at ambient and physiological temperatures. Additionally, rotational isomers are formed by hindered rotation about stereogenic axis (b). These two atropisomers of the compounds of Formula (I) were also found to be separable and stable in solution at ambient and physiological temperatures.

Chiral compounds, such as the compounds of Formula (A), can be separated by various techniques including Supercritical Fluid Chromatography (SFC). SFC, which is a form of normal phase HPLC, is a separation technique that uses super/subcritical fluid $CO_2$ and polar organic modifiers such as alcohols as mobile phases. (White et al., *J. Chromatography A*, 1074:175-185 (2005).)

The compounds of Formula (I) wherein Q is

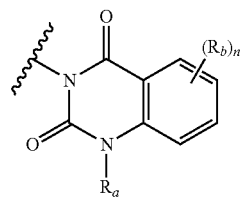

can be represented by the structure of Formula (II):

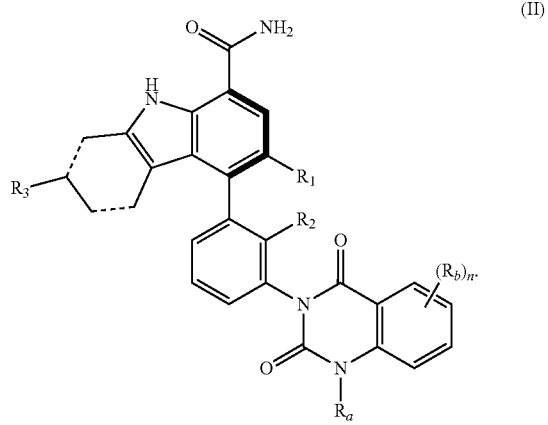

The four rotational isomers of the compound of Formula (A) wherein Q is

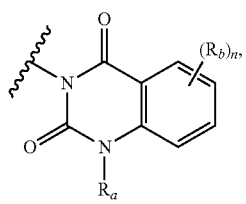

can be represented by compounds of Formula (II) having the structures of Formula (II-1) and (II-2):

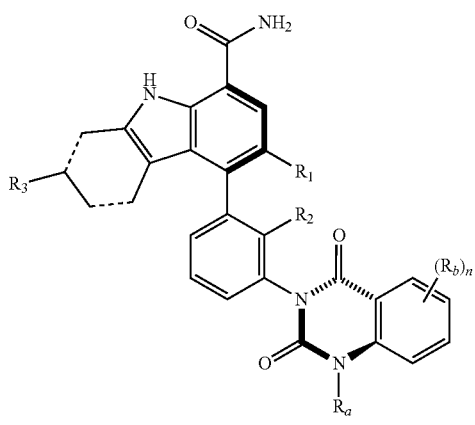
(II-1)
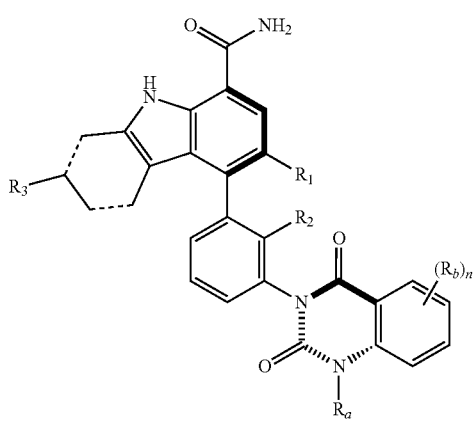
(II-2)
and the compounds of Formula (B) having the structures of Formula (B-1) and (B-2):
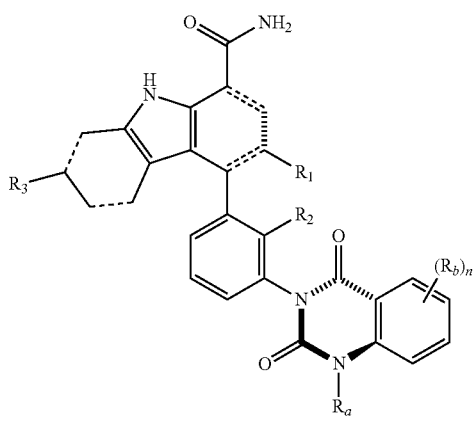
(B-1)
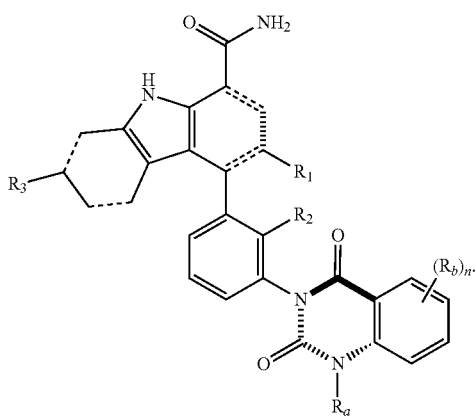
(B-2)
The compounds of Formula (I) wherein Q is
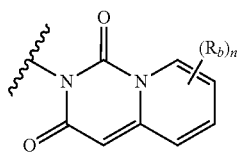
can be represented by the structure of Formula (III):
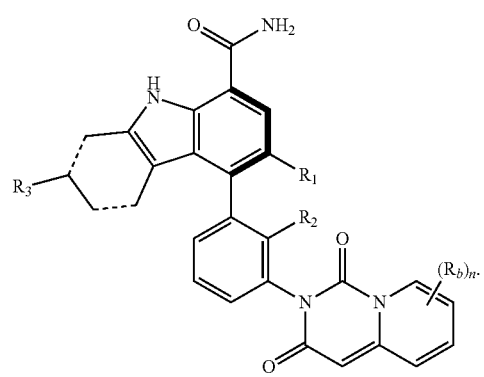
(III)
The four rotational isomers of the compound of Formula (A) wherein Q is
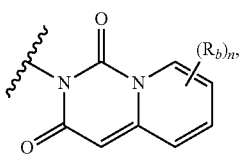
can be represented by the compounds of Formula (III) having the structures of Formula (III-1) and (III-2):

(III-1)
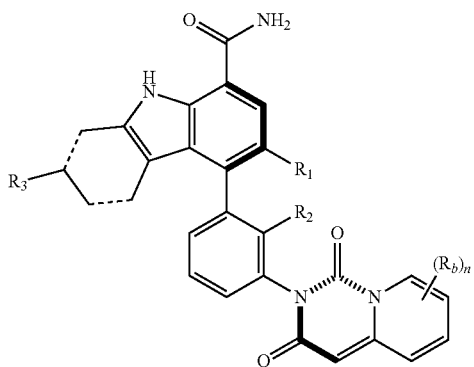
(B-4)
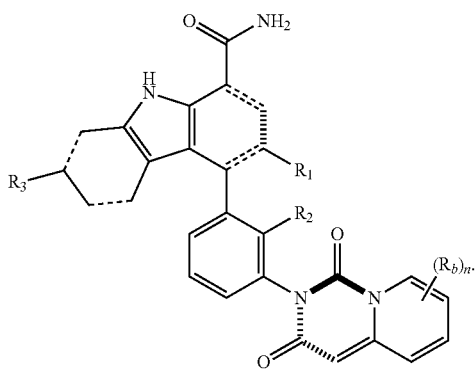
The compounds of Formula (I) wherein Q is
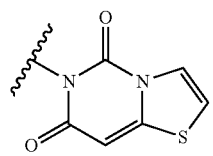 [SMILES: *n1c(=O)cc2sccn2c1=O]
can be represented by the structure of Formula (IV):
(III-2)
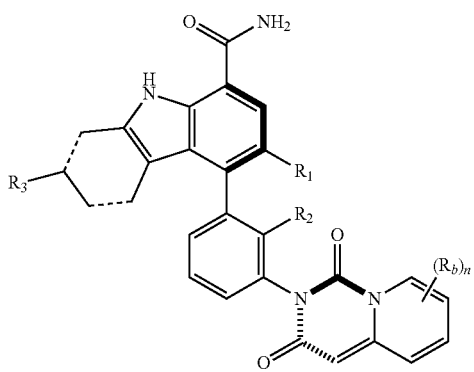
(IV)
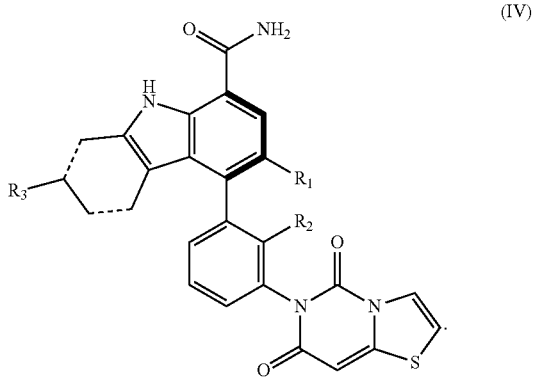
and the compounds of Formula (B) having the structures of Formula (B-3) and (B-4):
(B-3)
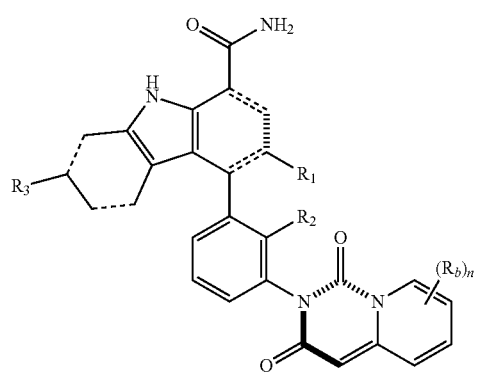
The four rotational isomers of the compound of Formula (A) wherein Q is
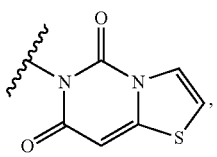 [SMILES: *n1c(=O)cc2sccn2c1=O]
can be represented by the compounds of Formula (IV) having the structures of Formula (IV-1) and (IV-2):

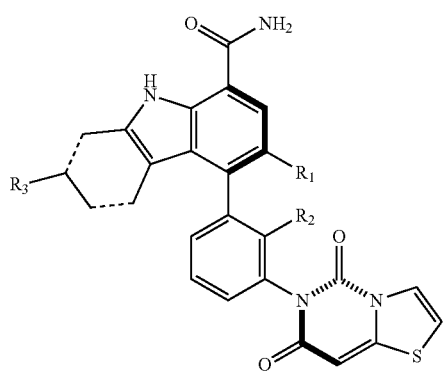
(IV-1)
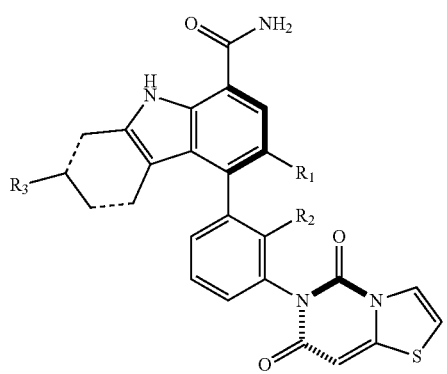
(IV-2)
and the compounds of Formula (B) having the structures of Formula (B-5) and B-6):
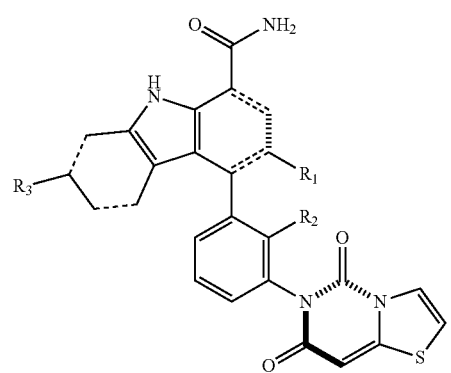
(B-5)
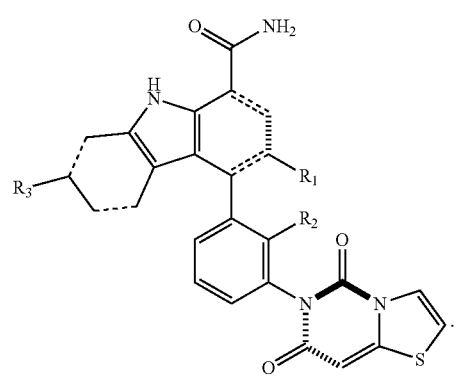
(B-6)
The compounds of Formula (I) wherein Q is
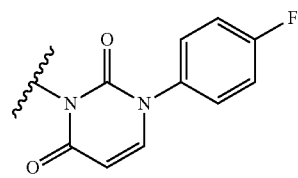 [SMILES: *n1c(=O)ccn(-c2ccc(F)cc2)c1=O]
can be represented by the structure of Formula (V):
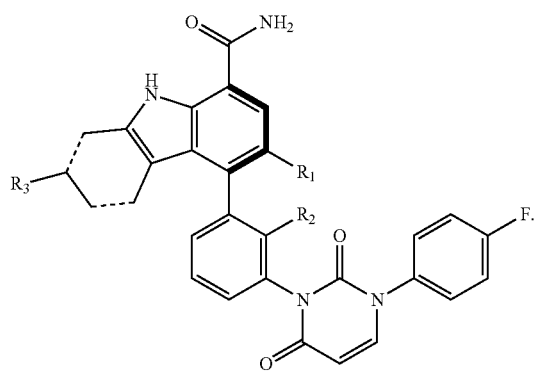
(V)
The four rotational isomers of the compound of Formula (A) wherein Q is
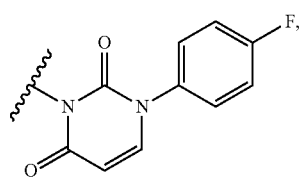 [SMILES: *n1c(=O)ccn(-c2ccc(F)cc2)c1=O]
can be represented by the compounds of Formula (V), having the structures of Formula (V-1) and (V-2):

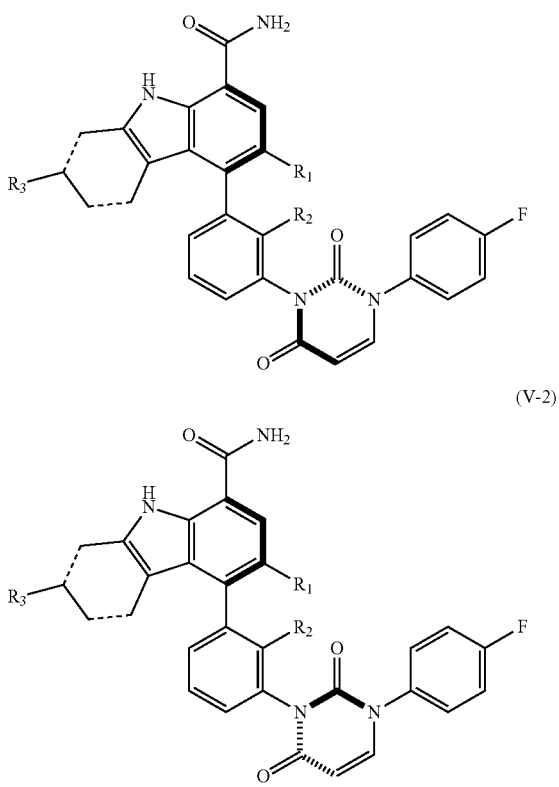

(V-1)

(V-2)

and the compounds of Formula (B) having the structures of Formula (B-7) and (B-8):

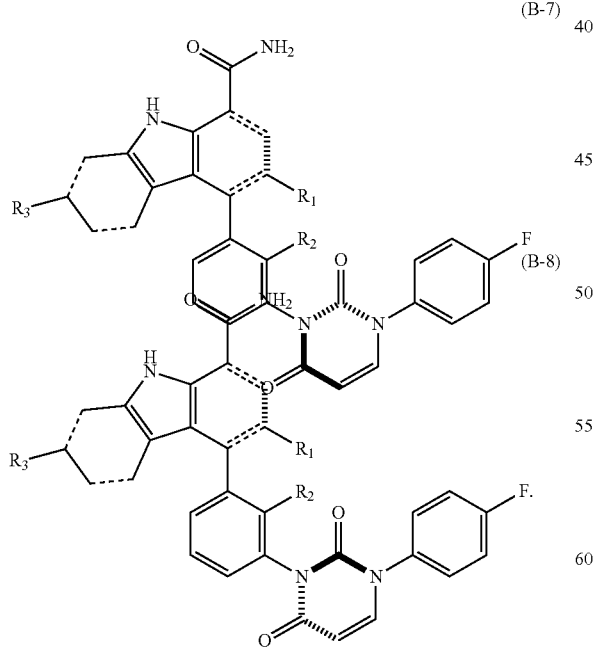

(B-7)

(B-8)

The absolute spacial configurations of the atropisomers can be determined by single crystal x-ray crystallography.

The compounds of Formula (I) can be provided as individual atropisomers or as mixtures comprising the two atropisomers of Formula (I) in any proportions. The mixture of the two atropisomers of Formula (I) may optionally contain one or both atropisomers of Formula (B) in any proportions.

The compounds of Formula (I) in which $R_1$ is F, Cl, or —$CH_3$ correspond to the (R)-atropisomer with respect to the stereogenic axis formed by bond (a). The compounds of Formula (B) in which $R_1$ is F, Cl, or —$CH_3$ correspond to the (S)-atropisomer with respect to the stereogenic axis formed by bond (a).

The compounds of Formula (I) in which $R_1$ is —CN correspond to the (S)-atropisomer with respect to the stereogenic axis formed by bond (a). The compounds of Formula (B) in which $R_1$ is —CN correspond to the (R)-atropisomer with respect to the stereogenic axis formed by bond (a).

As used herein, the phase "the two dotted lines represent either two single or two double bonds" refers to compounds of Formula (A), (B), (I), (II), (III), (IV), and (V) in which the two dotted lines are simultaneously single bonds or the two dotted lines are simultaneously double bonds. For example, the compounds of Formula (I) in which the two dotted lines are simultaneously single bonds are tetrahydrocarbazole compounds having the structure of Formula (IA) and the compounds of Formula (I) in which the two dotted lines are simultaneously double bonds are carbazole compounds having the structure of Formula (B):

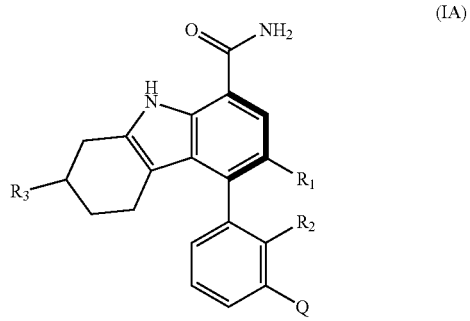

(IA)

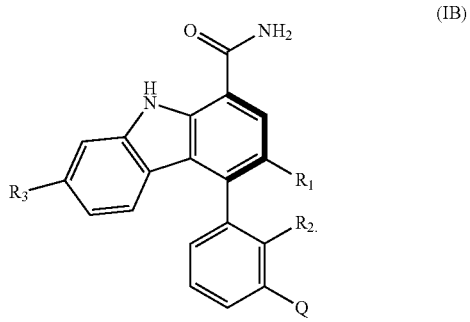

(IB)

The tetrahydrocarbazole compounds represented by Formula (IA) also have a chiral center at the carbon atom to which the substituent $R^3$ is attached, and thus can exist as S- and R-isomers at this chiral center.

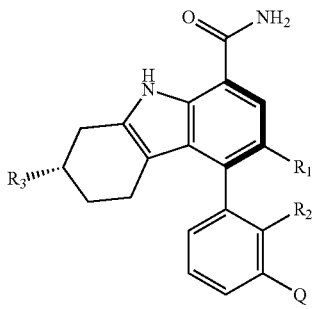

(IA-1)

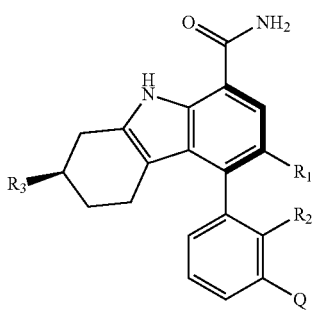

(IA-2)

These isomers are separable and are stable. One embodiment provides compounds of Formula (IA) with the carbon chiral center to which the $R^3$ substituent is attached, as the S-isomer. One embodiment provides the compounds of Formula (IA) with the carbon chiral center to which the $R^3$ substituent is attached, as the R-isomer.

One embodiment provides compounds of Formula (I) wherein $R_3$ is —C(CH$_3$)$_2$OH; and $R_1$, $R_2$, and Q are defined in the first aspect. Included in this embodiment are compounds in which Q is:

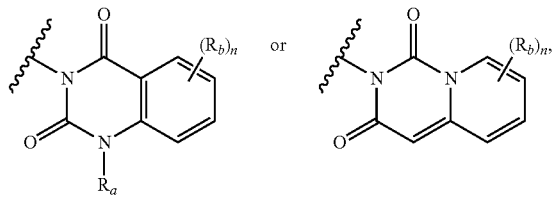

and $R_a$, $R_b$, and n are defined in the first aspect. Also included in this embodiment are compounds of Formula (IA). Other compounds included in this embodiment are the compounds of Formula (IB).

One embodiment provides compounds of Formula (II) wherein $R_3$ is —C(CH$_3$)$_2$OH; and $R_1$, $R_2$, $R_a$, $R_b$, and n are defined in the first aspect. Included in this embodiment are compounds in which in which $R_a$ is —CH$_3$ including —CD$_3$.

One embodiment provides compounds of Formula (III) wherein $R_3$ is —C(CH$_3$)$_2$OH; and $R_1$, $R_2$, $R_b$, and n are defined in the first aspect. Included in this embodiment are compounds in which in which each $R_b$ is independently F or Cl.

One embodiment provides compounds of Formula (IV) wherein $R_3$ is —C(CH$_3$)$_2$OH; and $R_1$ and $R_2$ are defined in the first aspect. Included in this embodiment are compounds in which $R_1$ is F, Cl, or —CH$_3$.

One embodiment provides compounds of Formula (V) wherein $R_3$ is —C(CH$_3$)$_2$OH; and $R_1$ and $R_2$ are defined in the first aspect. Included in this embodiment are compounds in which $R_1$ is F, Cl, or —CH$_3$.

One embodiment provides compounds of Formula (I) wherein $R_1$ is F. Included in this embodiment are compounds of Formula (IA). Other compounds included in this embodiment are the compounds of Formula (IB).

One embodiment provides compounds of Formula (I) wherein $R_1$ is Cl. Included in this embodiment are compounds of Formula (IA). Other compounds included in this embodiment are the compounds of Formula (IB).

One embodiment provides compounds of Formula (I) wherein $R_1$ is F or Cl. Included in this embodiment are compounds of Formula (IA). Other compounds included in this embodiment are the compounds of Formula (IB).

One embodiment provides compounds of Formula (I) wherein $R_1$ is —CH$_3$. Included in this embodiment are compounds of Formula (IA). Other compounds included in this embodiment are the compounds of Formula (IB).

One embodiment provides compounds of Formula (I) wherein $R_1$ is —CN. Included in this embodiment are compounds of Formula (IA). Other compounds included in this embodiment are the compounds of Formula (IB).

One embodiment provides compounds of Formula (I) wherein $R_1$ is F, Cl, or —CN. Included in this embodiment are compounds of Formula (IA). Other compounds included in this embodiment are the compounds of Formula (IB).

One embodiment provides compounds of Formula (I) wherein $R_1$ is —CH$_3$ or —CN. Included in this embodiment are compounds of Formula (IA). Other compounds included in this embodiment are the compounds of Formula (IB).

One embodiment provides compounds of Formula (I) wherein $R_1$ is F, Cl, or —CH$_3$. Included in this embodiment are compounds of Formula (IA). Other compounds included in this embodiment are the compounds of Formula (IB).

One embodiment provides compounds of Formula (I) wherein $R_2$ is Cl. Included in this embodiment are compounds of Formula (IA). Other compounds included in this embodiment are the compounds of Formula (IB). Also, included in this embodiment are compounds in which $R_3$ is —C(CH$_3$)$_2$OH.

One embodiment provides compounds of Formula (I) wherein $R_2$ is —CH$_3$. Included in this embodiment are compounds of Formula (IA). Other compounds included in this embodiment are the compounds of Formula (IB). Also, included in this embodiment are compounds in which $R_3$ is —C(CH$_3$)$_2$OH.

One embodiment provides compounds of Formula (I) wherein $R_3$ is —C(CH$_3$)$_2$OH. Included in this embodiment are compounds of Formula (IA). Other compounds included in this embodiment are the compounds of Formula (IB).

One embodiment provides compounds of Formula (I) wherein each $R_b$ is independently F and/or Cl. Included in this embodiment are compounds in which n is 1 or 2. Also included in this embodiment are compounds in which n is 2 and each $R_b$ is F.

One embodiment provides compounds of Formula (I) wherein n is 1 and $R_b$ is —CH$_3$ or —OCH$_3$.

One embodiment provides compounds of Formula (I) wherein n is zero. Included in this embodiment are compounds of Formula (IA). Other compounds included in this embodiment are the compounds of Formula (IB).

One embodiment provides compounds of Formula (II) in which the two dotted lines are simultaneously single bonds and $R_1$, $R_2$, $R_3$, $R_a$, $R_b$, and n are defined in the first aspect. Compounds of this embodiment have the structure of Formula (IIA):

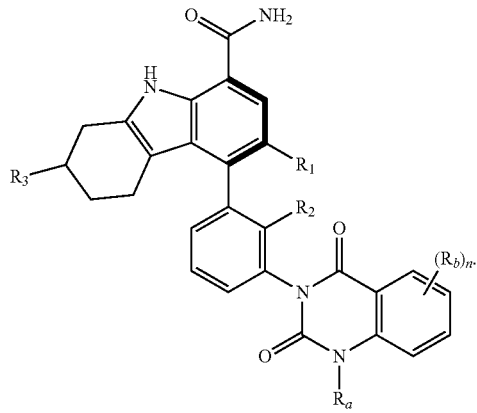

The two rotational isomers of the compound of Formula (IIA) are represented by the structures of Formula (IIA-1) and (IIA-2):

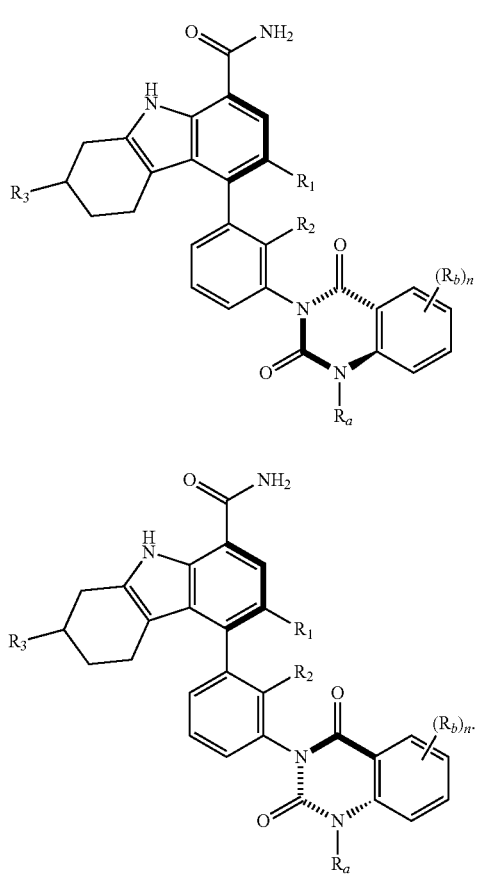

Included in this embodiment are compounds of Formula (IIA), (IIA-1), and (IIA-2) in which $R_3$ is —C(CH$_3$)$_2$OH.

One embodiment provides compounds of Formula (II) in which the two dotted lines are simultaneously double bonds and $R_1$, $R_2$, $R_3$, $R_a$, $R_b$, and n are defined in the first aspect. Compounds of this embodiment have the structure of Formula (IIB):

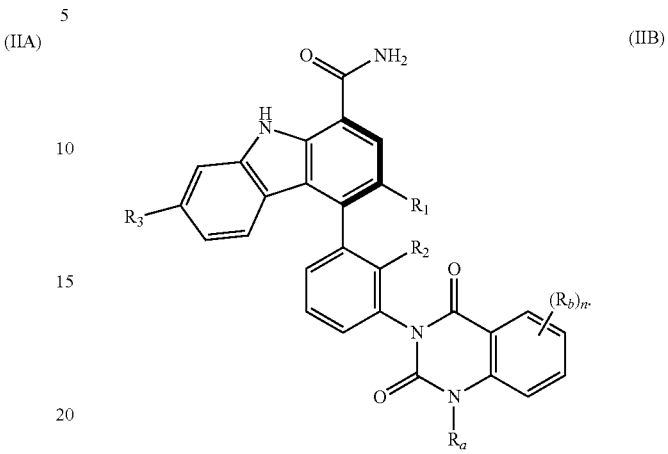

The two rotational isomers of the compound of Formula (IIB) are represented by the structures of Formula (IIB-1) and (IIB-2):

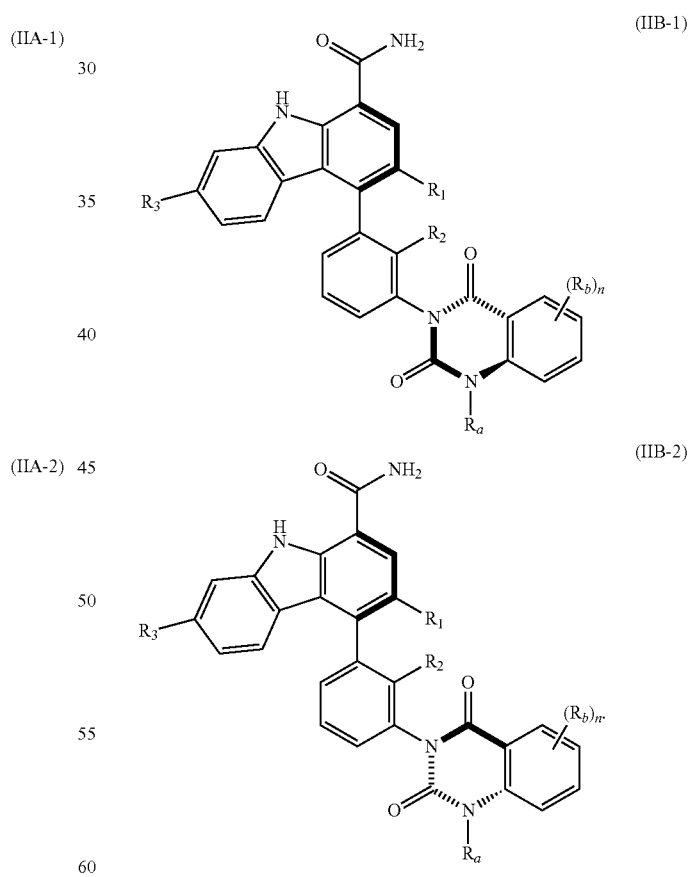

Included in this embodiment are compounds of Formula (IIB), (IIB-1), and (IIB-2) in which $R_3$ is —C(CH$_3$)$_2$OH.

One embodiment provides compounds of Formula (II) wherein $R_a$ is H. Included in this embodiment are compounds of Formula (IIA). Other compounds included in this embodiment are the compounds of Formula (IIB).

One embodiment provides compounds of Formula (II) wherein $R_a$ is —$CH_3$. Included in this embodiment are compounds in which $R_a$ is —$CD_3$. Also, included in this embodiment are compounds of Formula (IIA). Other compounds included in this embodiment are the compounds of Formula (IIB).

One embodiment provides compounds of Formula (III) in which the two dotted lines are simultaneously single bonds and $R_1$, $R_2$, $R_3$, $R_b$, and n are defined in the first aspect. Compounds of this embodiment have the structure of Formula (IIIA):

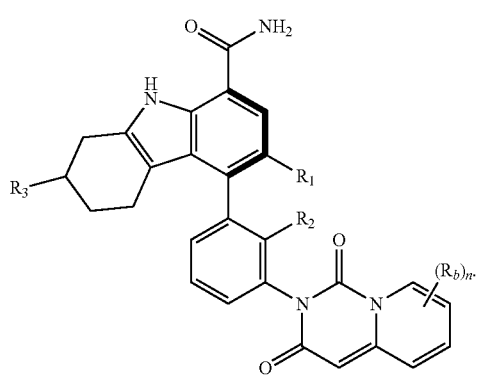

(IIIA)

The two rotational isomers of the compound of Formula (IIIA) are represented by the structures of Formula (IIIA-1) and (IIIA-2):

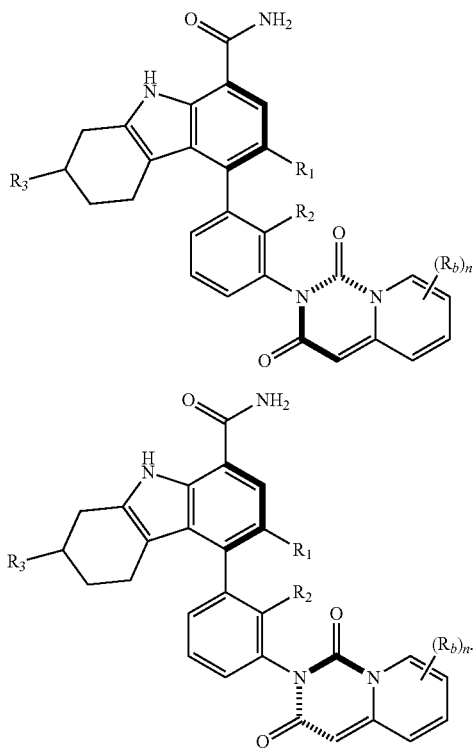

(IIIA-1)

(IIIA-2)

Included in this embodiment are compounds of Formula (IIIA), (IIIA-1), and (IIIA-2) in which $R_3$ is —$C(CH_3)_2OH$.

One embodiment provides compounds of Formula (III) in which the two dotted lines are simultaneously double bonds and $R_1$, $R_2$, $R_3$, $R_b$, and n are defined in the first aspect. Compounds of this embodiment have the structure of Formula (IIIB):

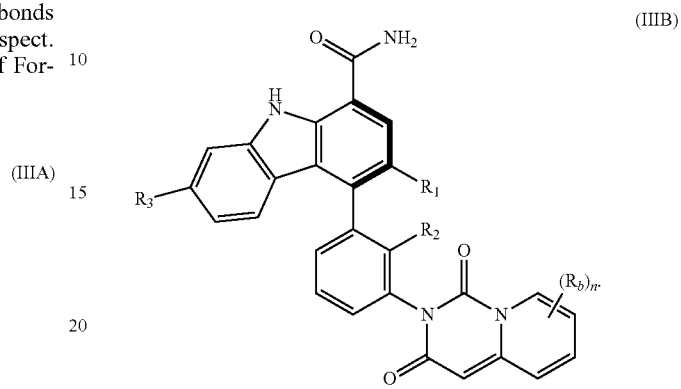

(IIIB)

The two rotational isomers of the compound of Formula (IIIB) are represented by the structures of Formula (IIIB-1) and (IIIB-2):

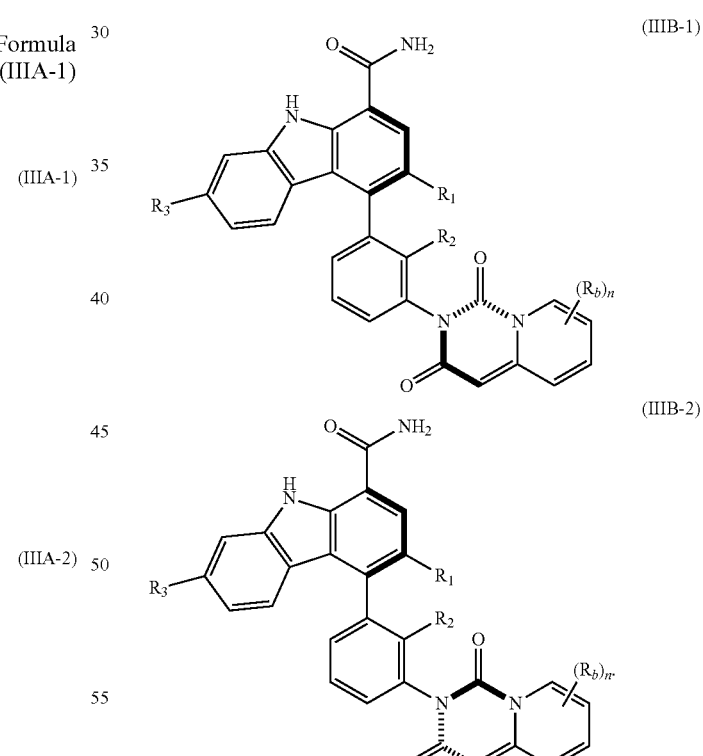

(IIIB-1)

(IIIB-2)

Included in this embodiment are compounds of Formula (IIIB), (IIIB-1), and (IIIB-2) in which $R_3$ is —$C(CH_3)_2OH$.

One embodiment provides compounds of Formula (IV) in which the two dotted lines are simultaneously single bonds and $R_1$, $R_2$, and $R_3$ are defined in the first aspect. Compounds of this embodiment have the structure of Formula (IVA);

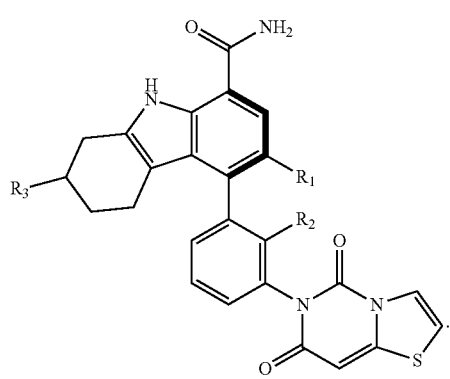

(IVA)

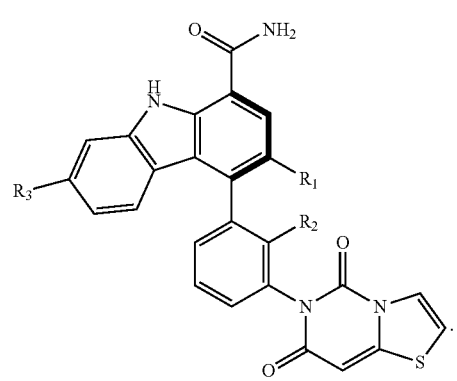

(IVB)

The two rotational isomers of the compound of Formula (IVA) are represented by the structures of Formula (IVA-1) and (IVA-2):

The two rotational isomers of the compound of Formula (IVB) are represented by the structures of Formula (IVB-1) and (IVB-2):

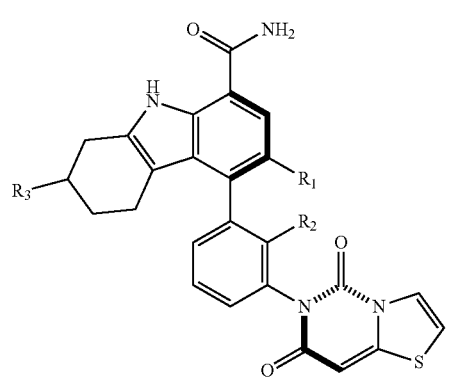

(IVA-1)

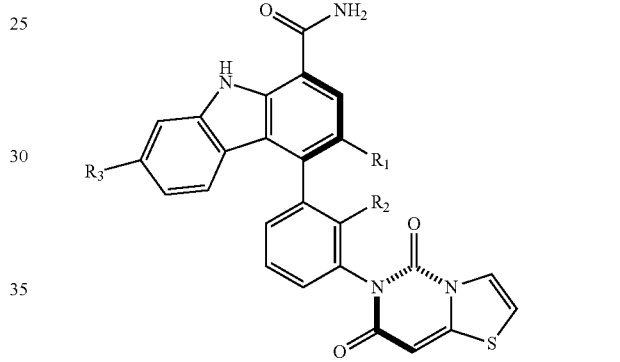

(IVB-1)

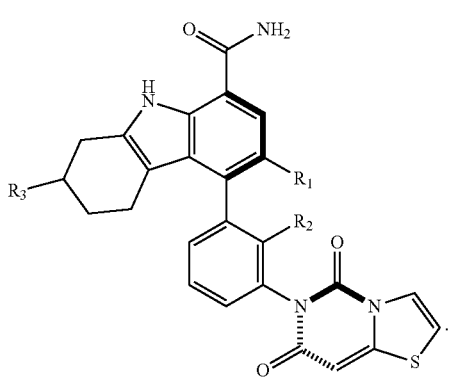

(IVA-2)

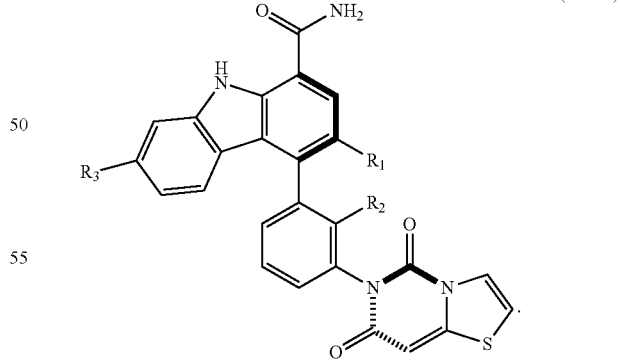

(IVB-2)

Included in this embodiment are compounds of Formula (IVA), (IVA-1), and (IVA-2) in which $R_3$ is —C(CH$_3$)$_2$OH.

One embodiment provides compounds of Formula (IV) in which the two dotted lines are simultaneously double bonds and $R_1$, $R_2$, and $R_3$ are defined in the first aspect. Compounds of this embodiment have the structure of Formula (IVB):

Included in this embodiment are compounds of Formula (IVB), (IVB-1), and (IVB-2) in which $R_3$ is —C(CH$_3$)$_2$OH.

One embodiment provides compounds of Formula (V) in which the two dotted lines are simultaneously single bonds and $R_1$, $R_2$, and $R_3$ are defined in the first aspect. Compounds of this embodiment have the structure of Formula (VA):

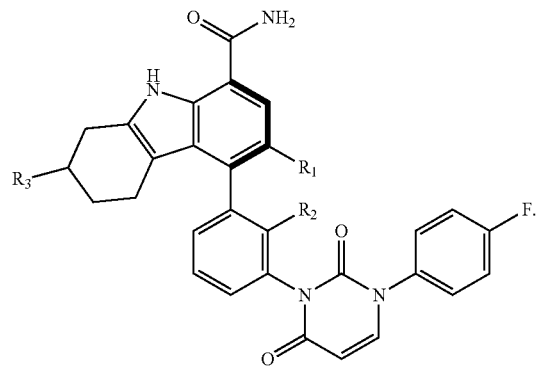

(VA)

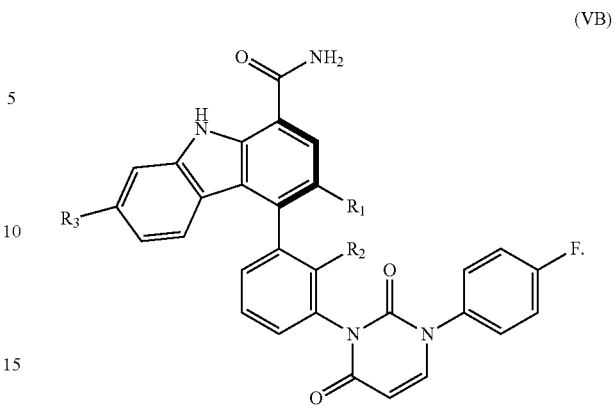

(VB)

The two rotational isomers of the compound of Formula (VA) are represented by the structures of Formula (VA-1) and (VA-2):

The two rotational isomers of the compound of Formula (VB) are represented by the structures of Formula (VB-1) and (VB-2):

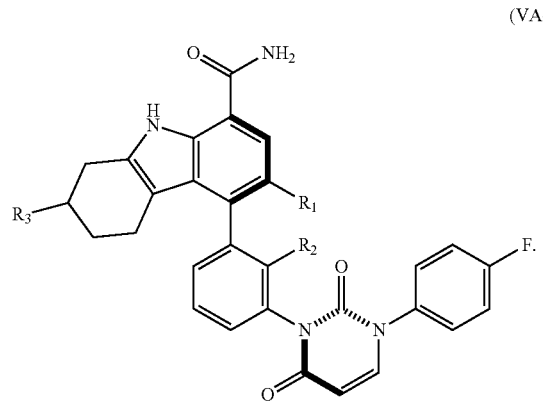

(VA-1)

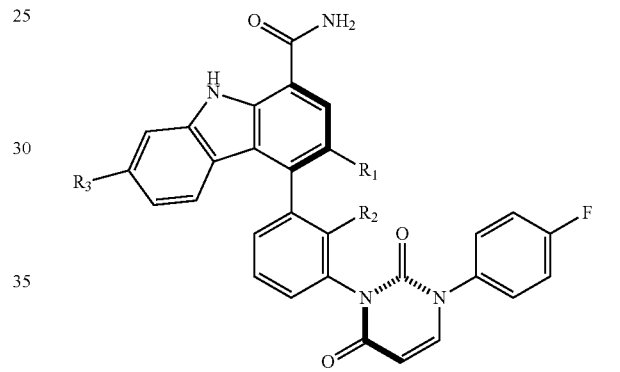

(VB-1)

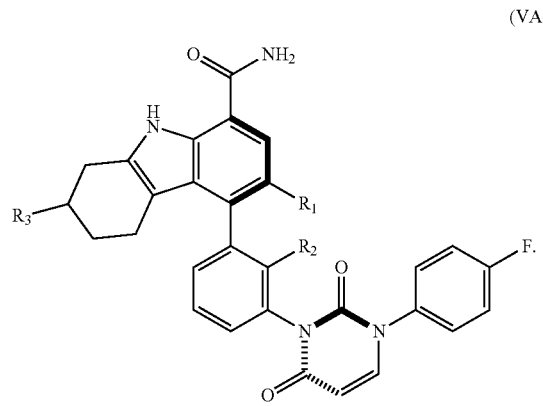

(VA-2)

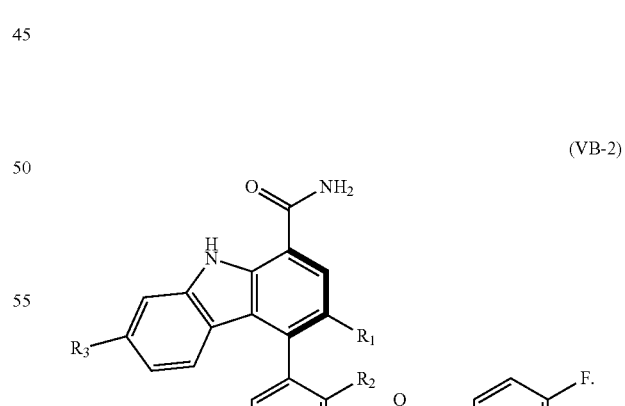

(VB-2)

Included in this embodiment are compounds of Formula (VA), (VA-1), and (VA-2) in which $R_3$ is —C(CH$_3$)$_2$OH.

One embodiment provides compounds of Formula (V) in which the two dotted lines are simultaneously double bonds and $R_1$, $R_2$, and $R_3$ are defined in the first aspect. Compounds of this embodiment have the structure of Formula (VB):

Included in this embodiment are compounds of Formula (VB), (VB-1), and (VB-2) in which $R_3$ is —C(CH$_3$)$_2$OH.

One embodiment provides a compound of Formula (I) having the structure:

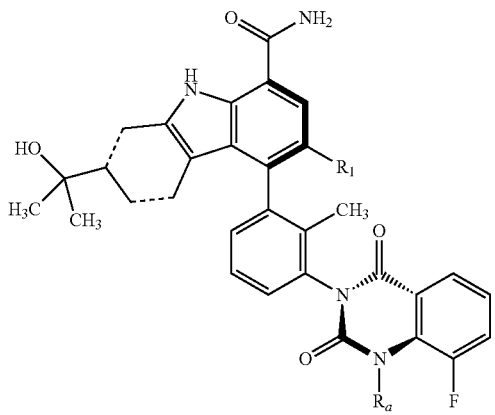

wherein R₁ is Cl or F; and $R_a$ is —CH₃ including —CD₃.

One embodiment provides a compound of Formula (I) having the structure:

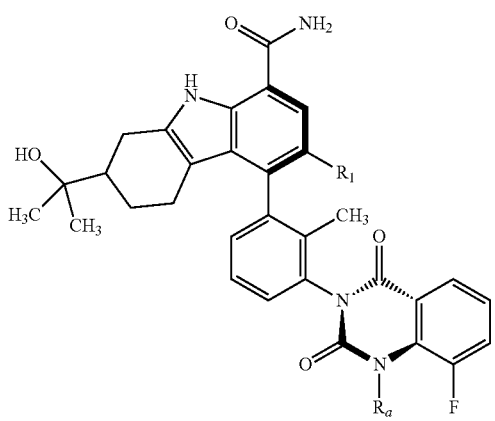

wherein R₁ is Cl or F; and $R_a$ is —CH₃ including —CD₃.

One embodiment provides a compound of Formula (I) having the structure:

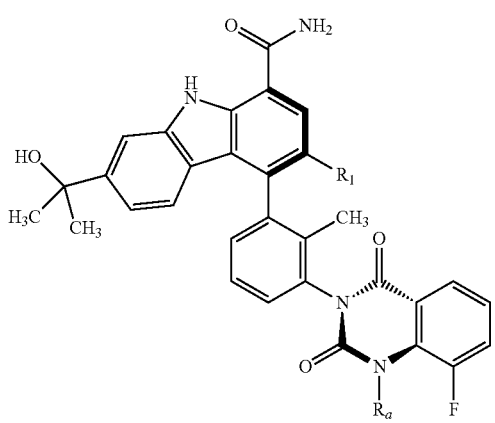

wherein R₁ is Cl or F; and $R_a$ is —CH₃ including —CD₃.

One embodiment provides a compound of Formula (I) having the structure:

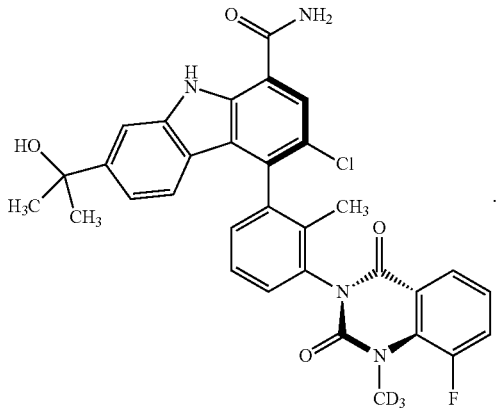

One embodiment provides a compound of Formula (I) or having the structure:

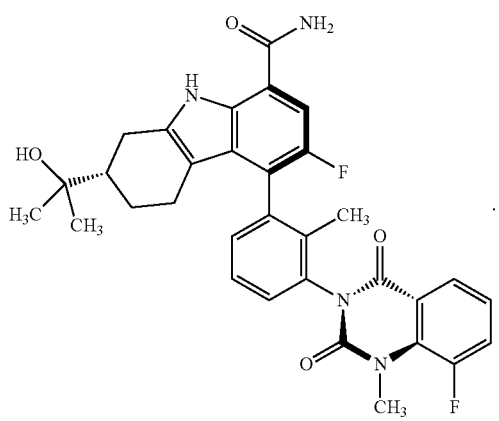

One embodiment provides a compound of Formula (I) having the structure:

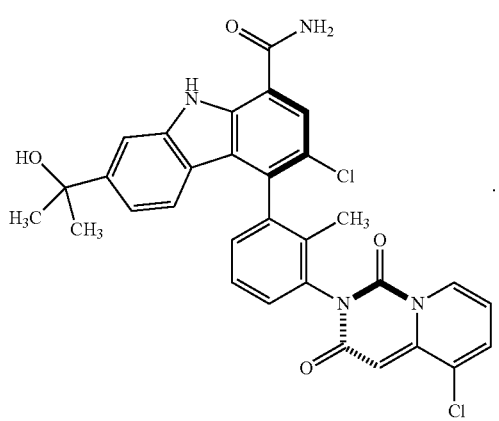

One embodiment provides a compound selected from the exemplified examples within the scope of the first aspect.

One embodiment provides a compound selected from any subset list of compounds within the scope of the first aspect or of any of the above embodiments.

One embodiment provides a compound of Formula (II) wherein the compound is: 3-chloro-4-(R)-(3-(R)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (1); 3-chloro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (2); 3-chloro-7-(2-hydroxypropan-2-yl)-4-(R)-(2-methyl-3-(1-methyl-2,4-dioxo-1,2-dihydroquinazolin-3(4H)-yl)phenyl)-9H-carbazole-1-carboxamide (3); 3-chloro-4-(R)-(3-(1,8-dimethyl-2,4-dioxo-1,2-dihydroquinazolin-3(4H)-yl)-2-methylphenyl)-7-(2-hydroxypropan-2-yl)-9H-carbazole-1-carboxamide (4); 3-chloro-7-(2-hydroxypropan-2-yl)-4-(R)-(3-(R)-(7-methoxy-1-methyl-2,4-dioxo-1,2-dihydroquinazolin-3(4H)-yl)-2-methylphenyl)-9H-carbazole-1-carboxamide (5); 3-chloro-7-(2-hydroxypropan-2-yl)-4-(R)-(3-(S)-(7-methoxy-1-methyl-2,4-dioxo-1,2-dihydroquinazolin-3(4H)-yl)-2-methylphenyl)-9H-carbazole-1-carboxamide (6); 3-chloro-7-(2-hydroxypropan-2-yl)-4-(R)-(3-(8-methoxy-1-methyl-2,4-dioxo-1,2-dihydroquinazolin-3(4H)-yl)-2-methylphenyl)-9H-carbazole-1-carboxamide (7); 3-chloro-4-(R)-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (8); 3-chloro-4-(R)-(3-(7-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (9); 3-chloro-4-(R)-(3-(6,8-difluoro-2,4-dioxo-1,2-dihydroquinazolin-3(4H)-yl)-2-methylphenyl)-7-(2-hydroxypropan-2-yl)-9H-carbazole-1-carboxamide (10); 3-chloro-4-(R)-(3-(S)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide (11); 3-chloro-4-(R)-(3-(R)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide (12); 3-chloro-4-(R)-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (13); 3-chloro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide (14); 3-cyano-4-(S)-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (15 and 16); 3-fluoro-4-(R)-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (17); 3-fluoro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (18); 3-fluoro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (19); 3-fluoro-4-(R)-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (20); 3-fluoro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide (21); 3-fluoro-4-(R)-(3-(S)-(8-fluoro-2,4-dioxo-1,2-dihydroquinazolin-3(4H)-yl)-2-methylphenyl)-7-(2-hydroxypropan-2-yl)-9H-carbazole-1-carboxamide (22); 6-chloro-5-(R)-(3-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (25); 6-chloro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (26); 6-fluoro-5-(R)-(3-(S)-(8-fluoro-1-methyl-2,4-dioxo-1,2-dihydroquinazolin-3(4H)-yl)-2-methylphenyl)-2-(R)-(2-hydroxypropan-2-yl)-2,3,4,9-tetrahydro-1H-carbazole-8-carboxamide (27); 6-fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (28); 4-(R)-(3-(S)-(8-fluoro-1-methyl-2,4-dioxo-1,2-dihydroquinazolin-3(4H)-yl)-2-methylphenyl)-7-(2-hydroxypropan-2-yl)-3-methyl-9H-carbazole-1-carboxamide (29); 3-chloro-4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (42); 3-chloro-4-(R)-(2-chloro-3-(R)-(1-methyl-2,4-dioxo-1,2-dihydroquinazolin-3(4H)-yl)phenyl)-7-(2-hydroxypropan-2-yl)-9H-carbazole-1-carboxamide (43); 3-chloro-4-(2-chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (44); 3-chloro-4-(R)-(2-chloro-3-(R)-(8-fluoro-1-methyl-2,4-dioxo-1,2-dihydroquinazolin-3(4H)-yl)phenyl)-7-(2-hydroxypropan-2-yl)-9H-carbazole-1-carboxamide (45); 4-(2-chloro-3-(8-fluoro-1-methyl-2,4-dioxo-1,2-dihydroquinazolin-3(4H)-yl)phenyl)-3-fluoro-7-(2-hydroxypropan-2-yl)-9H-carbazole-1-carboxamide (46); 3-chloro-4-(R)-(2-chloro-3-(8-fluoro-2,4-dioxo-1,2-dihydroquinazolin-3(4H)-yl)phenyl)-7-(2-hydroxypropan-2-yl)-9H-carbazole-1-carboxamide (47);

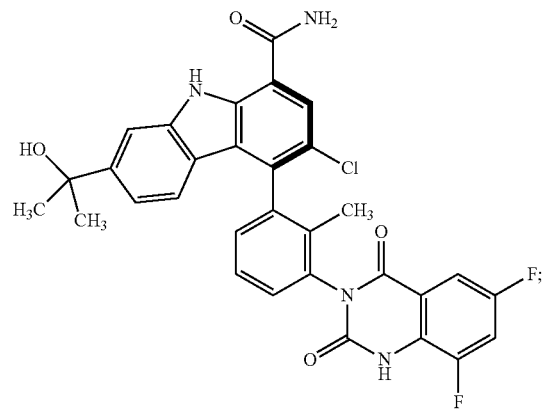

(48)

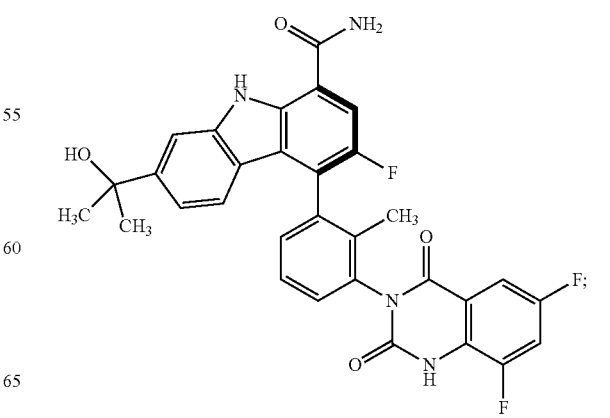

(50)

-continued
(51)
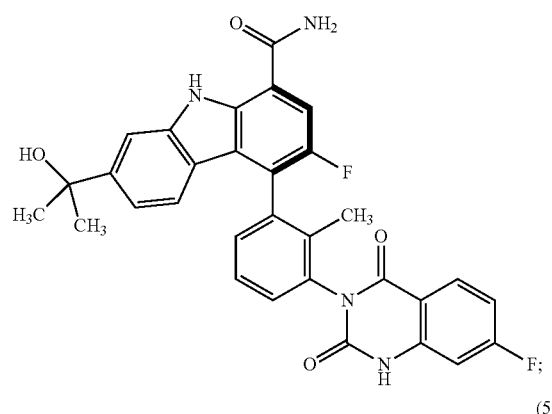
(52)
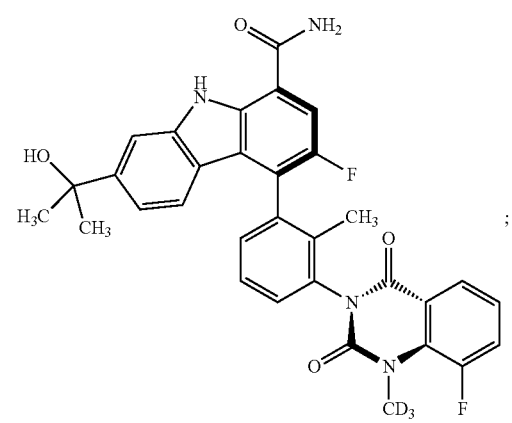
(53)
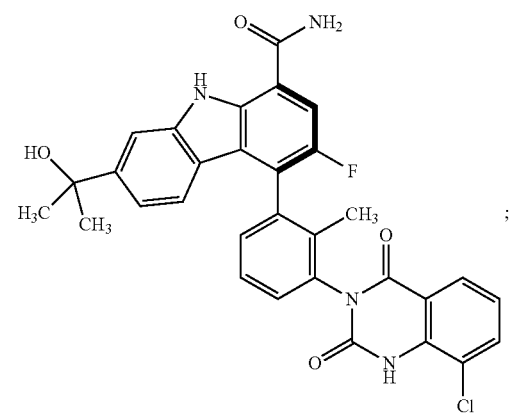
(54)
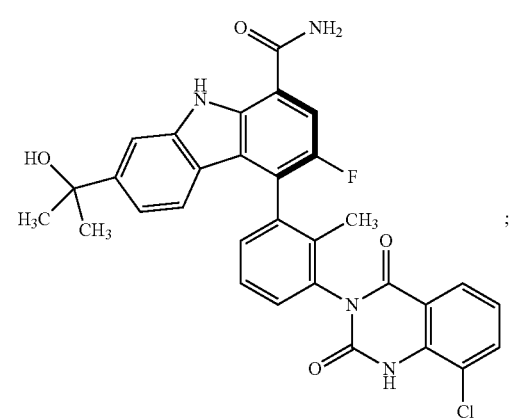
-continued
(55)
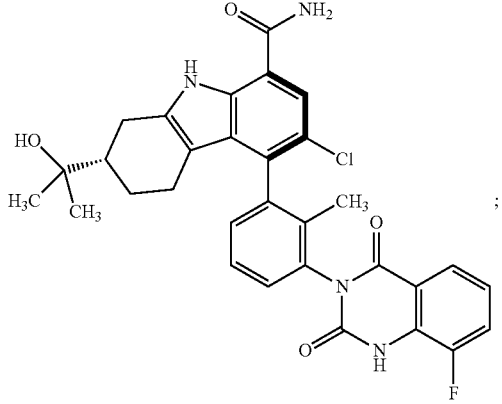
(56)
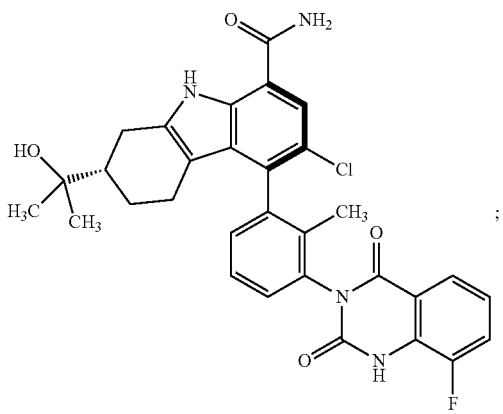
(57)
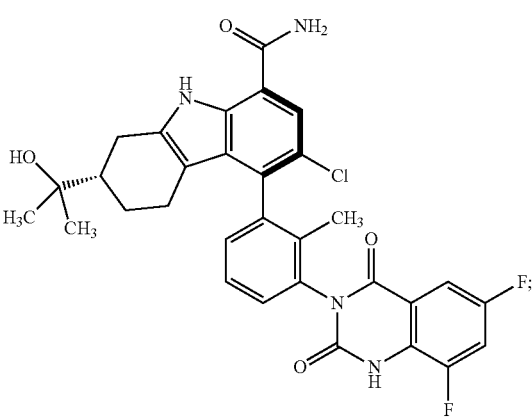
(58)
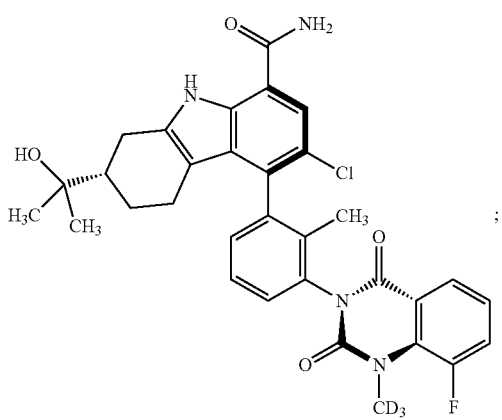

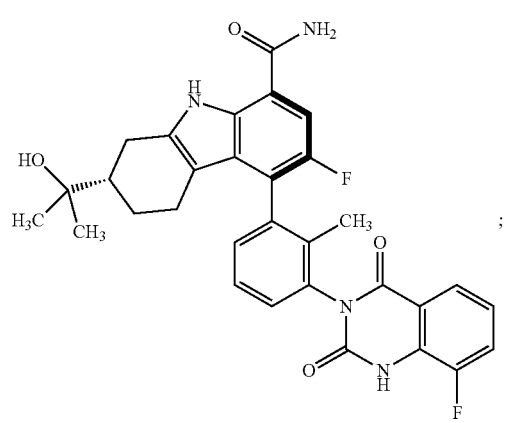
(59)
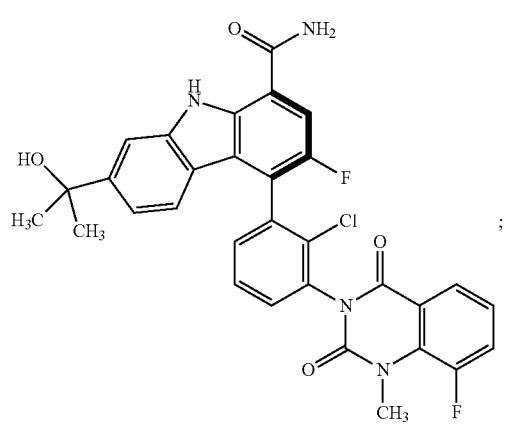
(60)
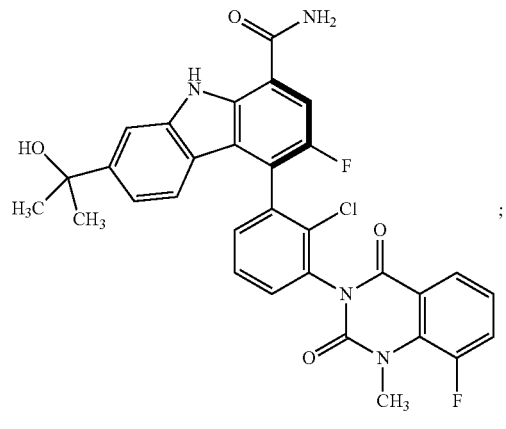
(61)
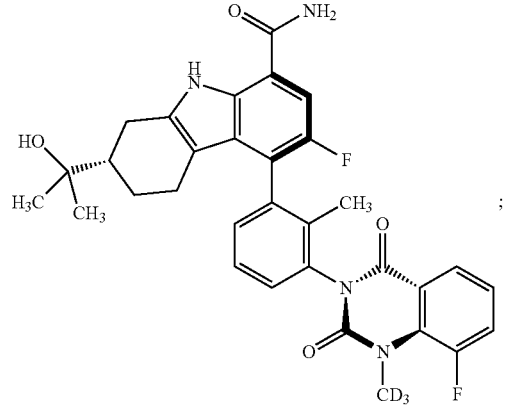
(62)
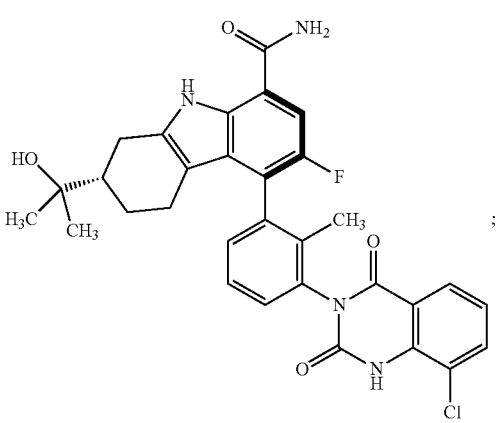
(63)
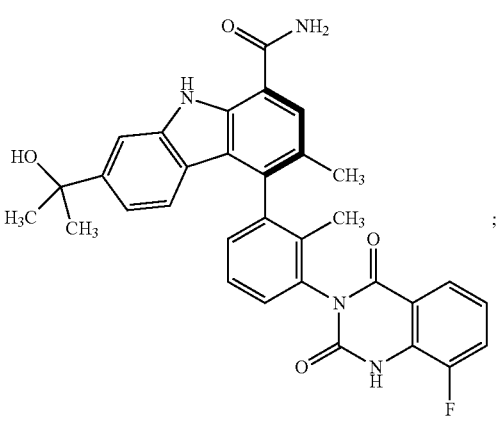
(66)
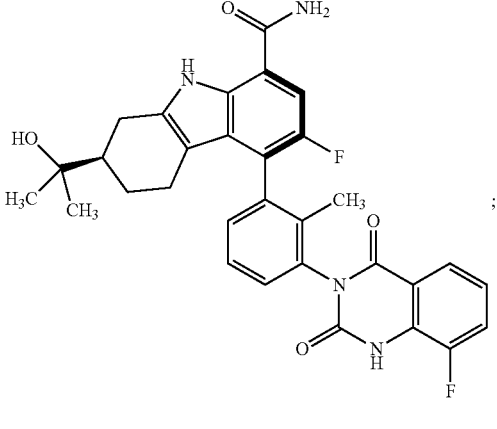
(67)
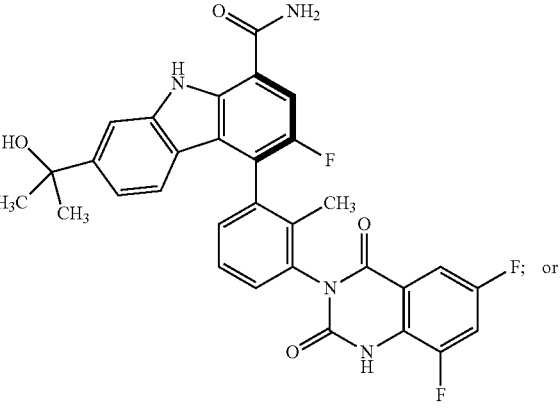
(73)

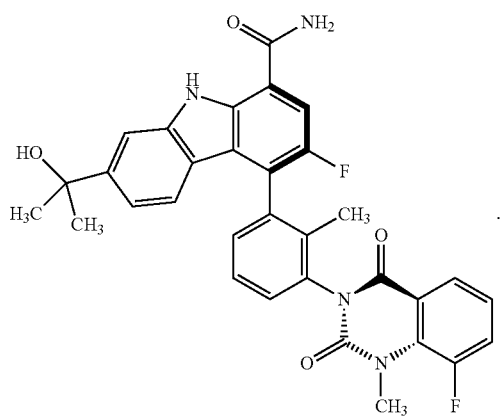

(74)

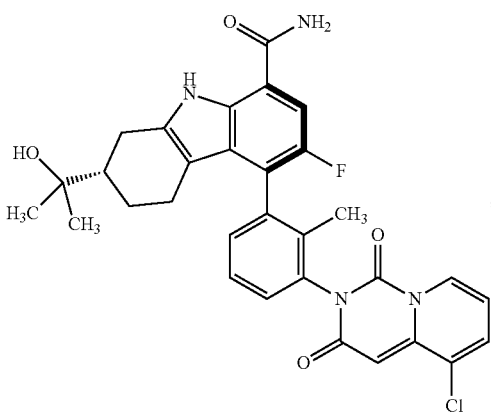

(65)

One embodiment provides a compound of Formula (III) wherein the compound is: 3-chloro-4-(R)-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (23); 4-(R)-(3-(5-chloro-1,3-dioxo-1H-pyrido[1,2-c]pyrimidin-2(3H)-yl)-2-methylphenyl)-3-fluoro-7-(2-hydroxypropan-2-yl)-9H-carbazole-1-carboxamide (30 and 31); 3-chloro-4-(R)-(3-(R)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (32); 3-chloro-4-(R)-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (33); 3-chloro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (34); 3-chloro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (35 and 36); 3-chloro-7-(2-hydroxypropan-2-yl)-4-(R)-(3-(5-methoxy-1,3-dioxo-1H-pyrido[1,2-c]pyrimidin-2(3H)-yl)-2-methylphenyl)-9H-carbazole-1-carboxamide (37); 3-fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (40 and 41);

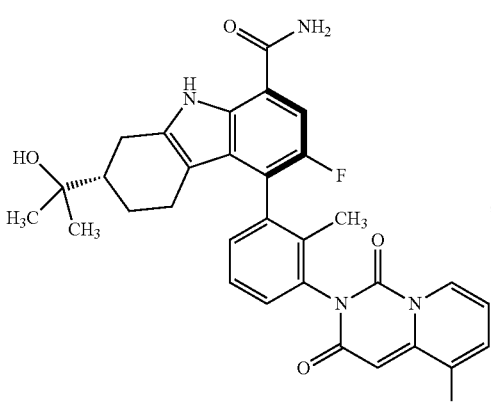

(68)

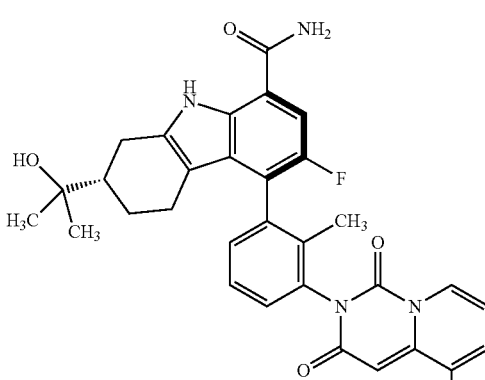

(69)

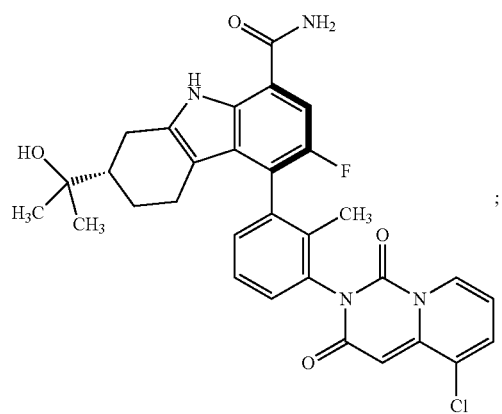

(64)

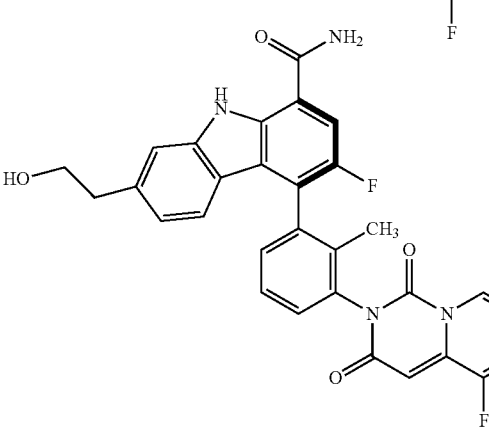

(70)

(71)

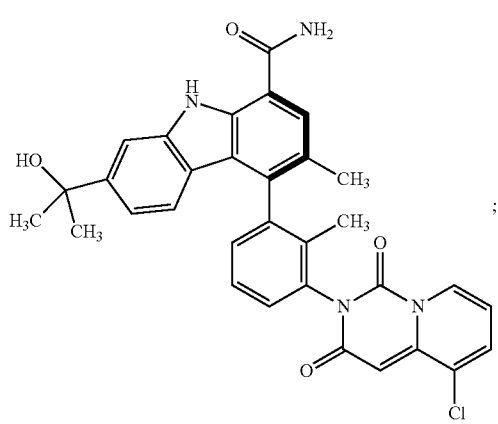

; or (72)

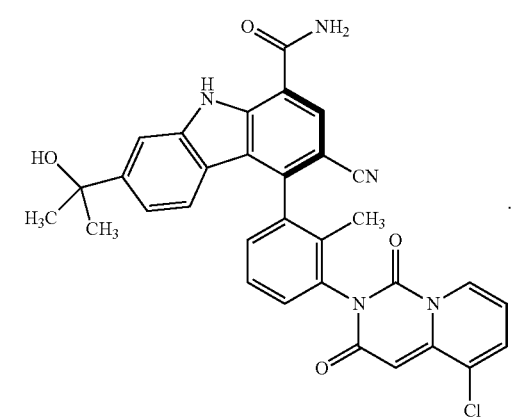

One embodiment provides a compound of Formula (IV) wherein the compound is: 3-chloro-4-(R)-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide (38 and 39).

One embodiment provides a compound of Formula (V) wherein the compound is: 3-chloro-4-(R)-(3-(3-(4-fluorophenyl)-2,6-dioxo-2,3-dihydropyrimidin-(6H)-yl)-2-methylphenyl)-7-(2-hydroxypropan-2-yl)-9H-carbazole-1-carboxamide (24).

In one embodiment, a composition is provided comprising a compound of Formula (I). Included in this embodiment is a composition comprising a mixture in any proportion of (i) a compound of Formula (I) and (ii) a compound of Formula (B).

In one embodiment, a composition is provided comprising at least 98 equivalent weight % of a compound of Formula (I), based on the total equivalent weight of the compound of Formula (I) and its atropisomer compound of Formula (B). Included in this embodiment, are compositions comprising at 99 equivalent weight %, 99.5 equivalent weight %, 99.8 equivalent weight %, and 99.9 equivalent weight % of a compound of Formula (I) based on the total equivalent weight of the compound of Formula (I) and its atropisomer compound of Formula (B). Compositions of this embodiment include pharmaceutical compositions.

In one embodiment, a composition is provided comprising a compound of Formula (II). Included in this embodiment is a composition comprising a mixture in any proportion of (i) a compound of Formula (II) and (ii) one or both of its atropisomer compounds of Formula (B-1) and (B-2).

In one embodiment, a composition is provided comprising at least 98 equivalent weight % of a compound of Formula (II), based on the total equivalent weight of the compound of Formula (II) and its atropisomer compounds of Formula (B-1) and (B-2). Included in this embodiment, are compositions comprising at 99 equivalent weight %, 99.5 equivalent weight %, 99.8 equivalent weight %, and 99.9 equivalent weight % of a compound of Formula (II) based on the total equivalent weight of the compound of Formula (II) and its atropisomer compounds of Formula (B-1) and (B-2). Compositions of this embodiment include pharmaceutical compositions.

In one embodiment, a composition is provided comprising a compound of Formula (III). Included in this embodiment is a composition comprising a mixture in any proportion of (i) a compound of Formula (III) and (ii) one or both of its atropisomer compounds of Formula (B-3) and (B-4).

In one embodiment, a composition is provided comprising at least 98 equivalent weight % of a compound of Formula (III), based on the total equivalent weight of the compound of Formula (III) and its atropisomer compounds of Formula (B-3) and (B-4). Included in this embodiment, are compositions comprising at 99 equivalent weight %, 99.5 equivalent weight %, 99.8 equivalent weight %, and 99.9 equivalent weight % of a compound of Formula (III) based on the total equivalent weight of the compound of Formula (III) and its atropisomer compounds of Formula (B-3) and (B-4). Compositions of this embodiment include pharmaceutical compositions.

In one embodiment, a composition is provided comprising a compound of Formula (IV). Included in this embodiment is a composition comprising a mixture in any proportion of (i) a compound of Formula (IV) and (ii) one or both of its atropisomer compounds of Formula (B-5) and (B-6).

In one embodiment, a composition is provided comprising at least 98 equivalent weight % of a compound of Formula (IV), based on the total equivalent weight of the compound of Formula (IV) and its atropisomer compounds of Formula (B-5) and (B-6). Included in this embodiment, are compositions comprising at 99 equivalent weight %, 99.5 equivalent weight %, 99.8 equivalent weight %, and 99.9 equivalent weight % of a compound of Formula (IV) based on the total equivalent weight of the compound of Formula (IV) and its atropisomer compounds of Formula (B-5) and (B-6). Compositions of this embodiment include pharmaceutical compositions.

In one embodiment, a composition is provided comprising a compound of Formula (V). Included in this embodiment is a composition comprising a mixture in any proportion of (i) a compound of Formula (V) and (ii) one or both of its atropisomer compounds of Formula (B-7) and (B-8).

In one embodiment, a composition is provided comprising at least 98 equivalent weight % of a compound of Formula (V), based on the total equivalent weight of the compound of Formula (V) and its atropisomer compounds of Formula (B-7) and (B-8). Included in this embodiment, are compositions comprising at 99 equivalent weight %, 99.5 equivalent weight %, 99.8 equivalent weight %, and 99.9 equivalent weight % of a compound of Formula (V) based on the total equivalent weight of the compound of Formula (V) and its atropisomer compounds of Formula (B-7) and (B-8). Compositions of this embodiment include pharmaceutical compositions.

In one embodiment, a composition is provided comprising a compound of Formula (II-1). Included in this embodiment is a composition comprising a mixture in any proportion of (i) a compound of Formula (II-1) and (ii) one or more of its atropisomer compounds of Formula (II-2), Formula (B-1) and (B-2).

In one embodiment, a composition is provided comprising at least 98 equivalent weight % of a compound of Formula (II-1), based on the total equivalent weight of the compounds of Formula (II-1), (II-2), (B-1), and (B-2). Included in this embodiment, are compositions comprising at 99 equivalent weight %, 99.5 equivalent weight %, 99.8 equivalent weight %, and 99.9 equivalent weight % of a compound of Formula (II-1) based on the total equivalent weight of the compounds of Formula (II-1), (II-2), (B-1), and (B-2). Compositions of this embodiment include pharmaceutical compositions.

In one embodiment, a composition is provided comprising a compound of Formula (II-2). Included in this embodiment is a composition comprising a mixture in any proportion of (i) a compound of Formula (II-2) and (ii) one or more of its atropisomer compounds of Formula (II-1), Formula (B-1) and (B-2).

In one embodiment, a composition is provided comprising at least 98 equivalent weight % of a compound of Formula (II-2), based on the total equivalent weight of the compounds of Formula (II-1), (II-2), (B-1), and (B-2). Included in this embodiment, are compositions comprising at 99 equivalent weight %, 99.5 equivalent weight %, 99.8 equivalent weight %, and 99.9 equivalent weight % of a compound of Formula (II-2) based on the total equivalent weight of the compounds of Formula (II-1), (II-2), (B-1), and (B-2). Compositions of this embodiment include pharmaceutical compositions.

In one embodiment, a composition is provided comprising a compound of Formula (III-1). Included in this embodiment is a composition comprising a mixture in any proportion of (i) a compound of Formula (III-1) and (ii) one or more of its atropisomer compounds of Formula (III-2), Formula (B-3) and (B-4).

In one embodiment, a composition is provided comprising at least 98 equivalent weight % of a compound of Formula (III-1), based on the total equivalent weight of the compounds of Formula (III-1), (III-2), (B-3), and (B-4). Included in this embodiment, are compositions comprising at 99 equivalent weight %, 99.5 equivalent weight %, 99.8 equivalent weight %, and 99.9 equivalent weight % of a compound of Formula (III-1) based on the total equivalent weight of the compounds of Formula (III-1), (III-2), (B-3), and (B-4). Compositions of this embodiment include pharmaceutical compositions.

In one embodiment, a composition is provided comprising a compound of Formula (III-2). Included in this embodiment is a composition comprising a mixture in any proportion of (i) a compound of Formula (III-2) and (ii) one or more of its atropisomer compounds of Formula (III-1), Formula (B-3) and (B-4).

In one embodiment, a composition is provided comprising at least 98 equivalent weight % of a compound of Formula (III-2), based on the total equivalent weight of the compounds of Formula (III-1), (III-2), (B-3), and (B-4). Included in this embodiment, are compositions comprising at 99 equivalent weight %, 99.5 equivalent weight %, 99.8 equivalent weight %, and 99.9 equivalent weight % of a compound of Formula (III-2) based on the total equivalent weight of the compounds of Formula (III-1), (III-2), (B-3), and (B-4). Compositions of this embodiment include pharmaceutical compositions.

In one embodiment, a composition is provided comprising a compound of Formula (IV-1). Included in this embodiment is a composition comprising a mixture in any proportion of (i) a compound of Formula (IV-1) and (ii) one or more of its atropisomer compounds of Formula (IV-2), Formula (B-5) and (B-6).

In one embodiment, a composition is provided comprising at least 98 equivalent weight % of a compound of Formula (IV-1), based on the total equivalent weight of the compounds of Formula (IV-1), (IV-2), (B-5), and (B-6). Included in this embodiment, are compositions comprising at 99 equivalent weight %, 99.5 equivalent weight %, 99.8 equivalent weight %, and 99.9 equivalent weight % of a compound of Formula (IV-1) based on the total equivalent weight of the compounds of Formula (IV-1), (IV-2), (B-5), and (B-6). Compositions of this embodiment include pharmaceutical compositions.

In one embodiment, a composition is provided comprising a compound of Formula (IV-2). Included in this embodiment is a composition comprising a mixture in any proportion of (i) a compound of Formula (IV-2) and (ii) one or more of its atropisomer compounds of Formula (IV-1), Formula (B-5) and (B-6).

In one embodiment, a composition is provided comprising at least 98 equivalent weight % of a compound of Formula (IV-2), based on the total equivalent weight of the compounds of Formula (IV-1), (IV-2), (B-5), and (B-6). Included in this embodiment, are compositions comprising at 99 equivalent weight %, 99.5 equivalent weight %, 99.8 equivalent weight %, and 99.9 equivalent weight % of a compound of Formula (IV-2) based on the total equivalent weight of the compounds of Formula (IV-1), (IV-2), (B-5), and (B-6). Compositions of this embodiment include pharmaceutical compositions.

In one embodiment, a composition is provided comprising a compound of Formula (V-1). Included in this embodiment is a composition comprising a mixture in any proportion of (i) a compound of Formula (V-1) and (ii) one or more of its atropisomer compounds of Formula (V-2), Formula (B-7) and (B-8).

In one embodiment, a composition is provided comprising at least 98 equivalent weight % of a compound of Formula (V-1), based on the total equivalent weight of the compounds of Formula (V-1), (V-2), (B-7), and (B-8). Included in this embodiment, are compositions comprising at 99 equivalent weight %, 99.5 equivalent weight %, 99.8 equivalent weight %, and 99.9 equivalent weight % of a compound of Formula (V-1) based on the total equivalent weight of the compounds of Formula (V-1), (V-2), (B-7), and (B-8). Compositions of this embodiment include pharmaceutical compositions.

In one embodiment, a composition is provided comprising a compound of Formula (V-2). Included in this embodiment is a composition comprising a mixture in any proportion of (i) a compound of Formula (V-2) and (ii) one or more of its atropisomer compounds of Formula (V-1), Formula (B-7) and (B-8).

In one embodiment, a composition is provided comprising at least 98 equivalent weight % of a compound of Formula (V-2), based on the total equivalent weight of the compounds of Formula (V-1), (V-2), (B-7), and (B-8). Included in this embodiment, are compositions comprising at 99 equivalent weight %, 99.5 equivalent weight %, 99.8 equivalent weight %, and 99.9 equivalent weight % of a compound of Formula (V-2) based on the total equivalent weight of the compounds of Formula (V-1), (V-2), (B-7), and (B-8). Compositions of this embodiment include pharmaceutical compositions.

Crystal Forms

TABLE 1

| Example | Form |
|---|---|
| 2 | M-1 |
| 11 | H-1 |
| 11 | N-2 |
| 11 | M-1 |
| 28 | M2-1 |
| 33 | M2-1 |

In one embodiment, the compound of Example 2 is provided as a crystalline material comprising Form M-1. This crystalline form of the compound of Example 2 comprises a methanol solvate crystalline form referred to herein as "Form M-1" or "M-1 Form" of Example 2. The M-1 Form of Example 2 comprises one molecule of methanol for each molecule of Example 2.

In one embodiment, the M-1 Form of the compound of Example 2 is characterized by unit cell parameters approximately equal to the following:
Cell dimensions:
a=9.75 Å
b=14.21 Å
c=21.26 Å
α=90.0°
β=90.0°
γ=90.0°
Space group: $P2_12_12_1$
Molecules of Example 2/asymmetric unit: 1
Volume/Number of molecules in the unit cell=736 Å$^3$
Density (calculated)=1.391 g/cm$^3$,
wherein the unit cell parameters of Form M-1 are measured at a temperature of about 203 K.

In yet an even further embodiment, the M-1 Form of Example 2 is characterized by fractional atomic coordinates substantially as listed in Table 2.

TABLE 2

Fractional Atomic Coordinates of Example 2, Form M-1 Calculated at a Temperature of about 203 K; Atomic Coordinates (×104)

| Atom | X | Y | Z |
|---|---|---|---|
| Cl1 | 0.5111 | 0.2098 | 0.2452 |
| N1 | 0.4284 | −0.0941 | 0.0651 |
| C1 | 0.4089 | 0.0402 | 0.2141 |
| C2 | 0.4430 | −0.0331 | 0.1143 |
| C3 | 0.5134 | −0.0987 | −0.0462 |
| C4 | 0.5311 | 0.0412 | 0.0962 |
| C5 | 0.5042 | −0.0618 | 0.0142 |
| C6 | 0.3830 | −0.0362 | 0.1748 |
| C7 | 0.6528 | 0.0676 | −0.0127 |
| C8 | 0.4911 | 0.1146 | 0.1945 |
| C9 | 0.5570 | 0.1167 | 0.1365 |
| C10 | 0.5928 | −0.0859 | −0.1587 |
| C11 | 0.5718 | 0.0218 | 0.0316 |
| C12 | 0.5929 | −0.0521 | −0.0902 |
| C13 | 0.6628 | 0.0308 | −0.0728 |
| O1 | 0.5612 | −0.1842 | −0.1607 |
| C14 | 0.4745 | −0.0373 | −0.1922 |
| C15 | 0.2943 | −0.1171 | 0.1922 |
| C16 | 0.7270 | −0.0662 | −0.1926 |
| O2 | 0.2647 | −0.1777 | 0.1522 |
| N2 | 0.2483 | −0.1213 | 0.2514 |
| C17 | 0.6935 | 0.3440 | 0.0689 |
| C18 | 0.8335 | 0.3314 | 0.0747 |
| C19 | 0.6506 | 0.1944 | 0.1165 |
| C20 | 0.5982 | 0.2769 | 0.0896 |
| C21 | 0.8827 | 0.2492 | 0.1010 |
| C22 | 0.7908 | 0.1819 | 0.1221 |
| C23 | 0.4470 | 0.2921 | 0.0824 |
| N3 | 0.6425 | 0.4284 | 0.0392 |
| C24 | 0.6079 | 0.5032 | 0.0785 |
| N4 | 0.5449 | 0.5793 | 0.0505 |
| C25 | 0.5043 | 0.5772 | −0.0128 |
| C26 | 0.6347 | 0.4289 | −0.0265 |
| C27 | 0.3810 | 0.6409 | −0.1018 |
| C28 | 0.5564 | 0.5079 | −0.0530 |
| C29 | 0.5260 | 0.5081 | −0.1169 |
| C30 | 0.4122 | 0.6409 | −0.0392 |
| C31 | 0.4401 | 0.5750 | −0.1415 |
| O3 | 0.6826 | 0.3654 | −0.0574 |
| O4 | 0.6337 | 0.5004 | 0.1344 |
| C32 | 0.5414 | 0.6667 | 0.0876 |
| F1 | 0.3478 | 0.7048 | −0.0014 |
| O5 | 0.4744 | −0.2738 | −0.2654 |
| C33 | 0.3392 | −0.2608 | −0.2825 |
| H1 | 0.3792 | −0.1452 | 0.0656 |
| H2 | 0.3702 | 0.0415 | 0.2546 |
| H3 | 0.4665 | −0.1543 | −0.0570 |
| H4 | 0.7002 | 0.1230 | −0.0020 |
| H5 | 0.7175 | 0.0617 | −0.1027 |
| H6 | 0.6298 | −0.2150 | −0.1502 |
| H7 | 0.4710 | −0.0582 | −0.2356 |
| H8 | 0.4881 | 0.0302 | −0.1910 |
| H9 | 0.3890 | −0.0531 | −0.1713 |
| H10 | 0.8030 | −0.0882 | −0.1671 |
| H11 | 0.7361 | 0.0009 | −0.1996 |
| H12 | 0.7275 | −0.0988 | −0.2327 |
| H13 | 0.1959 | −0.1676 | 0.2631 |
| H14 | 0.2709 | −0.0777 | 0.2782 |
| H15 | 0.8945 | 0.3782 | 0.0608 |
| H16 | 0.9776 | 0.2391 | 0.1046 |
| H17 | 0.8245 | 0.1265 | 0.1406 |
| H18 | 0.3989 | 0.2335 | 0.0902 |
| H19 | 0.4275 | 0.3135 | 0.0399 |
| H20 | 0.4165 | 0.3393 | 0.1122 |
| H21 | 0.3195 | 0.6857 | −0.1180 |
| H22 | 0.5646 | 0.4622 | −0.1434 |
| H23 | 0.4213 | 0.5761 | −0.1848 |
| H24 | 0.4485 | 0.6782 | 0.1021 |
| H25 | 0.5711 | 0.7190 | 0.0615 |
| H26 | 0.6021 | 0.6608 | 0.1234 |
| H27 | 0.4880 | −0.2496 | −0.2304 |
| H28 | 0.2809 | −0.3001 | −0.2565 |
| H29 | 0.3273 | −0.2780 | −0.3263 |
| H30 | 0.3142 | −0.1953 | −0.2767 |

In one embodiment, the compound of Example 11 is provided as a crystalline material comprising Form H-1. This crystalline form of the compound of Example 11 comprises a monohydrate crystalline form referred to herein as "Form H-1" or "H-1 Form" of Example 11. The H-1 Form of Example 11 comprises one molecule of water for each molecule of Example 11.

In one embodiment, the H-1 Form of the compound of Example 11 is characterized by unit cell parameters approximately equal to the following:
Cell dimensions:
a=9.41 Å
b=14.51 Å
c=21.12 Å
α=90.0°
β=90.0°
γ=90.0°
Space group: $P2_12_12_1$
Molecules of Example 11/asymmetric unit: 1
Volume/Number of molecules in the unit cell=721 Å$^3$
Density (calculated)=1.396 g/cm$^3$,
wherein the unit cell parameters of Form H-1 are measured at a temperature of about room temperature.

Figure 7:
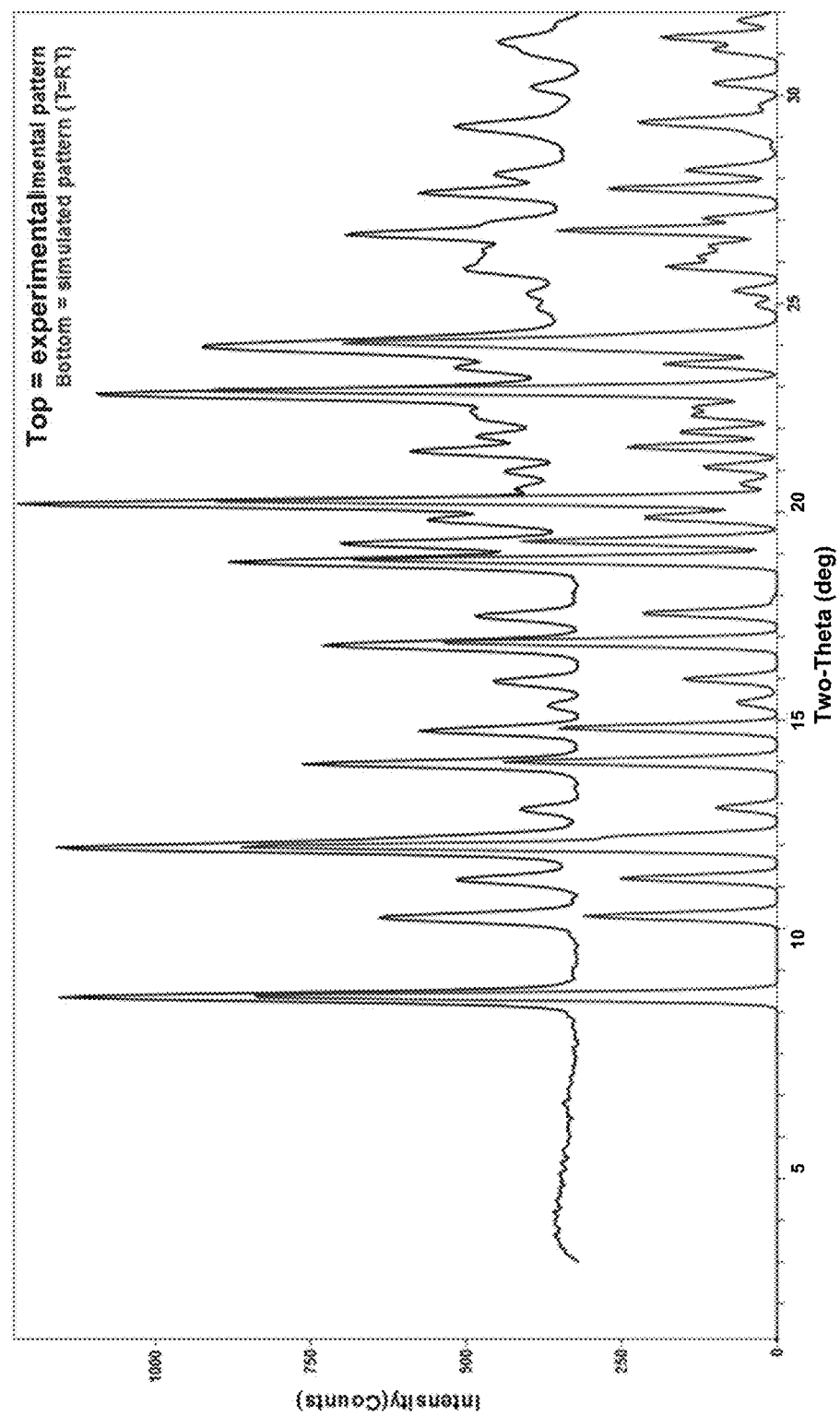
FIG. 7 shows the experimental and the simulated PXRD patterns at room temperature (Cu Kα radiation λ=1.5418 Å) of Example 11 monohydrate, crystal Form H-1.

In another embodiment, H-1 form of Example 11 is characterized by a simulated powder x-ray diffraction (PXRD) pattern substantially in accordance with the pattern shown in FIG. 7 and/or by an experimental PXRD pattern substantially in accordance with the pattern shown in FIG. 7.

In yet an even further embodiment, the H-1 Form of Example 11 is characterized by fractional atomic coordinates substantially as listed in Table 3.

TABLE 3

Fractional Atomic Coordinates of Example 11, Form H-1 Calculated at Room Temperature; Atomic Coordinates (×10$^4$)

| Atom | X | Y | Z |
|---|---|---|---|
| Cl1 | 0.4783 | 0.2052 | 0.2387 |
| N1 | 0.4348 | −0.0990 | 0.0600 |
| C1 | 0.4427 | −0.0381 | 0.1093 |
| C2 | 0.3961 | 0.0338 | 0.2082 |
| C3 | 0.5280 | 0.0384 | 0.0908 |
| C4 | 0.5215 | −0.0998 | −0.0525 |
| C5 | 0.3806 | −0.0431 | 0.1694 |
| C6 | 0.6503 | 0.0680 | −0.0190 |
| C7 | 0.5093 | −0.0648 | 0.0087 |
| C8 | 0.5466 | 0.1131 | 0.1314 |
| C9 | 0.4735 | 0.1097 | 0.1887 |
| C10 | 0.5719 | 0.0201 | 0.0261 |
| C11 | 0.6615 | 0.0322 | −0.0793 |
| C12 | 0.5970 | −0.0514 | −0.0970 |
| C13 | 0.5968 | −0.0824 | −0.1662 |
| O1 | 0.5643 | −0.1789 | −0.1705 |
| C14 | 0.7370 | −0.0628 | −0.1994 |
| C15 | 0.4767 | −0.0343 | −0.1997 |
| C16 | 0.3010 | −0.1271 | 0.1879 |
| O2 | 0.2749 | −0.1874 | 0.1484 |
| N2 | 0.2591 | −0.1344 | 0.2483 |
| C17 | 0.6425 | 0.1917 | 0.1143 |
| C18 | 0.6863 | 0.3413 | 0.0723 |
| C19 | 0.7866 | 0.1827 | 0.1254 |
| C20 | 0.8297 | 0.3327 | 0.0837 |
| C21 | 0.8807 | 0.2530 | 0.1104 |
| C22 | 0.5887 | 0.2724 | 0.0870 |
| C23 | 0.4341 | 0.2839 | 0.0745 |
| N3 | 0.6351 | 0.4252 | 0.0428 |
| C24 | 0.6028 | 0.4987 | 0.0826 |
| N4 | 0.5451 | 0.5756 | 0.0548 |
| C25 | 0.5048 | 0.5763 | −0.0091 |
| C26 | 0.5515 | 0.5068 | −0.0496 |
| C27 | 0.6265 | 0.4268 | −0.0234 |
| C28 | 0.5218 | 0.5088 | −0.1139 |
| C29 | 0.4158 | 0.6426 | −0.0357 |
| C30 | 0.3848 | 0.6446 | −0.0985 |
| C31 | 0.4396 | 0.5789 | −0.1388 |
| O3 | 0.6707 | 0.3631 | −0.0545 |
| O4 | 0.6282 | 0.4945 | 0.1389 |
| C32 | 0.5492 | 0.6607 | 0.0922 |
| D1 | 0.4548 | 0.6763 | 0.1057 |
| D2 | 0.5866 | 0.7098 | 0.0666 |
| D3 | 0.6089 | 0.6519 | 0.1285 |
| F1 | 0.3543 | 0.7073 | 0.0021 |
| O5 | 0.3852 | −0.2732 | −0.2607 |
| H1 | 0.3903 | −0.1507 | 0.0608 |
| H2 | 0.3536 | 0.0342 | 0.2480 |
| H3 | 0.4788 | −0.1556 | −0.0631 |
| H4 | 0.6945 | 0.1233 | −0.0086 |
| H5 | 0.7136 | 0.0645 | −0.1094 |
| H6 | 0.6241 | −0.2085 | −0.1509 |
| H7 | 0.8132 | −0.0904 | −0.1760 |
| H8 | 0.7514 | 0.0026 | −0.2019 |
| H9 | 0.7344 | −0.0882 | −0.2414 |
| H10 | 0.4742 | −0.0535 | −0.2431 |
| H11 | 0.4909 | 0.0312 | −0.1976 |
| H12 | 0.3885 | −0.0499 | −0.1795 |
| H13 | 0.2127 | −0.1822 | 0.2605 |
| H14 | 0.2789 | −0.0913 | 0.2748 |
| H15 | 0.8211 | 0.1285 | 0.1433 |
| H16 | 0.8915 | 0.3806 | 0.0735 |
| H17 | 0.9774 | 0.2462 | 0.1183 |

TABLE 3-continued

Fractional Atomic Coordinates of Example 11, Form H-1 Calculated at Room Temperature; Atomic Coordinates (×10$^4$)

| Atom | X | Y | Z |
|---|---|---|---|
| H18 | 0.3940 | 0.3251 | 0.1052 |
| H19 | 0.3878 | 0.2250 | 0.0774 |
| H20 | 0.4206 | 0.3088 | 0.0328 |
| H21 | 0.5571 | 0.4629 | −0.1402 |
| H22 | 0.3260 | 0.6907 | −0.1143 |
| H23 | 0.4216 | 0.5818 | −0.1821 |
| H24 | 0.4426 | −0.2428 | −0.2322 |
| H25 | 0.2940 | −0.2508 | −0.2576 |
| — | — | — | — |

In one embodiment, the compound of Example 11 is provided as a crystalline material comprising Form N-2. This crystalline form of the compound of Example 11 comprises a neat crystalline form referred to herein as "Form N-2" or "N-2 Form" of Example 11.

In one embodiment, the N-2 Form of the compound of Example 11 is characterized by unit cell parameters approximately equal to the following:

Cell dimensions:
a=10.89 Å
b=9.47 Å
c=14.28 Å
α=90.0°
β=105.5°
γ=90.0°
Space group: P2$_1$
Molecules of Example 11/asymmetric unit: 1
Volume/Number of molecules in the unit cell=710 Å$^3$
Density (calculated)=1.369 g/cm$^3$,
wherein the unit cell parameters of Form N-2 are measured at a temperature of about room temperature.

Figure 8:
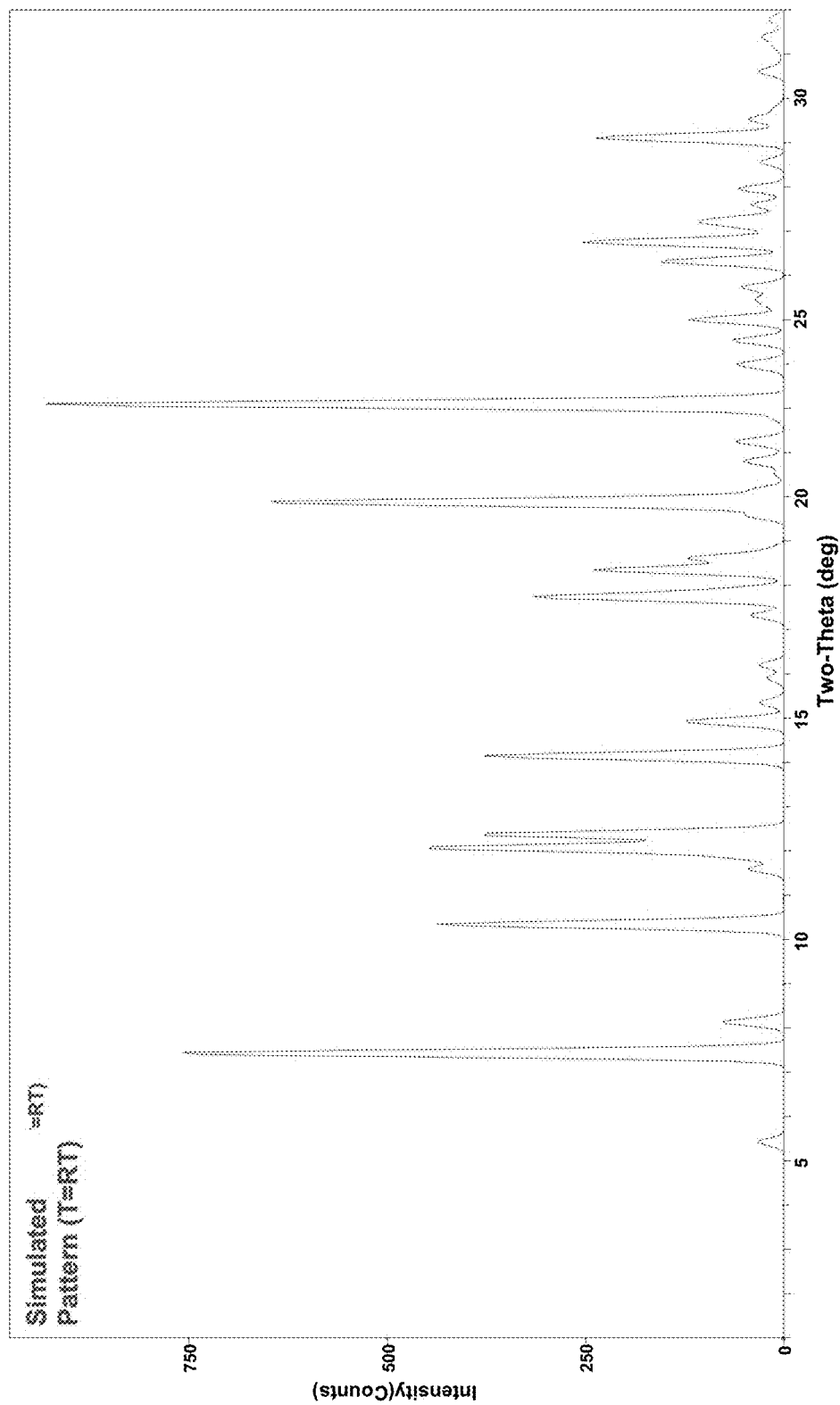
FIG. 8 shows the simulated PXRD pattern at room temperature (Cu Kα radiation λ=1.5418 Å) of the crystal Form N-2 of Example 11.

In another embodiment, N-2 form of Example 11 is characterized by a simulated powder x-ray diffraction (PXRD) pattern substantially in accordance with the pattern shown in FIG. 8.

In yet an even further embodiment, the N-2 Form of Example 11 is characterized by fractional atomic coordinates substantially as listed in Table 4.

TABLE 4

Fractional Atomic Coordinates of Example 11, Form N-2 Calculated at Room Temperature; Atomic Coordinates (×10$^4$)

| Atom | X | Y | Z |
|---|---|---|---|
| Cl1 | 0.0126 | 0.5814 | −0.0398 |
| N28 | 0.4096 | 0.6892 | −0.1985 |
| N1 | 0.3977 | 0.4748 | 0.3228 |
| C6 | 0.2421 | 0.6140 | 0.0877 |
| C3 | 0.1740 | 0.4291 | 0.2250 |
| C4 | 0.0901 | 0.4607 | 0.1367 |
| C7 | 0.3291 | 0.5833 | 0.1771 |
| C10 | 0.6696 | 0.7241 | 0.2527 |
| C8 | 0.4600 | 0.6251 | 0.2204 |
| C2 | 0.2949 | 0.4910 | 0.2436 |
| C5 | 0.1241 | 0.5497 | 0.0709 |
| C11 | 0.7085 | 0.6521 | 0.3424 |
| C12 | 0.6222 | 0.5671 | 0.3708 |
| C13 | 0.4986 | 0.5553 | 0.3100 |
| C9 | 0.5476 | 0.7104 | 0.1920 |
| C14 | 0.8476 | 0.6567 | 0.4037 |
| O15 | 0.8564 | 0.6165 | 0.5020 |
| C18 | 0.1439 | 0.3323 | 0.2987 |
| C17 | 0.9207 | 0.5431 | 0.3663 |
| C16 | 0.9095 | 0.7999 | 0.4029 |

TABLE 4-continued

Fractional Atomic Coordinates of Example 11, Form N-2 Calculated at Room Temperature; Atomic Coordinates (×10⁴)

| Atom | X | Y | Z |
|---|---|---|---|
| O19 | 0.2223 | 0.3164 | 0.3783 |
| N20 | 0.0317 | 0.2672 | 0.2766 |
| C21 | 0.2745 | 0.7085 | 0.0137 |
| C22 | 0.3280 | 0.6518 | −0.0566 |
| C23 | 0.3515 | 0.7447 | −0.1255 |
| C26 | 0.2482 | 0.8516 | 0.0138 |
| C24 | 0.3252 | 0.8854 | −0.1258 |
| C25 | 0.2734 | 0.9408 | −0.0553 |
| C27 | 0.3567 | 0.4978 | −0.0589 |
| C29 | 0.3283 | 0.6529 | −0.2889 |
| N30 | 0.3839 | 0.5912 | −0.3541 |
| C36 | 0.5943 | 0.5995 | −0.2422 |
| C31 | 0.5122 | 0.5507 | −0.3280 |
| C32 | 0.5654 | 0.4577 | −0.3830 |
| C35 | 0.7220 | 0.5668 | −0.2168 |
| C37 | 0.5426 | 0.6797 | −0.1732 |
| C34 | 0.7717 | 0.4812 | −0.2747 |
| C33 | 0.6929 | 0.4253 | −0.3569 |
| O38 | 0.6061 | 0.7269 | −0.0972 |
| O39 | 0.2156 | 0.6776 | −0.3073 |
| C40 | 0.3090 | 0.5904 | −0.4562 |
| F41 | 0.4905 | 0.3950 | −0.4631 |
| H1 | 0.3995 | 0.4230 | 0.3726 |
| H4 | 0.0089 | 0.4214 | 0.1210 |
| H10 | 0.7276 | 0.7822 | 0.2338 |
| H12 | 0.6458 | 0.5184 | 0.4295 |
| H9 | 0.5245 | 0.7578 | 0.1329 |
| H15 | 0.8171 | 0.6734 | 0.5263 |
| H17A | 1.0065 | 0.5391 | 0.4070 |
| H17B | 0.9217 | 0.5650 | 0.3009 |
| H17C | 0.8800 | 0.4535 | 0.3675 |
| H16A | 0.8623 | 0.8699 | 0.4274 |
| H16B | 0.9097 | 0.8236 | 0.3375 |
| H16C | 0.9956 | 0.7969 | 0.4432 |
| H20A | 0.0121 | 0.2121 | 0.3182 |
| H20B | −0.0212 | 0.2801 | 0.2206 |
| H26 | 0.2130 | 0.8882 | 0.0612 |
| H24 | 0.3419 | 0.9439 | −0.1733 |
| H25 | 0.2557 | 1.0368 | −0.0544 |
| H27A | 0.2879 | 0.4513 | −0.1048 |
| H27B | 0.3664 | 0.4581 | 0.0045 |
| H27C | 0.4341 | 0.4851 | −0.0779 |
| H35 | 0.7752 | 0.6032 | −0.1598 |
| H34 | 0.8585 | 0.4614 | −0.2581 |
| H33 | 0.7257 | 0.3648 | −0.3955 |
| D40A | 0.2768 | 0.4970 | −0.4739 |
| D40B | 0.3622 | 0.6185 | −0.4968 |
| D40C | 0.2390 | 0.6551 | −0.4647 |

In one embodiment, the compound of Example 11 is provided as a crystalline material comprising Form M-1. This crystalline form of the compound of Example 11 comprises a methanol solvate crystalline form referred to herein as "Form M-1" or "M-1 Form" of Example 11. The M-1 Form of Example 11 comprises one molecule of methanol for each molecule of Example 11.

In one embodiment, the M-1 Form of the compound of Example 11 is characterized by unit cell parameters approximately equal to the following:
Cell dimensions:
a=9.78 Å
b=14.26 Å
c=21.38 Å
α=90.0°
β=90.0°
γ=90.0°
Space group: P2₁2₁2₁
Molecules of Example 11/asymmetric unit: 1
Volume/Number of molecules in the unit cell=746 Å³
Density (calculated)=1.381 g/cm³, wherein the unit cell parameters of Form M-1 are measured at a temperature of about room temperature.

Figure 9:
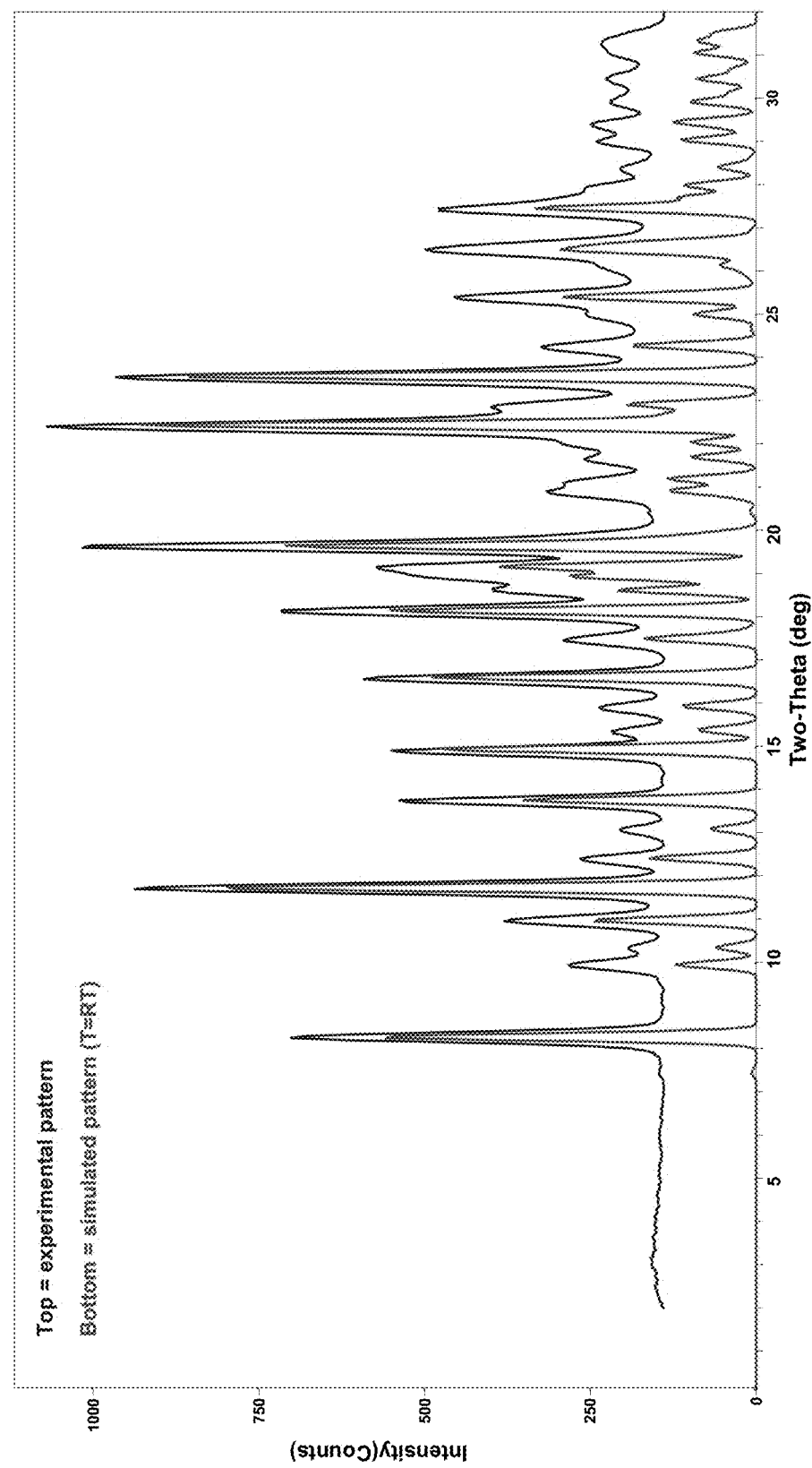
FIG. 9 shows the experimental and the simulated PXRD patterns at room temperature (Cu Kα radiation λ=1.5418 Å) of Example 11 methanolate, crystal Form M-1.

In another embodiment, M-1 form of Example 11 is characterized by a simulated powder x-ray diffraction (PXRD) pattern substantially in accordance with the pattern shown in FIG. 9 and/or by an experimental PXRD pattern substantially in accordance with the pattern shown in FIG. 9.

In yet an even further embodiment, the M-1 Form of Example 11 is characterized by fractional atomic coordinates substantially as listed in Table 5.

TABLE 5

Fractional Atomic Coordinates of Example 11, Form M-1 Calculated at Room Temperature; Atomic Coordinates (×10⁴)

| Atom | X | Y | Z |
|---|---|---|---|
| Cl1 | 0.5122 | 0.2066 | 0.2450 |
| N1 | 0.4273 | −0.0936 | 0.0641 |
| C1 | 0.5289 | 0.0415 | 0.0955 |
| C2 | 0.5116 | −0.0974 | −0.0464 |
| C3 | 0.5023 | −0.0607 | 0.0136 |
| C4 | 0.4097 | 0.0384 | 0.2129 |
| C5 | 0.3831 | −0.0373 | 0.1735 |
| C6 | 0.4422 | −0.0331 | 0.1135 |
| C7 | 0.5686 | 0.0224 | 0.0311 |
| C8 | 0.5550 | 0.1158 | 0.1358 |
| C9 | 0.6496 | 0.0688 | −0.0131 |
| C10 | 0.4913 | 0.1125 | 0.1938 |
| C11 | 0.5915 | −0.0838 | −0.1580 |
| C12 | 0.5911 | −0.0506 | −0.0901 |
| C13 | 0.6594 | 0.0319 | −0.0724 |
| O1 | 0.5610 | −0.1824 | −0.1606 |
| C14 | 0.2956 | −0.1183 | 0.1908 |
| C15 | 0.4743 | −0.0364 | −0.1918 |
| C16 | 0.7257 | −0.0643 | −0.1914 |
| O2 | 0.2663 | −0.1785 | 0.1512 |
| N2 | 0.2503 | −0.1229 | 0.2496 |
| C17 | 0.6898 | 0.3431 | 0.0697 |
| C18 | 0.8290 | 0.3311 | 0.0758 |
| C19 | 0.5954 | 0.2757 | 0.0893 |
| C20 | 0.6478 | 0.1941 | 0.1162 |
| C21 | 0.7878 | 0.1825 | 0.1226 |
| C22 | 0.8782 | 0.2501 | 0.1022 |
| C23 | 0.4452 | 0.2902 | 0.0817 |
| N3 | 0.6391 | 0.4273 | 0.0400 |
| C24 | 0.6052 | 0.5019 | 0.0789 |
| N4 | 0.5432 | 0.5777 | 0.0514 |
| C25 | 0.5035 | 0.5761 | −0.0117 |
| C26 | 0.6313 | 0.4281 | −0.0253 |
| C27 | 0.5542 | 0.5067 | −0.0516 |
| C28 | 0.5238 | 0.5074 | −0.1149 |
| C29 | 0.3824 | 0.6403 | −0.1003 |
| C30 | 0.4126 | 0.6400 | −0.0381 |
| C31 | 0.4398 | 0.5745 | −0.1396 |
| O3 | 0.6783 | 0.3646 | −0.0559 |
| O4 | 0.6315 | 0.4993 | 0.1345 |
| C32 | 0.5414 | 0.6652 | 0.0884 |
| D1 | 0.4501 | 0.6772 | 0.1028 |
| D2 | 0.5715 | 0.7164 | 0.0628 |
| D3 | 0.6014 | 0.6588 | 0.1237 |
| F1 | 0.3490 | 0.7042 | −0.0007 |
| O5 | 0.4716 | −0.2733 | −0.2643 |
| C33 | 0.3374 | −0.2588 | −0.2808 |
| H1 | 0.3791 | −0.1440 | 0.0644 |
| H2 | 0.4656 | −0.1521 | −0.0572 |
| H3 | 0.3719 | 0.0392 | 0.2528 |
| H4 | 0.6960 | 0.1235 | −0.0027 |
| H5 | 0.7131 | 0.0626 | −0.1019 |
| H6 | 0.6289 | −0.2124 | −0.1504 |
| H7 | 0.4747 | −0.0549 | −0.2350 |
| H8 | 0.4845 | 0.0304 | −0.1890 |
| H9 | 0.3894 | −0.0547 | −0.1729 |
| H10 | 0.8000 | −0.0891 | −0.1672 |
| H11 | 0.7373 | 0.0021 | −0.1964 |
| H12 | 0.7247 | −0.0938 | −0.2318 |
| H13 | 0.1990 | −0.1687 | 0.2610 |

TABLE 5-continued

Fractional Atomic Coordinates of Example 11, Form M-1 Calculated at Room Temperature; Atomic Coordinates (×10⁴)

| Atom | X | Y | Z |
|---|---|---|---|
| H14 | 0.2724 | −0.0800 | 0.2760 |
| H15 | 0.8889 | 0.3773 | 0.0621 |
| H16 | 0.8214 | 0.1281 | 0.1410 |
| H17 | 0.9719 | 0.2410 | 0.1065 |
| H18 | 0.4004 | 0.2305 | 0.0788 |
| H19 | 0.4283 | 0.3257 | 0.0444 |
| H20 | 0.4104 | 0.3238 | 0.1173 |
| H21 | 0.5610 | 0.4617 | −0.1409 |
| H22 | 0.3229 | 0.6851 | −0.1163 |
| H23 | 0.4215 | 0.5757 | −0.1823 |
| H24 | 0.4869 | −0.2481 | −0.2306 |
| H25 | 0.3304 | −0.2025 | −0.3052 |
| H26 | 0.2828 | −0.2527 | −0.2437 |
| H27 | 0.3053 | −0.3110 | −0.3050 |

In one embodiment, the compound of Example 28 is provided as a crystalline material comprising Form M2-1. This crystalline form of the compound of Example 28 comprises a methanol solvate crystalline form referred to herein as "Form M2-1" or "M2-1 Form" of Example 28. The M2-1 Form of Example 28 comprises two molecules of methanol for each molecule of Example 28.

In one embodiment, the M2-1 Form of the compound of Example 28 is characterized by unit cell parameters approximately equal to the following:

Cell dimensions:
a=9.24 Å
b=7.97 Å
c=22.12 Å
α=90.0°
β=94.1°
γ=90.0°
Space group: P2₁
Molecules of Example 28/asymmetric unit: 1
Volume/Number of molecules in the unit cell=813 Å³
Density (calculated)=1.301 g/cm³, wherein the unit cell parameters of Form M2-1 are measured at a temperature of about 173 K.

Figure 10:
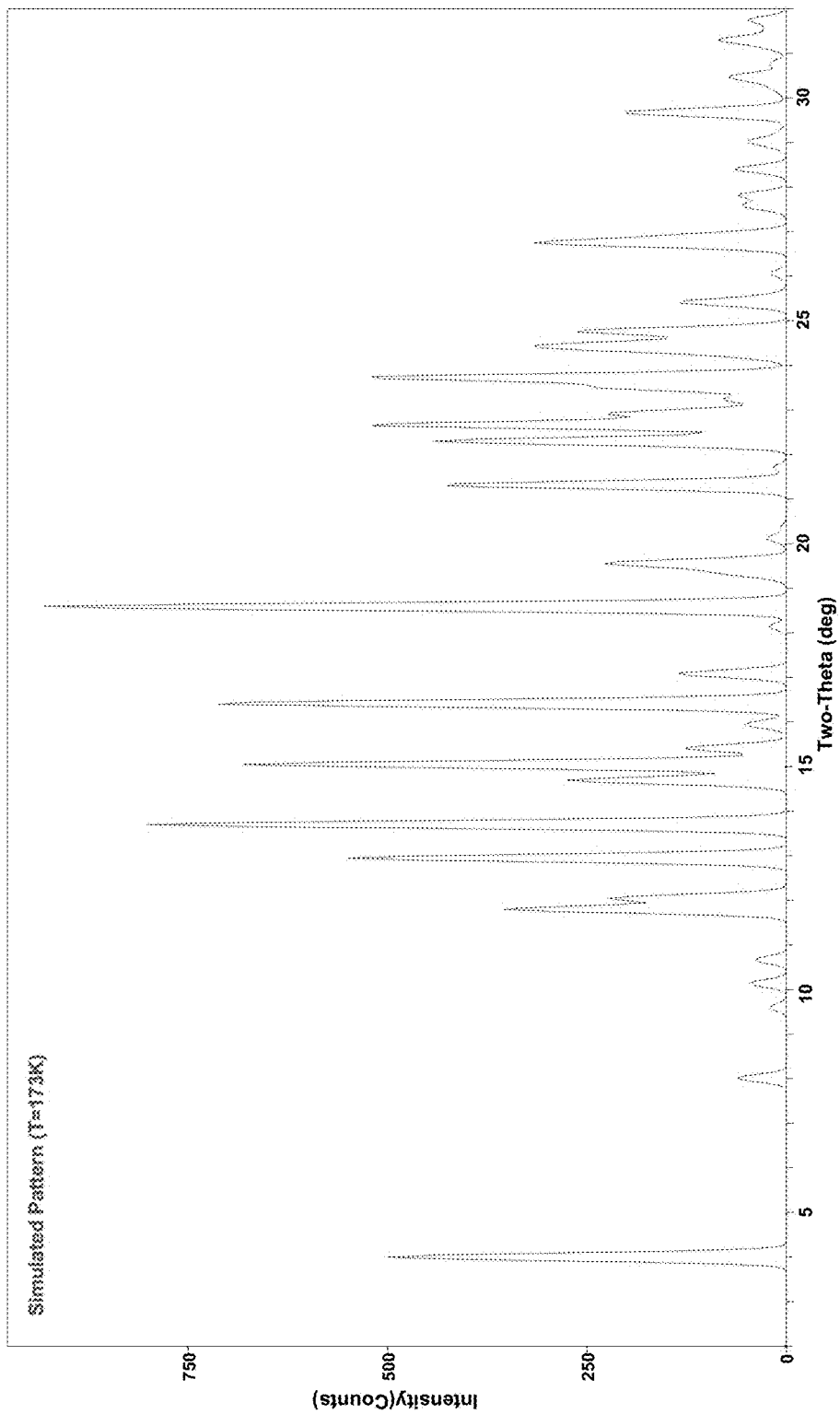
FIG. 10 shows the simulated PXRD pattern at 173 K (Cu Kα radiation λ=1.5418 Å) of Example 28 dimethanolate, crystal Form M2-1.

In another embodiment, M2-1 form of Example 28 is characterized by a simulated powder x-ray diffraction (PXRD) pattern substantially in accordance with the pattern shown in FIG. 10.

In yet an even further embodiment, the M2-1 Form of Example 28 is characterized by fractional atomic coordinates substantially as listed in Table 6.

TABLE 6

Fractional Atomic Coordinates of Example 28, Form M2-1 Calculated at a Temperature of about 173 K; Atomic Coordinates (×10⁴)

| Atom | X | Y | Z |
|---|---|---|---|
| N1 | 0.1027 | 0.4043 | 0.3748 |
| C1 | −0.2232 | 0.3960 | 0.2673 |
| C2 | 0.0404 | 0.5638 | 0.2929 |
| C3 | −0.0029 | 0.4268 | 0.3288 |
| C4 | −0.0521 | 0.6188 | 0.2437 |
| C5 | −0.1336 | 0.3399 | 0.3162 |
| C6 | −0.1814 | 0.5329 | 0.2339 |
| C7 | 0.5794 | 0.6873 | 0.4355 |
| C8 | 0.1792 | 0.6199 | 0.3196 |
| C9 | 0.3425 | 0.5311 | 0.4117 |
| C10 | 0.4312 | 0.7276 | 0.3333 |
| C11 | 0.4282 | 0.6926 | 0.4013 |
| C12 | 0.2800 | 0.7581 | 0.3027 |
| C13 | 0.2107 | 0.5221 | 0.3691 |
| O1 | 0.6379 | 0.8543 | 0.4304 |
| C14 | −0.1722 | 0.2005 | 0.3567 |
| C15 | 0.5688 | 0.6482 | 0.5022 |
| C16 | 0.6824 | 0.5649 | 0.4077 |
| O2 | −0.0922 | 0.1697 | 0.4030 |
| N2 | −0.2929 | 0.1124 | 0.3427 |
| C17 | 0.0680 | 1.0435 | 0.1406 |
| C18 | −0.0136 | 0.7640 | 0.2053 |
| C19 | −0.0685 | 0.9224 | 0.2173 |
| C20 | 0.0824 | 0.7434 | 0.1594 |
| C21 | −0.0291 | 1.0613 | 0.1851 |
| C22 | 0.1220 | 0.8874 | 0.1288 |
| C23 | 0.1432 | 0.5751 | 0.1445 |
| N3 | 0.2335 | 0.8729 | 0.0858 |
| C24 | 0.3767 | 0.8784 | 0.1096 |
| C25 | 0.4864 | 0.8571 | 0.0663 |
| N4 | 0.2979 | 0.8380 | −0.0149 |
| C26 | 0.4453 | 0.8370 | 0.0049 |
| C27 | 0.6314 | 0.8568 | 0.0885 |
| C28 | 0.5591 | 0.8157 | −0.0330 |
| C29 | 0.7023 | 0.8160 | −0.0107 |
| C30 | 0.1898 | 0.8520 | 0.0243 |
| C31 | 0.7397 | 0.8355 | 0.0497 |
| O3 | 0.4038 | 0.8977 | 0.1639 |
| O4 | 0.0618 | 0.8482 | 0.0081 |
| C32 | 0.2483 | 0.8261 | −0.0793 |
| F1 | −0.2771 | 0.5872 | 0.1879 |
| F2 | 0.5324 | 0.7902 | −0.0930 |
| O5 | −0.0788 | −0.0991 | 0.4776 |
| C33 | 0.0326 | −0.1899 | 0.4513 |
| O6 | 0.4799 | 1.1498 | 0.2473 |
| C34 | 0.3561 | 1.2372 | 0.2578 |
| H1 | 0.1019 | 0.3275 | 0.4033 |
| H2 | −0.3127 | 0.3410 | 0.2567 |
| H3 | 0.4049 | 0.4324 | 0.4058 |
| H4 | 0.3136 | 0.5287 | 0.4540 |
| H5 | 0.4925 | 0.8272 | 0.3274 |
| H6 | 0.4759 | 0.6309 | 0.3137 |
| H7 | 0.3737 | 0.7870 | 0.4190 |
| H8 | 0.2426 | 0.8676 | 0.3159 |
| H9 | 0.2850 | 0.7612 | 0.2582 |
| H10 | 0.7202 | 0.8591 | 0.4490 |
| H11 | 0.6640 | 0.6644 | 0.5240 |
| H12 | 0.5377 | 0.5317 | 0.5067 |
| H13 | 0.4979 | 0.7236 | 0.5189 |
| H14 | 0.7009 | 0.6021 | 0.3668 |
| H15 | 0.6384 | 0.4529 | 0.4058 |
| H16 | 0.7742 | 0.5607 | 0.4329 |
| H17 | −0.3176 | 0.0302 | 0.3664 |
| H18 | −0.3477 | 0.1365 | 0.3097 |
| H19 | 0.0970 | 1.1384 | 0.1185 |
| H20 | −0.1342 | 0.9351 | 0.2480 |
| H21 | −0.0683 | 1.1683 | 0.1933 |
| H22 | 0.1200 | 0.5506 | 0.1014 |
| H23 | 0.1005 | 0.4889 | 0.1693 |
| H24 | 0.2488 | 0.5761 | 0.1530 |
| H25 | 0.6555 | 0.8714 | 0.1307 |
| H26 | 0.7765 | 0.8024 | −0.0380 |
| H27 | 0.8387 | 0.8345 | 0.0646 |
| H28 | 0.2762 | 0.7168 | −0.0952 |
| H29 | 0.2933 | 0.9156 | −0.1019 |
| H30 | 0.1425 | 0.8377 | −0.0839 |
| H31 | −0.0943 | −0.0091 | 0.4585 |
| H32 | 0.1274 | −0.1480 | 0.4674 |
| H33 | 0.0232 | −0.1756 | 0.4072 |
| H34 | 0.0242 | −0.3092 | 0.4612 |
| H35 | 0.4597 | 1.0733 | 0.2219 |
| H36 | 0.3799 | 1.3281 | 0.2866 |
| H37 | 0.2857 | 1.1614 | 0.2746 |
| H38 | 0.3141 | 1.2845 | 0.2195 |

In one embodiment, the compound of Example 33 is provided as a crystalline material comprising Form M2-1. This crystalline form of the compound of Example 33 comprises a methanol solvate crystalline form referred to herein as "Form M2-1" or "M2-1 Form" of Example 33. The M2-1 Form of Example 33 comprises two molecules of methanol for each molecule of Example 33.

In one embodiment, the M2-1 Form of the compound of Example 33 is characterized by unit cell parameters approximately equal to the following:

Cell dimensions:
a=7.41 Å
b=9.74 Å
c=44.55 Å
α=90.0°
β=90.0°
γ=90.0°
Space group: $P2_12_12_1$
Molecules of Example 33/asymmetric unit: 1
Volume/Number of molecules in the unit cell=3214 Å$^3$
Density (calculated)=1.346 g/cm$^3$, wherein the unit cell parameters of Form M2-1 are measured at a temperature of about 173 K.

Figure 11:
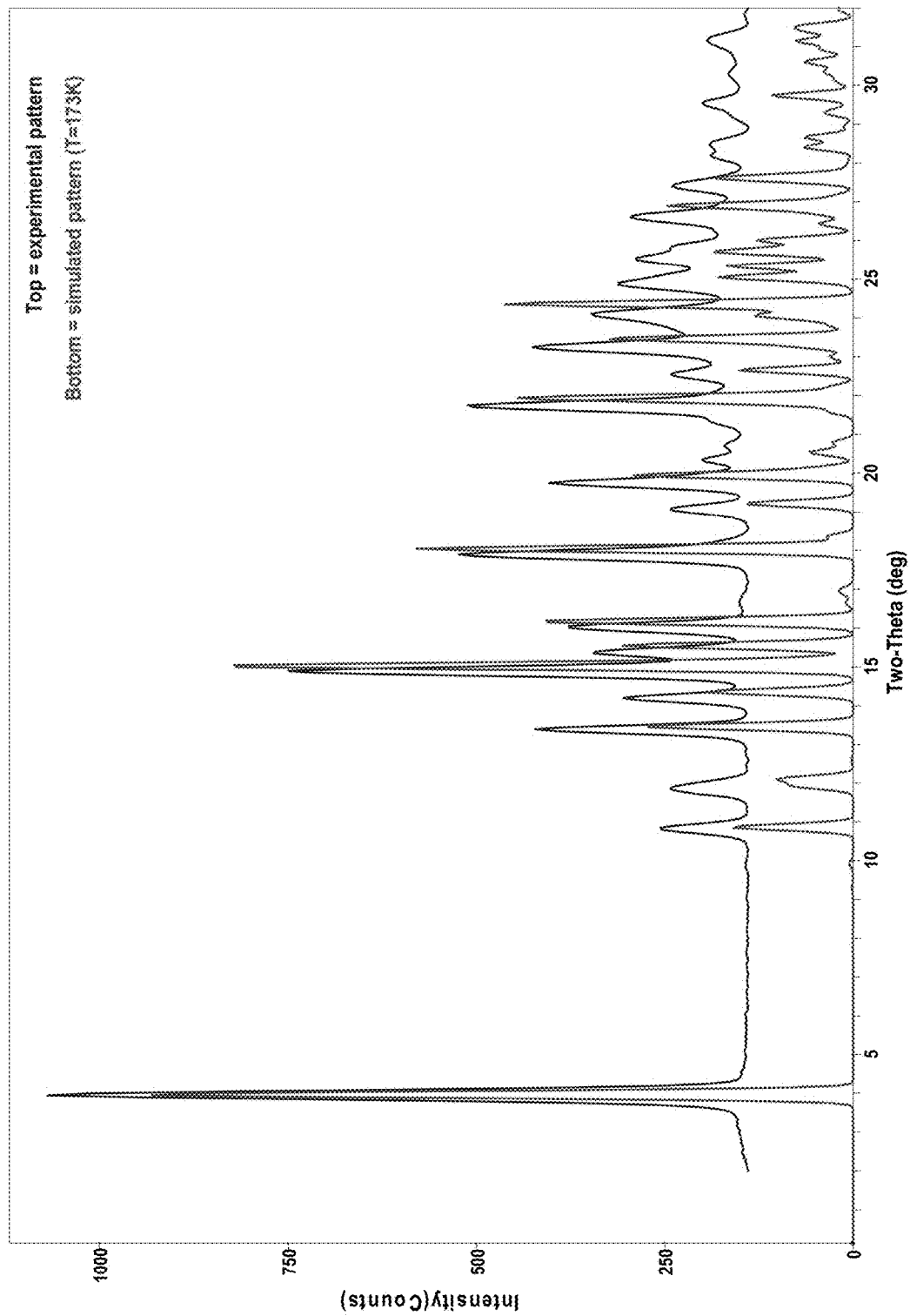
FIG. 11 shows the experimental PXRD pattern at room temperature and the simulated PXRD pattern at 173 K (Cu Kα radiation λ=1.5418 Å) of Example 33 dimethanolate, crystal Form M2-1.

In another embodiment, M2-1 form of Example 33 is characterized by a simulated powder x-ray diffraction (PXRD) pattern substantially in accordance with the pattern shown in FIG. 11 and/or by an experimental PXRD pattern substantially in accordance with the pattern shown in FIG. 11.

In yet an even further embodiment, the M2-1 Form of Example 33 is characterized by fractional atomic coordinates substantially as listed in Table 7.

TABLE 7

Fractional Atomic Coordinates of Example 33, Form M2-1 Calculated at a Temperature of about 173 K; Atomic Coordinates (×10$^4$)

| Atom | X | Y | Z |
|---|---|---|---|
| Cl1 | 0.4450 | −0.0974 | 0.0917 |
| Cl2 | 0.2679 | 0.9390 | −0.0104 |
| N1 | 0.7146 | 0.2778 | 0.1831 |
| C1 | 0.6840 | −0.0285 | 0.1346 |
| C2 | 0.4628 | 0.1463 | 0.1208 |
| C3 | 0.7574 | 0.0528 | 0.1572 |
| C4 | 0.5932 | 0.3851 | 0.1807 |
| C5 | 0.4797 | 0.3617 | 0.1559 |
| C6 | 0.4364 | 0.5908 | 0.1933 |
| C7 | 0.5330 | 0.2289 | 0.1438 |
| C8 | 0.3277 | 0.5712 | 0.1678 |
| C9 | 0.5744 | 0.4989 | 0.1993 |
| C10 | 0.3475 | 0.4586 | 0.1493 |
| C11 | 0.6778 | 0.1810 | 0.1617 |
| C12 | 0.5397 | 0.0174 | 0.1173 |
| C13 | 0.4025 | 0.7166 | 0.2133 |
| O1 | 0.2131 | 0.7465 | 0.2141 |
| C14 | 0.9038 | 0.0063 | 0.1779 |
| C15 | 0.4684 | 0.6951 | 0.2453 |
| C16 | 0.4889 | 0.8419 | 0.1994 |
| O2 | 0.9372 | 0.0751 | 0.2007 |
| N2 | 0.9916 | −0.1089 | 0.1715 |
| C17 | 0.3100 | 0.1985 | 0.1022 |
| C18 | 0.1348 | 0.1615 | 0.1093 |
| C19 | 0.1945 | 0.3479 | 0.0644 |
| C20 | 0.0197 | 0.3118 | 0.0715 |
| C21 | −0.0095 | 0.2166 | 0.0941 |
| C22 | 0.3427 | 0.2931 | 0.0791 |
| C23 | 0.5305 | 0.3367 | 0.0708 |
| N3 | 0.2226 | 0.4569 | 0.0426 |
| C24 | 0.2578 | 0.4191 | 0.0134 |
| N4 | 0.2870 | 0.5312 | −0.0066 |
| C25 | 0.2192 | 0.5925 | 0.0539 |

TABLE 7-continued

Fractional Atomic Coordinates of Example 33, Form M2-1 Calculated at a Temperature of about 173 K; Atomic Coordinates (×10$^4$)

| Atom | X | Y | Z |
|---|---|---|---|
| C26 | 0.2741 | 0.6673 | 0.0027 |
| C27 | 0.2455 | 0.6972 | 0.0321 |
| C28 | 0.2898 | 0.7686 | −0.0207 |
| C29 | 0.3530 | 0.5950 | −0.0567 |
| C30 | 0.3340 | 0.4967 | −0.0359 |
| C31 | 0.3249 | 0.7337 | −0.0493 |
| O3 | 0.1923 | 0.6096 | 0.0807 |
| O4 | 0.2649 | 0.3023 | 0.0050 |
| O5 | −0.0568 | 0.6980 | 0.1220 |
| C32 | −0.1535 | 0.5826 | 0.1313 |
| O6 | 0.9895 | 0.0341 | 0.2613 |
| C33 | 0.9227 | −0.0982 | 0.2682 |
| H1 | 0.8003 | 0.2727 | 0.1961 |
| H2 | 0.7322 | −0.1151 | 0.1310 |
| H3 | 0.2399 | 0.6362 | 0.1632 |
| H4 | 0.6524 | 0.5129 | 0.2154 |
| H5 | 0.2733 | 0.4474 | 0.1327 |
| H6 | 0.1580 | 0.6793 | 0.2204 |
| H7 | 0.4410 | 0.7750 | 0.2571 |
| H8 | 0.5965 | 0.6803 | 0.2452 |
| H9 | 0.4092 | 0.6166 | 0.2538 |
| H10 | 0.4409 | 0.8558 | 0.1796 |
| H11 | 0.6171 | 0.8286 | 0.1982 |
| H12 | 0.4636 | 0.9209 | 0.2116 |
| H13 | 1.0747 | −0.1382 | 0.1834 |
| H14 | 0.9653 | −0.1543 | 0.1555 |
| H15 | 0.1144 | 0.0986 | 0.1246 |
| H16 | −0.0771 | 0.3508 | 0.0613 |
| H17 | −0.1264 | 0.1899 | 0.0990 |
| H18 | 0.5554 | 0.3096 | 0.0504 |
| H19 | 0.6156 | 0.2937 | 0.0840 |
| H20 | 0.5405 | 0.4346 | 0.0725 |
| H21 | 0.2431 | 0.7886 | 0.0381 |
| H22 | 0.3851 | 0.5712 | −0.0762 |
| H23 | 0.3524 | 0.4052 | −0.0410 |
| H24 | 0.3306 | 0.8009 | −0.0641 |
| H25 | 0.0254 | 0.6742 | 0.1108 |
| H26 | −0.0765 | 0.5242 | 0.1430 |
| H27 | −0.1958 | 0.5332 | 0.1140 |
| H28 | −0.2548 | 0.6110 | 0.1432 |
| H29 | 0.9836 | 0.0467 | 0.2431 |
| H30 | 0.8087 | −0.1118 | 0.2584 |
| H31 | 0.9071 | −0.1064 | 0.2896 |
| H32 | 1.0070 | −0.1664 | 0.2614 |
| — | — | — | — |

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art, $\xi\!\!\!-$ is used in structural formulas herein to depict the bond that is the point of attachment of the moiety or substituent to the core or backbone structure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and insoluble solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to Btk, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I)

described herein, or a prodrug thereof, and a pharmaceutically acceptable carrier, adjuvant, or vehicle.

UTILITY

The compounds of the invention modulate kinase activity, including the modulation of Btk. Other types of kinase activity that may be modulated by the compounds of the instant invention include, but are not limited to, the Tec family of compounds, such as BMX, Btk, ITK, TXK and Tec, and mutants thereof.

Accordingly, compounds of Formula (I) have utility in treating conditions associated with the modulation of kinase activity, and particularly the selective inhibition of Btk activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of Btk, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the Btk inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

"Therapeutically effective amount" is intended to include an amount of a compound of the present invention that is effective when administered alone or in combination to inhibit Btk.

One embodiment provides methods for treating such Btk kinase-associated conditions, comprising administering to a subject in need thereof at least one compound of Formula (I). A therapeutically-effective amount for treating such conditions may be administered. The methods of the present embodiment may be employed to treat Btk kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating Btk kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to treat Btk kinase-associated conditions. The combination of compounds is preferably a synergistic combination. Synergy, as described, for example, by Chou et al., *Adv. Enzyme Regul.*, 22:27-55 (1984), occurs when the effect (in this case, inhibition of Btk) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-Btk effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment of prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of prophylaxis of an allergic disorder and/or autoimmune and/or inflammatory disease.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Examples of compounds of Formula (I) as specified in the "Examples" section below, have been tested in one or more of the assays described below.

In one embodiment, the compounds of Formula (I) inhibit Btk enzymes with $IC_{50}$ values of 6 nM or less, for example, from 0.001 to 6 nM, as measured by the Human Recombinant Btk enzyme assay. Preferably, the compounds of Formula (I) inhibit Btk enzymes with $IC_{50}$ values of 2 nM and less, for example, from 0.001 to 2 nM. Other preferred compounds inhibit Btk enzymes with $IC_{50}$ values of 1.0 nM and less, for example, from 0.001 to 1.0 nM.

In one embodiment, the compounds of Formula (I) have reduced inhibition of the Jak2 kinase characterized by $IC_{50}$ values above 50 nM, for example, greater than 250 nM, as measured by the Jak2 tyrosine kinase assay. Preferably, the compounds of Formula (I) inhibit Jak2 enzymes with $IC_{50}$ values of greater than 400 nM, for example, with $IC_{50}$ values of greater than 700 nM.

In one embodiment, the compounds of Formula (I) have kinase selectivity ratios of Btk inhibition activity over Jak2 inhibition activity characterized by ratios of Jak2 $IC_{50}$ inhibition values, as measured by the Jak2 tyrosine kinase assay, to Btk $IC_{50}$ inhibition values, as measured by the Human Recombinant Btk enzyme assay, of 150 and greater, for example, ratios of 300 and greater. Preferably, the compounds of Formula (I) have ratios of Jak2 $IC_{50}$ inhibition values to Btk $IC_{50}$ inhibition values of 400 and greater, for example, ratios of 500 and greater.

In one embodiment, the compounds of Formula (I) have improved potency in the whole blood BCR-stimulated CD69 expression assay with $IC_{50}$ values of 250 nM or less, for example, from 0.1 to 250 nM. More preferably, the compounds of Formula (I) have potency in the whole blood BCR-stimulated CD69 expression assay with $IC_{50}$ values of 160 nM or less, for example, from 0.1 to 160 nM; and with $IC_{50}$ values of 100 nM or less, for example, from 0.1 to 100 nM.

Methods of Preparation

Compounds of Formula (I) can be prepared using methods shown in Scheme 1.

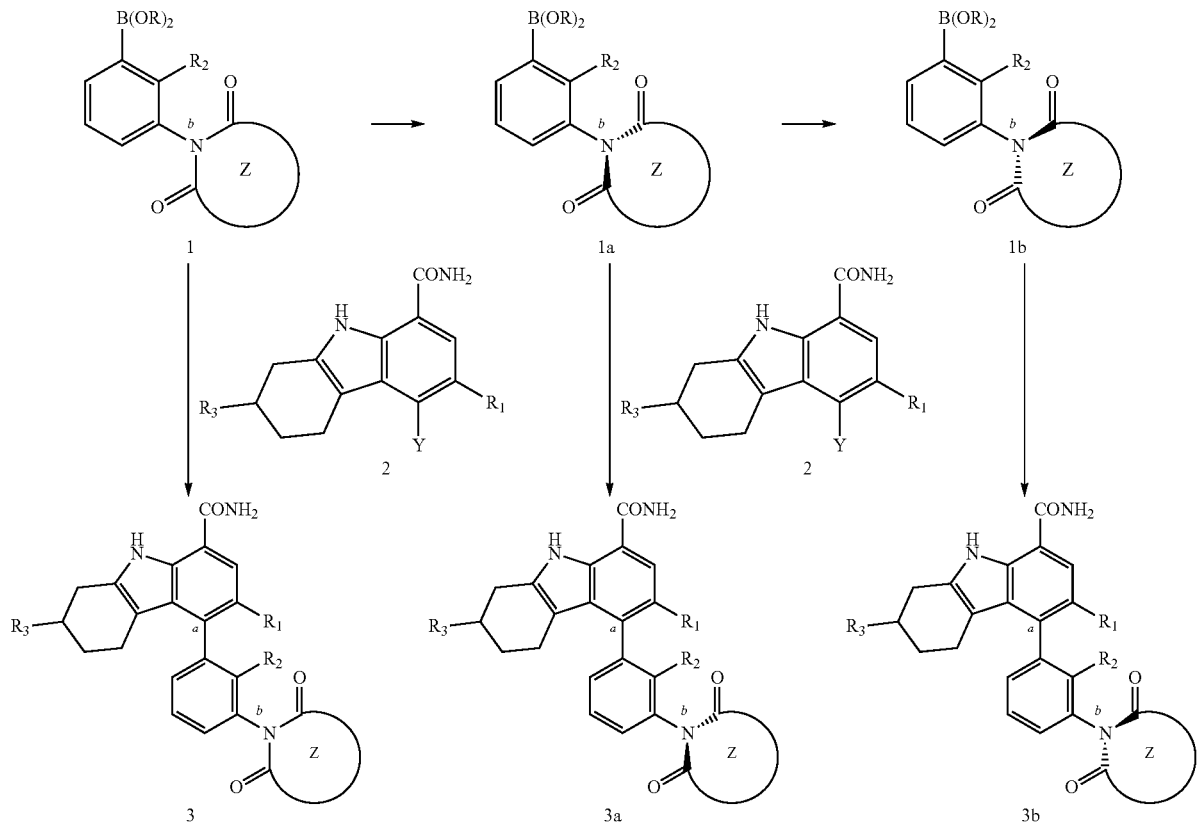

Scheme 1

Substituted boronic esters 1, wherein Z represents a substituted monocyclic or fused bicyclic heterocyclic ring (substituent Q in compounds of Formula (I)), can be reacted with substituted carbazolecarboxamides or tetrahydrocarbazolecarboxamides 2 (wherein Y is an appropriate group such as Br, Cl or trifluoromethanesulfonyloxy) to provide compounds 3. This reaction may be performed by using a suitable base such as potassium carbonate, cesium carbonate or tripotassium phosphate, and a suitable catalyst such as tetrakis(triphenylphosphine)palladium, 1,1'-bis(diphenylphosphino)ferrocene palladium(II) chloride, or 1,1'-bis(di-tert-butylphosphino)ferrocene palladium(II) chloride, in a suitable solvent such as dioxane or tetrahydrofuran, optionally with a suitable cosolvent such as water. Such coupling reactions are commonly known as Suzuki-Miyaura coupling reactions, and are well known in the chemical literature (see, for example, Heravi, M. M. et al., *Tetrahedron*, 68:9145 (2012), and references cited therein).

Due to the non-symmetric nature of the rings connected by the single bonds labeled a and b in Scheme 1, and due to limited rotation about these bonds caused by steric hindrance, compounds of the current invention display chirality, known as atropisomerism. Thus, under certain conditions, such as chromatography on a chiral stationary phase, the four diastereomeric atropisomers (arising from limited rotation about the two stereogenic axes) can be observed as four separate peaks in the chromatogram. Compounds of Formula (I) can be isolated either as stable mixtures of from two to four diastereomeric atropisomers, or as single stable atropisomers.

Since 1 is racemic, compounds 3 will normally be isolated as mixtures of four diastereomeric atropisomers. Alternatively, racemic compounds 1 can be converted into single atropisomers 1a and 1b, with the absolute configurations shown, using methods known in the art, such as preparative chromatography on a chiral stationary phase. Suzuki-Miyaura coupling reactions as described above can then convert 1a into compounds 3a, or 1b into 3b, having the absolute configurations shown about bond b but a mixture of two configurations about bond a, as long as the conditions of the Suzuki-Miyaura coupling reaction are such that isomerization about bond b does not occur. Compounds 3a and 3b will thus exist as a mixture of two diastereomeric atropisomers.

As shown in Scheme 2, compounds 3, which are mixtures of four diastereomeric atropisomers, can be separated into four single stable diastereomeric atropisomers 3c, 3d, 3e and 3f, using methods known in the art, such as chromatography on a chiral stationary phase. Alternatively, compounds 3a (mixtures of two diastereomeric atropisomers) can be separated into single stable atropisomers 3c and 3d, and compounds 3b (mixtures of two diastereomeric atropisomers) can likewise be separated into single stable atropisomers 3e and 3f.

Scheme 2
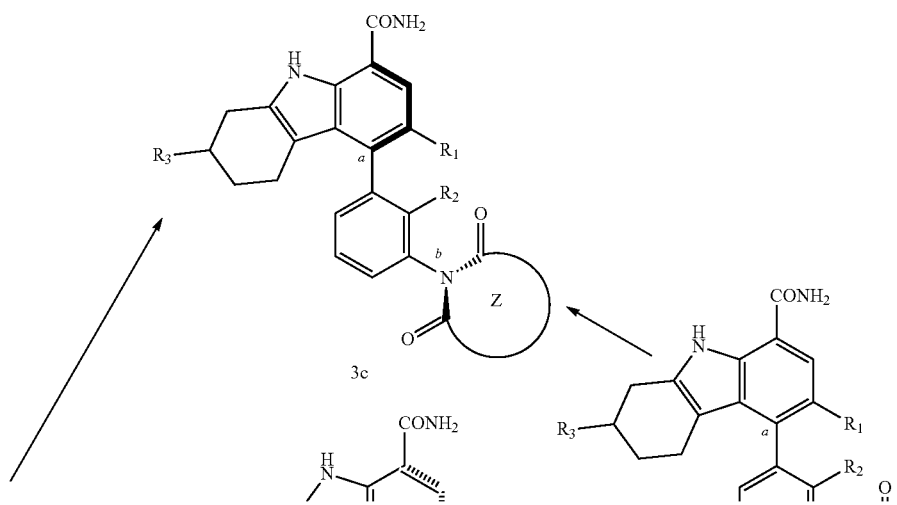
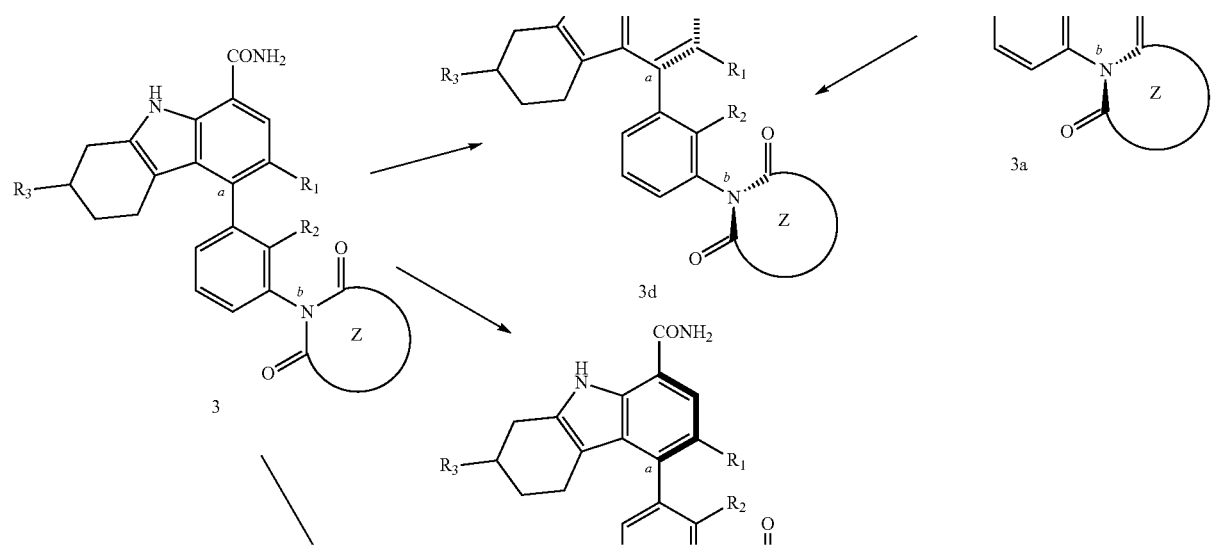

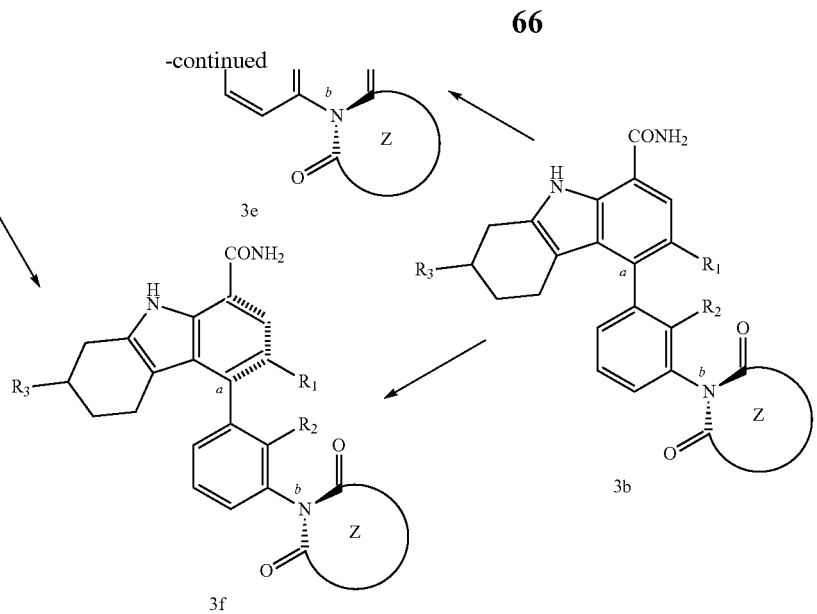

3e

3b

3f

In the case where 2 is a substituted tetrahydrocarbazole carboxamide (where the dashed lines represent single bonds), 2 also contains a chiral center, and thus can exist as a racemate. In this case, compounds 3 prepared from these compounds 2 will exist as a mixture of eight diastereomers, each of 3a and 3b will exist as a mixture of four diastereomers, and each of 3c, 3d, 3e and 3f will exist as a mixture of two diastereomers.

Any of these mixtures can also be separated into single stable diastereomers using methods known in the art, such as chromatography on a chiral stationary phase. Alternatively, compounds 2 can be converted into two separated enantiomers using methods known in the art, such as chromatography on a chiral stationary phase.

In some cases where one of the coupling intermediates 1 or 2 in Scheme 1 is non-racemic, chiral induction can occur during the Suzuki-Miyaura coupling reactions shown in Scheme 1. In these cases, mixtures of diastereomers can be obtained which are not equimolar mixtures; that is, the product 3 can be a mixture of diastereomers in which one or more of the diastereomers, having bond a with one absolute configuration, is present to a greater extent than one or more diastereomers having bond a with the opposite absolute configuration.

An alternative method for the synthesis of certain compounds of Formula (I) is shown in Scheme 3. A suitably substituted 4-arylimino-1H-benzo[d][1,3]oxazin-2(4H)-one 4 can react with 2 under conditions of the Suzuki-Miyaura coupling reaction as described above, to provide compounds of Formula (I) having structure 5. During the course of the reaction, the 4-arylimino-1H-benzo[d][1,3]oxazin-2(4H)-one moiety present in 4 rearranges to the 3-arylquinazoline-2,4(1H,3H)-dione moiety present in the reaction product 5.

Scheme 3

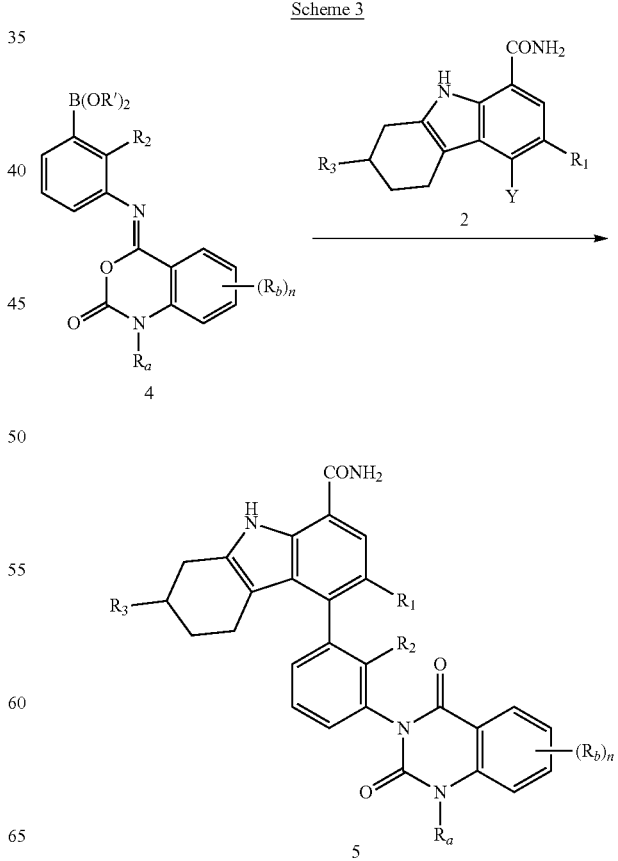

Compounds 1 of Scheme 1, used in the preparation of compounds of Formula (I), can be prepared by a variety of methods. Some of these methods are shown in Scheme 4. An isatoic anhydride 6 can react with a substituted aniline 7 (wherein Y' is an appropriate group such as Br, Cl or trifluoromethanesulfonyloxy) to produce an amide 8. Such reactions can be carried out under a variety of conditions, for example by heating in a suitable solvent, or by heating in the presence of an auxiliary reagent such as trimethylaluminum. A compound 8 can be converted into a substituted quinazolinedione 9, for example by treatment in a suitable solvent with phosgene or triphosgene. Optionally, 9 can be converted to the corresponding boronate ester 10 (which is an example of a compound 1 of Scheme 1) using methods well known in the chemical literature (see, for example, Ishiyama, T. et al., *Tetrahedron*, 57:9813 (2001), and references cited therein). Examples of such methods are the reaction of 9 with a borylating reagent such as 4,4,4',4',5,5,5',5'-octamethyl-2,2'-bi(1,3,2-dioxaborolane) or 5,5,5',5'-tetramethyl-2,2'-bi(1,3,2-dioxaborinane) in the presence of a base such as potassium acetate and a suitable catalyst such as 1,1'-bis(diphenylphosphino)ferrocene palladium(II) chloride in a suitable solvent.

Alternatively, a compound 9 can optionally be converted into a compound 11 where $R_a$ is an alkyl group, using methods known well known in the chemical literature, for example by treatment with an alkylating agent such as iodomethane or trideuteroiodomethane in the presence of a suitable base such as cesium carbonate. A compound 11 can then be converted into the corresponding boronate ester 12 (which is an example of compound 1 of Scheme 1) using the same methods described above. A compound 10 can also be optionally converted into the corresponding compound 12 by methods similar to those described for the conversion of 9 into 11.

Compounds 10 and 12 display chirality due to hindered rotation about the single bond connecting the substituted phenyl ring to the quinazolinedione moiety. If desired, these compounds can be resolved into separate enantiomeric atropisomers, for example by chromatography on a chiral stationary phase. The separated enantiomeric atropisomers of 10 can then optionally be converted into stable enantiomeric atropisomers of 12 as described above to provide certain examples of the compounds 1a or 1b of Scheme 1. Likewise, racemic quinazolinediones 12 can also be resolved into separate enantiomeric atropisomers.

Scheme 4

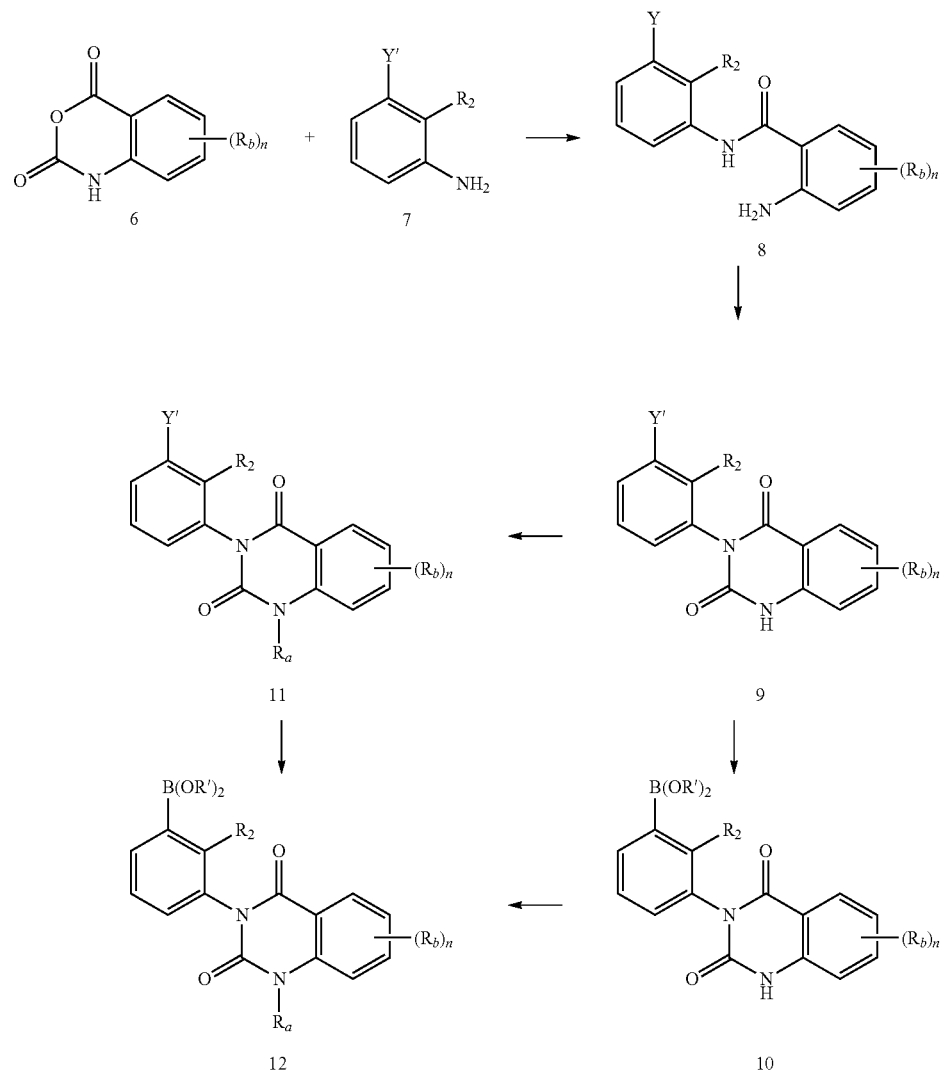

An alternative synthesis of intermediate compounds 8 of Scheme 4 is shown in Scheme 5. A substituted 2-nitrobenzoic acid 13 can be converted to a compound 14 using well-known amide bond forming reactions, for example by conversion of 8 to the corresponding carboxylic acid chloride and reaction with a substituted aniline 7, or by direct reaction of 13 and 7 in the presence of a suitable coupling reagent such O-(7-azabenzotriazol-1-yl)-1,1,3,3-tetramethyluronium hexafluorophosphate (HATU), or a mixture of 1-[3-(dimethylamino)propyl]-3-ethyl-carbodiimide hydrochloride (EDC) and 1-hydroxybenzotriazole hydrate (HOBT), using methods well known in the literature. The nitro group of 14 can then be reduced, using one of a wide variety of methods known in the literature, to give a compound 8 of Scheme 4.

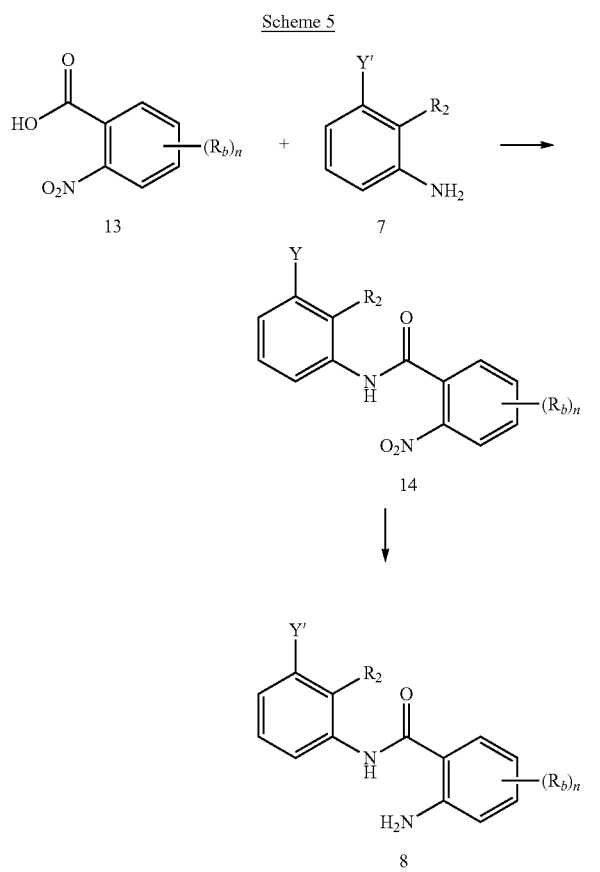

Compounds 4 of Scheme 3 can be prepared using the method shown in Scheme 6. An N-substituted isatoic anhydride 15, wherein $R_a$ is an alkyl group, can react with a substituted aniline 7 to produce an amide 16. Such reactions can be carried out under a variety of conditions as described above, for example by heating in a suitable solvent, or by heating in the presence of an auxiliary reagent such as trimethylaluminum. A compound 16 can be converted into a substituted aryliminobenzoxazinone 17, for example by treatment in a suitable solvent with phosgene or triphosgene. A compound 17 can then be converted into the corresponding boronate ester 4 using methods similar to those described above for the conversion of a compound 10 or a compound 11 into a compound 12 (see Scheme 4).

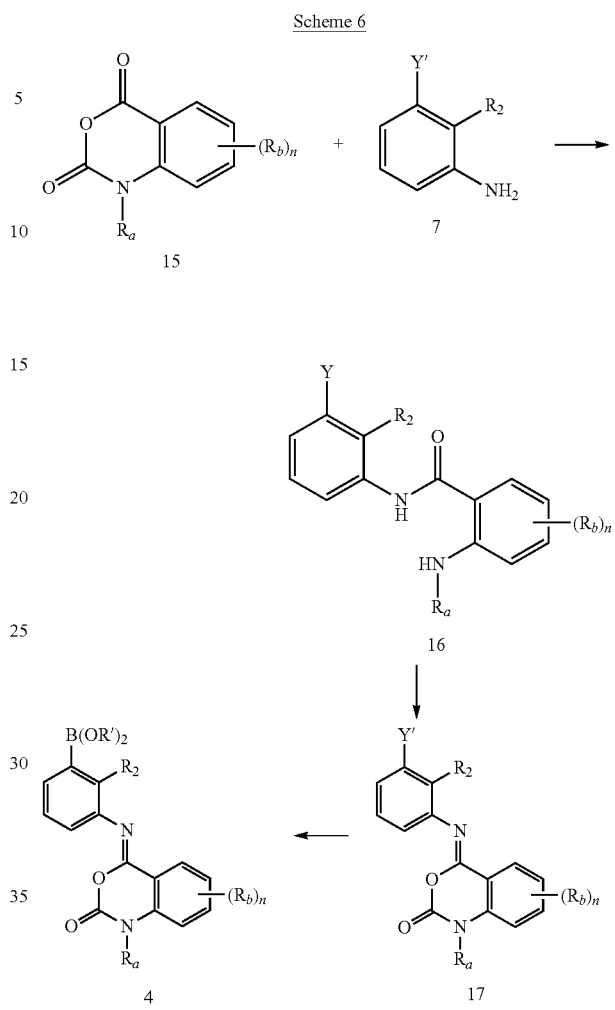

Some additional methods which can be used to prepare certain compounds 1, used in the preparation of compounds of Formula (I), are shown in Scheme 7. A substituted pyridyl-2-acetic acid 18, or a salt of a substituted pyridyl-2-acetic acid such as a sodium salt (which are either commercially available or can be prepared by methods well known in the chemical literature), can be reacted with an aniline 7 under a variety of methods well known in the chemical literature to provide an amide 19. For example, the reaction can be performed in the presence of a coupling reagent such as O-(7-azabenzotriazol-1-yl)-1,1,3,3-tetramethyluronium hexafluorophosphate (HATU), or a mixture of 1-[3-(dimethylamino)propyl]-3-ethyl-carbodiimide hydrochloride (EDC) and 1-hydroxybenzotriazole hydrate (HOBT). An amide 19 can be converted into the corresponding substituted 1H-pyrido[1,2-c]pyrimidine-1,3(2H)-dione 20 by heating with a reagent such as carbonyldiimidazole in an appropriate solvent such as toluene. A compound 20 can be converted into the corresponding boronate ester 21 (which is an example of an intermediate 1 of Scheme 1) using methods previously described (see Scheme 4). Alternatively, a compound 19 can be converted into the corresponding boronate ester 22 using methods previously described (see Scheme 4), followed by conversion of 22 to 21 by heating with a reagent such as carbonyldiimidazole.

Scheme 7

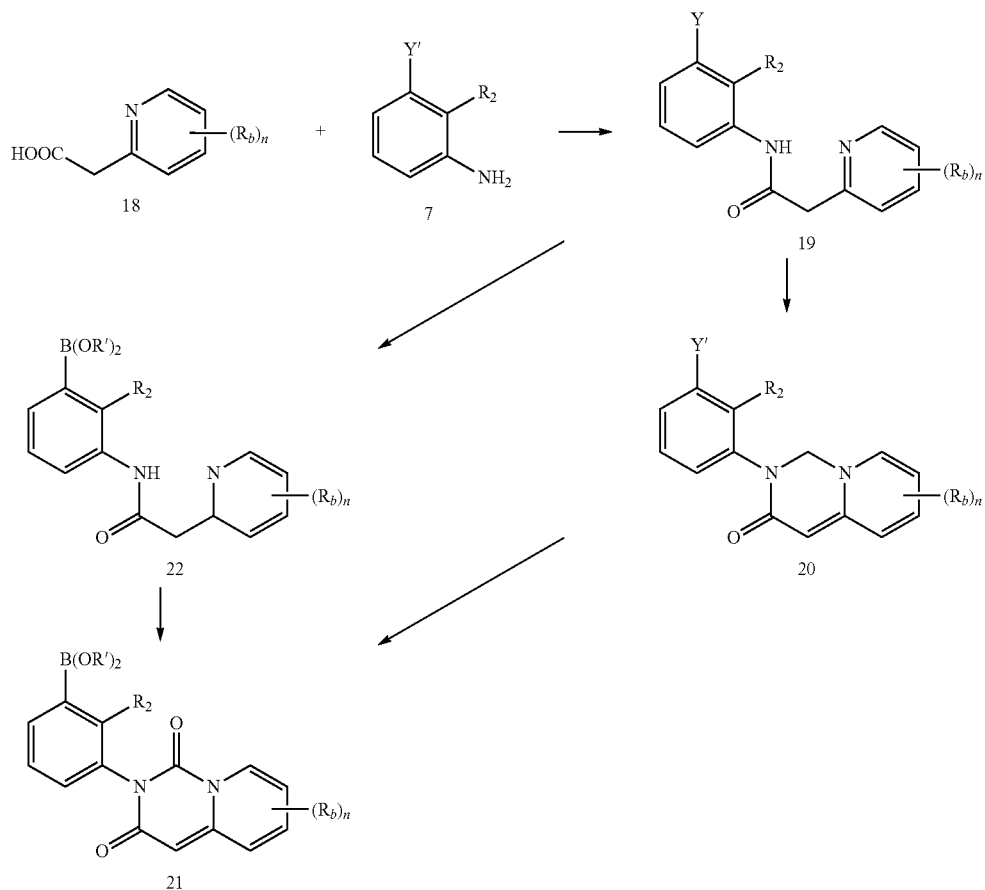

In Scheme 7, the pyridyl ring in the structures shown can also be replaced with another nitrogen heterocycle, such as a thiazole. In this case, the corresponding compounds 20 and 21 will contain a 5H-thiazolo[3,2-c]pyrimidine-5,7(6H)-dione moiety in place of the 1H-pyrido[1,2-c]pyrimidine-1,3 (2H)-dione moiety shown.

Compounds 21 display chirality due to hindered rotation about the single bond joining the substituted phenyl ring with the substituted 1H-pyrido[1,2-c]pyrimidine-1,3(2H)-dione moiety. If desired, these racemic compounds can be resolved into separate enantiomeric atropisomers, for example by chromatography on a chiral stationary phase, to provide certain examples of the intermediates 1a and 1b of Scheme 1.

Scheme 8

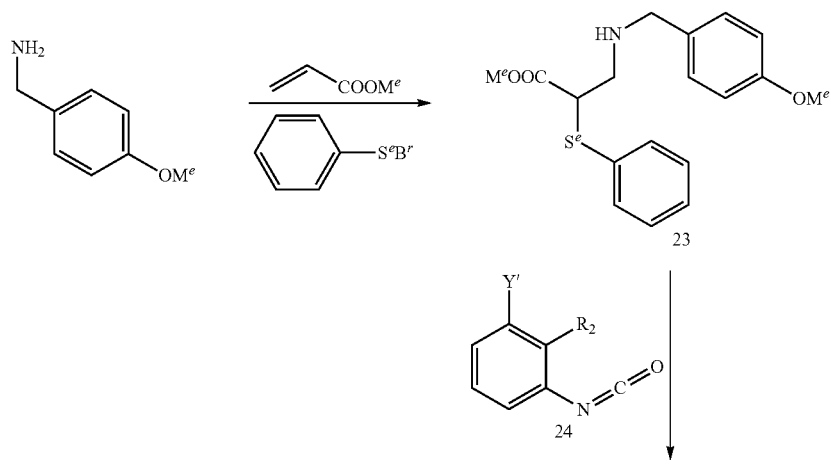

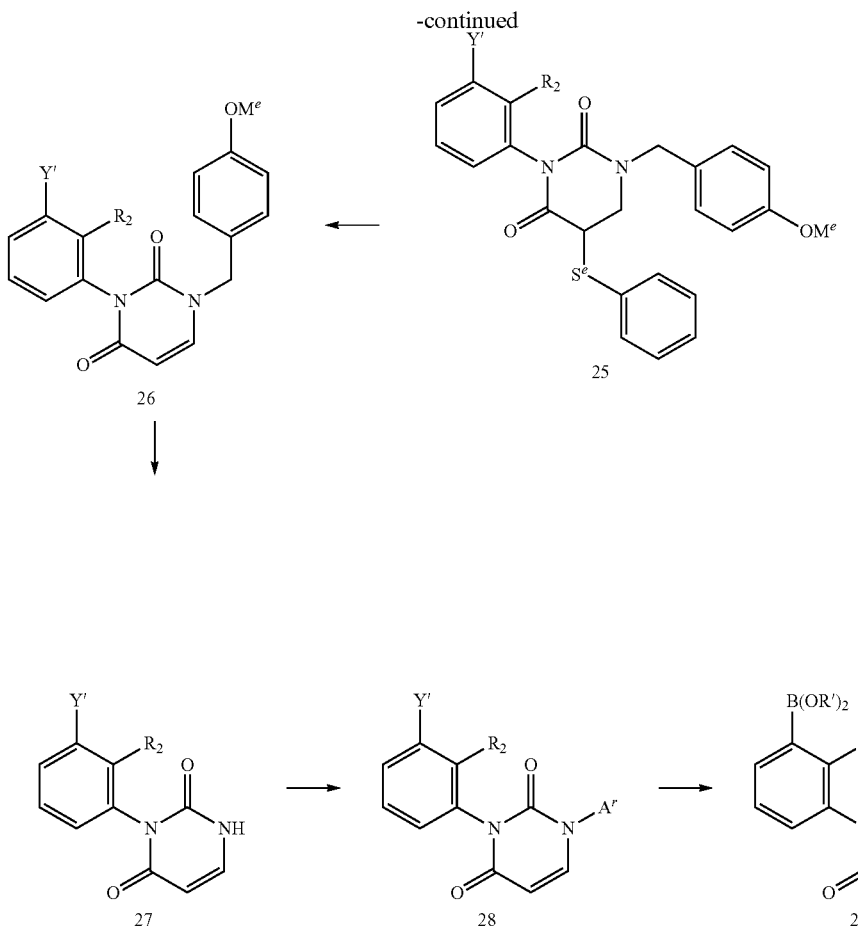

Preparation of a compound 1 of Scheme 1, wherein Z represents a substituted pyrimidine-1,3-dione moiety, can be achieved using the method shown in Scheme 8, following a general procedure reported by Cao, J. et al. (*Synthetic Commun.*, 39:205 (2009)). Compound 23 can be prepared by reacting p-methoxybenzylamine, methyl acrylate and phenyl hypobromoselenoite. This material can be reacted with an appropriate aryl isocyanate 24 (which can be prepared from the aniline 7 shown in Scheme 4, using methods well known in the chemical literature) to provide the substituted dihydropyrimidine-1,3-dione 25. Treatment of this compound with an oxidizing agent such as hydrogen peroxide can provide the substituted pyrimidine-1,3-dione 26. Removal of the p-methoxybenzyl group of 26 can be achieved using a number of methods reported in the chemical literature, for example by treatment with a mixture of trifluoromethanesulfonic acid and trifluoroacetic acid (as reported by Wu, F. et al., *J. Org. Chem.*, 69:9307 (2004)). The resulting pyrimidine-1,3-dione 27 can be reacted with an aryl boronic acid such as 4-fluorobenzeneboronic acid, for example using conditions described by Jacobsen, M. F. et al. (*J. Org. Chem.*, 71:9183 (2006)) to provide 28 (wherein Ar represents 4-fluorophenyl). This can then be converted to the boronate ester 29, which is an example of a compound 1 of Scheme 1, using methods similar to those described above.

Compounds 2 shown in Scheme 1, used in the preparation of compounds of Formula (I), can be prepared using procedures shown in Scheme 9. A substituted 2-aminobenzoic acid 30 (known in the literature, or prepared using procedures known in the literature) can be converted to the corresponding 2-hydrazinylbenzoic acid 31 as the hydrochloric acid salt using methods well known in the literature, for example by conversion to the corresponding diazonium salt by treatment with sodium nitrite in aqueous hydrochloric acid, followed by reduction with tin(II) chloride. Reaction of 31 with ethyl 3-oxocyclohexanecarboxylate 32 (which can be prepared from ethyl 3-hydroxybenzoate; see for example Hirsch, J. et al., *J. Org. Chem.*, 51:2218 (1986)) in a suitable solvent with an appropriate catalyst, for example ethanol with hydrochloric acid, toluene with p-toluenesulfonic acid or trifluoroacetic acid, or acetic acid (in which case the solvent also can serve as the catalyst), can provide the corresponding tetrahydrocarbazole derivative 33. This reaction is commonly known as the Fischer indole synthesis, and is well known in the chemical literature (for example, see Kamata, J. et al., *Chem. Pharm. Bull.*, 52:1071 (2004)). Alternatively, the Fischer indole synthesis can be carried out in two consecutive steps: 31 can react with 32 under suitable conditions (such as in an appropriate solvent such as ethanol or toluene, optionally with a suitable catalyst such as p-toluenesulfonic acid) to form an intermediate hydrazone, which can be isolated and then reacted further under suitable conditions (for example, ethanol with hydrochloric acid, acetic acid with zinc chloride, or toluene with trifluoroacetic acid) to provide 33.

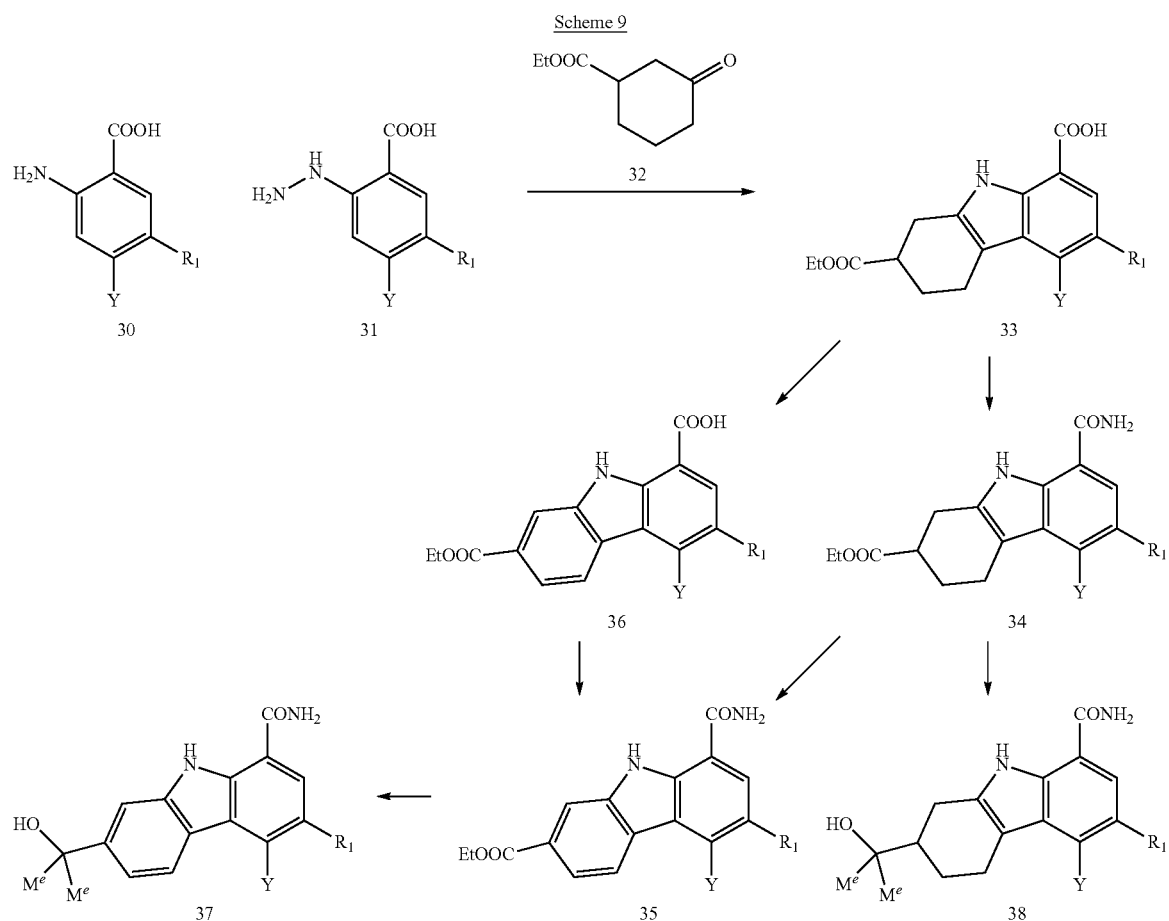

Scheme 9

A carboxylic acid 33 can be converted to the corresponding carboxamide 34 using methods well known in the chemical literature, for example by conversion of 33 to the acid chloride by treatment with oxalyl chloride or thionyl chloride, followed by treatment with ammonia; or by treatment of 33 with ammonia in the presence of a coupling reagent such as carbodiimide, or a mixture of N-(3-dimethylaminopropyl)-N'-ethylcarbodiimide hydrochloride and 1-hydroxybenzotriazole or 1-hydroxy-7-azabenzotriazole. Conversion of a tetrahydrocarbazole 34 to the corresponding carbazole 35 can be performed using methods well known in the chemical literature, for example by treatment of 34 with an oxidizing agent such as 2,3-dichloro-5,6-dicyanobenzoquinone in a suitable solvent.

Alternatively, the order of the amide formation and oxidation steps can be reversed to convert 33 to 35. Thus, a compound 33 can be oxidized using the procedure described above, or a similar procedure, to give the corresponding compound 36. The carboxylic acid of this compound can then be converted into the corresponding primary amide, again using a procedure described above or a similar procedure, to give the corresponding compound 35.

Conversion of 35 to the corresponding tertiary carbinol substituted carbazolecarboxamide 37 (which is an example of compound 2 in Scheme 1) can be performed using methods well known in the chemical literature, for example by treatment of 35 with a reagent such as methyllithium, methylmagnesium bromide or methylmagnesium chloride.

Alternatively, conversion of 34 to the corresponding tertiary carbinol substituted tetrahydrocarbazole carboxamide 38 (which is another example of compound 2 in Scheme 1) can be performed using a similar procedure.

Compounds 33, 34 and 38 contain a chiral center, and thus exist as two enantiomers. Preparation of 33, 34 and 38 as shown in Scheme 9 provides racemic products, which may be used to prepare compounds of Formula (I) as shown in Scheme 1. Alternatively, 33, 34 and 38 may be resolved into separated enantiomers, using well-known methods such as chromatography on a chiral stationary phase.

Certain compounds 2 of Scheme 1, used to prepare compounds of Formula (I), may also be prepared using procedures shown in Scheme 10. Compound 39, prepared from the appropriate 2-hydrazinylbenzoic acid as shown in Scheme 9 (see U.S. Pat. No. 8,084,620, Intermediate 48-1) can be treated with an appropriate halogenating reagent to give 40, where $R_1$ is a halogen atom. For example, treatment of 39 with a chlorinating reagent such as N-chlorosuccinimide can give 40 where $R_1$ is Cl, and treatment of 39 with a fluorinating reagent such as 1-(chloromethyl)-4-fluoro-1,4-diazoniabicyclo[2.2.2]octane-bis(tetrafluoroborate) [SELECTFLUOR®] can give 40 where $R_1$ is F. Treatment of 40 with methyllithium or a methylmagnesium halide as described for Scheme 9 can then provide compounds 37 where $R_1$ is F or Cl (which are examples of compounds 2 in Scheme 1).

Scheme 10

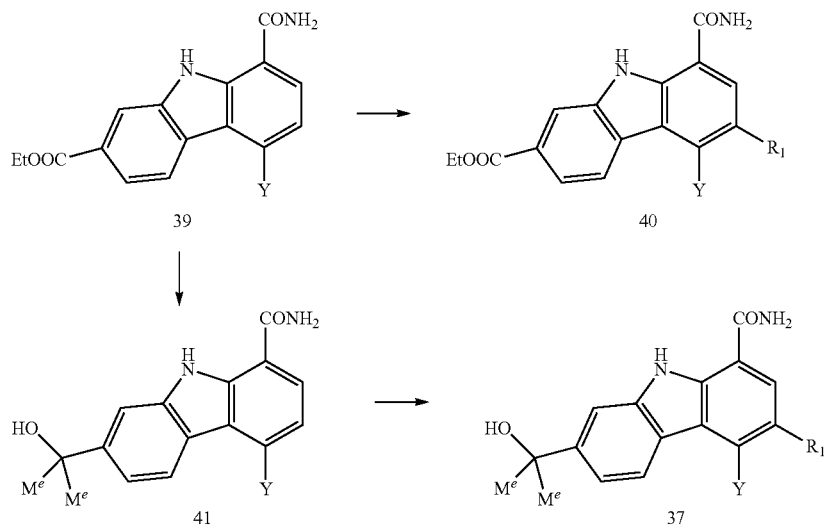

Compound 37 where $R_1$ is CN can be prepared by an alternative procedure, also shown in Scheme 10. Compound 41, which can be prepared from compound 39 (see U.S. Pat. No. 8,084,620, Example 73-2) can be treated with an iodinating reagent such as N-iodosuccinimide to provide 37 where $R_1$ is I. This compound can be converted to 37 where $R_1$ is CN (an example of compound 2 in Scheme 1), for example by treatment with zinc cyanide in the presence of a catalyst such as tetrakis(triphenylphosphine)palladium.

Another example of the preparation of a compound 2 of Scheme 1 is shown in Scheme 11. Using procedures described in Scheme 9 and similar procedures, the ketone 42 (which can be prepared by reaction of diethyl malonate with cyclohex-2-enone, using a number of methods reported in the literature) can be reacted with a hydrazinylbenzoic acid 31 to give a compound 43, which can then be converted to a compound 44 and subsequently to a compound 45 using methods described above for Scheme 9. Using methods known in the literature, for example heating with sodium chloride and water in a suitable solvent such as dimethyl sulfoxide, a compound 45 can be converted to a compound 46. The ester moiety of a compound 46 can then be reduced to the carbinol using procedures known in the literature, for example by treatment with lithium borohydride, to give a compound 47, which is an example of compound 2 of Scheme 1.

Scheme 11

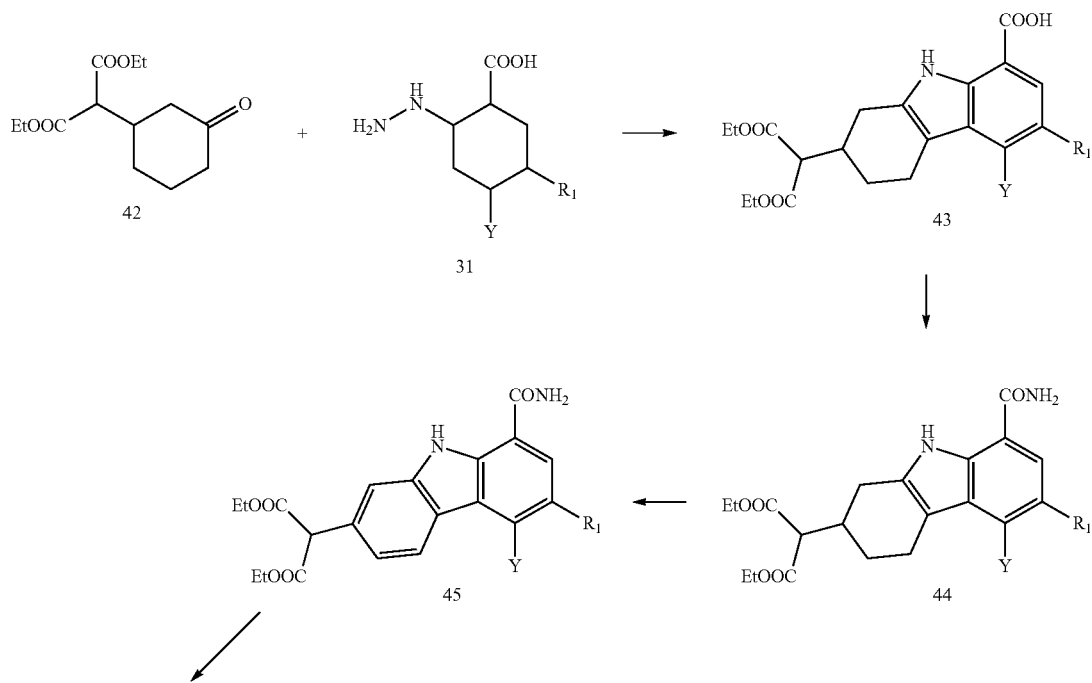

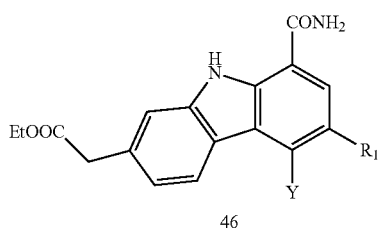

46

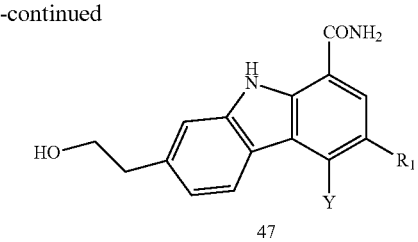

47

EXAMPLES

Compounds of the current invention, and intermediates used in the preparation of compounds of the current invention, can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared).

Column chromatography was generally performed using the flash chromatography technique (Still, W. C. et al., *J. Org. Chem.*, 43:2923 (1978)), or with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chiral super-critical fluid chromatographic separation of enantiomers or atropisomers was performed using conditions described for the individual cases. Mass spectral data were obtained by liquid chromatography-mass spectrometry using electrospray ionization.

Single crystal x-ray diffraction data were collected on a Bruker-AXS APEX2 CCD system using Cu Kα radiation (λ=1.5418 Å). Indexing and processing of the measured intensity data were carried out with the APEX2 software package/program suite (see the APEX2 User Manual, v1.27; Bruker AXS, Inc., WI 53711 USA). When indicated, crystals were cooled in the cold stream of an Oxford Cryosystems cryostream cooler (Cosier, J. et al., *J. Appl. Cryst.*, 19:105 (1986)) during data collection. The structures were solved by direct methods and refined on the basis of observed reflections using the crystallographic package SHELXTL (see the APEX2 User Manual, v1.27; Bruker AXS, Inc., WI 53711 USA). The derived atomic parameters (coordinates and temperature factors) were refined through full matrix least-squares. The function minimized in the refinements was $\Sigma w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied. Unit cell parameters were obtained according to the procedure described in Stout et al., *X-Ray Structure Determination: A Practical Guide*, MacMillan (1968).

Chemical names were determined using CHEMDRAW® Ultra, version 9.0.5 (CambridgeSoft). The following abbreviations are used:

| ABBREVIATIONS | |
|---|---|
| CDI | carbonyldiimidazole |
| DCM | dichloromethane |
| DIEA | diisopropylethylamine |
| DMF | N,N-dimethylformamide |
| DMSO | dimethyl sulfoxide |
| dppf | 1,1'-bis(diphenylphosphino)ferrocene |
| DSC | differential scanning calorimetry |
| DTT | dithiothreitol |
| EDC | 1-[3-(dimethylamino)propyl]-3-ethyl-carbodiimide hydrochloride |
| EDTA | ethylenediamine tetraacetate |
| EtOAc | ethyl acetate |
| EtOH | ethanol |
| g | gram(s) |
| h | hour(s) |
| HATU | O-(7-azabenzotriazol-1-yl)-1,1,3,3-tetramethyluronium hexafluorophosphate |
| HOBT | 1-hydroxybenzotriazole hydrate |
| HPLC | High Pressure Liquid Chromatography |
| IPA | isopropanol |
| MeCN | acetonitrile |
| MeOH | methanol |
| min | minute(s) |
| mmol | millimole(s) |
| NBS | N-bromosuccinimide |
| NCS | N-chlorosuccinimide |
| NMP | N-methylpyrrolidinone |
| t-butyl | tertiary butyl |
| TEA | triethylamine |
| TFA | trifluoroacetic acid |
| THF | tetrahydrofuran |

Intermediate 1

3-(3-Bromo-2-methylphenyl)-8-fluoroquinazoline-2,4(1H,3H)-dione

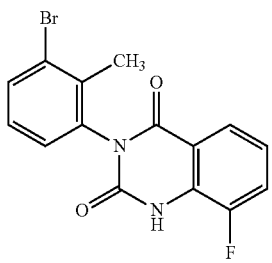

(I-1)

Intermediate 1A: 2-Amino-N-(3-bromo-2-methylphenyl)-3-fluorobenzamide

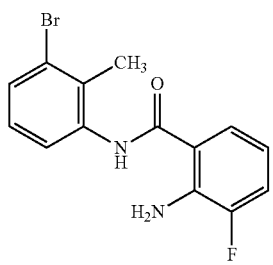

(I-1A)

Method 1: A solution of 8-fluoro-1H-benzo[d][1,3]oxazine-2,4-dione (2.00 g, 11.04 mmol) and 3-bromo-2-methylaniline (4.11 g, 22.08 mmol) in dioxane (20 mL) in sealed reaction vessels was heated at 110° C. for 4 days. The cooled mixture was treated with 10% aqueous $K_2CO_3$ and stirred at room temperature for 30 min. The mixture was extracted with DCM 3 times, and the combined organic phases were washed with water, dried and concentrated. The residue was triturated with ether to give a gray solid (2.50 g). The mother liquor was concentrated and the residue was again triturated with ether to give a gray solid (230 mg). The two solids were combined to provide 2-amino-N-(3-bromo-2-methylphenyl)-3-fluorobenzamide as a gray solid (2.73 g, 78% yield). Mass spectrum m/z 323, 325 (M+H)+.

Method 2. A suspension of 8-fluoro-1H-benzo[d][1,3]oxazine-2,4-dione (3.00 g, 16.6 mmol) in xylenes (50 mL) was treated with 3-bromo-2-methylaniline (3.08 g, 16.6 mmol) and heated to reflux. After 6 h the mixture was allowed to cool to room temperature overnight. The resulting suspension was diluted with hexanes and the precipitate was collected by filtration, rinsed with hexanes and air-dried to provide 2-amino-N-(3-bromo-2-methylphenyl)-3-fluorobenzamide as a white solid (4.50 g, 84% yield). $^1$H NMR (400 MHz, chloroform-d) δ 7.69 (d, J=7.9 Hz, 1H), 7.65 (br. s., 1H), 7.50-7.46 (m, 1H), 7.32 (d, J=8.1 Hz, 1H), 7.19-7.11 (m, 2H), 6.73-6.64 (m, 1H), 5.69 (br. s., 2H), 2.44 (s, 3H).

Intermediate 1:

A solution of 2-amino-N-(3-bromo-2-methylphenyl)-3-fluorobenzamide (5.70 g, 17.6 mmol) in THF (100 mL) was treated with bis(trichloromethyl) carbonate (triphosgene) (6.28 g, 21.2 mmol) at room temperature and stirred for 15 min. The mixture was diluted with EtOAc, carefully treated with saturated aqueous $NaHCO_3$ and stirred at room temperature until gas evolution stopped. The separated organic phase was washed sequentially with saturated aqueous $NaHCO_3$, water and brine, and was dried and concentrated. The residue was triturated with ether to provide 3-(3-bromo-2-methylphenyl)-8-fluoroquinazoline-2,4(1H,3H)-dione as an off-white solid (6.00 g, 97% yield). Mass spectrum m/z 349, 351 (M+H)+. $^1$H NMR (400 MHz, chloroform-d) δ 8.59 (d, J=17.6 Hz, 1H), 7.99 (d, J=8.1 Hz, 1H), 7.70 (dd, J=7.8, 1.2 Hz, 1H), 7.54-7.43 (m, 1H), 7.28-7.21 (m, 2H), 7.21-7.17 (m, 1H), 2.28 (s, 3H).

Intermediate 2

8-Fluoro-1-methyl-3-(2-methyl-3-(4,4,5,5-tetramethyl-1,3,2-dioxaborolan-2-yl)phenyl)quinazoline-2,4(1H,3H)-dione

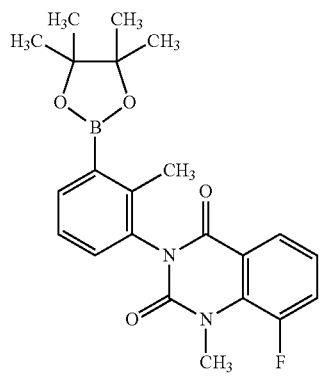

(I-2)

Intermediate 2A: 3-(3-Bromo-2-methylphenyl)-8-fluoro-1-methylquinazoline-2,4(1H,3H)-dione

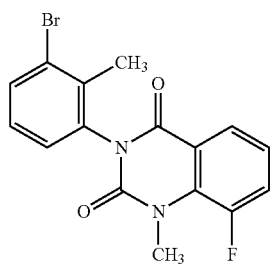

(I-24A)

A solution of 3-(3-bromo-2-methylphenyl)-8-fluoroquinazoline-2,4(1H,3H)-dione [Intermediate 1] (4.80 g, 13.8 mmol) in DMF (25 mL) was treated with $Cs_2CO_3$ (13.4 g, 41.2 mmol). The suspension was stirred at room temperature and treated dropwise (but quickly) with iodomethane (4.30 mL, 68.7 mmol) and stirred rapidly at room temperature for 1 h. The mixture was diluted with EtOAc and water (200 mL). The organic phase was separated and washed sequentially with water and brine, then was dried and concentrated to provide 3-(3-bromo-2-methylphenyl)-8-fluoro-1-methylquinazoline-2,4(1H,3H)-dione as a tan glassy foam (4.80 g, 96% yield). Mass spectrum m/z 363, 365 (M+H)+.

Intermediate 2:

A mixture of 3-(3-bromo-2-methylphenyl)-8-fluoro-1-methylquinazoline-2,4(1H,3H)-dione (4.80 g, 13.2 mmol), 4,4,4',4',5,5,5',5'-octamethyl-2,2'-bi(1,3,2-dioxaborolane) (4.36 g, 17.2 mmol), potassium acetate (3.89 g, 39.6 mmol) and PdCl$_2$(dppf) DCM adduct (0.540 g, 0.661 mmol) in dioxane (65 mL) was heated to reflux for 2 h. After cooling to room temperature, the mixture was filtered through CELITE® and the solids were rinsed with EtOAc. The filtrate was diluted with EtOAc, washed with water, and dried and concentrated. The residue was subjected to column chromatography on silica gel (80 g), eluting with EtOAc-hexanes (gradient from 20-50%), to provide 8-fluoro-1-methyl-3-(2-methyl-3-(4,4,5,5-tetramethyl-1,3,2-dioxaborolan-2-yl)phenyl) quinazoline-2,4(1H,3H)-dione as a white solid (4.61 g, 85% yield). Mass spectrum m/z 411 (M+H)+. $^1$H NMR (400 MHz, chloroform-d) δ 8.14-8.08 (m, 1H), 7.93 (dd, J=7.5, 1.3 Hz, 1H), 7.48 (ddd, J=14.0, 8.0, 1.5 Hz, 1H), 7.34 (t, J=7.6 Hz, 1H), 7.27-7.20 (m, 2H), 3.88 (d, J=7.9 Hz, 3H), 2.36 (s, 3H), 1.36 (s, 12H).

Intermediate 3

4-Bromo-3-chloro-7-(2-hydroxypropan-2-yl)-9H-carbazole-1-carboxamide

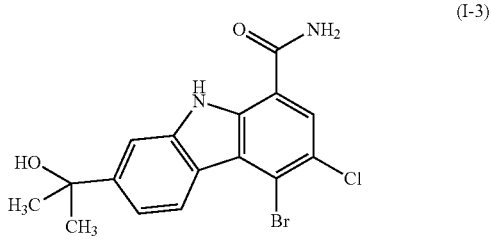 [SMILES: CC(C)(O)c1ccc2c(c1)[nH]c1c(C(N)=O)cc(Cl)c(Br)c12]

(I-3)

Intermediate 3A: Ethyl 5-bromo-8-carbamoyl-6-chloro-9H-carbazole-2-carboxylate

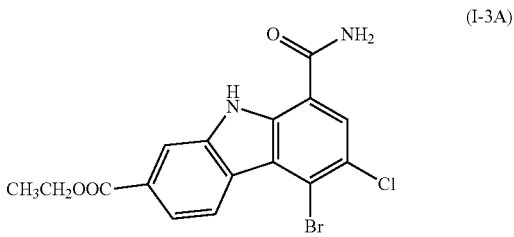

(I-3A)

A mixture of ethyl 5-bromo-8-carbamoyl-9H-carbazole-2-carboxylate [synthesized according to the procedure described in U.S. Pat. No. 8,084,620, Intermediate 48-1] (0.100 g, 0.277 mmol) and NCS (recrystallized from toluene; 0.037 g, 0.277 mmol) in CCl$_4$ (10 mL) and DMF (2 mL) was stirred at room temperature for 112 h. The mixture was filtered, and the collected precipitate was washed with CCl$_4$ and dried overnight under vacuum. The residue was purified by column chromatography on silica gel (40 g), eluting with hexanes, then with EtOAc-hexanes (30%, then 50%), to give ethyl 5-bromo-8-carbamoyl-6-chloro-9H-carbazole-2-carboxylate as a fluffy white solid (0.071 g, 65% yield). Mass spectrum m/z 395, 397, (M+H)+. $^1$H NMR (400 MHz, DMSO-d$_6$) δ 12.13 (s, 1H), 8.77 (d, J=8.6 Hz, 1H), 8.53 (d, J=1.1 Hz, 1H), 8.36 (br. s., 1H), 8.29 (s, 1H), 7.89 (dd, J=8.4, 1.5 Hz, 1H), 7.74 (br. s., 1H), 4.38 (q, J=7.0 Hz, 2H), 1.38 (t, J=7.0 Hz, 3H).

Alternative Preparation of Intermediate 3A:

To a mixture of ethyl 5-bromo-8-carbamoyl-9H-carbazole-2-carboxylate (90 g, 249 mmol), CCl$_4$ (2900 mL), and NMP (600 mL) was added NCS (36.1 g, 271 mmol). The reaction mixture was stirred at 45° C. for 2 h. After cooling to room temperature, the solid was collected by vacuum filtration. The solid was stirred in methanol (1 L) at 60° C. for 2 h and then cooled to room temperature. The solid was collected and dried to give ethyl 5-bromo-8-carbamoyl-6-choro-9H-carbazole-2-carboxylate (69.5 g, 167 mmol, 67% yield) (95% purity).

The filtrate was concentrated under reduced pressure to remove CCl$_4$. To the NMP residue was then added water (2 L). The resulting precipitate was collected and dried to give an additional 13.7 g of product (25% yield, 75% purity).

Intermediate 3:

A solution of ethyl 5-bromo-8-carbamoyl-6-chloro-9H-carbazole-2-carboxylate (4.14 g, 10.5 mmol) in THF (200 mL) cooled in a dry ice-acetone bath was treated portionwise over 30 min with 1.6 M methyllithium in hexanes (45.8 mL, 73.2 mmol). The mixture was stirred at −78° C. for 60 min, then was treated portionwise with saturated aqueous NH$_4$Cl. Water was added and the mixture was extracted twice with EtOAc. The combined organic phases were washed twice with water. All aqueous phases were combined and extracted with DCM, and this organic phase was washed with water. All organic phases were combined, dried and concentrated. The residue was crystallized from EtOAc to give a solid. The residue from concentration of the mother liquor was purified by chromatography on silica gel (330 g), eluting with EtOAc-hexanes (gradient from 0-100%), to give additional solid. The two solids were combined to give 4-bromo-3-chloro-7-(2-hydroxypropan-2-yl)-9H-carbazole-1-carboxamide as a light yellow solid (3.13 g, 78% yield). Mass spectrum m/z 363, 365, (M+H-H$_2$O)+. $^1$H NMR (400 MHz, DMSO-d$_6$) δ 11.71 (s, 1H), 8.56 (d, J=8.6 Hz, 1H), 8.29 (br. s., 1H), 8.17 (s, 1H), 7.97 (d, J=1.3 Hz, 1H), 7.66 (br. s., 1H), 7.42 (dd, J=8.6, 1.8 Hz, 1H), 1.52 (s, 6H).

Alternative Preparation of Intermediate 3:

A suspension of ethyl 5-bromo-8-carbamoyl-6-chloro-9H-carbazole-2-carboxylate (58.56 g, 148 mmol) in THF (700 mL) under nitrogen was cooled to −15° C. in an acetone-dry ice bath. The mixture was treated dropwise with 3 M methylmagnesium chloride in THF (395 mL, 1.19 mol) at a rate that the internal temperature remained between −15° C. and −10° C. After 5 h the mixture was poured into 3 vessels, each containing ca. 1.5 L of crushed ice and 500 mL of saturated aqueous NH$_4$Cl. The resulting mixtures were extracted with EtOAc, and the combined organic phases were dried and concentrated. The residue was combined with material from two additional batches, one starting from 146 mmol of ethyl 5-bromo-8-carbamoyl-6-chloro-9H-carbazole-2-carboxylate and the other starting from 142 mmol of ethyl 5-bromo-8-carbamoyl-6-chloro-9H-carbazole-2-carboxylate, and stirred for 1 h in acetone (250 mL). The precipitate was collected by filtration, washed with hexane and dried to provide 4-bromo-3-chloro-7-(2-hydroxypropan-2-yl)-9H-carbazole-1-carboxamide as a solid (134.56 g). The filtrate was concentrated and the residue was again stirred for 1 h in acetone, forming a precipitate which was collected by filtration, washed with hexane and dried to give additional 4-bromo-3-chloro-7-(2-hydroxypropan-2-yl)-9H-carbazole-1-carboxamide as a solid (7.36 g) for a total of 141.92 g (88% yield). The filtrate from the second filtration was combined with impure material from other batches and subjected to column chromatography on silica gel (2×1.5 kg), eluting with EtOAc-hexanes (gradient from 40-100%), providing additional product.

Intermediate 4

1-Methyl-3-(2-methyl-3-(4,4,5,5-tetramethyl-1,3,2-dioxaborolan-2-yl)phenyl)quinazoline-2,4(1H,3H)-dione

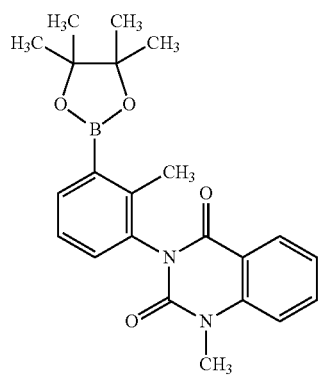

(I-4)

Intermediate 4A:
2-Amino-N-(3-bromo-2-methylphenyl)benzamide

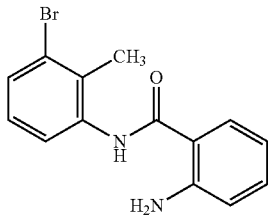

(I-4A)

Method 1. A solution of 2-aminobenzoic acid (5.00 g, 36.5 mmol) and thionyl chloride (8.68 g, 72.9 mmol) in toluene (50 mL) was heated at reflux for 60 min. The mixture was concentrated in vacuo, and the residue was suspended in THF (50 mL), cooled in an ice-water bath and treated with 3-bromo-2-methylaniline (20.35 g, 109 mmol). The resulting suspension was heated at reflux for 2 h. The cooled mixture was treated with 10% aqueous K$_2$CO$_3$ (50 mL), stirred vigorously for 15 min, and extracted with EtOAc. The organic phase was dried and concentrated. The residue was purified by column chromatography on silica gel to give 2-amino-N-(3-bromo-2-methylphenyl) benzamide as a light yellow solid (4.70 g, 42% yield). Mass spectrum m/z 305, 307 (M+H)$^+$. $^1$H NMR (400 MHz, chloroform-d) δ 7.72 (d, J=7.9 Hz, 1H), 7.67 (br. s., 1H), 7.54 (dd, J=8.3, 1.2 Hz, 1H), 7.48 (dd, J=7.9, 0.9 Hz, 1H), 7.36-7.31 (m, 1H), 7.15 (t, J=8.0 Hz, 1H), 6.81-6.73 (m, 2H), 5.59 (br. s., 2H), 2.45 (s, 3H).

Method 2. A suspension of 1H-benzo[d][1,3]oxazine-2,4-dione (5.00 g, 30.7 mmol) and 3-bromo-2-methylaniline (5.70 g, 30.7 mmol) in xylenes (50 mL) was heated at reflux for 8 h. The solvent was removed by distillation and the residue was purified by column chromatography on silica gel (120 g), eluting with EtOAc-hexanes (gradient from 0-50%), to give 2-amino-N-(3-bromo-2-methylphenyl)benzamide as an off-white solid (2.30 g, 24% yield).

Method 3. A suspension of 1H-benzo[d][1,3]oxazine-2,4-dione (10.00 g, 61.3 mmol) in DMF (150 mL) was treated with 3-bromo-2-methylaniline (13.69 g, 73.6 mmol) and heated to reflux overnight. The cooled mixture was diluted with water and extracted with EtOAc. The whole mixture was filtered to remove grey solids and the layers of the filtrate were separated. The organic phase was washed with water, dried and concentrated. The residue was purified by column chromatography on silica gel (330 g), eluting with EtOAc-hexanes (gradient from 0-50%), to give 2-amino-N-(3-bromo-2-methylphenyl)benzamide as tan solid (1.1 g, 6% yield). A second eluent from the column gave 3-(3-bromo-2-methylphenyl)quinazoline-2,4(1H,3H)-dione [Intermediate 4B] as a tan solid (3.4 g, 17% yield).

Intermediate 4B: 3-(3-Bromo-2-methylphenyl)quinazoline-2,4(1H,3H)-dione

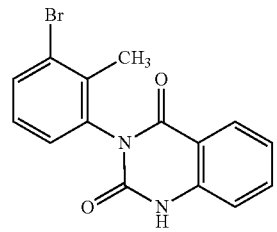

(I-4B)

A solution of 2-amino-N-(3-bromo-2-methylphenyl)benzamide (2.00 g, 6.55 mmol) in THF (50 mL) was treated with bis(trichloromethyl)carbonate[triphosgene] (2.92 g, 9.83 mmol) and heated at reflux for 60 min. The cooled mixture was treated with saturated aqueous NaHCO$_3$, extracted with EtOAc, and the combined organic phases were washed twice with saturated NaHCO$_3$, then with water, dried and concentrated. The residue was triturated with DCM to give a white solid which was collected by filtration. The residue from concentration of the filtrate was triturated with DCM to give additional white solid which was collected by filtration. The two solids were combined to give 3-(3-bromo-2-methylphenyl)quinazoline-2,4(1H,3H)-dione as a white solid (2.10 g, 97% yield). Mass spectrum m/z 331, 333 (M+H)$^+$. $^1$H NMR (400 MHz, MeOH-d$_4$) δ 8.07 (dd, J=7.92, 1.32 Hz, 1H), 7.65-7.75 (m, 2H), 7.21-7.32 (m, 4H), 2.20 (s, 3H). $^1$H NMR (400 MHz, chloroform-d) δ 9.38 (br. s., 1H), 8.19 (dd, J=7.9, 1.1 Hz, 1H), 7.76-7.69 (m, 1H), 7.69-7.60 (m, 1H), 7.35-7.17 (m, 3H), 7.04-6.97 (m, 1H), 2.28 (s, 3H).

Intermediate 4C: 3-(3-Bromo-2-methylphenyl)-1-methylquinazoline-2,4(1H,3H)-dione

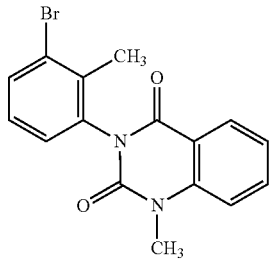

(I-4C)

A suspension of 3-(3-bromo-2-methylphenyl)quinazoline-2,4(1H,3H)-dione (23.02 g, 69.5 mmol) and $Cs_2CO_3$ (34.0 g, 104 mmol) in DMF (70 mL) cooled in an ice-water bath was treated portionwise with iodomethane (5.22 mL, 83 mmol). The mixture was warmed to room temperature and stirred for 30 min. The mixture was filtered and the filtrate was concentrated. The residue was partitioned between EtOAc and water. A precipitate which formed was collected by filtration. The collected solid was washed with water and dried overnight under vacuum to give a white solid. The organic phase of the filtrate was separated, washed 3 times with 10% aqueous LiCl, then was washed twice with water, dried and concentrated to give additional solid. The two solids were combined to give 3-(3-bromo-2-methylphenyl)-1-methylquinazoline-2,4(1H,3H)-dione as a white solid (15.56 g, 92% yield). Mass spectrum m/z 345, 347 $(M+H)^+$.

Intermediate 4:

A mixture of 3-(3-bromo-2-methylphenyl)-1-methylquinazoline-2,4(1H,3H)-dione (36.39 g, 105 mmol), 4,4,4',4',5,5,5',5'-octamethyl-2,2'-bi(1,3,2-dioxaborolane) (40.2 g, 158 mmol), $PdCl_2$(dppf) DCM adduct (4.30 g, 5.27 mmol) and potassium acetate (31.0 g, 316 mmol) in dioxane (500 mL) and DMSO (50 mL) was heated at reflux for 24 h. Additional $PdCl_2$(dppf) DCM adduct (1.47 g) was added and the mixture was heated at reflux for 6 h more. The cooled mixture was filtered through CELITE® and the filtrate was concentrated. The residue was diluted with EtOAc, shaken with water, and both phases were filtered through CELITE® to remove a black precipitate. The organic phase of the filtrate was separated, washed sequentially with water and brine, dried and concentrated. The residue was purified by column chromatography on silica gel (two 330 g columns), eluting with EtOAc-hexanes (gradient from 20-100%). The resulting solid was triturated with EtOAc to give a solid which was collected by filtration. The filtrate was concentrated and crystallized from EtOAc to give additional solid. The mother liquor from this crystallization was concentrated and the residue was purified by column chromatography on silica gel (330 g), eluting with EtOAc-hexanes (gradient from 20-50%), to give additional solid. The three solids were combined to give 1-methyl-3-(2-methyl-3-(4,4,5,5-tetramethyl-1,3,2-dioxaborolan-2-yl)phenyl)quinazoline-2,4(1H,3H)-dione as a white solid (21.2 g, 51% yield). Mass spectrum m/z 393 $(M+H)^+$. $^1$H NMR (400 MHz) δ 8.35 (d, J=7.9 Hz, 1H), 7.64 (ddd, J=8.5, 7.3, 1.5 Hz, 1H), 7.59 (dd, J=7.4, 1.4 Hz, 1H), 7.33-7.27 (m, 1H), 7.24-7.17 (m, 1H), 7.12 (d, J=8.1 Hz, 2H), 3.55 (s, 3H), 1.59 (s, 3H), 1.39 (s, 12H).

Intermediate 5

8-Chloro-1-methyl-3-(2-methyl-3-(4,4,5,5-tetramethyl-1,3,2-dioxaborolan-2-yl)phenyl)quinazoline-2,4(1H,3H)-dione

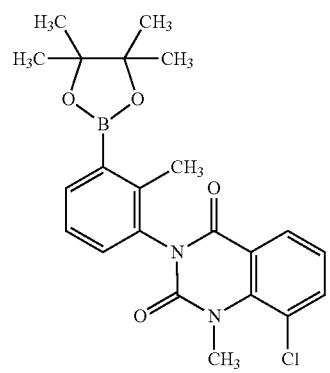

(I-5)

Intermediate 5A: 2-Amino-N-(3-bromo-2-methylphenyl)-3-chlorobenzamide

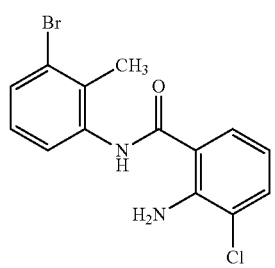

(I-5A)

A suspension of 8-chloro-1H-benzo[d][1,3]oxazine-2,4-dione (4.00 g, 20.3 mmol) and 3-bromo-2-methylaniline (5.65 g, 30.4 mmol) in xylene (20 mL) was heated at reflux for 2.5 h. The cooled mixture formed a yellow precipitate. The mixture was diluted with hexanes, and the precipitate was collected by filtration, washed with hexanes and dried to give 2-amino-N-(3-bromo-2-methylphenyl)-3-chlorobenzamide as a yellow solid (6.28 g, 91% yield). Mass spectrum m/z 339, 341 $(M+H)^+$. $^1$H NMR (400 MHz, chloroform-d) δ 7.68 (d, J=8.1 Hz, 1H), 7.61 (br. s., 1H), 7.52-7.43 (m, 3H), 7.15 (t, J=8.0 Hz, 1H), 6.70 (t, J=7.8 Hz, 1H), 6.12 (br. s., 2H), 2.44 (s, 3H).

Intermediate 5B: 3-(3-Bromo-2-methylphenyl)-8-chloroquinazoline-2,4(1H,3H)-dione

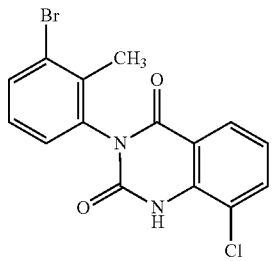

(I-5B)

A solution of 2-amino-N-(3-bromo-2-methylphenyl)-3-chlorobenzamide (780 mg, 2.30 mmol) in THF (20 mL) was treated with bis(trichloromethyl) carbonate (1.02 g, 3.45 mmol) and the solution stirred at room temperature for 21 h. The mixture was diluted with DCM and washed sequentially with saturated aqueous NaHCO$_3$, water and brine. The organic phase was dried and concentrated. The residue was purified by column chromatography on silica gel (80 g), eluting with EtOAc-hexanes (gradient from 25-50%), to give 3-(3-bromo-2-methylphenyl)-8-chloroquinazoline-2,4(1H,3H)-dione as a white solid (800 mg, 95% yield). Mass spectrum m/z 365, 367 (M+H)$^+$.

Intermediate 5C: 3-(3-Bromo-2-methylphenyl)-8-chloro-1-methylquinazoline-2,4(1H,3H)-dione

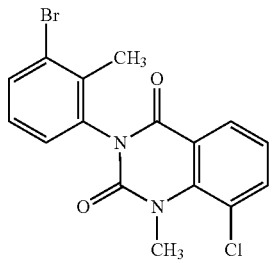

(I-5C)

A solution of 3-(3-bromo-2-methylphenyl)-8-chloroquinazoline-2,4(1H,3H)-dione (1.45 g, 3.97 mmol) in DMF (15 mL) was treated with Cs$_2$CO$_3$ (3.88 g, 11.9 mmol) and iodomethane (2.48 mL, 39.7 mmol) and stirred at room temperature for 1.5 h. The mixture was diluted with water and a mixture of EtOAc and hexanes. The organic phase was washed with water, dried and concentrated. The residue was purified by column chromatography on silica gel (80 g), eluting with EtOAc-hexanes (gradient from 5-40%), to give 3-(3-bromo-2-methylphenyl)-8-chloro-1-methylquinazoline-2,4(1H,3H)-dione as a white solid (1.3 g, 81% yield). Mass spectrum m/z 379, 391 (M+H)$^+$.

Intermediate 5:

A solution of 3-(3-bromo-2-methylphenyl)-8-chloro-1-methylquinazoline-2,4(1H,3H)-dione (1.14 g, 3.00 mmol) in dioxane (20 mL) was treated with 4,4,4',4',5,5,5',5'-octamethyl-2,2'-bi(1,3,2-dioxaborolane) (0.915 g, 3.60 mmol), potassium acetate (0.884 g, 9.01 mmol), and PdCl$_2$(dppf) DCM adduct (0.123 g, 0.150 mmol). The mixture was sealed in a pressure reaction vial and heated at 110° C. for 4 h. The cooled mixture was diluted with EtOAc, filtered through CELITE®, and the filtrate was washed with water, dried and concentrated. The residue was purified by column chromatography on silica gel (80 g), eluting with EtOAc-hexanes (gradient from 20-50%), to give 8-chloro-1-methyl-3-(2-methyl-3-(4,4,5,5-tetramethyl-1,3,2-dioxaborolan-2-yl)phenyl)quinazoline-2,4(1H,3H)-dione as a white solid (1.00 g, 78% yield). Mass spectrum m/z 427 (M+H)$^+$. $^1$H NMR (400 MHz, chloroform-d) δ 8.23 (dd, J=7.8, 1.7 Hz, 1H), 7.93 (dd, J=7.5, 1.3 Hz, 1H), 7.76 (dd, J=7.9, 1.5 Hz, 1H), 7.37-7.31 (m, 1H), 7.27-7.20 (m, 2H), 3.94 (s, 3H), 2.36 (s, 3H), 1.36 (s, 15H).

Intermediates 6 and 7

8-Chloro-1-methyl-3-(S)-(2-methyl-3-(4,4,5,5-tetramethyl-1,3,2-dioxaborolan-2-yl)phenyl)quinazoline-2,4(1H,3H)-dione (I-6), and 8-Chloro-1-methyl-3-(R)-(2-methyl-3-(4,4,5,5-tetramethyl-1,3,2-dioxaborolan-2-yl)phenyl)quinazoline-2,4(1H,3H)-dione (I-7)

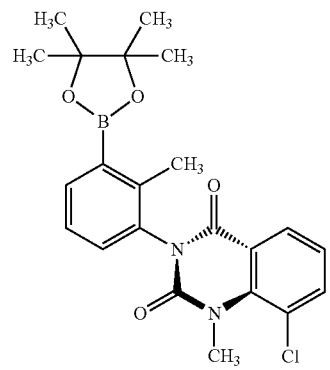

(I-6)

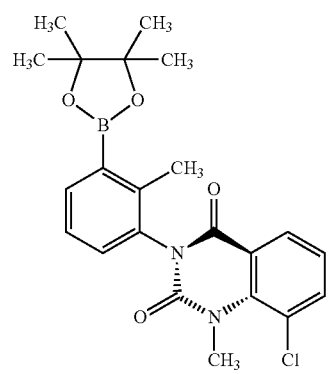

(I-7)

A sample of racemic 8-chloro-1-methyl-3-(2-methyl-3-(4,4,5,5-tetramethyl-1,3,2-dioxaborolan-2-yl)phenyl)quinazoline-2,4(1H,3H)-dione [Intermediate 5] was separated by chiral super-critical fluid chromatography as follows: column: Regis WHELK-O® R,R (3×25 cm, 5 μm); Mobile Phase: CO$_2$-MeOH (60:40) at 85 mL/min; sample preparation: 17 mg/mL in MeOH-MeCN (1:1). The first peak eluting from the column provided the S enantiomer, 8-chloro-1-methyl-3-(S)-(2-methyl-3-(4,4,5,5-tetramethyl-1,3,2-dioxaborolan-2-yl)phenyl)quinazoline-2,4(1H,3H)-dione [Intermediate 6]. The second peak eluting from the column gave the R enantiomer, 8-chloro-1-methyl-3-(R)-(2-methyl-3-(4,4,5,5-tetramethyl-1,3,2-dioxaborolan-2-yl)phenyl)quinazoline-2,4(1H,3H)-dione [Intermediate 7]. The mass spectrum and ¹H NMR for each enantiomeric atropisomer were the same as those for Intermediate 5.

Intermediate 8

8-Chloro-3-(2-methyl-3-(4,4,5,5-tetramethyl-1,3,2-dioxaborolan-2-yl)phenyl)quinazoline-2,4(1H,3H)-dione

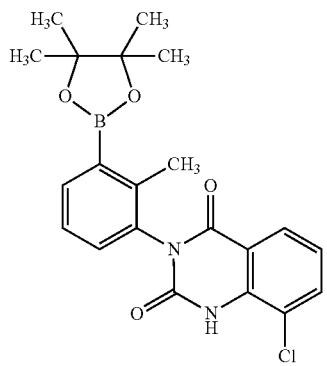

(I-8)

A mixture of 3-(3-bromo-2-methylphenyl)-8-chloroquinazoline-2,4(1H,3H)-dione [Intermediate 5B] (1.00 g, 2.74 mmol), 4,4,4',4',5,5,5',5'-octamethyl-2,2'-bi(1,3,2-dioxaborolane) (0.833 g, 3.28 mmol), potassium acetate (0.805 g, 8.21 mmol) and PdCl₂(dppf) DCM adduct (0.112 g, 0.137 mmol) in dioxane (20 mL) was heated at 90° C. for 8 h. The cooled mixture was filtered, concentrated, and the residue was partitioned between DCM and water. The organic phase was dried and concentrated, and the residue was purified by column chromatography on silica gel (120 g), eluting with EtOAc-DCM (gradient from 0-10%), to give 8-chloro-3-(2-methyl-3-(4,4,5,5-tetramethyl-1,3,2-dioxaborolan-2-yl)phenyl)quinazoline-2,4(1H,3H)-dione (782 mg, 58% yield). Mass spectrum m/z 413 (M+H)⁺.

Intermediate 9

1,8-Dimethyl-3-(2-methyl-3-(4,4,5,5-tetramethyl-1,3,2-dioxaborolan-2-yl)phenyl)quinazoline-2,4(1H,3H)-dione

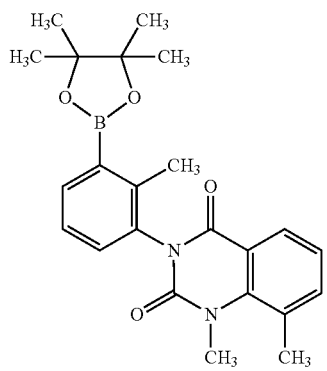

(I-9)

Intermediate 9A: 2-Amino-N-(3-bromo-2-methylphenyl)-3-methylbenzamide

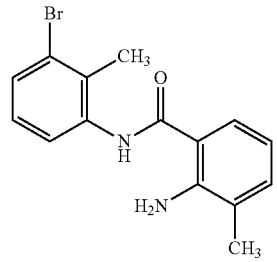

(I-9A)

A mixture of thionyl chloride (3.15 g, 26.5 mmol) and 2-amino-3-methylbenzoic acid (2.00 g, 13.23 mmol) in THF (50 mL) was heated at reflux for 2 h. The cooled mixture was concentrated and the residue was combined with 3-bromo-2-methylaniline (4.92 g, 26.5 mmol) in THF (50 mL) and heated at reflux for 5 h. The mixture was cooled to room temperature, treated with 10% aqueous K₂CO₃ and stirred at room temperature for 30 min. The resulting mixture was extracted 3 times with DCM, and the combined organic phases were washed with water, dried and concentrated. The residue was purified by column chromatography on silica gel (330 g), eluting with EtOAc-hexanes (gradient from 0-20%), to give 2-amino-N-(3-bromo-2-methylphenyl)-3-methylbenzamide as a yellow solid (1.71 g, 40% yield). Mass spectrum m/z 319, 321 (M+H)⁺. ¹H NMR (400 MHz, chloroform-d) δ 7.70 (d, J=7.9 Hz, 1H), 7.64 (br. s., 1H), 7.50-7.40 (m, 2H), 7.24 (d, J=7.3 Hz, 1H), 7.14 (t, J=8.0 Hz, 1H), 6.70 (t, J=7.6 Hz, 1H), 5.67 (br. s., 2H), 2.44 (s, 3H), 2.23 (s, 3H).

Intermediate 9B: 3-(3-Bromo-2-methylphenyl)-8-methylquinazoline-2,4(1H,3H)-dione

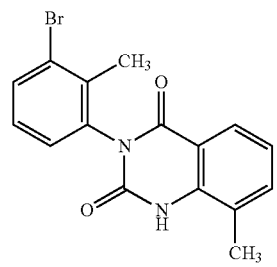

(I-9B)

A solution of 2-amino-N-(3-bromo-2-methylphenyl)-3-methylbenzamide (1.71 g, 5.36 mmol) and triphosgene (2.07 g, 6.96 mmol) in THF (20 mL) was heated at reflux for 1 h. The mixture was cooled on an ice-water bath and treated with saturated aqueous NaHCO₃. Stirring was continued until gas evolution ceased. The resulting mixture was extracted 3 times with DCM. The combined organic phases were washed with water, dried and concentrated. The residue was triturated with ether to give a white solid, collected by filtration. A second trituration of the concentrated filtrate gave additional solid, collected by filtration. The filtrate from this was concentrated and purified by column chromatography on silica gel (40 g), eluting with EtOAc-hexanes (gradient from 0-100%), to provide additional solid. The three solids were combined to provide 3-(3-bromo-2-methylphenyl)-8-methylquinazoline-2,4(1H,3H)-dione as a white solid (1.69 g, 91% yield). Mass spectrum m/z 345, 347 (M+H)+. 1H NMR (400 MHz, chloroform-d): δ 8.07 (d, J=7.9 Hz, 1H), 7.70 (dd, J=7.9, 1.3 Hz, 1H), 7.54 (d, J=7.3 Hz, 1H), 7.27-7.17 (m, 3H), 2.41 (s, 3H), 2.28 (s, 3H).

Intermediate 9C: 3-(3-Bromo-2-methylphenyl)-1,8-dimethylquinazoline-2,4(1H,3H)-dione

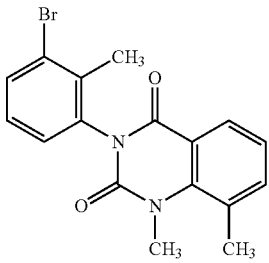

(I-9C)

A mixture of 3-(3-bromo-2-methylphenyl)-8-methylquinazoline-2,4(1H,3H)-dione (470 mg, 1.36 mmol) and Cs2CO3 (1.33 g, 4.08 mmol) in DMF (8 mL) was treated with iodomethane (0.85 mL, 13.6 mmol) and stirred at room temperature for 1.5 h. The mixture was diluted with EtOAc, washed sequentially with water and two portions of 10% aqueous LiCl. The combined aqueous phases were extracted with EtOAc. The combined organic phases were washed sequentially with 10% aqueous LiCl and water, dried and concentrated to give impure 3-(3-bromo-2-methylphenyl)-1,8-dimethylquinazoline-2,4(1H,3H)-dione as a white solid (510 mg), used without further purification. Mass spectrum m/z 359, 361 (M+H)+.

Intermediate 9:

Using the same procedure described for the preparation of Intermediate 2, 3-(3-bromo-2-methylphenyl)-1,8-dimethylquinazoline-2,4(1H,3H)-dione (489 mg, 1.36 mmol) was converted to 1,8-dimethyl-3-(2-methyl-3-(4,4,5,5-tetramethyl-1,3,2-dioxaborolan-2-yl)phenyl)quinazoline-2,4(1H,3H)-dione as a white solid (410 mg, 74% yield). Mass spectrum m/z 407 (M+H)+.

Intermediates 10 and 11

8-Fluoro-1-methyl-3-(S)-(2-methyl-3-(4,4,5,5-tetramethyl-1,3,2-dioxaborolan-2-yl) phenyl)quinazoline-2,4(1H,3H)-dione (I-10), and 8-Fluoro-1-methyl-3-(R)-(2-methyl-3-(4,4,5,5-tetramethyl-1,3,2-dioxaborolan-2-yl)phenyl)quinazoline-2,4(1H,3H)-dione (I-11)

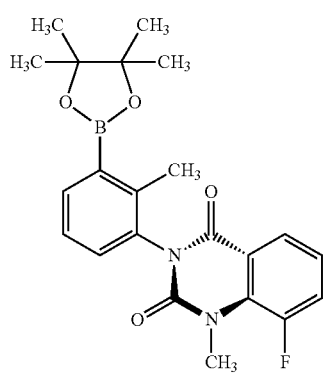

(I-10)

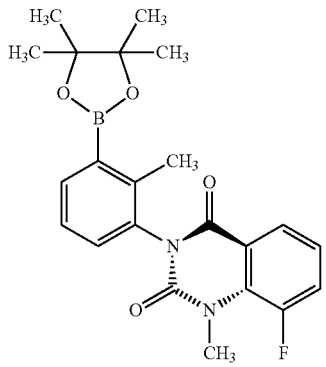

(I-11)

A sample of racemic 8-fluoro-1-methyl-3-(2-methyl-3-(4,4,5,5-tetramethyl-1,3,2-dioxaborolan-2-yl)phenyl)quinazoline-2,4(1H,3H)-dione [Intermediate 2] was separated by chiral super-critical fluid chromatography as follows: column: (R,R)-WHELK-O® 1 (3×25 cm, 5 μm); Mobile Phase: CO2-MeOH (70:30) at 200 mL/min, 100 bar, 30° C.; sample preparation: 97.3 mg/mL in MeOH:DCM (1:1); injection; 4 mL. The first peak eluting from the column provided the (S) isomer, 8-fluoro-1-methyl-3-(S)-(2-methyl-3-(4,4,5,5-tetramethyl-1,3,2-dioxaborolan-2-yl)phenyl)quinazoline-2,4 (1H,3H)-dione [Intermediate 10] as a white solid. Mass spectrum m/z 411 (M+H)+. 1H NMR (400 MHz, chloroform-d) δ 8.14-8.08 (m, 1H), 7.93 (dd, J=7.5, 1.3 Hz, 1H), 7.48 (ddd, J=14.0, 8.0, 1.5 Hz, 1H), 7.34 (t, J=7.6 Hz, 1H), 7.27-7.20 (m, 2H), 3.88 (d, J=7.9 Hz, 3H), 2.36 (s, 3H), 1.36 (s, 12H).

The second peak eluting from the column provided the (R) isomer, 8-fluoro-1-methyl-3-(R)-(2-methyl-3-(4,4,5,5-tetramethyl-1,3,2-dioxaborolan-2-yl)phenyl) quinazoline-2,4(1H,3H)-dione [Intermediate 11] as a white solid. Mass spectrum m/z 411 (M+H)+. 1H NMR (400 MHz, chloroform-d) δ 8.13-8.08 (m, 1H), 7.93 (dd, J=7.5, 1.3 Hz, 1H), 7.48 (ddd, J=13.9, 8.1, 1.5 Hz, 1H), 7.37-7.31 (m, 1H), 7.27-7.20 (m, 2H), 3.88 (d, J=7.9 Hz, 3H), 2.36 (s, 3H), 1.36 (s, 12H).

Alternative Preparation of Intermediate 10:

A solution of 8-fluoro-3-(2-methyl-3-(S)-(4,4,5,5-tetramethyl-1,3,2-dioxaborolan-2-yl)phenyl)quinazoline-2,4(1H, 3H)-dione [Intermediate 19] (40 g, 101 mmol) in tetrahydrofuran (400 mL) was treated with cesium carbonate (99 g, 303 mmol) and iodomethane (12.6 mL, 202 mmol). The resulting cloudy solution was stirred at room temperature overnight. Water (300 mL) was added and the reaction mixture was extracted with EtOAc (3×150 mL). The combined organic phases were washed sequentially with brine and water, and dried and concentrated. The residue was purified by recrystallization from EtOAc to provide 8-fluoro-1-methyl-3-(S)-(2-methyl-3-(4,4,5,5-tetramethyl-1,3,2-dioxaborolan-2-yl)phenyl)quinazoline-2,4(1H,3H)-dione as a white solid (38 g, 92% yield).

Intermediate 12

3-(3-Bromo-2-methylphenyl)-8-methoxy-1-methyl quinazoline-2,4(1H,3H)-dione

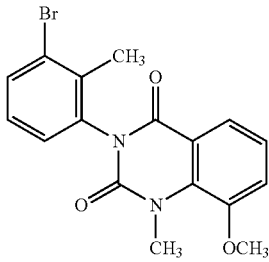

(I-12)

Intermediate 12A: 2-Amino-N-(3-bromo-2-methylphenyl)-3-methoxybenzamide

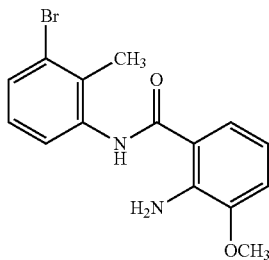

(I-12A)

A mixture of 3-bromo-2-methylaniline (482 mg, 2.59 mmol) and 8-methoxy-1H-benzo[d][1,3]oxazine-2,4-dione (500 mg, 2.59 mmol) in toluene (20 mL) was treated with 2 M trimethylaluminum in toluene (3.24 mL, 6.47 mmol) at 0° C. The mixture was stirred at room temperature for 10 minutes, then was heated at 70° C. overnight. The mixture was cooled to room temperature, treated with 1 N aqueous HCl and extracted 3 times with EtOAc. The combined organic phases were washed sequentially with saturated aqueous NaHCO₃ and water, dried and concentrated. The residue was subjected to column chromatography on silica gel (40 g), eluting with EtOAc-hexanes (gradient from 0-100%), to provide 2-amino-N-(3-bromo-2-methylphenyl)-3-methoxybenzamide as a white solid (302 mg, 35% yield). Mass spectrum m/z 335, 337 (M+H)⁺. ¹H NMR (400 MHz, chloroform-d) δ 7.72 (d, J=7.3 Hz, 2H), 7.46 (dd, J=8.0, 0.8 Hz, 1H), 7.17-7.10 (m, 2H), 6.90 (dd, J=7.9, 0.9 Hz, 1H), 6.72-6.66 (m, 1H), 5.88 (br. s., 2H), 3.92 (s, 3H), 2.43 (s, 3H).

Intermediate 12B: 3-(3-Bromo-2-methylphenyl)-8-methoxyquinazoline-2,4(1H,3H)-dione

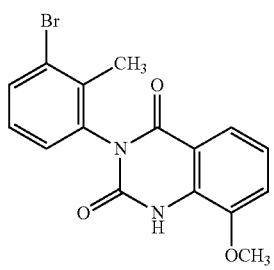

(I-12B)

A solution of 2-amino-N-(3-bromo-2-methylphenyl)-3-methoxybenzamide (302 mg, 0.901 mmol) and triphosgene (321 mg, 1.081 mmol) in THF (20 mL) was stirred at room temperature for 2 h. The mixture was treated carefully with saturated aqueous NaHCO₃ and stirred until gas evolution ceased. The mixture was extracted twice with DCM, and the combined organic phases were washed with water, dried and concentrated to provide 3-(3-bromo-2-methylphenyl)-8-methoxyquinazoline-2,4(1H,3H)-dione (339 mg) which was used without further purification. Mass spectrum m/z 361, 363 (M+H)⁺.

Intermediate 12C: 3-(3-Bromo-2-methylphenyl)-8-methoxy-1-methylquinazoline-2,4(1H,3H)-dione

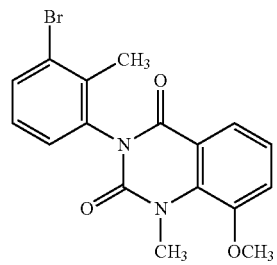

(I-12C)

A mixture of 3-(3-bromo-2-methylphenyl)-8-methoxyquinazoline-2,4(1H,3H)-dione (535 mg, 1.48 mmol), iodomethane (0.185 mL, 2.96 mmol) and Cs₂CO₃ (965 mg, 2.96 mmol) in THF (20 mL) was stirred at room temperature overnight. The mixture was filtered and concentrated. The residue was dissolved in DCM, washed sequentially with saturated aqueous NaHCO₃ and water, dried and concentrated. The residue was purified by column chromatography on silica gel (40 g silica), eluting with EtOAc-hexanes (gradient from 0-100%), to give 3-(3-bromo-2-methylphenyl)-8-methoxy-1-methylquinazoline-2,4(1H,3H)-dione (442 mg). Mass spectrum m/z 375, 377 (M+H)⁺. ¹H NMR (400 MHz, chloroform-d) δ 7.90 (dd, J=7.2, 2.3 Hz, 1H), 7.66 (dd, J=8.0, 1.2 Hz, 1H), 7.31-7.22 (m, 2H), 7.22-7.19 (m, 1H), 7.17-7.13 (m, 1H), 3.97 (s, 3H), 3.89 (s, 3H), 2.23 (s, 3H).

Intermediate 12:

A mixture of 3-(3-bromo-2-methylphenyl)-8-methoxy-1-methylquinazoline-2,4(1H,3H)-dione (380 mg, 1.01 mmol), 4,4,4',4',5,5,5',5'-octamethyl-2,2'-bi(1,3,2-dioxaborolane) (309 mg, 1.22 mmol), potassium acetate (298 mg, 3.04 mmol) and PdCl₂(dppf) DCM adduct (41.4 mg, 0.051 mmol) in dioxane (20 mL) was heated at 90° C. overnight. The cooled mixture was filtered and the filtrate was concentrated. The residue was purified by column chromatography on silica gel (24 g), eluting with EtOAc-hexanes (gradient from 20-55%), to give 8-methoxy-1-methyl-3-(2-methyl-3-(4,4,5,5-tetramethyl-1,3,2-dioxaborolan-2-yl)phenyl)quinazoline-2,4(1H,3H)-dione in 75% purity, used without further purification (486 mg, 85% yield). Mass spectrum m/z 423 (M+H)⁺.

Intermediate 13

3-(3-Bromo-2-methylphenyl)-6-fluoro-1-methylquinazoline-2,4(1H,3H)-dione

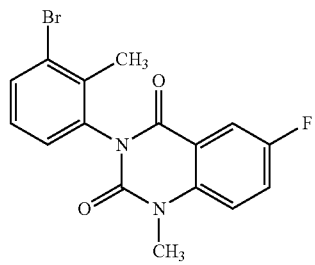

(I-13)

Intermediate 13A: 2-Amino-N-(3-bromo-2-methylphenyl)-5-fluorobenzamide

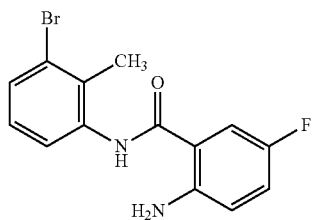

(I-13A)

A mixture of 3-bromo-2-methylaniline (1.50 g, 8.06 mmol) and 6-fluoro-1H-benzo[d][1,3]oxazine-2,4-dione (1.46 g, 8.06 mmol) in toluene (40 mL) was cooled on an ice-water bath and treated portionwise with 2 M trimethylaluminum in toluene (10.1 mL, 20.2 mmol). The mixture was stirred at room temperature for 30 min, then was heated at 70° C. overnight. The mixture was cooled to 0° C., carefully treated with 1 M aqueous HCl, and extracted 3 times with EtOAc. The combined organic phases were washed sequentially with saturated aqueous $NaHCO_3$ and water, dried and concentrated. The residue was subjected to column chromatography on silica gel (120 g), eluting with EtOAc-hexanes (gradient from 5-40%), to provide 2-amino-N-(3-bromo-2-methylphenyl)-5-fluorobenzamide (0.893 g, 87% purity, 30% yield). Mass spectrum m/z 323, 325 (M+H)+. $^1$H NMR (400 MHz, MeOH-$d_4$) δ 7.54 (1H, dd, J=8.03, 0.99 Hz), 7.48 (1H, dd, J=9.68, 3.08 Hz), 7.33 (1H, d, J=7.26 Hz), 7.16 (1H, t, J=7.92 Hz), 7.04-7.12 (1H, m), 6.83 (1H, dd, J=9.02, 4.62 Hz), 2.39 (3H, s).

Intermediate 13B: 3-(3-Bromo-2-methylphenyl)-6-fluoroquinazoline-2,4(1H,3H)-dione

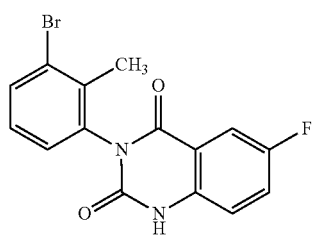

(I-13B)

A solution of 2-amino-N-(3-bromo-2-methylphenyl)-5-fluorobenzamide (0.893 g, 2.76 mmol) and triphosgene (0.984 g, 3.32 mmol) in THF (30 mL) was stirred at room temperature for 2 h. The mixture was carefully treated with saturated aqueous $NaHCO_3$ and stirred until gas evolution ceased. The mixture was extracted twice with DCM. The combined organic phases were washed with water, dried and concentrated. The residue was triturated with DCM to give a white solid, isolated by filtration. The filtrate was concentrated and subjected to column chromatography on silica gel (40 g), eluting with EtOAc-hexanes (gradient from 0-80%), to provide additional solid. The two solids were combined to provide 3-(3-bromo-2-methylphenyl)-6-fluoroquinazoline-2,4(1H,3H)-dione as a white solid (845 mg, 87% yield). Mass spectrum m/z 349, 351 (M+H)+.

Intermediate 13C: 3-(3-Bromo-2-methylphenyl)-6-fluoro-1-methylquinazoline-2,4(1H,3H)-dione

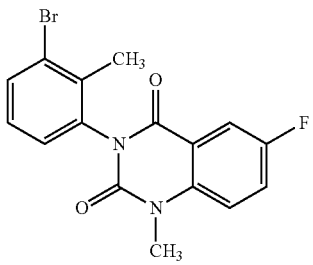

(I-13C)

A mixture of 3-(3-bromo-2-methylphenyl)-6-fluoroquinazoline-2,4(1H,3H)-dione (742 mg, 2.13 mmol), iodomethane (0.159 mL, 2.55 mmol) and $Cs_2CO_3$ (1.039 g, 3.19 mmol) in THF (20 mL) was stirred at room temperature overnight. The mixture was filtered and concentrated. The residue was dissolved in DCM and washed sequentially with saturated aqueous $NaHCO_3$ and water, dried and concentrated to provide 3-(3-bromo-2-methylphenyl)-6-fluoro-1-methylquinazoline-2,4(1H,3H)-dione (742 mg, 96% yield). Mass spectrum m/z 363, 365 (M+H)+.

Intermediate 13:

A mixture of 3-(3-bromo-2-methylphenyl)-6-fluoro-1-methylquinazoline-2,4(1H,3H)-dione (742 mg, 2.04 mmol), 4,4,4',4',5,5,5',5'-octamethyl-2,2'-bi(1,3,2-dioxaborolane) (623 mg, 2.45 mmol), potassium acetate (602 mg, 6.13 mmol) and $PdCl_2$(dppf) DCM adduct (83 mg, 0.102 mmol) in dioxane (20 mL) was heated at 90° C. overnight. The cooled mixture was filtered and the filtrate was concentrated. The residue was purified by column chromatography on silica gel (120 g), eluting with EtOAc-hexanes (gradient from 0-40%), to give 6-fluoro-1-methyl-3-(2-methyl-3-(4,4,5,5-tetramethyl-1,3,2-dioxaborolan-2-yl)phenyl)quinazoline-2,4(1H,3H)-dione (866 mg), used without further purification. Mass spectrum m/z 411 (M+H)+.

Intermediate 14

7-Methoxy-1-methyl-3-(2-methyl-3-(4,4,5,5-tetramethyl-1,3,2-dioxaborolan-2-yl) phenyl)quinazoline-2,4(1H,3H)-dione

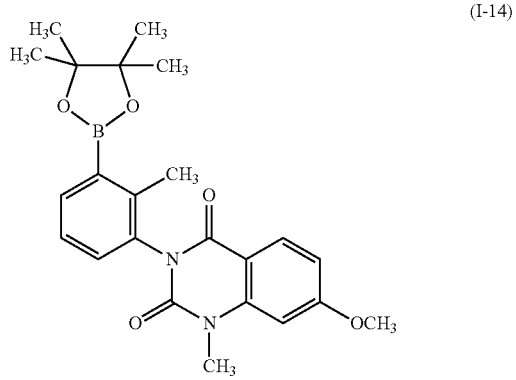 [SMILES: COc1ccc2c(=O)n(-c3cccc(B4OC(C)(C)C(C)(C)O4)c3C)c(=O)n(C)c2c1]
(I-14)

Intermediate 14A: 2-Amino-N-(3-bromo-2-methylphenyl)-4-methoxybenzamide

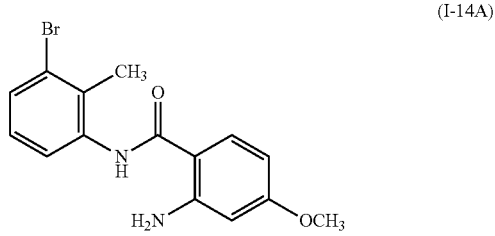 [SMILES: COc1ccc(C(=O)Nc2cccc(Br)c2C)c(N)c1]
(I-14A)

A mixture of 3-bromo-2-methylaniline (482 mg, 2.59 mmol) 7-methoxy-1H-benzo[d][1,3]oxazine-2,4-dione (500 mg, 2.59 mmol) in toluene (20 mL) was treated with 2 M trimethylaluminum in toluene (3.24 mL, 6.48 mmol) at 0° C. The mixture was stirred at room temperature for 10 min, then heated at 70° C. overnight. The cooled mixture was treated with 1 M aqueous HCl, extracted 3 times with EtOAc, and the combined organic phases were washed sequentially with saturated aqueous NaHCO$_3$ and water, dried and concentrated. The residue was purified by column chromatography on silica gel (40 g), eluting with EtOAc-hexanes (gradient from 0-100%), to give a 4:1 mixture of 2-amino-N-(3-bromo-2-methylphenyl)-4-methoxybenzamide and 3-(3-bromo-2-methylphenyl)-7-methoxyquinazoline-2,4(1H,3H)-dione (592 mg). Mass spectrum m/z 335, 337 (M+H)$^+$.

Intermediate 14B: 3-(3-Bromo-2-methylphenyl)-7-methoxyquinazoline-2,4(1H,3H)-dione

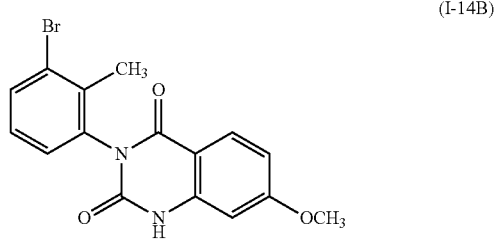 [SMILES: COc1ccc2c(=O)n(-c3cccc(Br)c3C)c(=O)[nH]c2c1]
(I-14B)

A solution of 2-amino-N-(3-bromo-2-methylphenyl)-4-methoxybenzamide (596 mg, 1.78 mmol) and triphosgene (633 mg, 2.13 mmol) in THF (30 mL) was stirred at room temperature for 2 h. The mixture was treated with saturated aqueous NaHCO$_3$ and stirred until gas evolution ceased. The resulting mixture was extracted twice with DCM, and the combined organic phases were washed with water, dried and concentrated. The residue was purified by column chromatography on silica gel (40 g), eluting with EtOAc-hexanes (gradient from 0-100%), to give 3-(3-bromo-2-methylphenyl)-7-methoxyquinazoline-2,4(1H,3H)-dione as a white solid (440 mg, 68% yield). Mass spectrum m/z 361, 363 (M+H)$^+$.

Intermediate 14C: 3-(3-Bromo-2-methylphenyl)-7-methoxy-1-methylquinazoline-2,4(1H,3H)-dione

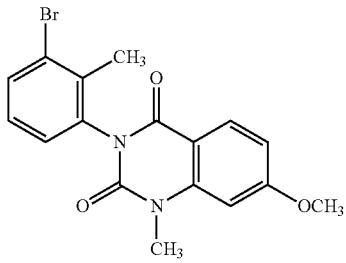
(I-14C)

A solution of 3-(3-bromo-2-methylphenyl)-7-methoxyquinazoline-2,4(1H,3H)-dione (440 mg, 1.22 mmol) in THF (30 mL) was treated with iodomethane (303 mg, 2.13 mmol) and Cs$_2$CO$_3$ (869 mg, 2.67 mmol) at room temperature. The mixture was stirred at room temperature overnight, then was filtered and concentrated. The residue was dissolved in DCM and washed sequentially with saturated aqueous NaHCO$_3$ and water, dried and concentrated to give 3-(3-bromo-2-methylphenyl)-7-methoxy-1-methylquinazoline-2,4(1H,3H)-dione (502 mg), used without further purification. Mass spectrum m/z 375, 377 (M+H)$^+$. $^1$H NMR (400 MHz, chloroform-d) δ 8.21 (d, J=8.8 Hz, 1H), 7.67 (dd, J=7.9, 1.3 Hz, 1H), 7.24-7.18 (m, 1H), 7.17-7.13 (m, 1H), 6.88 (dd, J=8.8, 2.2 Hz, 1H), 6.72 (d, J=2.2 Hz, 1H), 3.99 (s, 3H), 3.64 (s, 3H), 2.24 (s, 3H).

Intermediate 14:

A mixture of 3-(3-bromo-2-methylphenyl)-7-methoxy-1-methylquinazoline-2,4(1H,3H)-dione (390 mg, 1.04 mmol), 4,4,4',4',5,5,5',5'-octamethyl-2,2'-bi(1,3,2-dioxaborolane) (317 mg, 1.25 mmol), potassium acetate (306 mg, 3.12 mmol) and PdCl$_2$(dppf) DCM adduct (42.4 mg, 0.052 mmol) in dioxane (20 mL) was heated at 90° C. overnight. The cooled mixture was filtered and concentrated. The residue was purified by column chromatography on silica gel (40 g), eluting with EtOAc-hexanes (gradient from 10-55%), to give 7-methoxy-1-methyl-3-(2-methyl-3-(4,4,5,5-tetramethyl-1,3,2-dioxaborolan-2-yl)phenyl)quinazoline-2,4(1H,3H)-dione (504 mg, 76% purity, 87% yield), used without further purification. Mass spectrum m/z 423 (M+H)$^+$.

Intermediate 15

7-Fluoro-1-methyl-3-(2-methyl-3-(4,4,5,5-tetramethyl-1,3,2-dioxaborolan-2-yl) phenyl)quinazoline-2,4(1H,3H)-dione

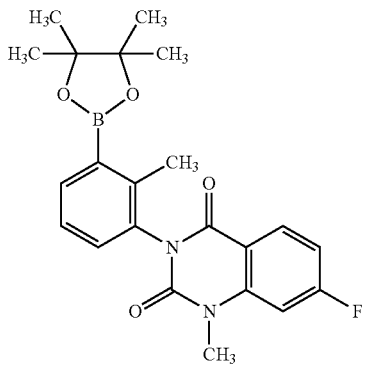
(I-15)

Intermediate 15A: 2-Amino-N-(3-bromo-2-methylphenyl)-4-fluorobenzamide

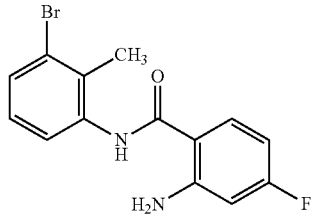
(I-15A)

A mixture of 7-fluoro-1H-benzo[d][1,3]oxazine-2,4-dione (5.00 g, 27.6 mmol) and 3-bromo-2-methylaniline (5.14 g, 27.6 mmol) in xylene (50 mL) was heated at reflux for 8 h. The cooled mixture was filtered. The collected solid was washed with 3 times with DCM and the combined filtrates were concentrated. The residue was purified by column chromatography on silica gel (330 g), eluting with EtOAc-hexanes (gradient from 0-45%), to give 2-amino-N-(3-bromo-2-methylphenyl)-4-fluorobenzamide (3.65 g, 41% yield). Mass spectrum m/z 323, 325 (M+H)$^+$. $^1$H NMR (400 MHz, chloroform-d) δ 7.65 (1H, d, J=8.14 Hz), 7.45-7.57 (3H, m), 7.14 (1H, t, J=8.03 Hz), 6.39-6.50 (2H, m), 5.80 (2H, br. s.), 2.43 (3H, s).

Intermediate 15B: 3-(3-Bromo-2-methylphenyl)-7-fluoroquinazoline-2,4(1H,3H)-dione

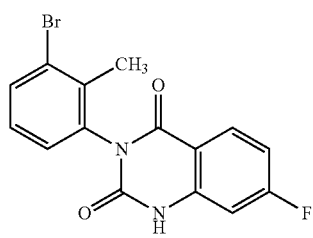
(I-15B)

A solution of 2-amino-N-(3-bromo-2-methylphenyl)-4-fluorobenzamide (3.65 g, 11.3 mmol) in THF (50 mL) was treated with triphosgene (3.69 g, 12.4 mmol) at room temperature. The solution was stirred at room temperature for 2 h, then was treated slowly with saturated aqueous NaHCO$_3$ and stirred until no more gas evolution was observed. The resulting mixture was extracted twice with EtOAc. The combined organic phases were washed twice with water, then with brine, dried and concentrated to give 3-(3-bromo-2-methylphenyl)-7-fluoroquinazoline-2,4(1H,3H)-dione (4.20 g), used without further purification. Mass spectrum m/z 349, 351 (M+H)$^+$.

Intermediate 15C: 3-(3-Bromo-2-methylphenyl)-7-fluoro-1-methylquinazoline-2,4(1H,3H)-dione

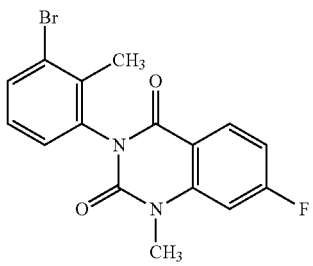
(I-15C)

A mixture of 3-(3-bromo-2-methylphenyl)-7-fluoroquinazoline-2,4(1H,3H)-dione (2.70 g, 7.73 mmol), iodomethane (0.580 mL, 9.28 mmol) and Cs$_2$CO$_3$ (3.78 g, 11.6 mmol) in THF (20 mL) was stirred at room temperature for 3 h. The mixture was filtered and the filtrate was diluted with DCM and washed with water. The aqueous phase was extracted with DCM, and the combined organic phases were dried and concentrated to give 3-(3-bromo-2-methylphenyl)-7-fluoro-1-methylquinazoline-2,4(1H,3H)-dione (2.85 g), used without further purification. Mass spectrum m/z 363, 365 (M+H)$^+$, 385, 387 (M+Na)$^+$.

Intermediate 15:

A mixture of 3-(3-bromo-2-methylphenyl)-7-fluoro-1-methylquinazoline-2,4(1H,3H)-dione (2.81 g, 7.74 mmol), 4,4,4',4',5,5,5',5'-octamethyl-2,2'-bi(1,3,2-dioxaborolane) (2.36 g, 9.28 mmol), potassium acetate (1.52 g, 15.5 mmol) and PdCl$_2$(dppf) DCM adduct (0.190 g, 0.232 mmol) in dioxane (20 mL) was heated at 90° C. for 8 h. Additional PdCl$_2$(dppf) DCM adduct (0.190 g, 0.232 mmol) and potassium acetate (0.80 g) were added and the mixture was heated at 90° C. for another 7 h. The cooled mixture was diluted with EtOAc and washed sequentially with saturated aqueous NaHCO$_3$ and water. The combined aqueous phases were extracted with EtOAc. The combined organic phases were filtered through CELITE® and concentrated. The residue was purified by column chromatography on silica gel (220 g), eluting with EtOAc-hexanes (gradient from 0-40%), to give 7-fluoro-1-methyl-3-(2-methyl-3-(4,4,5,5-tetramethyl-1,3,2-dioxaborolan-2-yl)phenyl)quinazoline-2,4(1H,3H)-dione (1.76 g, 56% yield). Mass spectrum m/z 411 (M+H)$^+$.

Intermediate 16

6,8-Difluoro-3-(2-methyl-3-(4,4,5,5-tetramethyl-1,3,2-dioxaborolan-2-yl) phenyl)quinazoline-2,4(1H,3H)-dione

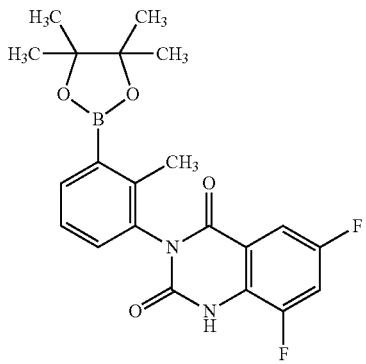

(I-16)

Intermediate 16A: N-(3-Bromo-2-methylphenyl)-3,5-difluoro-2-nitrobenzamide

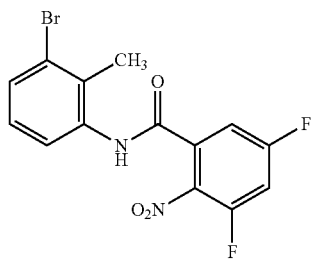

(I-16A)

A solution of 3,5-difluoro-2-nitrobenzoic acid (522 mg, 2.57 mmol) in DCM (10 mL) was treated with oxalyl chloride (0.337 mL, 3.86 mmol), then with DMF (3 drops). The resulting solution was stirred at room temperature for 60 min. The mixture was concentrated and the residue was re-concentrated twice from dry DCM. The residue was dissolved in DCM (10 mL) and treated dropwise with 3-bromo-2-methylaniline (478 mg, 2.57 mmol), followed by dropwise addition of TEA (0.537 mL, 3.86 mmol). The resulting mixture was stirred at room temperature overnight. The mixture was treated with saturated aqueous NaHCO$_3$, forming a white precipitate. The organic phase was separated, and the aqueous phase and the white solid were extracted twice with DCM, then filtered. The collected solid was washed with water and dried. The combined organic phases were dried and concentrated, and the residue was triturated with DCM to give additional solid. Both solids were combined with DCM and MeOH and concentrated to give N-(3-bromo-2-methylphenyl)-3,5-difluoro-2-nitrobenzamide (821 mg, 86% yield). Mass spectrum m/z 371, 373 (M+H)$^+$ 393, 395 (M+Na)$^+$. $^1$H NMR (400 MHz, DMSO-d$_6$) δ 10.65 (s, 1H), 7.98-7.90 (m, 1H), 7.81 (d, J=8.1 Hz, 1H), 7.55 (d, J=7.9 Hz, 1H), 7.40 (d, J=7.7 Hz, 1H), 7.21 (t, J=7.9 Hz, 1H), 2.32 (s, 3H).

Intermediate 16B: 2-Amino-N-(3-bromo-2-methylphenyl)-3,5-difluorobenzamide

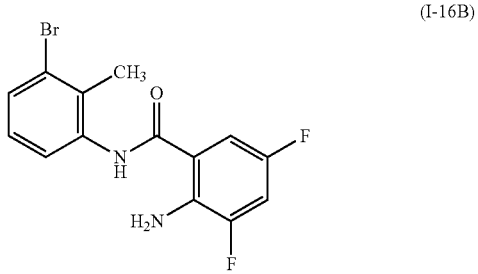 [SMILES: Cc1c(Br)cccc1NC(=O)c1cc(F)cc(F)c1N]

(I-16B)

A mixture of N-(3-bromo-2-methylphenyl)-3,5-difluoro-2-nitrobenzamide (821 mg, 2.21 mmol), NH$_4$Cl (1.18 g, 22.1 mmol) and zinc (1.45 g, 22.1 mmol) in MeOH (10 mL) was stirred at room temperature for 60 min. The mixture was filtered and the filtrate was concentrated. The residue was suspended in DCM and washed with saturated aqueous NaHCO$_3$. The organic phase, with an insoluble precipitate, was separated from the aqueous phase and concentrated to give 2-amino-N-(3-bromo-2-methylphenyl)-3,5-difluorobenzamide (760 mg), used without further purification. Mass spectrum m/z 341, 343 (M+H)$^+$, 363, 365 (M+Na)$^+$.

Intermediate 16C: 3-(3-Bromo-2-methylphenyl)-6,8-difluoroquinazoline-2,4(1H,3H)-dione

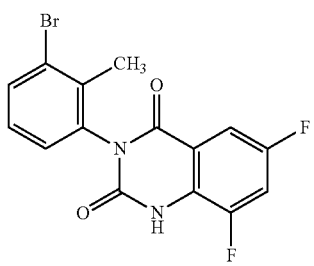

(I-16C)

A solution of 2-amino-N-(3-bromo-2-methylphenyl)-3,5-difluorobenzamide (760 mg, 2.23 mmol) in THF (10 mL) was treated portionwise with triphosgene (722 mg, 2.43 mmol). The solution was stirred at room temperature for 60 min, then was treated dropwise with saturated aqueous NaHCO$_3$ and stirred until no more gas evolution was observed. The organic phase was separated, washed with water, dried and concentrated. The residue was purified by column chromatography on silica gel (40 g), eluting with EtOAc-hexanes (gradient from 0-100%), to give 3-(3-bromo-2-methylphenyl)-6,8-difluoroquinazoline-2,4(1H,3H)-dione (820 mg), used without further purification. Mass spectrum m/z 367, 369 (M+H)⁺, 389, 391 (M+Na)⁺.

Intermediate 16:

A mixture of 3-(3-bromo-2-methylphenyl)-6,8-difluoroquinazoline-2,4(1H,3H)-dione (1.43 g, 3.89 mmol), 4,4,4',4',5,5,5',5'-octamethyl-2,2'-bi(1,3,2-dioxaborolane) (1.29 g, 5.06 mmol), potassium acetate (0.956 g, 9.74 mmol) and PdCl$_2$(dppf) DCM adduct (0.159 g, 0.195 mmol) in dioxane (20 mL) was heated at 100° C. for 5 h. The cooled mixture was filtered and the filtrate was concentrated. The residue was purified by column chromatography on silica gel (40 g+12 g stacked columns), eluting with EtOAc-hexanes (gradient from 0-100%), to give 6,8-difluoro-3-(2-methyl-3-(4,4,5,5-tetramethyl-1,3,2-dioxaborolan-2-yl)phenyl)quinazoline-2,4(1H,3H)-dione (1.20 g, 74% yield). Mass spectrum m/z 415 (M+H)⁺.

Intermediate 17

8-Fluoro-3-(RS)-(2-methyl-3-(4,4,5,5-tetramethyl-1,3,2-dioxaborolan-2-yl) phenyl)quinazoline-2,4(1H,3H)-dione

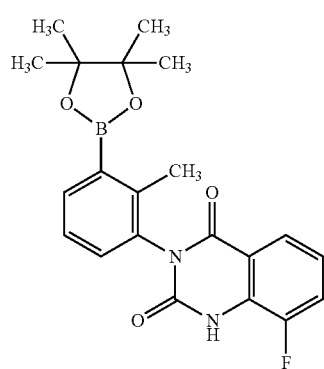

(I-17)

A stirred mixture of 3-(3-bromo-2-methylphenyl)-8-fluoroquinazoline-2,4(1H,3H)-dione [Intermediate 1] (0.349 g, 1.00 mmol), 4,4,4',4',5,5,5',5'-octamethyl-2,2'-bi(1,3,2-dioxaborolane) (0.305 g, 1.20 mmol), PdCl$_2$(dppf) DCM adduct (0.041 g, 0.050 mmol) and potassium acetate (0.245 g, 2.50 mmol) in dioxane (20 mL) and DMSO (4 mL) was bubbled with nitrogen for 5 min, then heated at 90° C. overnight. The cooled mixture was partitioned between EtOAc and water. The organic phase was washed sequentially with saturated aqueous NaHCO$_3$, water and brine, and dried and concentrated. The residue was purified by column chromatography on silica gel, eluting with EtOAc-hexanes (20:80) to give 8-fluoro-3-(RS)-(2-methyl-3-(4,4,5,5-tetramethyl-1,3,2-dioxaborolan-2-yl)phenyl)quinazoline-2,4(1H,3H)-dione as a white solid (0.326 g, 82% yield). Mass spectrum m/z 397 (M+H)⁺. ¹H NMR (500 MHz, DMSO-d$_6$) δ 11.78 (s, 1H), 7.80 (d, J=7.2 Hz, 1H), 7.72 (dd, J=7.4, 1.5 Hz, 1H), 7.71-7.56 (m, 1H), 7.45-7.35 (m, 1H), 7.35-7.29 (m, 1H), 7.29-7.16 (m, 1H), 2.22 (s, 3H), 1.33 (s, 12H).

Intermediates 18 and 19

8-Fluoro-3-(R)-(2-methyl-3-(4,4,5,5-tetramethyl-1,3,2-dioxaborolan-2-yl) phenyl)quinazoline-2,4(1H,3H)-dione (18), and 8-Fluoro-3-(S)-(2-methyl-3-(4,4,5,5-tetramethyl-1,3,2-dioxaborolan-2-yl)phenyl)quinazoline-2,4(1H,3H)-dione (19)

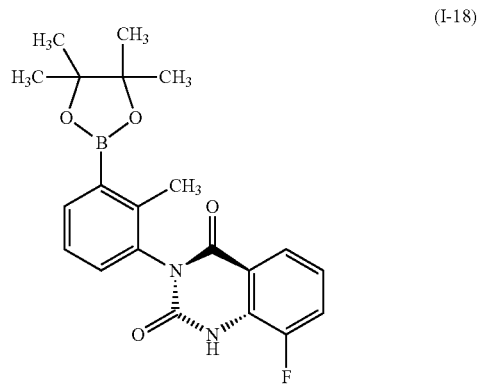

(I-18)

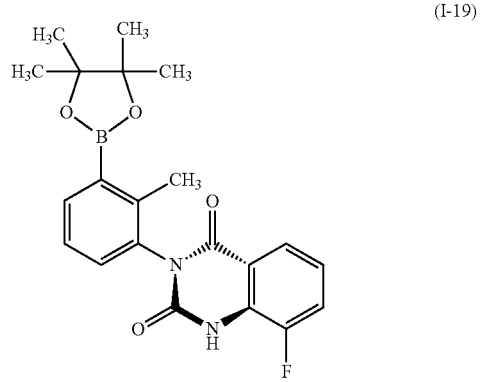

(I-19)

A sample of 8-fluoro-3-(RS)-(2-methyl-3-(4,4,5,5-tetramethyl-1,3,2-dioxaborolan-2-yl)phenyl)quinazoline-2,4(1H,3H)-dione [Intermediate 17] was separated by supercritical fluid chromatography as follows: column: CHIRALCEL® OD-H (5×25 cm, 5 μm); Mobile Phase: CO$_2$-MeOH (70:30) at 300 mL/min, 100 bar, 40° C.; sample preparation: 103 mg/mL in DCM-MeOH (44:56); injection: 5.0 mL. The first peak eluting from the column provided the R enantiomer, 8-fluoro-3-(R)-(2-methyl-3-(4,4,5,5-tetramethyl-1,3,2-dioxaborolan-2-yl)phenyl)quinazoline-2,4(1H,3H)-dione [Intermediate 18] as a white solid. The second peak eluting from the column provided the S enantiomer, 8-fluoro-3-(S)-(2-methyl-3-(4,4,5,5-tetramethyl-1,3,2-dioxaborolan-2-yl)phenyl)quinazoline-2,4(1H,3H)-dione [Intermediate 19] as a white solid. The mass spectrum and ¹H NMR for each enantiomeric atropisomer were the same as those for Intermediate 17.

Intermediate 20

8-Fluoro-1-methyl(d₃)-3-(RS)-(2-methyl-3-(4,4,5,5-tetramethyl-1,3,2-dioxaborolan-2-yl) phenyl)quinazoline-2,4(1H,3H)-dione

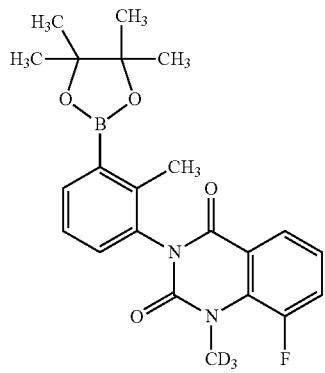

(I-20)

Intermediate 20A: 3-(3-Bromo-2-methylphenyl)-8-fluoro-1-methyl(d₃)quinazoline-2,4(1H,3H)-dione

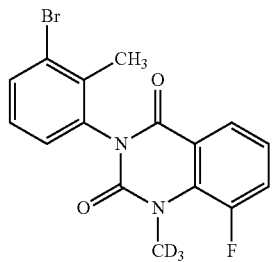

(I-20A)

A mixture of 3-(3-bromo-2-methylphenyl)-8-fluoroquinazoline-2,4(1H,3H)-dione [Intermediate 1] (3.00 g, 8.59 mmol) and Cs₂CO₃ (5.60 g, 17.2 mmol) in DMF (45 mL) was treated with iodomethane-d₃ (0.80 mL, 12.9 mmol) and the mixture was stirred at room temperature for 1.75 h. The mixture was poured into rapidly-stirred water (400 mL) and stirred at room temperature, forming a suspended solid. The precipitate was collected by filtration, washed with water and dried under vacuum to provide 3-(3-bromo-2-methylphenyl)-8-fluoro-1-methyl(d₃) quinazoline-2,4(1H,3H)-dione as an off-white solid (3.05 g, 97% yield). Mass spectrum m/z 366, 368 (M+H)⁺. ¹H NMR (400 MHz, DMSO-d₆) δ 7.93 (dt, J=7.9, 0.7 Hz, 1H), 7.82-7.63 (m, 2H), 7.45-7.18 (m, 3H), 2.12 (s, 3H).

Intermediate 20:

A mixture of 3-(3-bromo-2-methylphenyl)-8-fluoro-1-methyl(d₃)quinazoline-2,4(1H,3H)-dione (3.00 g, 8.19 mmol), 4,4,4',4',5,5,5',5'-octamethyl-2,2'-bi(1,3,2-dioxaborolane) (2.70 g, 10.7 mmol) and potassium acetate (2.41 g, 24.6 mmol) in dioxane (40 mL) was bubbled with argon with sonication for ca. 2 min, then was treated with PdCl₂(dppf) DCM adduct (0.335 g, 0.410 mmol). The mixture was heated at 90° C. for 15.75 h. The cooled mixture was diluted with EtOAc, filtered through CELITE®, and the solids were rinsed with EtOAc. The combined filtrates were concentrated, and the residue was purified by column chromatography on silica gel (330 g), eluting with EtOAc-hexanes (gradient from 0-40%), to give 8-fluoro-1-methyl(d₃)-3-(RS)-(2-methyl-3-(4,4,5,5-tetramethyl-1,3,2-dioxaborolan-2-yl)phenyl)quinazoline-2,4(1H,3H)-dione as an off-white solid (3.23 g, 95% yield). Mass spectrum m/z 414 (M+H)⁺. ¹H NMR (400 MHz, chloroform-d) δ 8.14-8.07 (m, 1H), 7.93 (dd, J=7.4, 1.4 Hz, 1H), 7.48 (ddd, J=13.9, 8.1, 1.5 Hz, 1H), 7.37-7.31 (m, 1H), 7.27-7.19 (m, 2H), 2.36 (s, 3H), 1.36 (s, 12H).

Intermediates 21 and 22

8-Fluoro-1-methyl(d₃)-3-(S)-(2-methyl-3-(4,4,5,5-tetramethyl-1,3,2-dioxaborolan-2-yl) phenyl)quinazoline-2,4(1H,3H)-dione (21), and 8-Fluoro-1-methyl(d₃)-3-(R)-(2-methyl-3-(4,4,5,5-tetramethyl-1,3,2-dioxaborolan-2-yl)phenyl)quinazoline-2,4(1H,3H)-dione (22)

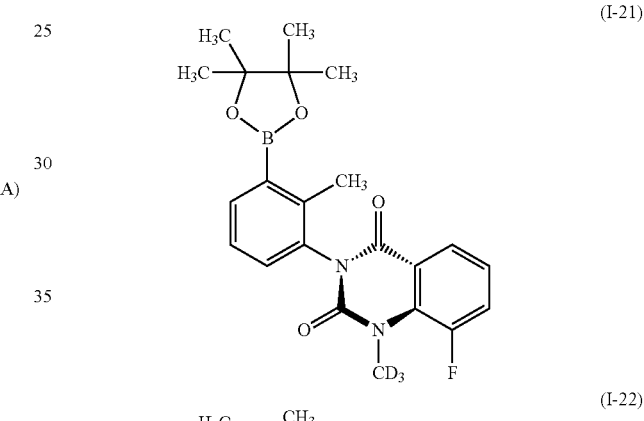

(I-21)

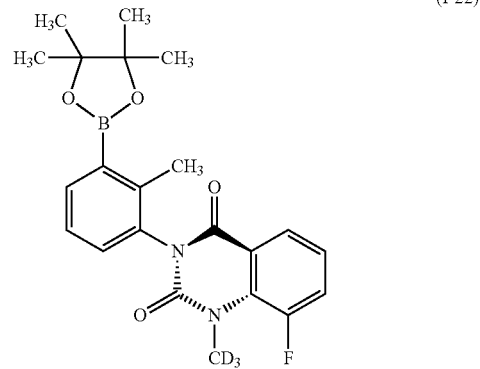

(I-22)

A sample of 8-fluoro-1-methyl(d₃)-3-(RS)-(2-methyl-3-(4,4,5,5-tetramethyl-1,3,2-dioxaborolan-2-yl)phenyl)quinazoline-2,4(1H,3H)-dione [Intermediate 20] was separated by super-critical fluid chromatography as follows: column: WHELK-O® R,R (3×25 cm, 5 μm); Mobile Phase: CO₂-MeOH (70:30) at 200 mL/min, 100 bar, 30° C.; sample preparation: 97.3 mg/mL in MeOH:DCM (1:1); injection: 4 mL. The first peak eluting from the column provided the S enantiomer, 8-fluoro-1-methyl(d₃)-3-(S)-(2-methyl-3-(4,4,5,5-tetramethyl-1,3,2-dioxaborolan-2-yl)phenyl)quinazoline-2,4(1H,3H)-dione [Intermediate 21] as a white solid. The second peak eluting from the column provided the R enantiomer, 8-fluoro-1-methyl(d₃)-3-(R)-(2-methyl-3-(4,4, 5,5-tetramethyl-1,3,2-dioxaborolan-2-yl)phenyl)quinazoline-2,4(1H,3H)-dione [Intermediate 22] as a white solid. The mass spectrum and $^1$H NMR for each enantiomeric atropisomer were the same as those for Intermediate 20.

Alternative Synthesis of 8-Fluoro-1-methyl(d$_3$)-3-(S)-(2-methyl-3-(4,4,5,5-tetramethyl-1,3,2-dioxaborolan-2-yl)phenyl)quinazoline-2,4(1H,3H)-dione [Intermediate 21]

A solution of 8-fluoro-3-(S)-(2-methyl-3-(4,4,5,5-tetramethyl-1,3,2-dioxaborolan-2-yl)phenyl)quinazoline-2,4(1H,3H)-dione [Intermediate 19] (5.42 g, 13.7 mmol) in THF (100 mL) was stirred on an ice-water bath and treated with Cs$_2$CO$_3$ (6.24 g, 19.2 mmol), then with iodomethane-d$_3$ (1.02 mL, 16.4 mmol) and the mixture was stirred at room temperature for 16.25 h. The mixture was filtered, the solid was rinsed with EtOAc, and the combined filtrates were concentrated. The residue was dissolved in EtOAc and washed sequentially with water and brine, dried and concentrated to provide 8-fluoro-1-methyl(d$_3$)-3-(S)-(2-methyl-3-(4,4,5,5-tetramethyl-1,3,2-dioxaborolan-2-yl)phenyl) quinazoline-2,4(1H,3H)-dione as a white solid (5.538 g, 98% yield). Mass spectrum m/z 414 (M+H)$^+$. $^1$H NMR (400 MHz, chloroform-d) δ 8.11 (dq, J=7.8, 0.8 Hz, 1H), 7.93 (dd, J=7.5, 1.3 Hz, 1H), 7.48 (ddd, J=13.9, 8.1, 1.5 Hz, 1H), 7.38-7.30 (m, 1H), 7.27-7.20 (m, 2H), 2.36 (s, 3H), 1.36 (s, 12H).

Intermediate 23

3-4-Bromo-3-cyano-7-(2-hydroxypropan-2-yl)-9H-carbazole-1-carboxamide

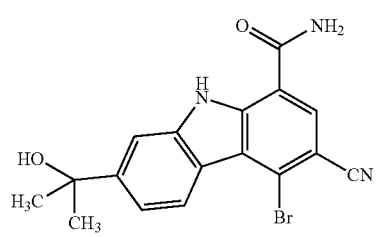

(I-23)

Intermediate 23A: 4-Bromo-7-(2-hydroxypropan-2-yl)-3-iodo-9H-carbazole-1-carboxamide

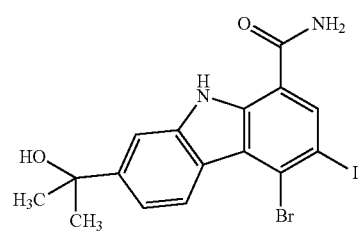

(I-23A)

A mixture of 4-bromo-7-(2-hydroxypropan-2-yl)-9H-carbazole-1-carboxamide [synthesized according to the procedure described in U.S. Pat. No. 8,084,620, Example 73-2] (2.00 g, 5.76 mmol), N-iodosuccinimide (1.69 g, 7.49 mmol), and pyridine (1.9 mL, 23.0 mmol) in DMF (20 mL) was heated at 65° C. for 2 days. The cooled mixture was diluted with EtOAc, washed twice with 10% aqueous LiCl and then with brine. The aqueous layers were extracted with EtOAc. The combined organic layers were dried and concentrated, and the residue was purified by column chromatography on silica gel, eluting with EtOAc-hexanes (gradient from 50%-65%), to provide 4-bromo-7-(2-hydroxypropan-2-yl)-3-iodo-9H-carbazole-1-carboxamide as a yellow solid (0.609 g, 23% yield). Mass spectrum m/z 473, 475 (M+H-H$_2$O)$^+$. $^1$H NMR (500 MHz, DMSO-d$_6$) δ 11.66 (s, 1H), 8.49 (d, J=8.6 Hz, 1H), 8.38 (s, 1H), 8.26 (br. s., 1H), 7.94 (d, J=1.1 Hz, 1H), 7.58 (br. s., 1H), 7.40 (dd, J=8.6, 1.4 Hz, 1H), 5.09 (s, 1H), and 1.51 (s, 6H).

Intermediate 23:

A mixture of 4-bromo-7-(2-hydroxypropan-2-yl)-3-iodo-9H-carbazole-1-carboxamide (0.609 g, 1.29 mmol) and zinc cyanide (0.076 g, 0.644 mmol) in DMF (7 mL) was subjected to three evacuate-fill cycles with nitrogen. The mixture was treated with tetrakis(triphenylphosphine)palladium (0.074 g, 0.064 mmol) and heated overnight at 95° C. The cooled mixture was diluted with EtOAc, washed twice with 10% aqueous LiCl, then with brine. The aqueous layers were extracted with EtOAc. The combined organic layers were dried and concentrated. The residue was triturated and sonicated with DCM and the precipitate was collected by filtration to give 4-bromo-3-cyano-7-(2-hydroxypropan-2-yl)-9H-carbazole-1-carboxamide as a pale yellow solid (0.400 g, 83% yield). Mass spectrum m/z 372, 374 (M+H-H$_2$O)$^+$. $^1$H NMR (500 MHz, DMSO-d$_6$) δ 12.12 (s, 1H), 8.55 (d, J=8.6 Hz, 1H), 8.38 (s, 1H), 8.31 (br. s., 1H), 8.03 (s, 1H), 7.74 (br. s., 1H), 7.49 (dd, J=8.6, 1.1 Hz, 1H), and 1.52 (s, 6H).

Intermediate 24

5-Bromo-6-fluoro-2-(2-hydroxypropan-2-yl)-2,3,4,9-tetrahydro-1H-carbazole-8-carboxamide (racemic)

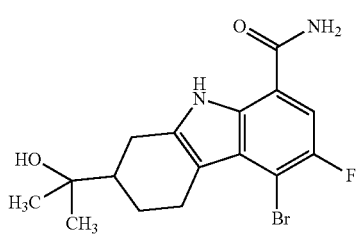

(I-24)

Intermediate 24A: 4-Bromo-2,5-difluorobenzoic acid

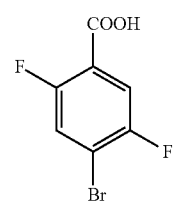

(I-24A)

A solution of 1,4-dibromo-2,5-difluorobenzene (640 mg, 2.35 mmol) in dry diethyl ether (10 mL) cooled in a dry ice-acetone bath was treated dropwise with 2.5 M n-butyllithium in hexanes (1.04 mL, 2.59 mmol). The solution was stirred at −78° C. for 30 min, then was treated with a piece of dry ice. The cooling bath was removed after 5 min and the mixture was stirred for another 30 min while warming to room temperature. The mixture was diluted with EtOAc and water. The organic phase was separated and washed twice with saturated aqueous NaHCO₃. The combined aqueous phases were acidified with 1 M aqueous HCl, extracted twice with DCM, and the combined organic phases were dried and concentrated to give 4-bromo-2,5-difluorobenzoic acid as a white solid (297 mg, 53% yield).

Intermediate 24B:
4-Bromo-5-fluoro-2-hydrazinylbenzoic acid hydrochloride

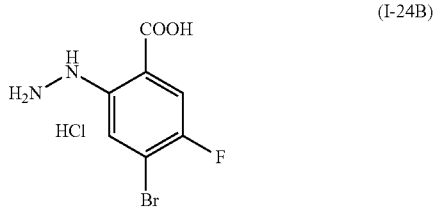 [SMILES: NNc1cc(Br)c(F)cc1C(=O)O ; Cl]

(I-24B)

A mixture of 4-bromo-2,5-difluorobenzoic acid (2.50 g, 10.6 mmol) and hydrazine (3.81 mL, 121 mmol) in N-methyl-2-pyrrolidinone (2 mL) was heated at 95° C. for 4 h. The cooled mixture was poured into vigorously stirred 6 M aqueous HCl (400 mL) which was cooled in an NaCl-ice bath. The resulting precipitate was collected by filtration, washed with 6 M aqueous HCl (200 mL) and dried under vacuum to give 4-bromo-5-fluoro-2-hydrazinylbenzoic acid hydrochloride as a yellow solid (1.88 g, 71% purity, 44% yield), used without further purification.

Alternative Synthesis of 4-Bromo-5-fluoro-2-hydrazinylbenzoic acid hydrochloride:

A suspension of 2-amino-4-bromo-5-fluorobenzoic acid (10.0 g, 42.7 mmol) in a mixture of 37% aqueous HCl (42.7 mL) and water (14.3 mL), cooled with a NaCl-ice bath, was treated dropwise with a solution of sodium nitrite (3.24 g, 47.0 mmol) in water (15.7 mL). When addition was complete, the mixture was stirred for 30 min more. A solution of tin(II) chloride dihydrate (28.9 g, 128 mmol) in 37% aqueous HCl (27.5 mL) was added dropwise. The cooling bath was removed and the mixture was stirred at room temperature for 45 min. The thick suspension was filtered and the collected precipitate was washed thoroughly with water and dried overnight under reduced pressure. The solid was triturated with MeOH with sonication, and the precipitate was collected by filtration, washed with MeOH and dried. The filtrate was concentrated, and the residue was triturated with DCM. The resulting solid was collected by filtration, dried and combined with the other solid to give 4-bromo-5-fluoro-2-hydrazinylbenzoic acid hydrochloride (5.37 g, 44% yield) as a white solid. Mass spectrum m/z 249, 251 (M+H)⁺.

Intermediate 24C: 5-Bromo-2-(ethoxycarbonyl)-6-fluoro-2,3,4,9-tetrahydro-1H-carbazole-8-carboxylic acid

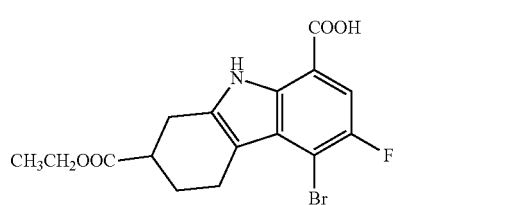

(I-24C)

A mixture of 4-bromo-5-fluoro-2-hydrazinylbenzoic acid hydrochloride (5.37 g, 18.8 mmol), ethyl 3-oxocyclohexanecarboxylate (3.52 g, 20.7 mmol) and acetic acid (3.23 mL, 56.4 mmol) in toluene (90 mL) was heated at 110° C. for 20 h. The solvent was removed under reduced pressure, and the residue was diluted with toluene (43 mL) and trifluoroacetic acid (11 mL). The mixture was stirred at 90-94° C. overnight. The cooled mixture was diluted with EtOAc, sonicated, and the precipitate was collected by filtration. The filtrate was concentrated and resuspended in EtOAc with sonication, resulting in another precipitate which was also collected by filtration and washed with EtOAc. The combined solids were triturated twice with MeOH to give a solid. The combined filtrates were concentrated and the residue was triturated with MeOH to give additional solid. The solids were combined to give 5-bromo-2-ethoxycarbonyl-6-fluoro-2,3,4,9-tetrahydro-1H-carbazole-8-carboxylic acid as a pale yellow solid (3.38 g). Mass spectrum m/z 384, 386 (M+H)⁺.

Intermediate 24D: Ethyl 5-bromo-8-carbamoyl-6-fluoro-2,3,4,9-tetrahydro-1H-carbazole-2-carboxylate

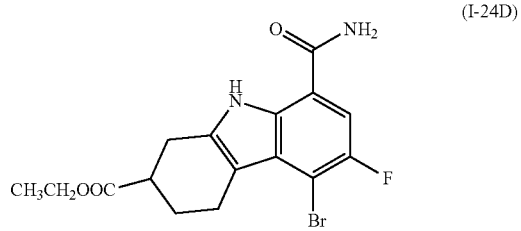

(I-24D)

A mixture of 5-bromo-2-(ethoxycarbonyl)-6-fluoro-2,3,4,9-tetrahydro-1H-carbazole-8-carboxylic acid (0.513 g, 1.34 mmol), EDC (0.384 g, 2.00 mmol), and HOBT (0.307 g, 2.00 mmol) in THF (10 mL) and DCM (1.65 mL) was stirred at room temperature for 20 min. Ammonium hydroxide (0.078 mL, 2.00 mmol) was added, and the mixture was stirred at room temperature for 60 min. The mixture was diluted with EtOAc and washed twice with saturated aqueous of NaHCO₃, then with brine. The aqueous layers were extracted with EtOAc, and the combined organic layers were dried and concentrated. The residue was triturated in MeOH with sonication to provide ethyl 5-bromo-8-carbamoyl-6-fluoro-2,3,4,9-tetrahydro-1H-carbazole-2-carboxylate as a yellow solid (0.432 g, 84% yield). Mass spectrum m/z 383, 385 (M+H)⁺.

Intermediate 24:

A solution of ethyl 5-bromo-8-carbamoyl-6-fluoro-2,3,4,9-tetrahydro-1H-carbazole-2-carboxylate (10.0 g, 26.1 mmol) in THF (200 mL) at −78° C. was treated dropwise over 30 min with 1.6 M methyllithium in ether (49 mL, 78 mmol). The mixture was stirred at −78° C. for 45 min, then was treated with additional methyllithium solution (33 mL) over 25 min. The mixture was stirred at −78° C. for an additional 90 min, then was treated with saturated aqueous $NH_4Cl$ and warmed to room temperature. The mixture was diluted with EtOAc and washed sequentially with water and brine. The aqueous layers were extracted with EtOAc. The combined organic layers were dried and concentrated. The residue was dissolved in EtOAc (about 100 mL) and filtered through a pad of CELITE® topped with a pad of silica gel, washing further with EtOAc (about 1000 mL). Concentration of the filtrate gave racemic 5-bromo-6-fluoro-2-(2-hydroxypropan-2-yl)-2,3,4,9-tetrahydro-1H-carbazole-8-carboxamide as a pale yellow solid (9.24 g, 96% yield). Mass spectrum m/z 369, 371 (M+H)⁺.

Alternative Synthesis of Intermediate 24:

To a solution of ethyl 5-bromo-8-carbamoyl-6-fluoro-2,3,4,9-tetrahydro-1H-carbazole-2-carboxylate (10.0 g, 26.1 mmol) in tetrahydrofuran (200 mL) at −78° C. was added methyllithium (1.6 M in ether) (3 equiv.; 49 mL, 78 mmol) dropwise over 30 min. The reaction mixture was stirred at −78° C. for 45 minutes. An additional 2 equivalents of methyllithium (33 mL) was added over 25 min., and the reaction mixture was stirred at −78° C. for an additional 1.5 h. The reaction was quenched at −78° C. with a saturated aqueous solution of ammonium chloride and warmed to room temperature. The mixture was diluted with ethyl acetate, washed with water, and washed with brine. The organic layer was collected, and the aqueous layers were sequentially extracted with ethyl acetate. The combined organic layers were dried over anhydrous sodium sulfate and concentrated under reduced pressure. The residue was dissolved in ~100 mL of ethyl acetate and filtered through a pad of CELITE® topped with a pad of silica gel in a 600 mL fritted funnel using ethyl acetate (~1 L). Concentration under reduced pressure afforded 5-bromo-6-fluoro-2-(2-hydroxypropan-2-yl)-2,3,4,9-tetrahydro-1H-carbazole-3-carboximide (9.24 g, 25.03 mmol, 96% yield) as a pale yellow solid.

Intermediates 25 and 26

(R)-5-Bromo-6-fluoro-2-(2-hydroxypropan-2-yl)-2,3,4,9-tetrahydro-1H-carbazole-8-carboxamide (I-25), and (S)-5-Bromo-6-fluoro-2-(2-hydroxypropan-2-yl)-2,3,4,9-tetrahydro-1H-carbazole-8-carboxamide (I-26)

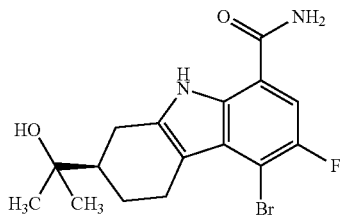

(I-25)

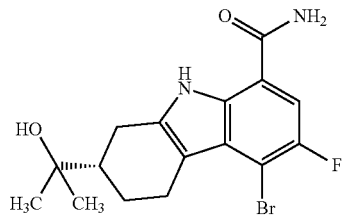

(I-26)

A sample of racemic 5-bromo-6-fluoro-2-(2-hydroxypropan-2-yl)-2,3,4,9-tetrahydro-1H-carbazole-8-carboxamide [Intermediate 24] was separated by chiral super-critical fluid chromatography as follows: column: CHIRALPAK® OD-H (3×25 cm, 5 μm); Mobile Phase: $CO_2$-MeOH (70:30) at 150 mL/min, 40° C. The first peak eluting from the column provided (R)-5-bromo-6-fluoro-2-(2-hydroxypropan-2-yl)-2,3,4,9-tetrahydro-1H-carbazole-8-carboxamide [Intermediate 25]. The second peak eluting from the column provided (S)-5-bromo-6-fluoro-2-(2-hydroxypropan-2-yl)-2,3,4,9-tetrahydro-1H-carbazole-8-carboxamide [Intermediate 26]. The mass spectra and ¹H NMR spectra of the two enantiomers were the same. Mass spectrum m/z 369, 371 (M+H)⁺. ¹H NMR (500 MHz, DMSO-$d_6$) δ 10.96 (s, 1H), 8.07 (br. s., 1H), 7.55 (d, J=10.3 Hz, 1H), 7.50 (br. s., 1H), 4.24 (s, 1H), 3.26 (dd, J=15.8, 4.4 Hz, 1H), 2.93 (dd, J=17.1, 4.6 Hz, 1H), 2.72 (t, J=11.7 Hz, 1H), 2.48-2.40 (m, 1H), 2.12 (d, J=9.2 Hz, 1H), 1.70-1.62 (m, 1H), and 1.32 (qd, J=12.4, 5.3 Hz, 1H).

Alternative SFC Separation to Give Intermediate 26:

CHIRALPAK® AD-H (3×25 cm, 5 μm); Mobile Phase: $CO_2$-MeOH (55:45) at 150 mL/min, 40° C. The first peak eluting from the column provided (S)-5-bromo-6-fluoro-2-(2-hydroxypropan-2-yl)-2,3,4,9-tetrahydro-1H-carbazole-8-carboxamide [Intermediate 26]. The second peak eluting from the column provided (R)-5-bromo-6-fluoro-2-(2-hydroxypropan-2-yl)-2,3,4,9-tetrahydro-1H-carbazole-8-carboxamide [Intermediate 25].

Intermediate 27

4-Bromo-3-fluoro-7-(2-hydroxypropan-2-yl)-9H-carbazole-1-carboxamide

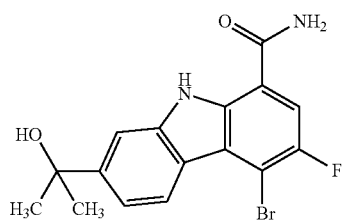

(I-27)

Intermediate 27A: 4-Bromo-7-ethoxycarbonyl-3-fluoro-9H-carbazole-1-carboxylic acid

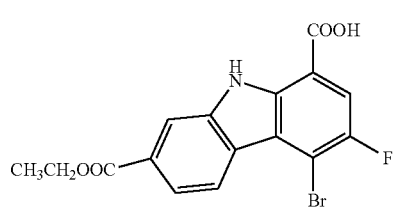

(I-27A)

A solution of 5-bromo-2-(ethoxycarbonyl)-6-fluoro-2,3,4,9-tetrahydro-1H-carbazole-8-carboxylic acid (2.87 g, 7.47 mmol) and 2,3-dichloro-5,6-dicyanobenzoquinone (3.73 g, 16.4 mmol) in THF (45 mL) was heated at 60° C. for 90 min. The cooled mixture was diluted with EtOAc (about 50 mL) and stirred for 60 min. The resulting precipitate was collected by filtration, washed with EtOAc and dried. The filtrate was concentrated, and the residue was triturated with MeOH with sonication, filtered, and the precipitate was washed with MeOH and dried. The two precipitates were combined to give 4-bromo-7-ethoxycarbonyl-3-fluoro-9H-carbazole-1-carboxylic acid as a pale yellow solid (2.39 g, 84% yield). Mass spectrum m/z 380, 382 (M+H)+.

Intermediate 26B: Ethyl 5-bromo-8-carbamoyl-6-fluoro-9H-carbazole-2-carboxylate

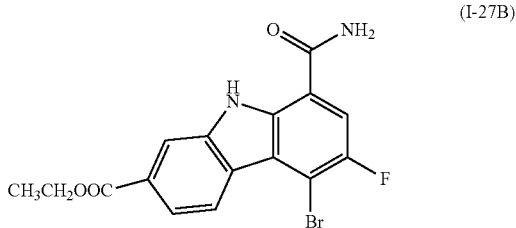

(I-27B)

A mixture of 4-bromo-7-(ethoxycarbonyl)-3-fluoro-9H-carbazole-1-carboxylic acid (2.39 g, 6.29 mmol), EDC (1.81 g, 9.43 mmol) and HOBT (1.44 g, 9.43 mmol) in THF (30 mL) and DCM (5 mL) was stirred at room temperature for 20 min. Ammonium hydroxide (0.367 mL, 9.43 mmol) was added, and the mixture was stirred at room temperature for 4 h. The mixture was diluted with EtOAc, washed twice with saturated aqueous $NaHCO_3$, then with brine. The aqueous layers were extracted with EtOAc, and the combined organic layers were dried and concentrated. The residue was triturated with MeOH with sonication to provide ethyl 5-bromo-8-carbamoyl-6-fluoro-9H-carbazole-2-carboxylate as a pale yellow solid (2.26 g, 95% yield). Mass spectrum m/z 379, 381 (M+H)+. 1H NMR (500 MHz, DMSO-$d_6$) δ 12.02 (s, 1H), 8.70 (d, J=8.3 Hz, 1H), 8.51 (d, J=1.1 Hz, 1H), 8.29 (br. s., 1H), 8.10 (d, J=10.3 Hz, 1H), 7.87 (dd, J=8.5, 1.5 Hz, 1H), 7.74 (br. s., 1H), 4.37 (q, J=6.9 Hz, 2H), and 1.37 (t, J=7.1 Hz, 3H). 1H NMR (500 MHz, MeOH-$d_4$) δ 8.77 (d, J=8.2 Hz, 1H), 8.36 (d, J=0.9 Hz, 1H), 7.83 (d, J=8.2 Hz, 1H), 7.46 (d, J=8.2 Hz, 1H), 4.12 (q, J=7.0 Hz, 2H), 1.58-1.36 (m, 4H), and 1.26 (t, J=7.2 Hz, 3H).

Alternative Synthesis of Ethyl 5-bromo-8-carbamoyl-6-fluoro-9H-carbazole-2-carboxylate:

A mixture of ethyl 5-bromo-8-carbamoyl-9H-carbazole-2-carboxylate [synthesized according to the procedure described in U.S. Pat. No. 8,084,620, Intermediate 48-1] (0.100 g, 0.277 mmol) and 1-(chloromethyl)-4-fluoro-1,4-diazoniabicyclo[2.2.2]octane bis(tetrafluoroborate) [SELECTFLUOR®] (0.100 g, 0.554 mmol) in THF (2 mL) and MeCN (2 mL) was heated at 60° C. overnight. The cooled mixture was filtered and the filtrate was concentrated. The residue was purified using reverse-phase preparative HPLC to give ethyl 5-bromo-8-carbamoyl-3-fluoro-9H-carbazole-2-carboxylate as a tan solid (0.035 g).

Intermediate 27:

A solution of ethyl 5-bromo-8-carbamoyl-6-fluoro-9H-carbazole-2-carboxylate (0.500 g, 1.32 mmol) in THF (9.0 mL) at −78° C. was treated dropwise over 10 min with 1.6 M methyllithium in ether (2.47 mL, 3.96 mmol). The mixture was stirred at −78° C. for 30 min, then was treated with additional methyllithium solution (1.65 mL, 2.64 mmol) and the mixture was stirred at −78° C. for 45 min more. The mixture was treated with saturated aqueous $NH_4Cl$ and allowed to warm to room temperature. The mixture was diluted with EtOAc and washed sequentially with water and brine. The aqueous layers were extracted with EtOAc and the combined organic layers were dried and concentrated to provide a pale yellow solid which was purified by reverse phase preparative HPLC. The appropriate fractions were neutralized with saturated aqueous $NaHCO_3$ and concentrated. The residue was partitioned between EtOAc and water, and the organic layer was washed with brine. The aqueous layers were extracted with EtOAc, and the combined organic layers were dried and concentrated to provide 4-bromo-3-fluoro-7-(2-hydroxypropan-2-yl)-9H-carbazole-1-carboxamide as a pale yellow solid (0.240 g, 50% yield). Mass spectrum m/z 347, 349 (M+H−$H_2O$)+. 1H NMR (500 MHz, DMSO-$d_6$) δ 11.58 (s, 1H), 8.50 (d, J=8.6 Hz, 1H), 8.22 (br. s., 1H), 7.96 (d, J=10.3 Hz, 1H), 7.94 (d, J=1.1 Hz, 1H), 7.65 (br. s., 1H), 7.39 (dd, J=8.5, 1.5 Hz, 1H), 5.09 (s, 1H), and 1.51 (s, 6H).

Alternative Synthesis of 4-Bromo-3-fluoro-7-(2-hydroxypropan-2-yl)-9H-carbazole-1-carboxamide:

A solution of ethyl 5-bromo-8-carbamoyl-6-fluoro-9H-carbazole-2-carboxylate (10 g, 26.4 mmol) in THF (300 mL) was cooled in an ice-water bath and treated dropwise with 3.0 M methylmagnesium chloride in THF (70.3 mL, 211 mmol). The solution was stirred at 0° C. for 18 h. The mixture was poured into 1000 mL of well-stirred saturated aqueous $NH_4Cl$ cooled in an ice-water bath. The resulting mixture was diluted with water and extracted twice with EtOAc. The combined organic phases were washed twice with water, then with brine, and dried and concentrated. The residue was purified by column chromatography on silica gel (330 g), eluting with EtOAc-DCM (gradient from 20-100%), to give 4-bromo-3-fluoro-7-(2-hydroxypropan-2-yl)-9H-carbazole-1-carboxamide (6.36 g, 65% yield).

Intermediate 28

4-Bromo-7-(2-hydroxypropan-2-yl)-3-methyl-9H-carbazole-1-carboxamide

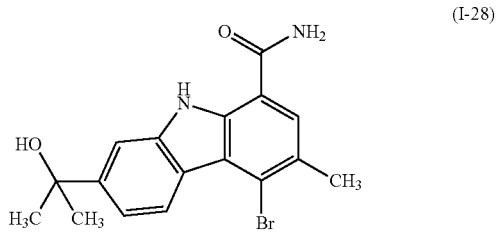 [SMILES: Cc1cc(C(N)=O)c2[nH]c3cc(C(C)(C)O)ccc3c2c1Br]

(I-28)

Intermediate 28A: 5-Bromo-2-iodo-4-methylaniline

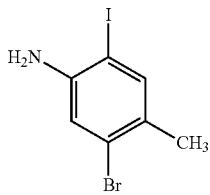

(I-28A)

A solution of 3-bromo-4-methylaniline (5.00 g, 26.9 mmol), N-iodosuccinimide (4.53 g, 20.2 mmol) and bis(pyridine)iodonium tetrafluoroborate (2.70 g, 7.26 mmol) in DCM (100 mL) was stirred at room temperature overnight. The mixture was diluted with DCM, washed sequentially with saturated aqueous NaHSO$_3$ and water, and dried and concentrated. The residue was purified by column chromatography on silica gel, eluting with EtOAc-hexanes (sequentially 1%, 2% and 3%), to provide 5-bromo-2-iodo-4-methylaniline as a yellow solid (5.27 g, 63% yield). Mass spectrum m/z 312, 314 (M+H)$^+$. $^1$H NMR (500 MHz, CDCl$_3$) δ 7.49 (d, J=0.6 Hz, 1H), 6.94 (s, 1H), 4.17-3.91 (br.s, 2H), and 2.25 (s, 3H).

Intermediate 28B: 2-Amino-4-bromo-5-methylbenzonitrile

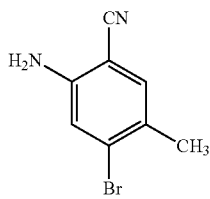

(I-28B)

A mixture of 5-bromo-2-iodo-4-methylaniline (5.25 g, 16.8 mmol) and zinc cyanide (0.988 g, 8.41 mmol) in DMF (80 mL) was subjected to three evacuate-fill cycles with nitrogen. The mixture was treated with tetrakis(triphenylphosphine)palladium (0.972 g, 0.841 mmol) and heated at 90° C. overnight. The cooled mixture was diluted with EtOAc and washed sequentially with 10% aqueous LiCl (twice) and brine. The aqueous layers were extracted with EtOAc, and the combined organic layers were dried and concentrated. The residue was purified by column chromatography on silica gel, eluting with EtOAc-hexanes (sequentially 1%, 2.5%, 5% and 50%), to give a brown solid. The residue was further purified by trituration with MeOH to give three crops of solid. The filtrate was again purified by column chromatography on silica gel, eluting with EtOAc-hexanes (5%, then 10%). The resulting solid was combined with the other crops to provide 2-amino-4-bromo-5-methylbenzonitrile as a tan solid (2.95 g, 83% yield). Mass spectrum m/z 211, 213 (M+H)$^+$.

Intermediate 28C: 2-Amino-4-bromo-5-methylbenzoic acid

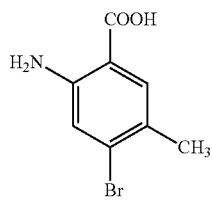

(I-28C)

A mixture of 2-amino-4-bromo-5-methylbenzonitrile (2.95 g, 14.0 mmol) in a mixture of EtOH (21 mL) and 2 M aqueous NaOH (34.9 mL, 69.9 mmol) was heated at reflux overnight. After cooling to room temperature, the ethanol was removed under reduced pressure, and the aqueous residue was diluted with water. After adjustment of the pH to about 5 with concentrated aqueous HCl, the mixture was stirred for 30 min and the precipitate was collected by filtration and washed with water. The resulting wet solid was dissolved in EtOAc, washed with brine, dried and concentrated to provide 2-amino-4-bromo-5-methylbenzoic acid as a pale yellow solid (2.92 g, 91% yield). Mass spectrum m/z 212, 214 (M+H)$^+$.

Intermediate 28D: 4-Bromo-2-hydrazinyl-5-methylbenzoic acid hydrochloride

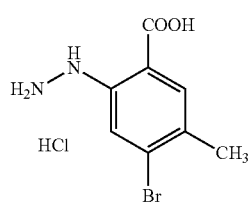

(I-28D)

A suspension of 2-amino-4-bromo-5-methylbenzoic acid (2.92 g, 12.7 mmol) in a mixture of 37% aqueous HCl (12.7 mL) and water (4.3 mL), cooled in a NaCl-ice bath, was treated slowly dropwise with a solution of sodium nitrite (0.963 g, 14.0 mmol) in water (4.5 mL). The resulting mixture was stirred for 45 min, then was treated slowly dropwise with a solution of tin(II) chloride dihydrate (8.59 g, 38.1 mmol) in 37% aqueous HCl (8.2 mL). The cooling bath was removed, and the mixture was stirred at room temperature for 60 min. The mixture was filtered, and the collected precipitate was washed with water and dried. The solid was triturated and sonicated in MeOH, and the mixture was concentrated. The residue was triturated and sonicated with DCM, and the precipitate was collected by filtration and washed with DCM to give 4-bromo-2-hydrazinyl-5-methylbenzoic acid hydrochloride as a white solid (2.17 g, 61% yield). Mass spectrum m/z 245, 247 (M+H)$^+$.

Intermediate 28E: 5-Bromo-2-(ethoxycarbonyl)-6-methyl-2,3,4,9-tetrahydro-1H-carbazole-8-carboxylic acid

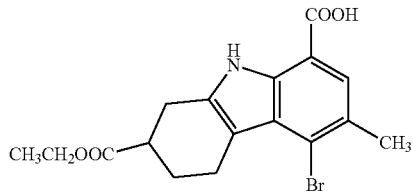

(I-28E)

A mixture of 4-bromo-2-hydrazinyl-5-methylbenzoic acid hydrochloride (2.17 g, 7.71 mmol), ethyl 3-oxocyclohexanecarboxylate (1.44 g, 8.48 mmol) and acetic acid (1.32 mL, 23.1 mmol) in toluene (40 mL) was heated in an oil bath at 117° C. for 5 h. The mixture was concentrated and dried under vacuum, and the residue was diluted with toluene (18 mL) and TFA (4.5 mL). The mixture was heated at 90° C. overnight. The cooled mixture was diluted with EtOAc, sonicated, and the precipitate was collected by filtration and washed with EtOAc to give a yellow solid. The filtrate was concentrated and the residue was suspended in EtOAc with sonication. The precipitate was collected by filtration and combined with the first precipitate. The solid was triturated with MeOH to give 5-bromo-2-(ethoxycarbonyl)-6-methyl-2,3,4,9-tetrahydro-1H-carbazole-8-carboxylic acid as a pale yellow solid (1.60 g, 55% yield). Mass spectrum m/z 380, 382 (M+H)+.

Intermediate 28F: 4-Bromo-7-(ethoxycarbonyl)-3-methyl-9H-carbazole-1-carboxylic acid

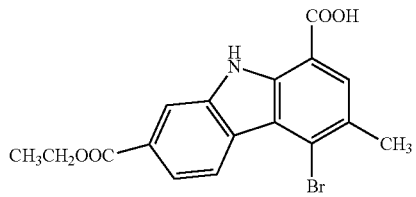

(I-28F)

A solution of 5-bromo-2-(ethoxycarbonyl)-6-methyl-2,3,4,9-tetrahydro-1H-carbazole-8-carboxylic acid (1.60 g, 4.21 mmol) and 2,3-dichloro-5,6-dicyanobenzoquinone (2.10 g, 9.26 mmol) in THF (45 mL) was heated at 60° C. for 60 min. The cooled mixture was diluted with EtOAc (about 70 mL), stirred for 15 min, and the precipitate was collected by filtration, washed with EtOAc and dried. The filtrate was concentrated, and the residue was triturated with MeOH, filtered, and the collected precipitate was washed with MeOH. The two solids were combined to give 4-bromo-7-(ethoxycarbonyl)-3-methyl-9H-carbazole-1-carboxylic acid as a pale yellow solid (1.40 g, 88% yield). Mass spectrum m/z 376, 378 (M+H)+.

Intermediate 28G: Ethyl 5-bromo-8-carbamoyl-6-methyl-9H-carbazole-2-carboxylate

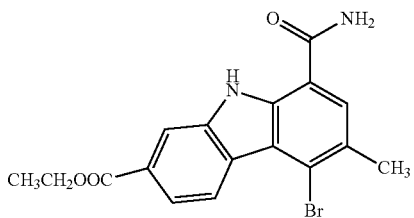

(I-28F)

A mixture of 4-bromo-7-(ethoxycarbonyl)-3-methyl-9H-carbazole-1-carboxylic acid (1.40 g, 3.72 mmol), EDC (1.070 g, 5.58 mmol), and HOBT (0.855 g, 5.58 mmol) in a mixture of THF (30 mL) and DCM (5 mL) was stirred at room temperature for 60 min. Ammonium hydroxide (0.217 mL, 5.58 mmol) was added, and the mixture was stirred at room temperature overnight. The mixture was diluted with EtOAc and washed with saturated aqueous NaHCO$_3$. Phase separation could not be achieved, so the mixture was filtered, and the collected solid was washed sequentially with water and EtOAc, triturated with MeOH and dried. The EtOAc-water filtrate was separated and the organic phase was washed with brine, dried and concentrated. The residue was triturated with MeOH, and the resulting solid was combined with the first solid to give ethyl 5-bromo-8-carbamoyl-6-methyl-9H-carbazole-2-carboxylate as an off-white solid (1.27 g, 91% yield). Mass spectrum m/z 375, 377 (M+H)+. $^1$H NMR (400 MHz, DMSO-d$_6$) δ 11.88 (s, 1H), 8.77 (d, J=8.6 Hz, 1H), 8.48 (d, J=0.9 Hz, 1H), 8.20 (br. s., 1H), 7.84 (dd, J=8.5, 1.4 Hz, 1H), 7.59 (br. s., 1H), 4.37 (q, J=7.0 Hz, 2H), 2.55 (s, 3H), and 1.37 (t, J=7.0 Hz, 3H).

Intermediate 28:

A solution of ethyl 5-bromo-8-carbamoyl-6-methyl-9H-carbazole-2-carboxylate (0.500 g, 1.33 mmol) in THF (12 mL) at −78° C. was treated dropwise over 10 min with 1.6 M methyllithium in ether (2.50 mL, 4.00 mmol). The mixture was stirred at −78° C. for 30 min, then was treated with additional methyllithium solution (1.67 mL, 2.67 mmol). After 30 min more, additional methyllithium solution (1.67 mL, 2.67 mmol) was added and stirring was continued for 45 min. The mixture was then treated with saturated aqueous NH$_4$Cl and allowed to warm to room temperature. The mixture was diluted with EtOAc and washed sequentially with water and brine. The aqueous layers were extracted with EtOAc, and the combined organic layers were dried and concentrated to provide an off-white solid. The solid was triturated and sonicated with MeOH and collected by filtration. The filtrate was purified by reverse-phase preparative HPLC. The appropriate fractions were treated with saturated aqueous NaHCO$_3$ and concentrated. The residue was partitioned between EtOAc and water. The organic phase was washed with brine, and the aqueous layers were extracted with EtOAc. The combined organic layers were dried and concentrated, and the residue was combined with the first solid to give 4-bromo-7-(2-hydroxypropan-2-yl)-3-methyl-9H-carbazole-1-carboxamide as a tan solid (0.409 g, 85% yield). Mass spectrum m/z 343, 345 (M+H-H$_2$O)+. $^1$H NMR (500 MHz, DMSO-d$_6$) δ 11.42 (s, 1H), 8.56 (d, J=8.6 Hz, 1H), 8.12 (br. s., 1H), 7.91-7.89 (m, 2H), 7.48 (br. s., 1H), 7.36 (dd, J=8.3, 1.7 Hz, 1H), 5.06 (s, 1H), 2.53 (s, 3H), and 1.51 (s, 6H).

Intermediate 29

5-Bromo-6-chloro-2-(RS)-(2-hydroxypropan-2-yl)-2,3,4,9-tetrahydro-1H-carbazole-8-carboxamide (racemic mixture)

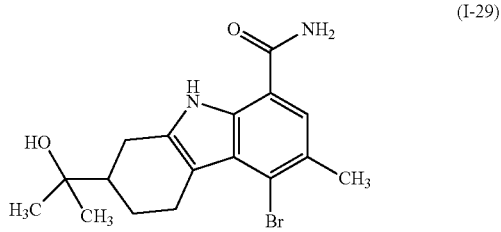 [SMILES: Cc1cc(C(N)=O)c2[nH]c3c(c2c1Br)CCC(C(C)(C)O)C3]
(I-29)

Intermediate 29A: 4-Bromo-5-chloro-2-hydrazinylbenzoic acid hydrochloride

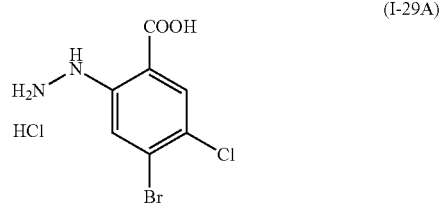 [SMILES: Cl ; NNc1cc(Br)c(Cl)cc1C(=O)O]
(I-29A)

A solution of sodium nitrite (3.03 g, 43.9 mmol) in water (14.8 mL) was added dropwise to a cooled (−10° C., NaCl-ice bath) suspension of 2-amino-4-bromo-5-chlorobenzoic acid (10.0 g, 39.9 mmol) in 37% aqueous HCl (39.9 mL) and water (13.3 mL), at such rate that the temperature did not exceed 0° C. The resulting suspension was stirred at 0° C. for 15 min, then was treated with a solution of tin(II) chloride hydrate (22.7 g, 120 mmol) in 37% aqueous HCl (17 mL). The resulting mixture was warmed to room temperature and stirred for 60 min. The precipitate was collected by filtration, washed with water and air-dried overnight to give 4-bromo-5-chloro-2-hydrazinylbenzoic acid hydrochloride as an off-white solid (12.86 g, 96% yield). Mass spectrum m/z 365, 267 (M+H)+. $^1$H NMR (400 MHz, DMSO-d$_6$) δ 9.05 (br. s., 1H), 7.95 (s, 1H), 7.55 (s, 1H).

Intermediate 29B: 5-Bromo-6-chloro-2-(ethoxycarbonyl)-2,3,4,9-tetrahydro-1H-carbazole-8-carboxylic acid

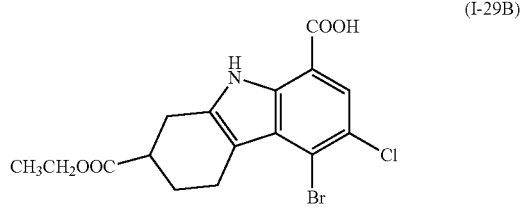
(I-29B)

A suspension of 4-bromo-5-chloro-2-hydrazinylbenzoic acid hydrochloride (12.89 g, 37.6 mmol), ethyl 3-oxocyclohexanecarboxylate (7.03 g, 41.3 mmol), and acetic acid (6.45 mL, 113 mmol) in toluene (188 mL) was heated at 105° C. overnight. After 16 h, more acetic acid (6 mL) and ethyl 3-oxocyclohexanecarboxylate (2.00 g) were added and the mixture was heated at 110° C. for 4.5 h. The mixture was concentrated, and the residue was combined with toluene (100 mL) and TFA (20 mL). The suspension was heated at 90° C. overnight. The cooled mixture was concentrated and the residue was suspended in EtOAc. The resulting solid was collected by filtration, washed with EtOAc and air-dried to give 5-bromo-6-chloro-2-(ethoxycarbonyl)-2,3,4,9-tetrahydro-1H-carbazole-8-carboxylic acid as a yellow solid (11.0 g, 73% yield). Mass spectrum m/z 400, 402 (M+H)+. $^1$H NMR (400 MHz, DMSO-d$_6$) δ 13.44 (br. s., 1H), 11.24 (s, 1H), 7.69 (s, 1H), 4.12 (qd, J=7.1, 2.3 Hz, 2H), 3.23-2.81 (m, 5H), 2.23-2.09 (m, 1H), 1.91-1.75 (m, 1H), 1.22 (t, J=7.0 Hz, 3H).

Intermediate 29C: Ethyl 5-bromo-8-carbamoyl-6-chloro-2,3,4,9-tetrahydro-1H-carbazole-2-carboxylate

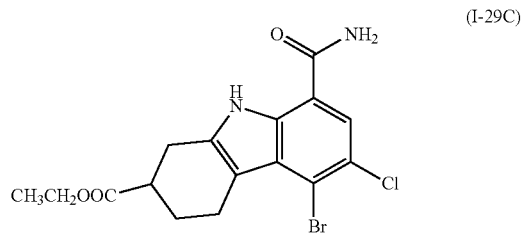
(I-29C)

Following the procedure used to prepare Intermediate 24D, 5-bromo-6-chloro-2-(ethoxycarbonyl)-2,3,4,9-tetrahydro-1H-carbazole-8-carboxylic acid was converted into ethyl 5-bromo-8-carbamoyl-6-chloro-2,3,4,9-tetrahydro-1H-carbazole-2-carboxylate as a light brown solid (8.54 g, 78% yield). Mass spectrum m/z 399, 401 (M+H)+. $^1$H NMR (400 MHz, DMSO-d$_6$) δ 13.44 (br. s., 1H), 11.24 (s, 1H), 7.69 (s, 1H), 4.12 (qd, J=7.1, 2.3 Hz, 2H), 3.23-2.81 (m, 5H), 2.23-2.09 (m, 1H), 1.91-1.75 (m, 1H), 1.22 (t, J=7.0 Hz, 3H).

Intermediate 29:

A solution of ethyl 5-bromo-8-carbamoyl-6-chloro-2,3,4,9-tetrahydro-1H-carbazole-2-carboxylate (7.03 g, 17.6 mmol) in THF (200 mL) was cooled in a dry ice-acetone bath and treated portionwise over 40 min with 1.6 M methyllithium in THF (66.0 mL, 106 mmol). After 60 min, the mixture was treated slowly at −78° C. with saturated aqueous NH$_4$Cl and stirred for 10 min while warming to room temperature. The mixture was extracted 3 times with DCM, and the combined organic phases were washed sequentially with water and brine, and dried and concentrated. The residue was purified by column chromatography on silica gel (120 g), eluting with EtOAc-hexanes (gradient from 0-100%), to give 5-bromo-6-chloro-2-(2-hydroxypropan-2-yl)-2,3,4,9-tetrahydro-1H-carbazole-8-carboxamide as a yellow solid (4.66 g). Mass spectrum m/z 385, 387 (M+H)+. $^1$H NMR (400 MHz, DMSO-d$_6$) δ 11.08 (s, 1H), 8.13 (br. s., 1H), 7.76 (s, 1H), 7.50 (br. s., 1H), 3.28 (d, J=5.5 Hz, 1H), 2.94 (dd, J=17.1, 4.7 Hz, 1H), 2.79-2.66 (m, 1H), 2.49-2.39 (m, 1H), 2.14 (d, J=9.5 Hz, 1H), 1.66 (td, J=11.4, 4.1 Hz, 1H), 1.33 (qd, J=12.4, 5.2 Hz, 1H), 1.15 (s, 6H).

Intermediates 30 and 31

(R)-5-Bromo-6-chloro-2-(2-hydroxypropan-2-yl)-2,3,4,9-tetrahydro-1H-carbazole-8-carboxamide (I-30), and (S)-5-Bromo-6-chloro-2-(2-hydroxypropan-2-yl)-2,3,4,9-tetrahydro-1H-carbazole-8-carboxamide (I-31)

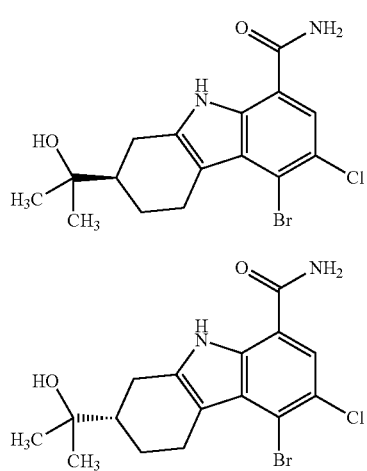

A sample of racemic 5-bromo-6-chloro-2-(2-hydroxypropan-2-yl)-2,3,4,9-tetrahydro-1H-carbazole-8-carboxamide [Intermediate 29] (2.35 g) was separated by chiral supercritical fluid chromatography as follows: column: CHIRALPAK® IA (3×25 cm, 5 μm); Mobile Phase: $CO_2$-MeOH (50:50) at 124 mL/min, 100 bar, 45° C.; sample preparation: 39 mg/mL in MeOH-DMSO (4:1); injection: 2.33 mL. The first peak eluting from the column provided the (R) isomer, (R)-5-bromo-6-chloro-2-(2-hydroxypropan-2-yl)-2,3,4,9-tetrahydro-1H-carbazole-8-carboxamide [Intermediate 30] as a yellow solid (1.15 g). Mass spectrum m/z 385, 387 (M+H)+. $^1$H NMR (500 MHz, DMSO-$d_6$) δ 11.07 (s, 1H), 8.12 (br. s., 1H), 7.75 (s, 1H), 7.57-7.45 (m, 1H), 4.23 (s, 1H), 3.27 (d, J=4.7 Hz, 1H), 2.93 (dd, J=17.2, 4.7 Hz, 1H), 2.78-2.67 (m, 1H), 2.48-2.39 (m, 1H), 2.16-2.08 (m, 1H), 1.69-1.59 (m, 1H), 1.37-1.26 (m, 1H), 1.14 (s, 6H).

The second peak eluting from the column provided the (S) isomer, (S)-5-bromo-6-chloro-2-(2-hydroxypropan-2-yl)-2,3,4,9-tetrahydro-1H-carbazole-8-carboxamide [Intermediate 31] as an off-white solid (0.92 g). Mass spectrum m/z 385, 387 (M+H)+. $^1$H NMR (500 MHz, DMSO-$d_6$) δ 11.06 (s, 1H), 8.12 (br. s., 1H), 7.74 (s, 1H), 7.49 (br. s., 1H), 4.23 (s, 1H), 3.27 (d, J=5.0 Hz, 1H), 2.93 (dd, J=17.1, 4.6 Hz, 1H), 2.72 (t, J=11.8 Hz, 1H), 2.48-2.37 (m, 1H), 2.12 (d, J=9.2 Hz, 1H), 1.69-1.59 (m, 1H), 1.38-1.24 (m, 1H), 1.14 (s, 6H).

The absolute configuration of Intermediate 30 was confirmed by single crystal x-ray analysis of crystals prepared by dissolving the compound in excess 1,2-dichloroethane/EtOAc/acetic acid and slowly evaporating the solvent at room temperature to provide a di-acetic acid solvate. Unit cell dimensions: a=11.690(2) Å, b=7.0901(9) Å, c=14.427(3) Å, α=90°, β=110.607(5)°, γ=90°; Volume=1119.2(3) Å³; Volume/Number of molecules in the unit cell=560 Å³; Space group: P2$_1$; Molecules of Intermediate 30/asymmetric unit (Z'): 1; Density, calc g-cm$^{-3}$: 1.501. Fractional atomic coordinates at room temperature are given in Table 8, and a depiction of the structure is given in FIG. 1.

TABLE 8

Fractional Atomic Coordinates for the Di-acetic Acid Solvate of Intermediate 30 at Room Temperature

| Atom | X | Y | Z |
|---|---|---|---|
| Br1 | 0.7129 | 0.3740 | 0.6642 |
| Cl1 | 0.7740 | 0.3738 | 0.4607 |
| N1 | 0.2665 | 0.3652 | 0.4430 |
| O1 | 0.2004 | 0.3636 | 0.2416 |
| C1 | 0.1772 | 0.3609 | 0.5790 |
| C2 | 0.5901 | 0.3791 | 0.5379 |
| C3 | 0.2812 | 0.3738 | 0.5418 |
| C4 | 0.3773 | 0.3661 | 0.4329 |
| C5 | 0.4669 | 0.3740 | 0.5291 |
| C6 | 0.3082 | 0.3690 | 0.2482 |
| C7 | 0.5312 | 0.3740 | 0.3598 |
| C8 | 0.4074 | 0.3753 | 0.3462 |
| C9 | 0.4036 | 0.3762 | 0.5976 |
| C10 | 0.4463 | 0.3870 | 0.7085 |
| C11 | 0.6203 | 0.3747 | 0.4534 |
| C12 | 0.2289 | 0.3165 | 0.6913 |
| N2 | 0.3387 | 0.3721 | 0.1672 |
| O2 | 0.1932 | 0.2852 | 0.8423 |
| C13 | 0.1290 | 0.3293 | 0.7384 |
| C14 | 0.0723 | 0.5210 | 0.7302 |
| C15 | 0.0325 | 0.1757 | 0.6967 |
| C16 | 0.3389 | 0.4360 | 0.7413 |
| O3 | 0.0996 | 0.3570 | −0.0085 |
| C17 | 0.0053 | 0.3621 | 0.0046 |
| O4 | −0.0020 | 0.3642 | 0.0929 |
| C18 | −0.1174 | 0.3580 | −0.0772 |
| C19 | 0.6259 | 0.3810 | 0.0872 |
| O5 | 0.5910 | 0.4309 | 0.1503 |
| O6 | 0.7118 | 0.4731 | 0.0663 |
| C20 | 0.5791 | 0.2200 | 0.0206 |
| H1 | 0.1973 | 0.3602 | 0.3950 |
| H2 | 0.1212 | 0.2621 | 0.5441 |
| H3 | 0.1327 | 0.4793 | 0.5676 |
| H4 | 0.5548 | 0.3721 | 0.3046 |
| H5 | 0.5091 | 0.4833 | 0.7321 |
| H6 | 0.4813 | 0.2674 | 0.7370 |
| H7 | 0.2569 | 0.1852 | 0.6979 |
| H8 | 0.2826 | 0.3705 | 0.1095 |
| H9 | 0.4142 | 0.3755 | 0.1729 |
| H10 | 0.1460 | 0.2951 | 0.8728 |
| H11 | 0.0219 | 0.5258 | 0.7703 |
| H12 | 0.0232 | 0.5455 | 0.6624 |
| H13 | 0.1355 | 0.6145 | 0.7528 |
| H14 | 0.0720 | 0.0559 | 0.7005 |
| H15 | −0.0148 | 0.2037 | 0.6289 |
| H16 | −0.0205 | 0.1714 | 0.7347 |
| H17 | 0.3637 | 0.4190 | 0.8124 |
| H18 | 0.3175 | 0.5675 | 0.7267 |
| H19 | 0.0671 | 0.3654 | 0.1347 |
| H20 | −0.1430 | 0.4843 | −0.0980 |
| H21 | −0.1761 | 0.2992 | −0.0536 |
| H22 | −0.1116 | 0.2873 | −0.1321 |
| H23 | 0.7379 | 0.5591 | 0.1062 |
| H24 | 0.6424 | 0.1271 | 0.0321 |
| H25 | 0.5538 | 0.2622 | −0.0469 |
| H26 | 0.5107 | 0.1656 | 0.0330 |

Intermediate 32

5-Methoxy-2-(2-methyl-3-(4,4,5,5-tetramethyl-1,3,2-dioxaborolan-2-yl)phenyl)-1H-pyrido[1,2-c]pyrimidine-1,3(2H)-dione

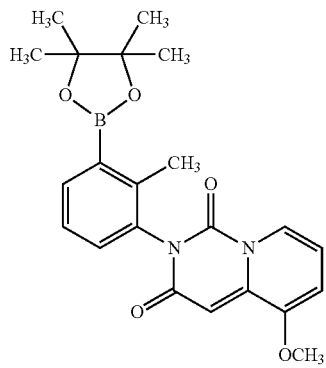
(I-32)

Intermediate 32A: Ethyl 2-(3-methoxypyridin-2-yl)acetate

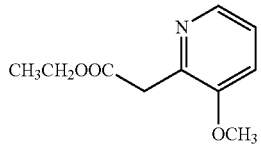
(I-32A)

A stirred solution of diisopropylamine (0.385 mL, 2.70 mmol) in THF (2 mL) at 0° C. was treated slowly with 1.6 M n-butyllithium in hexanes (1.69 mL, 2.70 mmol). The mixture was stirred for 15 min, then was added over 5 min to a stirred solution of 3-methoxy-2-picoline (0.133 g, 1.08 mmol) and diethyl carbonate (0.262 mL, 2.16 mmol) in THF (5 mL) at −78° C. After stirring for 45 min more, the cooling bath was removed and stirring was continued overnight at room temperature. The mixture was treated with saturated aqueous NH₄Cl and diluted with EtOAc. The organic phase was separated, washed sequentially with saturated aqueous NaHCO₃ and brine, and dried and concentrated. The residue was purified by column chromatography on silica gel (12 g), eluting with 50% EtOAc-hexanes, to provide ethyl 2-(3-methoxypyridin-2-yl)acetate as an oil (0.17 g, 81% yield). Mass spectrum m/z 196 (M+H)$^+$.

Intermediate 32B: Sodium 2-(3-methoxypyridin-2-yl)acetate

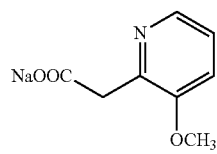
(I-32B)

A stirred solution of ethyl 2-(3-methoxypyridin-2-yl)acetate (0.17 g, 0.871 mmol) in THF (2.5 mL) at room temperature was treated with 3 M aqueous NaOH (0.581 mL, 1.74 mmol). After 7 h, the mixture was concentrated to remove the THF and the aqueous residue was frozen on dry ice and lyophilized to provide sodium 2-(3-methoxypyridin-2-yl)acetate as a white solid. A quantitative yield was assumed and the material used without further purification. Mass spectrum m/z 168 (M+H)$^+$.

Intermediate 32C: N-(3-Bromo-2-methylphenyl)-2-(3-methoxypyridin-2-yl) acetamide

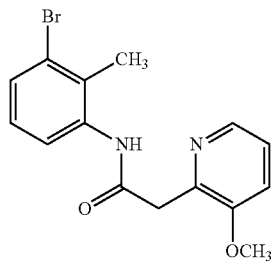
(I-32C)

A mixture of sodium 2-(3-methoxypyridin-2-yl)acetate (0.166 g, 0.871 mmol), 3-bromo-2-methylaniline (0.118 mL, 0.958 mmol), DIEA (0.608 mL, 3.48 mmol) and HATU (0.397 g, 1.05 mmol) in DMF (4.0 mL) was stirred at room temperature. After 1 h, the mixture was diluted with EtOAc and washed twice with 10% aqueous LiCl, then with brine, dried and concentrated. The residue was purified by column chromatography on silica gel to provide N-(3-bromo-2-methylphenyl)-2-(3-methoxypyridin-2-yl)acetamide as a pale yellow solid (0.213 g, 73% yield). Mass spectrum m/z 335, 337 (M+H)$^+$.

Intermediate 32D: 2-(3-Methoxypyridin-2-yl)-N-(2-methyl-3-(4,4,5,5-tetramethyl-1,3,2-dioxaborolan-2-yl)phenyl)acetamide

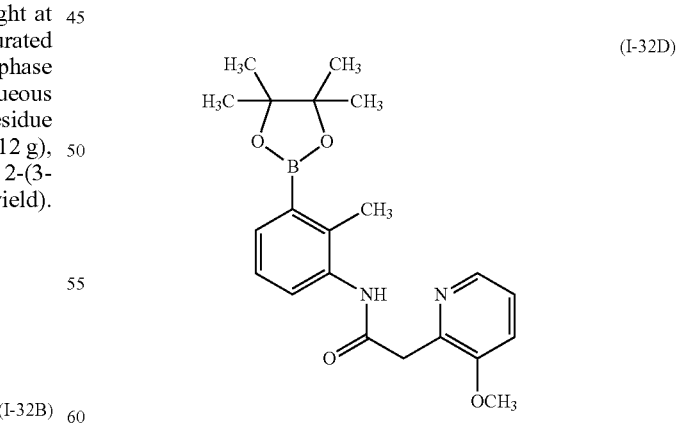
(I-32D)

A mixture of N-(3-bromo-2-methylphenyl)-2-(3-methoxypyridin-2-yl)acetamide (4.00 g, 11.9 mmol) and 4,4,4',4',5,5,5',5'-octamethyl-2,2'-bi(1,3,2-dioxaborolane) (3.48 g, 13.7 mmol) in DMSO (7 mL) and dioxane (35 mL) was bubbled with argon for 5 min, then was treated with potassium acetate (2.93 g, 29.8 mmol). Bubbling was continued for 2 min, then the mixture was treated with PdCl$_2$(dppf) DCM adduct (0.487 g, 0.597 mmol). The reaction vessel was sealed and heated at 90° C. overnight. The cooled mixture was diluted with EtOAc and washed sequentially with water and brine. The combined aqueous layers were extracted with EtOAc, and the combined organic layers were dried and concentrated. The residue was filtered through a plug of silica gel with 60% EtOAc-hexanes, and the filtrate was concentrated. The residue was purified by column chromatography on silica gel, eluting with EtOAc-hexanes, to give 2-(3-methoxypyridin-2-yl)-N-(2-methyl-3-(4,4,5,5-tetramethyl-1,3,2-dioxaborolan-2-yl)phenyl)acetamide as a tan solid (5.1 g, 82% yield). $^1$H NMR (400 MHz, chloroform-d) δ 9.65 (br. s., 1H), 8.20 (dd, J=4.3, 1.7 Hz, 1H), 8.14 (d, J=8.1 Hz, 1H), 7.54 (d, J=7.3 Hz, 1H), 7.24-7.17 (m, 3H), 4.01 (s, 2H), 3.88 (s, 3H), 2.45 (s, 3H), 1.35 (s, 12H).

Intermediate 32:

A mixture of 2-(3-methoxypyridin-2-yl)-N-(2-methyl-3-(4,4,5,5-tetramethyl-1,3,2-dioxaborolan-2-yl)phenyl)acetamide (1.45 g, 3.78 mmol) and CDI (2.45 g, 15.1 mmol) in toluene (19 mL) was heated at 110° C. for 3 h. The cooled mixture was partitioned between EtOAc and water. The organic layer was washed sequentially with water and brine, dried and concentrated. The residue was purified by column chromatography on silica gel, eluting with EtOAc-hexanes, to give 5-methoxy-2-(2-methyl-3-(4,4,5,5-tetramethyl-1,3,2-dioxaborolan-2-yl)phenyl)-1H-pyrido[1,2-c]pyrimidine-1,3(2H)-dione as a yellow solid (0.571 g, 37% yield). Mass spectrum m/z 409 (M+H)$^+$. $^1$H NMR (400 MHz, chloroform-d) δ 7.96 (d, J=7.0 Hz, 1H), 7.91 (dd, J=7.4, 1.2 Hz, 1H), 7.33 (t, J=7.6 Hz, 1H), 7.22 (dd, J=7.8, 1.2 Hz, 1H), 6.39-6.30 (m, 2H), 6.24 (s, 1H), 3.93 (s, 3H), 2.34 (s, 3H), 1.34 (s, 12H).

Intermediate 33

5-Chloro-2-(2-methyl-3-(4,4,5,5-tetramethyl-1,3,2-dioxaborolan-2-yl)phenyl)-1H-pyrido[1,2-c]pyrimidine-1,3(2H)-dione (racemic mixture)

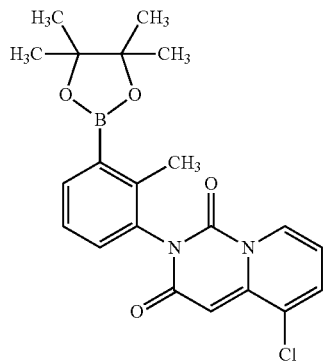

(I-33)

Intermediate 33A: Diethyl 2-(3-chloropyridin-2-yl)malonate

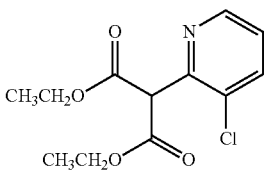

(I-33A)

A mixture of 3-chloro-2-fluoropyridine (5.00 g, 38.0 mmol), diethyl malonate (14.6 g, 91 mmol) and Cs$_2$CO$_3$ (29.7 g, 91 mmol) in DMSO (42 mL) was heated at 100° C. for 7 h. After stirring overnight at room temperature, the mixture was diluted with EtOAc, washed twice with water, then with brine. The combined aqueous layers were extracted with EtOAc, and the combined organic phases were dried and concentrated to give crude diethyl 2-(3-chloropyridin-2-yl) malonate as a colorless oil, used without further purification. Mass spectrum m/z 272 (M+H)$^+$.

Intermediate 33B: Ethyl 2-(3-chloropyridin-2-yl)acetate

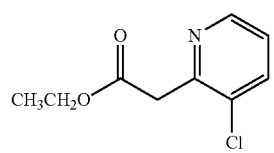

(I-33B)

A mixture of diethyl 2-(3-chloropyridin-2-yl) malonate (10.32 g, 38 mmol), sodium chloride (5.55 g, 95 mmol) and water (3.42 mL, 190 mmol) in DMSO (40 mL) was heated at 145° C. for 8 h. The mixture was cooled to room temperature, diluted with EtOAc and washed twice with water, then with brine. The organic phase was dried and concentrated to provide crude ethyl 2-(3-chloropyridin-2-yl) acetate, used without further purification. Mass spectrum m/z 200 (M+H)$^+$.

Intermediate 33C: Sodium 2-(3-chloropyridin-2-yl)acetate

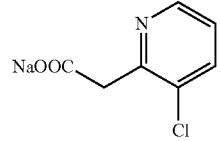

(I-33C)

A solution of ethyl 2-(3-chloropyridin-2-yl)acetate (7.59 g, 38 mmol) in THF (76 mL) was treated at room temperature with 3 M aqueous NaOH (25.3 mL, 76 mmol). The mixture was stirred at room temperature overnight and concentrated to remove the THF. The aqueous residue was frozen on dry ice and lyophilized to give sodium 2-(3-chloropyridin-2-yl)acetate as an off-white solid, used without further purification. Mass spectrum m/z 172 (M+H)$^+$.

Intermediate 33D: N-(3-Bromo-2-methylphenyl)-2-(3-chloropyridin-2-yl)acetamide

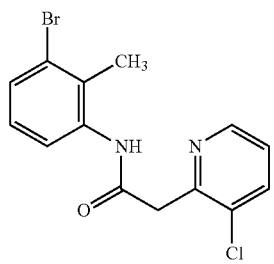

(I-33D)

A mixture of sodium 2-(3-chloropyridin-2-yl)acetate (7.39 g, 38 mmol), 3-bromo-2-methylaniline (4.7 mL, 38.4 mmol), DIEA (13.3 mL, 76 mmol) and HATU (14.6 g, 38.4 mmol) in DMF (127 mL) was stirred at room temperature. After 90 min the mixture was diluted with EtOAc and washed twice with 10% LiCl, then with brine. The combined aqueous layers were extracted with EtOAc, and the combined organic phases were dried and concentrated to a small volume. The solution was seeded with a crystal from an earlier batch and allowed to stand overnight to provide a precipitate which was collected by filtration and washed with 50% EtOAc-hexanes to provide a white solid. The filtrate was concentrated and recrystallized similarly three times to provide additional solid. The solids were combined to give N-(3-bromo-2-methylphenyl)-2-(3-chloropyridin-2-yl)acetamide as a white solid (11.43 g, 89% yield). Mass spectrum m/z 339, 341 (M+H)+. 1H NMR (400 MHz, chloroform-d) δ 9.76 (br. s., 1H), 8.52 (d, J=3.5 Hz, 1H), 7.92 (d, J=7.9 Hz, 1H), 7.80 (dd, J=8.1, 1.1 Hz, 1H), 7.36 (d, J=7.9 Hz, 1H), 7.32-7.23 (m, 1H), 7.06 (t, J=8.0 Hz, 1H), 4.16 (s, 2H), 2.39 (s, 3H).

Intermediate 33E: 2-(3-Chloropyridin-2-yl)-N-(2-methyl-3-(4,4,5,5-tetramethyl-1,3,2-dioxaborolan-2-yl)phenyl)acetamide

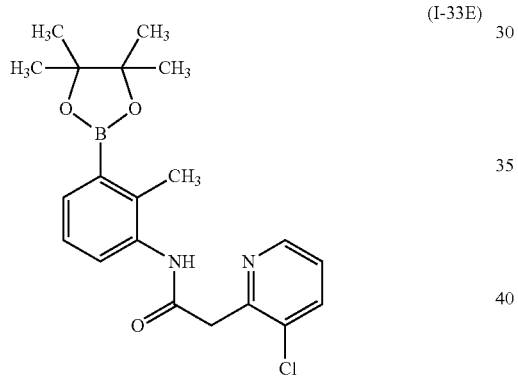

(I-33E)

A mixture of N-(3-bromo-2-methylphenyl)-2-(3-chloropyridin-2-yl)acetamide (4.0 g, 11.78 mmol) and 4,4,4',4',5,5,5',5'-octamethyl-2,2'-bi(1,3,2-dioxaborolane) (3.29 g, 12.96 mmol) in DMSO (5 mL) and dioxane (25 mL) was bubbled with argon for 7 min, followed by addition of potassium acetate (2.89 g, 29.4 mmol). Argon bubbling was continued for 7 min after which PdCl2(dppf) DCM adduct (0.481 g, 0.589 mmol) was added. The mixture was heated at 90° C. for 7 h. The cooled mixture was diluted with EtOAc and filtered through CELITE®. The filtrate was washed sequentially with water and brine. The combined aqueous layers were extracted with EtOAc, and the combined organic phases were dried and concentrated. The residue was recrystallized from EtOAc to provide a white solid. The mother liquor was concentrated and the residue was recrystallized from EtOAc. The two solids were combined to provide 2-(3-chloropyridin-2-yl)-N-(2-methyl-3-(4,4,5,5-tetramethyl-1,3,2-dioxaborolan-2-yl)phenyl)acetamide as a white solid (3.88 g, 85% yield). Mass spectrum m/z 387 (M+H)+.

Intermediate 33:

A mixture of 2-(3-chloropyridin-2-yl)-N-(2-methyl-3-(4,4,5,5-tetramethyl-1,3,2-dioxaborolan-2-yl)phenyl)acetamide (0.192 g, 0.497 mmol) and CDI (0.322 g, 1.986 mmol) in toluene (2 mL) was heated at 110° C. After 5 h, the cooled mixture was diluted with EtOAc and washed sequentially with water and brine. The combined aqueous layers were extracted with EtOAc, and the combined organic phases were dried and concentrated. The residue was purified by column chromatography on silica gel, eluting with EtOAc-hexanes, to provide racemic 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione as a bright yellow solid (0.133 g, 65% yield). Mass spectrum m/z 413 (M+H)+. 1H NMR (400 MHz, chloroform-d) δ 8.26 (dt, J=7.6, 0.9 Hz, 1H), 7.94 (dd, J=7.5, 1.3 Hz, 1H), 7.36 (t, J=7.6 Hz, 1H), 7.27-7.18 (m, 2H), 6.36 (t, J=7.3 Hz, 1H), 6.31 (s, 1H), 1.57 (s, 3H), 1.36 (s, 12H).

Intermediates 34 and 35

5-Chloro-2-(R)-(2-methyl-3-(4,4,5,5-tetramethyl-1,3,2-dioxaborolan-2-yl)phenyl)-1H-pyrido[1,2-c]pyrimidine-1,3(2H)-dione (I-34), and 5-Chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione (I-35)

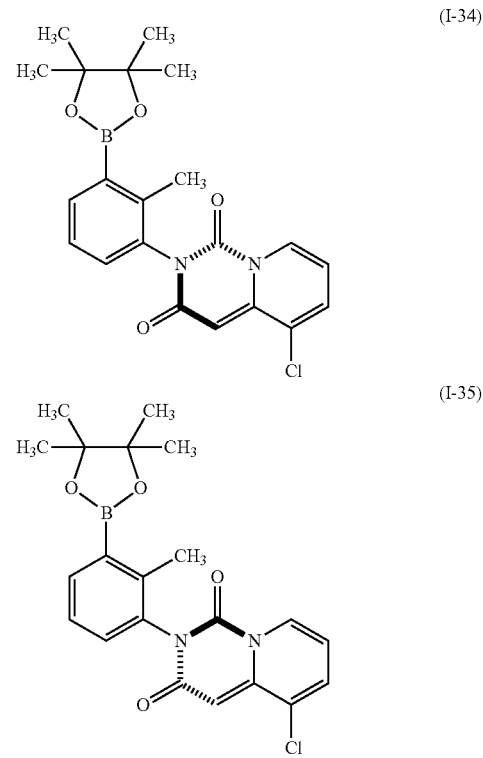

A sample of racemic 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 33] was separated by chiral super-critical fluid chromatography as follows: column: WHELK-O® R,R (3×25 cm, 5 μm); Mobile Phase: CO2-MeOH (55:45) at 200 mL/min, 100 bar, 35° C.; sample preparation: 96 mg/mL in MeCN-DCM (1:4); injection: 5 mL. The first peak eluting from the column provided 5-chloro-2-(R)-(2-methyl-3-(4,4,5,5-tetramethyl-1,3,2-dioxaborolan-2-yl)phenyl)-1H-pyrido[1,2-c]pyrimidine-1,3(2H)-dione [Intermediate 34]. The second peak eluting from the column provided 5-chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione [Intermediate 35]. The mass spectrum and $^1$H NMR for each enantiomeric atropisomer were the same as those for Intermediate 33.

Alternatively, a sample of racemic 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 33] was separated by chiral super-critical fluid chromatography as follows: column: WHELK-0® R,R (3×25 cm, 5 µm); Mobile Phase: $CO_2$—$CH_3CN$ (55:45) at 200 mL/min, 100 bar, 35° C.; sample preparation: 96 mg/mL in MeCN-DCM (1:4); injection: 5 mL. The first peak eluting from the column provided 5-chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione [Intermediate 35]. The material could be further purified by dissolving in THF, diluting with hexanes and collecting the precipitate by filtration.

Figure 2:
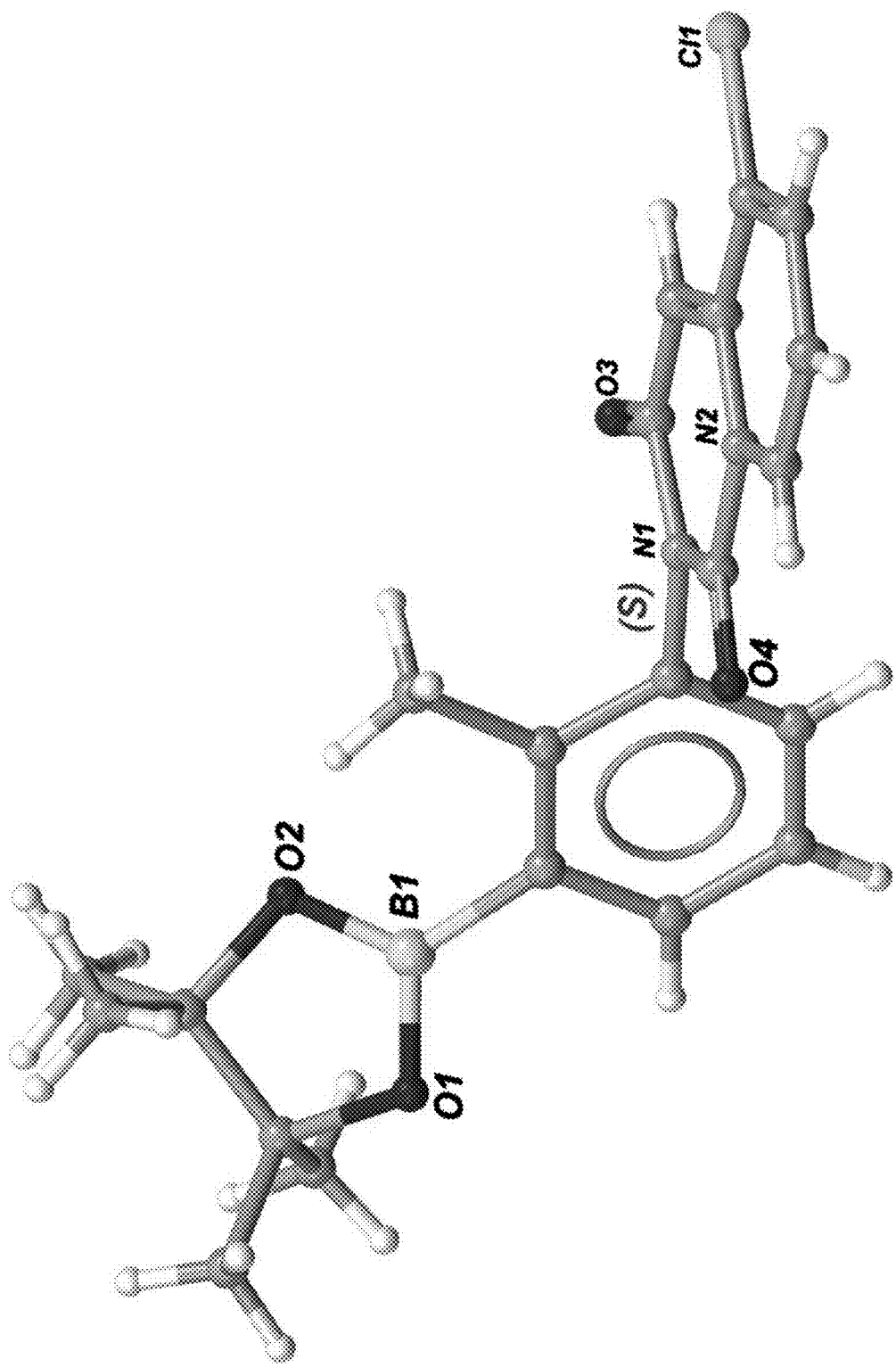
FIG. 2 shows the absolute stereochemistry of Intermediate 35.

The absolute configuration of Intermediate 35 was confirmed by single crystal x-ray analysis of crystals prepared by dissolving the compound in excess acetone and slowly evaporating the solvent at room temperature. Unit cell dimensions: a=19.6161(8) Å, b=9.1411(4) Å, c=12.7541(6) Å, α=90°, β=113.165(2)°, γ=90°; Space group: C2; Molecules of Intermediate 35/asymmetric unit (Z'): 1; Density, calc g-cm$^{-3}$: 1.304. Fractional atomic coordinates at room temperature are given in Table 9, and a depiction of the structure is given in FIG. 2.

TABLE 9

| \multicolumn{4}{c}{Fractional Atomic Coordinates for Intermediate 35 at Room Temperature} |
| Atom | X | Y | Z |
| --- | --- | --- | --- |
| Cl1 | −0.1755 | −0.1003 | 0.3365 |
| O1 | 0.2261 | 0.6937 | 0.2037 |
| C1 | 0.2132 | 0.8050 | 0.1156 |
| C2 | 0.1347 | 0.7655 | 0.0313 |
| O2 | 0.1028 | 0.6968 | 0.1045 |
| B1 | 0.1597 | 0.6467 | 0.1980 |
| C3 | 0.1403 | 0.4028 | 0.4772 |
| C4 | 0.1906 | 0.5142 | 0.4966 |
| C5 | 0.1012 | 0.4308 | 0.2727 |
| C6 | 0.1966 | 0.5843 | 0.4048 |
| C7 | 0.0966 | 0.3615 | 0.3668 |
| C8 | 0.1517 | 0.5466 | 0.2926 |
| C9 | 0.0863 | 0.8966 | −0.0281 |
| C10 | 0.0532 | 0.3809 | 0.1539 |
| C11 | 0.1298 | 0.6565 | −0.0585 |
| C12 | 0.2226 | 0.9474 | 0.1724 |
| C13 | 0.2710 | 0.7829 | 0.0643 |
| N1 | 0.0457 | 0.2404 | 0.3528 |
| C14 | 0.0746 | 0.1035 | 0.3564 |
| N2 | 0.0270 | −0.0148 | 0.3551 |
| C15 | −0.0287 | 0.2712 | 0.3397 |
| C16 | −0.0453 | 0.0086 | 0.3467 |
| C17 | −0.0720 | 0.1477 | 0.3375 |
| C18 | 0.0561 | −0.1540 | 0.3608 |
| C19 | −0.0563 | −0.2557 | 0.3562 |
| C20 | −0.0863 | −0.1218 | 0.3472 |
| C21 | 0.0166 | −0.2724 | 0.3622 |
| O3 | −0.0487 | 0.3988 | 0.3318 |
| O4 | 0.1356 | 0.0809 | 0.3596 |
| H1 | 0.1356 | 0.3551 | 0.5384 |
| H2 | 0.2203 | 0.5422 | 0.5706 |
| H3 | 0.2313 | 0.6587 | 0.4179 |
| H4 | 0.0388 | 0.8624 | −0.0807 |
| H5 | 0.1101 | 0.9509 | −0.0687 |
| H6 | 0.0796 | 0.9586 | 0.0279 |

TABLE 9-continued

| \multicolumn{4}{c}{Fractional Atomic Coordinates for Intermediate 35 at Room Temperature} |
| Atom | X | Y | Z |
| --- | --- | --- | --- |
| H7 | 0.0613 | 0.2788 | 0.1461 |
| H8 | 0.0655 | 0.4356 | 0.0994 |
| H9 | 0.0019 | 0.3967 | 0.1400 |
| H10 | 0.1556 | 0.5689 | −0.0231 |
| H11 | 0.1519 | 0.6967 | −0.1073 |
| H12 | 0.0787 | 0.6339 | −0.1029 |
| H13 | 0.1871 | 0.9571 | 0.2066 |
| H14 | 0.2151 | 1.0241 | 0.1175 |
| H15 | 0.2718 | 0.9545 | 0.2304 |
| H16 | 0.3176 | 0.8231 | 0.1147 |
| H17 | 0.2550 | 0.8312 | −0.0083 |
| H18 | 0.2769 | 0.6801 | 0.0543 |
| H19 | −0.1208 | 0.1615 | 0.3296 |
| H20 | 0.1039 | −0.1652 | 0.3637 |
| H21 | −0.0838 | −0.3378 | 0.3584 |
| H22 | 0.0370 | −0.3652 | 0.3671 |

Intermediate 36

6-(2-Methyl-3-(4,4,5,5-tetramethyl-1,3,2-dioxaborolan-2-yl)phenyl)-5H-thiazolo[3,2-c]pyrimidine-5,7(6H)-dione

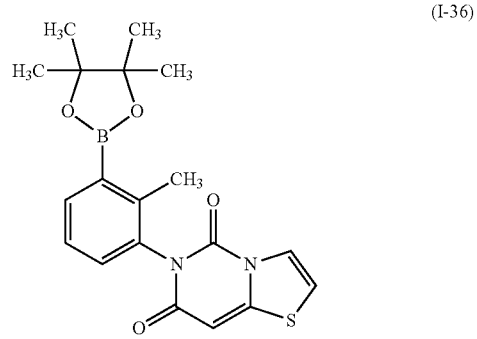 [SMILES: Cc1c(B2OC(C)(C)C(C)(C)O2)cccc1-n1c(=O)cc2sccn2c1=O]

(I-36)

Intermediate 36A: N-(3-Bromo-2-methylphenyl)-2-(thiazol-2-yl)acetamide

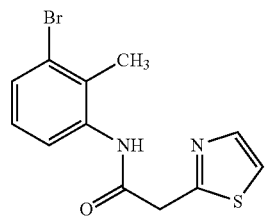

(I-36A)

A mixture of 3-bromo-2-methylaniline (0.764 mL, 6.20 mmol), 1,3-thiazol-2-ylacetic acid (0.74 g, 5.17 mmol) and DIEA (1.63 mL, 9.30 mmol) in DMF (15 mL) was treated with HATU (2.36 g, 6.20 mmol). After stirring overnight, the mixture was diluted with EtOAc, washed twice with 10% aqueous LiCl followed by brine, and the combined aqueous layers were extracted with EtOAc. The combined organic layers were dried and concentrated, and the residue was purified by column chromatography on silica gel, eluting with EtOAc-hexanes, to give N-(3-bromo-2-methylphenyl)-2-(thiazol-2-yl)acetamide as a white solid (0.681 g, 42% yield). ¹H NMR (400 MHz, chloroform-d) δ 9.84-9.65 (m, 1H), 7.91 (d, J=7.9 Hz, 1H), 7.84 (d, J=3.3 Hz, 1H), 7.42-7.35 (m, 2H), 7.07 (t, J=8.0 Hz, 1H), 4.18 (s, 2H), 2.38 (s, 3H).

Intermediate 36B: N-(2-Methyl-3-(4,4,5,5-tetramethyl-1,3,2-dioxaborolan-2-yl)phenyl)-2-(thiazol-2-yl)acetamide

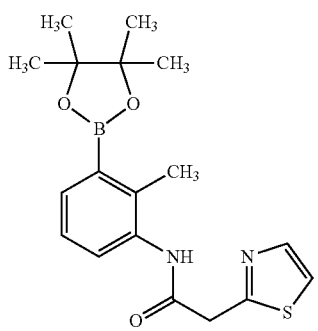

(I-36B)

A mixture of N-(3-bromo-2-methylphenyl)-2-(thiazol-2-yl)acetamide (0.53 g, 1.70 mmol) 4,4,4',4',5,5,5',5'-octamethyl-2,2'-bi(1,3,2-dioxaborolane) (0.476 g, 1.87 mmol) and potassium acetate (0.418 g, 4.26 mmol) in DMSO (1.6 mL) and dioxane (8 mL) was bubbled with nitrogen for 5 min, followed by the addition of PdCl₂(dppf) DCM adduct (0.070 g, 0.085 mmol). After bubbling with nitrogen for another 5 min, the mixture was heated at 90° C. for 7 h. The cooled mixture was diluted with EtOAc and filtered through CELITE®. The filtrate was washed sequentially with water and brine, and dried and concentrated. The residue was purified by column chromatography on silica gel (40 g), eluting with 50% EtOAc-hexanes, to give N-(2-methyl-3-(4,4,5,5-tetramethyl-1,3,2-dioxaborolan-2-yl)phenyl)-2-(thiazol-2-yl)acetamide as an off-white solid (0.45 g, 74% yield). Mass spectrum m/z 359 (M+H)⁺.

Intermediate 36:

A mixture of N-(2-methyl-3-(4,4,5,5-tetramethyl-1,3,2-dioxaborolan-2-yl) phenyl)-2-(thiazol-2-yl)acetamide (0.45 g, 1.26 mmol) and CDI (0.815 g, 5.02 mmol) in toluene (6.5 mL) was heated at 110° C. for 2 h. The cooled mixture was partitioned between EtOAc and water. The organic layer was washed with brine, and the combined aqueous layers were extracted with EtOAc. The combined organic layers were dried and concentrated. The residue was purified by column chromatography on silica gel (40 g), eluting with 70% EtOAc-hexanes, to give slightly impure 6-(2-methyl-3-(4,4,5,5-tetramethyl-1,3,2-dioxaborolan-2-yl)phenyl)-5H-thiazolo[3,2-c]pyrimidine-5,7(6H)-dione as a tan solid (34% yield). The material was used without further purification. Mass spectrum m/z 385 (M+H)⁺.

Intermediate 37

Racemic 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione

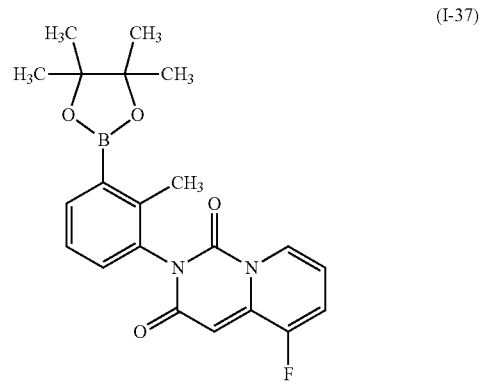 [SMILES: Cc1c(B2OC(C)(C)C(C)(C)O2)cccc1-n1c(=O)cc2c(F)cccn2c1=O]

(I-37)

Intermediate 37A: Diethyl 2-(3-fluoropyridin-2-yl)malonate

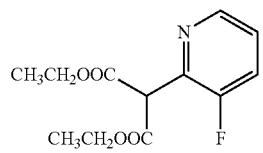

(I-37A)

A mixture of 2,3-difluoropyridine (2.00 g, 17.4 mmol), Cs₂CO₃ (13.59 g, 41.7 mmol) and diethyl malonate (6.68 g, 41.7 mmol) in DMSO (19 mL) was heated at 100° C. for 4.5 h. The mixture was poured onto ice, diluted with EtOAc, and the organic phase was separated, washed sequentially with water and brine, and dried and concentrated. The residue was purified by column chromatography on silica gel (80 g), eluting with EtOAc-hexanes (sequentially 10%, 20% and 30%), to provide diethyl 2-(3-fluoropyridin-2-yl)malonate as a pale colored oil (2.68 g, 60% yield). ¹H NMR (400 MHz, chloroform-d) δ 8.42 (dt, J=4.6, 1.3 Hz, 1H), 7.43 (ddd, J=9.4, 8.3, 1.4 Hz, 1H), 7.30 (dt, J=8.5, 4.3 Hz, 1H), 5.09 (d, J=1.1 Hz, 1H), 4.30 (q, J=7.0 Hz, 4H), 1.33-1.26 (m, 6H).

Intermediate 37B: Ethyl 2-(3-fluoropyridin-2-yl)acetate

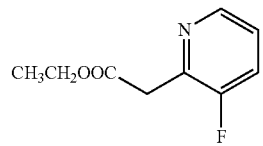

(I-37B)

A mixture of diethyl 2-(3-fluoropyridin-2-yl)malonate (2.68 g, 10.5 mmol), sodium chloride (0.675 g, 11.6 mmol)

and water (0.378 mL, 21.0 mmol) in DMSO (15 mL) was heated at 145° C. for 4.5 h. The mixture was cooled, diluted with EtOAc and washed sequentially with water and brine. The organic phase was dried and concentrated to provide ethyl 2-(3-fluoropyridin-2-yl)acetate as a pale colored oil (1.90 g, 99% yield) which was used without further purification. Mass spectrum m/z 184 (M+H)+.

Intermediate 37C: Sodium 2-(3-fluoropyridin-2-yl)acetate

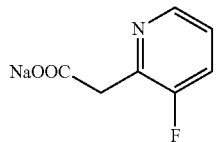

(I-37C)

A stirred solution of ethyl 2-(3-fluoropyridin-2-yl)acetate (1.90 g, 10.4 mmol) in THF (26 mL) was treated with 3 M aqueous NaOH (6.9 mL, 20.7 mmol) and stirred at room temperature overnight. The mixture was concentrated to remove the THF, and the residual aqueous solution was frozen and lyophilized to provide sodium 2-(3-fluoropyridin-2-yl)acetate as a white solid (assumed 100% yield), which was used without further purification. Mass spectrum m/z 156 (M+H)+.

Intermediate 37D: N-(3-Bromo-2-methylphenyl)-2-(3-fluoropyridin-2-yl)acetamide

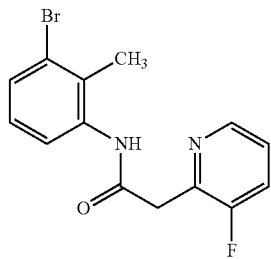

(I-37D)

A mixture of sodium 2-(3-fluoropyridin-2-yl)acetate (1.847 g, 10.37 mmol), 3-bromo-2-methylaniline (1.41 mL, 11.4 mmol), DIEA (5.4 mL, 31.1 mmol) and HATU (4.73 g, 12.4 mmol) in DMF (30 mL) was stirred at room temperature for 1.25 h. The mixture was diluted with EtOAc and washed twice with 10% aqueous LiCl, then with brine. The combined aqueous layers were extracted with EtOAc, and the combined organic phases were dried and concentrated. The residue was dissolved in hot EtOAc, allowed to cool, and the resulting white solid collected by filtration and washed with 60% EtOAc-hexanes. The combined filtrates were concentrated and the residue was recrystallized twice using the same procedure. The residue from concentration of the final filtrate was purified by column chromatography on silica gel, eluting with EtOAc-hexanes, to provide a solid which was combined with the recrystallized batches to provide N-(3-bromo-2-methylphenyl)-2-(3-fluoropyridin-2-yl)acetamide as a white solid (2.03 g, 61% yield). Mass spectrum m/z 323, 325 (M+H)+.

Intermediate 37E: 2-(3-Fluoropyridin-2-yl)-N-(2-methyl-3-(4,4,5,5-tetramethyl-1,3,2-dioxaborolan-2-yl)phenyl)acetamide

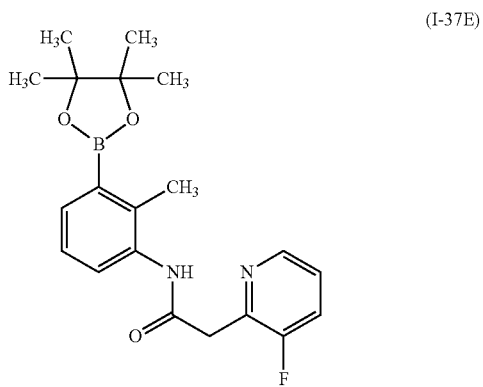 [SMILES: Cc1c(NC(=O)Cc2ncccc2F)cccc1B1OC(C)(C)C(C)(C)O1]

(I-37E)

A mixture of N-(3-bromo-2-methylphenyl)-2-(3-fluoropyridin-2-yl)acetamide (4.20 g, 13.6 mmol) and 4,4,4',4',5,5,5',5'-octamethyl-2,2'-bi(1,3,2-dioxaborolane) (3.80 g, 14.9 mmol) in dioxane (40 mL) was bubbled with nitrogen for 10 min. Potassium acetate (3.33 g, 34.0 mmol) was added to the mixture, bubbling was continued for another 5 min, and PdCl$_2$(dppf) DCM adduct (0.555 g, 0.679 mmol) was added. The mixture was heated at 100° C. overnight. The cooled mixture was diluted with EtOAc, washed sequentially with water and brine, dried and concentrated. The residue was purified by column chromatography on silica gel, eluting with DCM-methyl t-butyl ether, to provide 2-(3-fluoropyridin-2-yl)-N-(2-methyl-3-(4,4,5,5-tetramethyl-1,3,2-dioxaborolan-2-yl)phenyl)acetamide as a white solid (3.80 g, 76% yield). Mass spectrum m/z 371 (M+H)+.

Intermediate 37:

A mixture of 2-(3-fluoropyridin-2-yl)-N-(2-methyl-3-(4,4,5,5-tetramethyl-1,3,2-dioxaborolan-2-yl)phenyl)acetamide (9.01 g, 24.3 mmol) and CDI (15.78 g, 97 mmol) in toluene (97 mL) was heated at 120° C. for 7 h. The cooled mixture was diluted with EtOAc and washed sequentially with water and brine. The combined aqueous layers were extracted with EtOAc, and the combined organic phases were dried and concentrated. The residue was purified by column chromatography on silica gel (220 g), eluting with EtOAc-hexanes (gradient from 20-100%), to provide 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione as a yellow solid (6.26 g, 65% yield). Mass spectrum m/z 397 (M+H)+. $^1$H NMR (400 MHz, chloroform-d) δ 8.11 (dd, J=7.6, 0.8 Hz, 1H), 7.94 (dd, J=7.5, 1.3 Hz, 1H), 7.35 (t, J=7.5 Hz, 1H), 7.23 (dd, J=7.8, 1.4 Hz, 1H), 6.85-6.76 (m, 1H), 6.35 (td, J=7.4, 5.0 Hz, 1H), 6.09 (s, 1H), 2.36 (s, 3H), 1.36 (s, 12H).

Intermediates 38 and 39

5-Fluoro-2-(2-methyl-3-(4,4,5,5-tetramethyl-1,3,2-dioxaborolan-2-yl)phenyl)-1H-pyrido[1,2-c]pyrimidine-1,3(2H)-dione (single atropisomers)

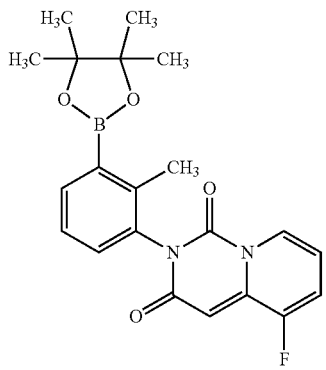

(I-38, I-39)

A sample of racemic 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 37] (7.5 g) was separated by chiral super-critical fluid chromatography as follows: column: CHIRALCEL® OD-H (5×25 cm, 5 µm); Mobile Phase: $CO_2$-MeOH (76:24) at 280 mL/min, 100 bar, 40° C.; sample preparation: 62.5 mg/mL in DCM-MeOH (1:1); injection: 0.83 mL. The first peak eluting from the column provided one atropisomer of 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 38] as a yellow solid (3.2 g, chiral purity 99.3%). The second peak eluting from the column provided the other atropisomer of 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 39] as a yellow solid (2.98 g, chiral purity 98.6%). The mass spectrum and $^1$H NMR for both enantiomers were the same as those for Intermediate 37.

Intermediate 40

(Z)-4-((2-Chloro-3-(4,4,5,5-tetramethyl-1,3,2-dioxaborolan-2-yl)phenyl)imino)-1-methyl-1H-benzo[d][1,3]oxazin-2(4H)-one

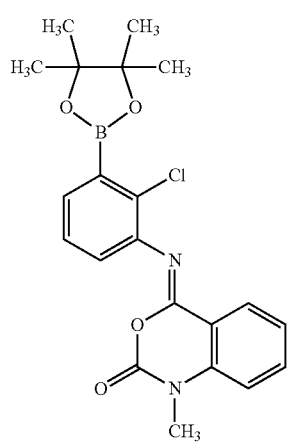

(I-40)

Intermediate 40A: N-(3-Bromo-2-chlorophenyl)-2-(methylamino)benzamide

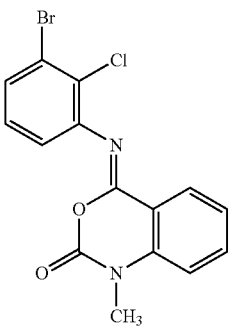

(I-40A)

A mixture of 3-bromo-2-chloroaniline [prepared according to the procedure described in U.S. Pat. No. 8,242,260] (240 mg, 1.162 mmol) and toluene (10 mL) at 0° C. was slowly treated with 2 M trimethylaluminum in toluene (0.99 mL, 1.98 mmol). The mixture was allowed to warm to room temperature and stirred for 15 min. A partial suspension of 1-methyl-1H-benzo[d][1,3]oxazine-2,4-dione (300 mg, 1.52 mmol) in toluene (4 mL) was added slowly. The resulting mixture was heated at 50° C. for 4 h, cooled to 0° C., and treated dropwise with 1 M aqueous HCl until no more gas evolution was observed. The mixture was stirred for 2 h while warming to room temperature, then was extracted with EtOAc. The organic phase was washed sequentially with $NaHCO_3$ and brine, dried and concentrated. The residue was purified by column chromatography on silica gel (80 g), eluting with EtOAc-hexanes (gradient from 0-30%), to provide N-(3-bromo-2-chlorophenyl)-2-(methylamino)benzamide as a yellow solid (110 mg, 28% yield). Mass spectrum m/z 339, 341 (M+H)$^+$. $^1$H NMR (400 MHz, DMSO-$d_6$) δ 10.00 (s, 1H), 7.78 (dd, J=7.9, 1.5 Hz, 1H), 7.67 (dd, J=8.1, 1.5 Hz, 1H), 7.57 (dd, J=8.0, 1.4 Hz, 1H), 7.53 (d, J=1.3 Hz, 1H), 7.38 (ddd, J=8.4, 7.1, 1.4 Hz, 1H), 7.32 (t, J=8.0 Hz, 1H), 6.70 (d, J=8.4 Hz, 1H), 6.68-6.61 (m, 1H), 2.79 (d, J=5.1 Hz, 3H).

Intermediate 40B: (Z)-4-((3-Bromo-2-chlorophenyl)imino)-1-methyl-1H-benzo[d][1,3]oxazin-2(4H)-one (I-40B)

A solution of N-(3-bromo-2-chlorophenyl)-2-(methylamino)benzamide (150 mg, 0.442 mmol) in THF (15 mL) cooled to 0° C. and treated with triphosgene (197 mg, 0.663 mmol). The mixture was stirred at room temperature for 1 h, then was cooled to 0° C. and treated with water until gas evolution ceased. The mixture was concentrated, and the residue was dissolved in EtOAc and washed sequentially with saturated aqueous NaHCO$_3$, water and brine, dried and concentrated. The residue was purified by column chromatography on silica gel, eluting with EtOAc-hexanes (gradient from 0-50%), to provide (Z)-4-((3-bromo-2-chlorophenyl)imino)-1-methyl-1H-benzo[d][1,3]oxazin-2(4H)-one as a beige solid (130 mg, 81% yield). $^1$H NMR (400 MHz, chloroform-d) δ 8.33 (dd, J=7.8, 1.4 Hz, 1H), 7.72-7.61 (m, 1H), 7.41 (dd, J=7.9, 1.5 Hz, 1H), 7.36-7.28 (m, 1H), 7.16-7.08 (m, 2H), 7.07-7.01 (m, 1H), 3.55 (s, 3H).

Intermediate 40:

A mixture of (Z)-4-((3-bromo-2-chlorophenyl)imino)-1-methyl-1H-benzo[d][1,3]oxazin-2(4H)-one (130 mg, 0.356 mmol), 4,4,4',4',5,5,5',5'-octamethyl-2,2'-bi(1,3,2-dioxaborolane) (117 mg, 0.462 mmol) and potassium acetate (87 mg, 0.889 mmol) in dioxane (4 mL) was bubbled with nitrogen for 10 min. The mixture was treated with PdCl$_2$ (dppf) DCM adduct (14.5 mg, 0.018 mmol), and heated at 90° C. overnight. The cooled mixture was partitioned between EtOAc and water. The organic phase was dried and concentrated and the residue was purified by column chromatography on silica gel, eluting with EtOAc-hexanes (gradient from 0-50%), to provide (Z)-4-((2-chloro-3-(4,4,5,5-tetramethyl-1,3,2-dioxaborolan-2-yl)phenyl)imino)-1-methyl-1H-benzo[d][1,3]oxazin-2(4H)-one as a yellow solid (120 mg, 82% yield). Mass spectrum m/z 413 (M+H)$^+$. $^1$H NMR (400 MHz, chloroform-d) δ 8.40-8.30 (m, 1H), 7.67-7.58 (m, 1H), 7.48-7.44 (m, 1H), 7.27 (s, 4H), 7.16-7.07 (m, 2H), 3.55-3.47 (m, 3H), 1.40-1.37 (m, 12H).

Intermediate 41

3-(2-Chloro-3-(4,4,5,5-tetramethyl-1,3,2-dioxaborolan-2-yl)phenyl)-8-fluoro-1-methylquinazoline-2,4(1H,3H)-dione

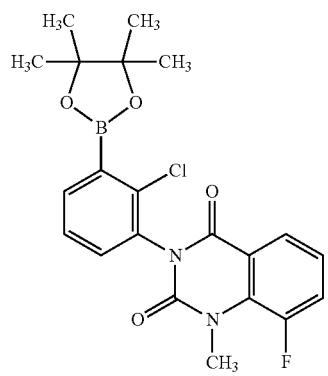

(I-41)

Intermediate 41A: 2-Amino-N-(3-bromo-2-chlorophenyl)-3-fluorobenzamide

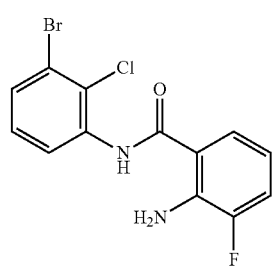

(I-41A)

A mixture of 3-bromo-2-chloroaniline [prepared according to the procedure described in U.S. Pat. No. 8,242,260] (600 mg, 2.91 mmol) and toluene (10 mL) was cooled to 0° C. and slowly treated with 2 M trimethylaluminum in toluene (2.47 mL, 4.94 mmol). The mixture was allowed to warm to room temperature and stirred for 15 min. The mixture was treated with 8-fluoro-1H-benzo[d][1,3]oxazine-2,4-dione (684 mg, 3.78 mmol) and heated at 50° C. for 16 h. The mixture was cooled to 0° C. and treated dropwise with 1 M aqueous HCl until gas evolution stopped, and stirred for 2 h while allowing to warm to room temperature. The mixture was extracted three times with EtOAc. The combined organic phases were washed sequentially with saturated aqueous NaHCO$_3$ and brine, dried and concentrated. The residue was purified by column chromatography on silica gel (24 g), eluting with EtOAc-hexanes (gradient from 0-30%), to provide 2-amino-N-(3-bromo-2-chlorophenyl)-3-fluorobenzamide as a pale yellow solid (350 mg, 35% yield). Mass spectrum m/z 343, 345 (M+H)$^+$. $^1$H NMR (400 MHz, chloroform-d) δ 8.46 (dd, J=8.4, 1.3 Hz, 1H), 8.42 (br. s., 1H), 7.43 (dd, J=8.0, 1.4 Hz, 1H), 7.34 (d, J=8.1 Hz, 1H), 7.22 (t, J=8.3 Hz, 1H), 7.15 (ddd, J=11.0, 8.0, 1.2 Hz, 1H), 6.69 (td, J=8.0, 5.1 Hz, 1H), 5.72 (br. s., 2H).

Intermediate 41B: 3-(3-Bromo-2-chlorophenyl)-8-fluoroquinazoline-2,4(1H,3H)-dione

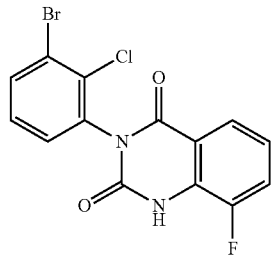

(I-41B)

Triphosgene (453 mg, 1.53 mmol) was added in one portion to a solution of amino-N-(3-bromo-2-chlorophenyl)-3-fluorobenzamide (350 mg, 1.019 mmol) in THF (10 mL) at 0° C. The mixture was stirred at room temperature for 1 h, then was cooled to 0° C. and treated with water until no more gas evolution was observed. The mixture was concentrated and the residue was dissolved in EtOAc, washed sequentially with saturated aqueous NaHCO$_3$, water and brine, and dried and concentrated. The residue was purified by column chromatography on silica gel (24 g), eluting with EtOAc-hexanes (gradient from 0-50%), to provide 3-(3-bromo-2-chlorophenyl)-8-fluoroquinazoline-2,4(1H,3H)-dione as a yellow solid (320 mg, 85% yield). Mass spectrum m/z 369, 371 (M+H)$^+$. $^1$H NMR (400 MHz, chloroform-d) δ 8.54 (br. s., 1H), 7.97 (d, J=8.1 Hz, 1H), 7.77 (dd, J=6.8, 2.6 Hz, 1H), 7.46 (ddd, J=9.8, 8.3, 1.2 Hz, 1H), 7.36-7.29 (m, 2H), 7.24 (td, J=8.0, 4.8 Hz, 1H).

141

Intermediate 41C: 3-(3-Bromo-2-chlorophenyl)-8-fluoro-1-methylquinazoline-2,4(1H,3H)-dione

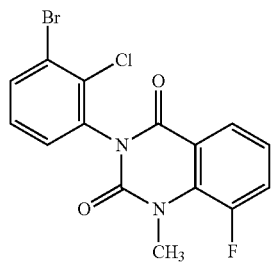

(I-41C)

Iodomethane (0.102 mL, 1.62 mmol) was added slowly to a mixture of 3-(3-bromo-2-chlorophenyl)-8-fluoroquinazoline-2,4(1H,3H)-dione (300 mg, 0.812 mmol), DMF (5 mL) and $Cs_2CO_3$ (529 mg, 1.62 mmol). The mixture was stirred at room temperature for 2 h, then was diluted with EtOAc, washed sequentially with water and brine, and dried and concentrated. The residue was purified by column chromatography on silica gel (24 g), eluting with EtOAc-hexanes (gradient from 0-30%), to provide 3-(3-bromo-2-chlorophenyl)-8-fluoro-1-methylquinazoline-2,4(1H,3H)-dione as a yellow solid (280 mg, 90% yield). Mass spectrum m/z 383, 385 (M+H)$^+$. $^1$H NMR (400 MHz, chloroform-d) δ 8.09 (dq, J=7.8, 0.8 Hz, 1H), 7.79-7.71 (m, 1H), 7.49 (ddd, J=13.9, 8.1, 1.5 Hz, 1H), 7.32-7.29 (m, 2H), 7.29-7.22 (m, 2H), 3.88 (s, 1.5H), 3.86 (s, 1.5H).

Intermediate 41:

A mixture of 3-(3-bromo-2-chlorophenyl)-8-fluoro-1-methylquinazoline-2,4(1H,3H)-dione (150 mg, 0.391 mmol), 4,4,4',4',5,5,5',5'-octamethyl-2,2'-bi(1,3,2-dioxaborolane) (129 mg, 0.508 mmol), potassium acetate (96 mg, 0.978 mmol) and dioxane (8 mL) was bubbled with nitrogen for 10 min and treated with PdCl$_2$(dppf) DCM adduct (16 mg, 0.020 mmol). The mixture was heated at 90° C. for 16 h, then was cooled and partitioned between EtOAc and water. The organic phase was dried and concentrated, and the residue was purified by column chromatography on silica gel (12 g), eluting with EtOAc-hexanes (gradient from 0-50%), to give 3-(2-chloro-3-(4,4,5,5-tetramethyl-1,3,2-dioxaborolan-2-yl)phenyl)-8-fluoro-1-methylquinazoline-2,4(1H,3H)-dione as a white glassy solid (52 mg, 31% yield). Mass spectrum m/z 431 (M+H)$^+$. $^1$H NMR (400 MHz, chloroform-d) δ 8.14-8.05 (m, 1H), 7.90-7.82 (m, 1H), 7.51-7.35 (m, 3H), 7.26-7.19 (m, 1H), 3.86 (d, J=8.1 Hz, 3H), 1.36 (s, 12H).

142

Intermediate 42

3-(2-Chloro-3-(4,4,5,5-tetramethyl-1,3,2-dioxaborolan-2-yl)phenyl)-8-fluoroquinazoline-2,4(1H,3H)-dione

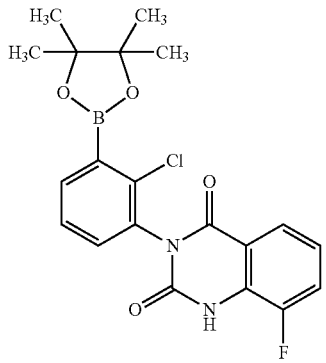

(I-42)

A mixture of 3-(3-bromo-2-chlorophenyl)-8-fluoroquinazoline-2,4(1H,3H)-dione [Intermediate 41B] (990 mg, 2.68 mmol), 4,4,4',4',5,5,5',5'-octamethyl-2,2'-bi(1,3,2-dioxaborolane) (884 mg, 3.48 mmol) and potassium acetate (657 mg, 6.70 mmol) in dioxane (8 mL) was bubbled with nitrogen for 10 min. PdCl$_2$(dppf) DCM adduct (109 mg, 0.134 mmol) was added and the mixture was heated at 90° C. overnight. The cooled mixture was diluted with EtOAc, filtered, and the filtrate was concentrated. The residue was purified by column chromatography on silica gel, eluting with MeOH-DCM (gradient from 0-5%), to give 3-(2-chloro-3-(4,4,5,5-tetramethyl-1,3,2-dioxaborolan-2-yl)phenyl)-8-fluoroquinazoline-2,4(1H,3H)-dione as a brown solid (710 mg, 64% yield). Mass spectrum m/z 416 (M+H)$^+$. $^1$H NMR (400 MHz, chloroform-d) δ 8.55-8.38 (m, 1H), 8.06-7.93 (m, 1H), 7.90-7.75 (m, 1H), 7.51-7.38 (m, 3H), 7.26-7.13 (m, 1H), 1.26 (br. s., 12H)

Intermediate 43

7-Fluoro-3-(2-methyl-3-(4,4,5,5-tetramethyl-1,3,2-dioxaborolan-2-yl)phenyl)quinazoline-2,4(1H,3H)-dione

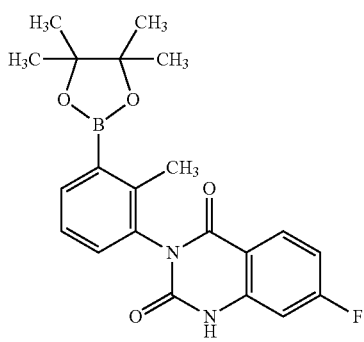

(I-43)

Using the procedure used to prepare Intermediate 8, 3-(3-bromo-2-methylphenyl)-7-fluoroquinazoline-2,4(1H, 3H)-dione [Intermediate 15B] was converted into 7-fluoro-3-(2-methyl-3-(4,4,5,5-tetramethyl-1,3,2-dioxaborolan-2-yl)phenyl)quinazoline-2,4(1H,3H)-dione. Mass spectrum m/z 397 (M+H)$^+$.

Intermediate 44

1-(4-Fluorophenyl)-3-(2-methyl-3-(4,4,5,5-tetramethyl-1,3,2-dioxaborolan-2-yl) phenyl)pyrimidine-2,4(1H,3H)-dione

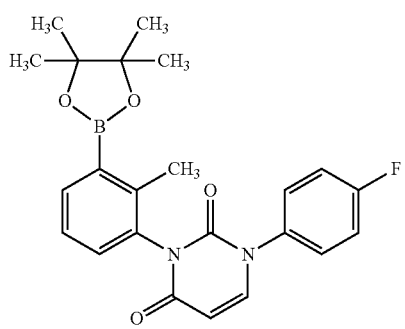

(I-44)

Intermediate 44A: Methyl 3-(4-methoxybenzylamino)-2-(phenylselanyl)propanoate

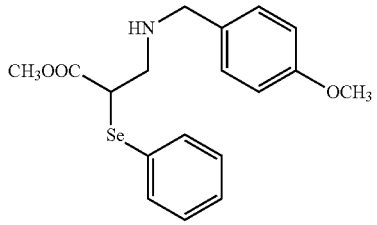

(I-44A)

A suspension of phenyl hypobromoselenoite (5.54 g, 23.5 mmol) and zinc(II) chloride (1.27 g, 9.29 mmol) in DCM (116 mL) was treated with methyl acrylate (2.09 mL, 23.2 mmol). The mixture was stirred at room temperature for 30 min, then was treated with (4-methoxyphenyl)methanamine (6.4 mL, 48.8 mmol), forming a thick suspension. After stirring for 16 h, the mixture was filtered, the collected precipitate was washed with EtOAc, and the combined filtrates were concentrated. The residue was purified by column chromatography on silica gel (120 g), eluting with EtOAc-hexanes (gradient from 0-50%), to provide methyl 3-(4-methoxybenzylamino)-2-(phenylselanyl) propanoate as a light brown oil (3.68 g, 42% yield). Mass spectrum m/z 380 (M+H)$^+$. $^1$H NMR (400 MHz, DMSO-d$_6$) δ 7.53-7.49 (m, 2H), 7.39-7.28 (m, 3H), 7.18 (d, J=8.6 Hz, 2H), 6.88-6.82 (m, 2H), 3.89 (dd, J=8.8, 5.9 Hz, 1H), 3.73 (s, 3H), 3.61 (s, 2H), 3.55 (s, 3H), 2.93-2.78 (m, 2H).

Intermediate 44B: 1-Bromo-3-isocyanato-2-methylbenzene

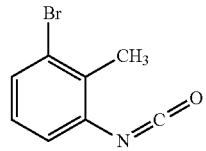

(I-44B)

A solution of triphosgene (2.25 g, 7.58 mmol) in toluene (27 mL), cooled in an ice-water bath, was treated slowly with a solution of 3-bromo-2-methylaniline (3.00 g, 16.1 mmol) and DIEA (5.6 mL, 32.2 mmol) in toluene (5.4 mL). The resulting suspension was stirred at room temperature for 2 h. The precipitate was removed by filtration and washed with EtOAc. The combined filtrates were diluted with EtOAc, washed with brine, dried and concentrated to provide 1-bromo-3-isocyanato-2-methylbenzene as a brown oil (3.68 g, 98% yield), used without purification. $^1$H NMR (400 MHz, DMSO-d$_6$) δ 7.49 (dd, J=8.1, 0.9 Hz, 1H), 7.31 (dd, J=7.9, 0.7 Hz, 1H), 7.15 (td, J=8.0, 0.7 Hz, 1H), 2.38 (s, 3H).

Intermediate 44C: 3-(3-Bromo-2-methylphenyl)-1-(4-methoxybenzyl)-5-(phenylselanyl) dihydropyrimidine-2,4(1H,3H)-dione

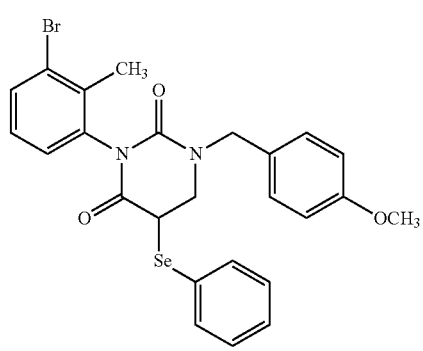

(I-44C)

A mixture of methyl 3-((4-methoxybenzyl)amino)-2-(phenylselanyl)propanoate (3.68 g, 9.73 mmol), 1-bromo-3-isocyanato-2-methylbenzene (2.27 g, 10.7 mmol), and K$_2$CO$_3$ (0.672 g, 4.86 mmol) in DMF (49 mL) was heated at 65° C. for 5 h. The cooled mixture was partitioned between water and EtOAc. And the organic phase was washed with brine, dried and concentrated to provide 3-(3-bromo-2-methylphenyl)-1-(4-methoxybenzyl)-5-(phenylselanyl)dihydropyrimidine-2,4(1H,3H)-dione as a light brown solid (5.43 g), used without further purification. Mass spectrum m/z 557, 559, 561 (M+H)$^+$.

Intermediate 44D: 3-(3-Bromo-2-methylphenyl)-1-(4-methoxybenzyl)pyrimidine-2,4(1H,3H)-dione

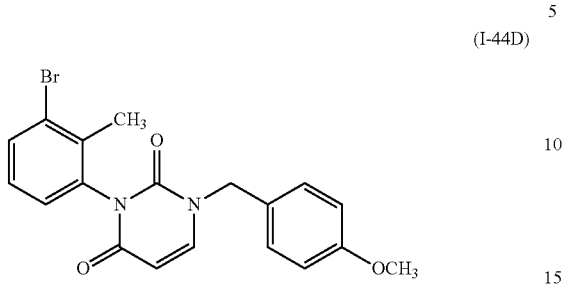

(I-44D)

A solution of 3-(3-bromo-2-methylphenyl)-1-(4-methoxybenzyl)-5-(phenylselanyl)dihydropyrimidine-2,4 (1H,3H)-dione (5.43 g, 9.73 mmol) in THF (97 mL) was treated with 30% aqueous hydrogen peroxide (5.0 mL, 48.6 mmol) and the mixture was stirred at room temperature for 30 min. Water was added and the mixture was extracted with EtOAc. The organic phase was washed with brine, dried and concentrated. The residue was purified by column chromatography on silica gel (220 g), eluting with EtOAc-hexanes (gradient from 25-70%), to provide 3-(3-bromo-2-methylphenyl)-1-(4-methoxybenzyl)pyrimidine-2,4(1H,3H)-dione as a white solid (2.10 g, 54% yield). Mass spectrum m/z 401, 403 (M+H)$^+$. $^1$H NMR (400 MHz, DMSO-d$_6$) δ 7.95 (d, J=7.9 Hz, 1H), 7.70-7.65 (m, 1H), 7.32-7.28 (m, 2H), 7.25-7.22 (m, 2H), 6.96-6.91 (m, 2H), 5.86 (d, J=7.9 Hz, 1H), 4.89 (d, J=2.4 Hz, 2H), 3.74 (s, 3H), 2.02 (s, 3H).

Intermediate 44E: 3-(3-Bromo-2-methylphenyl)pyrimidine-2,4(1H,3H)-dione

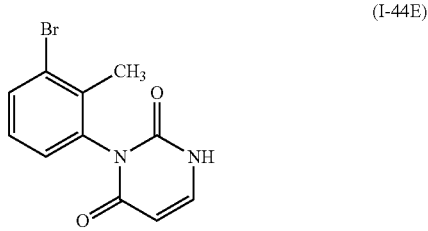 [SMILES: Cc1c(Br)cccc1-n1c(=O)cc[nH]c1=O]

(I-44E)

A solution of 3-(3-bromo-2-methylphenyl)-1-(4-methoxybenzyl)pyrimidine-2,4(1H,3H)-dione (0.87 g, 2.17 mmol) in TFA (5.5 mL) was treated with trifluoromethanesulfonic acid (0.55 mL) and the mixture was stirred at room temperature overnight. The mixture was slowly poured onto ice and stirred while warming to room temperature. The precipitate was collected by filtration, washed with water and dried to provide 3-(3-bromo-2-methylphenyl)pyrimidine-2,4(1H,3H)-dione as a purple solid (0.62 g, 96% yield). Mass spectrum m/z 281, 283 (M+H)$^+$. $^1$H NMR (400 MHz, DMSO-d$_6$) δ 11.36 (d, J=4.4 Hz, 1H), 7.67 (dd, J=6.5, 2.8 Hz, 1H), 7.60 (dd, J=7.7, 5.9 Hz, 1H), 7.27-7.21 (m, 2H), 5.72 (dd, J=7.7, 1.3 Hz, 1H), 2.07 (s, 3H).

Intermediate 44F: 3-(3-Bromo-2-methylphenyl)-1-(4-fluorophenyl)pyrimidine-2,4(1H,3H)-dione

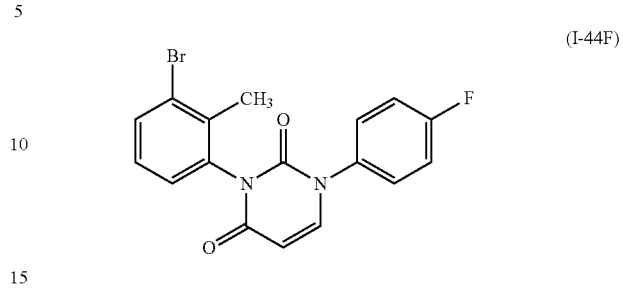

(I-44F)

A stirred suspension of copper(II) acetate (0.543 g, 2.99 mmol), 3-(3-bromo-2-methylphenyl)pyrimidine-2,4(1H, 3H)-dione (0.42 g, 1.49 mmol), (4-fluorophenyl) boronic acid (0.418 g, 2.99 mmol), and activated molecular sieves (750 mg) in dry DCM (25 mL) was treated with pyridine (0.363 mL, 4.48 mmol) and stirred at room temperature overnight. The mixture was diluted with DCM, filtered through CELITE®, and the solids were washed with DCM and THF. The combined filtrates were washed with water, dried and concentrated. The residue was purified by column chromatography on silica gel (40 g), eluting with EtOAc-hexanes (gradient from 20-40%), to give 3-(3-bromo-2-methylphenyl)-1-(4-fluorophenyl)pyrimidine-2,4(1H,3H)-dione as a yellow glassy solid (0.36 g, 43% yield). Mass spectrum m/z 375, 377 (M+H)$^+$. $^1$H NMR (400 MHz, DMSO-d$_6$) δ 7.91 (d, J=7.9 Hz, 1H), 7.68 (dd, J=7.9, 1.3 Hz, 1H), 7.60-7.51 (m, 2H), 7.40-7.22 (m, 4H), 5.95 (d, J=7.9 Hz, 1H), 2.21-2.12 (m, 3H).

Intermediate 44:

A mixture of 3-(3-bromo-2-methylphenyl)-1-(4-fluorophenyl)pyrimidine-2,4(1H,3H)-dione (250 mg, 0.666 mmol), 4,4,4',4',5,5,5',5'-octamethyl-2,2'-bi(1,3,2-dioxaborolane) (186 mg, 0.733 mmol), potassium acetate (131 mg, 1.33 mmol), and PdCl$_2$(dppf) DCM adduct (16 mg, 0.020 mmol) in dioxane (4.4 mL) was heated at 110° C. After 3 h, additional PdCl$_2$(dppf) DCM adduct was added and the mixture was heated at 110° C. for 6 h more. The cooled mixture was diluted with EtOAc, filtered through CELITE® and the solids were washed with EtOAc. The combined filtrates were washed sequentially with saturated aqueous NaHCO$_3$ and brine, and dried and concentrated. The residue was purified by column chromatography on silica gel (24 g), eluting with EtOAc-hexanes (gradient from 25-100%), to give impure 1-(4-fluorophenyl)-3-(2-methyl-3-(4,4,5,5-tetramethyl-1,3,2-dioxaborolan-2-yl)phenyl) pyrimidine-2,4(1H,3H)-dione as a yellow glassy solid (217 mg), used without further purification. Mass spectrum m/z 423 (M+H)$^+$. $^1$H NMR (400 MHz, DMSO-d$_6$) δ 7.90 (d, J=7.9 Hz, 1H), 7.69 (dd, J=7.0, 1.8 Hz, 1H), 7.61-7.52 (m, 2H), 7.40-7.26 (m, 4H), 5.94 (d, J=7.9 Hz, 1H), 2.24 (s, 3H), 1.32 (s, 12H).

Intermediate 45

4-Bromo-3-fluoro-7-(2-hydroxyethyl)-9H-carbazole-1-carboxamide

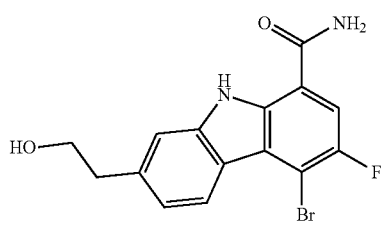

(I-45)

Intermediate 45A: Diethyl 2-(3-oxocyclohexyl)malonate

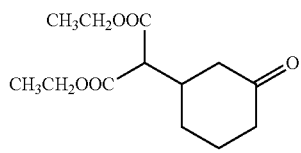

(I-45A)

A solution of cyclohex-2-enone (3.05 mL, 30 mmol) and diethyl malonate (4.58 mL, 30.0 mmol) in THF (30 mL) was treated with 1,8-diazabicyclo[5.4.0]undec-7-ene (4.52 mL, 30.0 mmol) and heated at 50° C. for 16 h. The cooled mixture was poured into EtOAc and washed sequentially with 1 M aqueous HCl and brine. The combined aqueous layers were extracted with EtOAc, and the combined organic phases were dried and concentrated to give diethyl 2-(3-oxocyclohexyl)malonate as an oil (8.0 g), used without further purification. Mass spectrum m/z 257 (M+H)$^+$.

Intermediate 45B: 5-Bromo-2-(1,3-diethoxy-1,3-dioxopropan-2-yl)-6-fluoro-2,3,4,9-tetrahydro-1H-carbazole-8-carboxylic acid

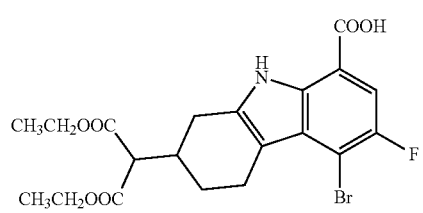

(I-45B)

A solution of diethyl 2-(3-oxocyclohexyl)malonate (15.26 g, 59.5 mmol) and 4-bromo-5-fluoro-2-hydrazinylbenzoic acid hydrochloride [Intermediate 24B] (17.0 g, 59.5 mmol) in acetic acid (120 mL) was heated at reflux for 2 h, then was stirred overnight at room temperature. The precipitate which formed was collected by filtration to provide a white solid. The filtrate was concentrated and purified by column chromatography on silica gel (80 g), eluting with EtOAc-hexanes (gradient from 0-100%). The resulting oily product was crystallized from a mixture of EtOAc, ether and hexanes to provide additional solid, which was combined with the first solid to provide 5-bromo-2-(1,3-diethoxy-1,3-dioxopropan-2-yl)-6-fluoro-2,3,4,9-tetrahydro-1H-carbazole-8-carboxylic acid as a white solid (10.5 g, 49% yield). Mass spectrum m/z 470, 472 (M+H)$^+$.

Intermediate 45C: Diethyl 2-(5-bromo-8-carbamoyl-6-fluoro-2,3,4,9-tetrahydro-1H-carbazol-2-yl)malonate

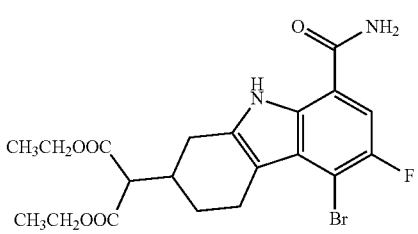

(I-45C)

A mixture of 5-bromo-2-(1,3-diethoxy-1,3-dioxopropan-2-yl)-6-fluoro-2,3,4,9-tetrahydro-1H-carbazole-8-carboxylic acid (0.981 g, 2.09 mmol), EDC (0.600 g, 3.13 mmol) and HOBT (0.383 g, 2.50 mmol) in THF (5 mL) was stirred at room temperature for 60 min. The mixture was treated with NH$_4$OH (1.74 mL, 12.5 mmol) and stirred at room temperature overnight. The mixture was diluted with EtOAc, washed sequentially with saturated aqueous Na$_2$CO$_3$ and brine. The combined aqueous layers were extracted with EtOAc, and the combined organic phases were dried and concentrated. The residue was purified by column chromatography on silica gel (40 g), eluting with EtOAc-hexanes (gradient from 0-100%), to provide diethyl 2-(5-bromo-8-carbamoyl-6-fluoro-2,3,4,9-tetrahydro-1H-carbazol-2-yl)malonate as a slightly yellow solid (440 mg, 45% yield). Mass spectrum m/z 469, 471 (M+H)$^+$.

Intermediate 45D: Diethyl 2-(5-bromo-8-carbamoyl-6-fluoro-9H-carbazol-2-yl)malonate

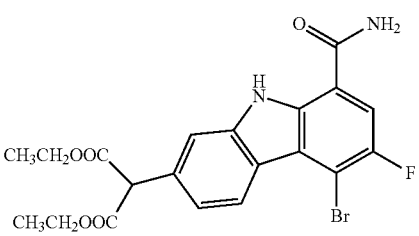

(I-45D)

A solution of diethyl 2-(5-bromo-8-carbamoyl-6-fluoro-2,3,4,9-tetrahydro-1H-carbazol-2-yl)malonate (2.26 g, 4.82 mmol) and 2,3-dichloro-5,6-dicyanobenzoquinone (2.30 g, 10.1 mmol) in THF (30 mL) was heated at reflux for 3 h. The cooled mixture was diluted with EtOAc and washed sequentially with saturated aqueous Na$_2$CO$_3$ and brine. The combined aqueous layers were extracted with EtOAc, and the combined organic phases were dried and partially concentrated. A white solid which formed was collected by filtration. The filtrate was passed through a pad of silica gel, eluting with EtOAc, and the effluent was concentrated to provide additional solid. The two solids were combined to provide diethyl 2-(5-bromo-8-carbamoyl-6-fluoro-9H-carbazol-2-yl) malonate as a white solid (1.86 g, 83% yield). Mass spectrum m/z 465, 467 (M+H)$^+$.

Intermediate 45E: Ethyl 2-(5 bromo-carbamoyl-6-furo-9H-carbazol-2-yl)acetate

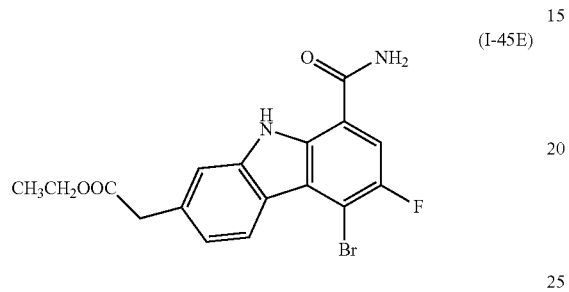

(I-45E)

A mixture of diethyl 2-(5-bromo-8-carbamoyl-6-fluoro-9H-carbazol-2-yl) malonate (1.30 g, 2.80 mmol), sodium chloride (0.28 g, 7.01 mmol) and water (0.25 mL, 14.01 mmol) in DMSO (6 mL) was heated at 150° C. for 20 h. The cooled mixture was poured into water, forming a precipitate. The precipitate was collected by filtration and dried, then was triturated with DCM. The solid was collected by filtration and dried to provide ethyl 2-(5-bromo-8-carbamoyl-6-fluoro-9H-carbazol-2-yl)acetate as a gray solid (930 mg, 84% yield). Mass spectrum m/z 393, 395 (M+H)$^+$. $^1$H NMR (400 MHz, DMSO-d$_6$) δ 11.70 (s, 1H), 8.54 (d, J=8.4 Hz, 1H), 8.25 (br. s., 1H), 8.00 (d, J=10.1 Hz, 1H), 7.72 (s, 1H), 7.69 (br. s., 1H), 7.19 (dd, J=8.4, 1.5 Hz, 1H), 4.11 (q, J=7.0 Hz, 2H), 3.82 (s, 2H), 1.21 (t, J=7.2 Hz, 3H).

Intermediate 45:

A solution of ethyl 2-(5-bromo-8-carbamoyl-6-fluoro-9H-carbazol-2-yl)acetate (500 mg, 1.27 mmol) in THF (10 mL) was treated with lithium borohydride (139 mg, 6.36 mmol) and stirred at room temperature overnight. The mixture was treated with saturated aqueous NH$_4$Cl and stirred for 15 min. The mixture was diluted with water and extracted twice with EtOAc. The combined organic phases were dried and concentrated, and the residue was purified by column chromatography on silica gel (40 g), eluting with EtOAc-hexanes (gradient from 30-100%), to provide 4-bromo-3-fluoro-7-(2-hydroxyethyl)-9H-carbazole-1-carboxamide as a white solid (310 mg, 69% yield). Mass spectrum m/z 351, 353 (M+H)$^+$. $^1$H NMR (400 MHz, DMSO-d$_6$) δ 11.58 (s, 1H), 8.50 (d, J=8.4 Hz, 1H), 8.24 (br. s., 1H), 7.98 (d, J=10.3 Hz, 1H), 7.72-7.63 (m, 2H), 7.15 (dd, J=8.4, 1.3 Hz, 1H), 4.68 (t, J=5.3 Hz, 1H), 3.73-3.64 (m, 2H), 2.90 (t, J=7.0 Hz, 2H).

Examples 1 and 2

3-Chloro-4-(R)-(3-(R)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (1), and 3-Chloro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (2)

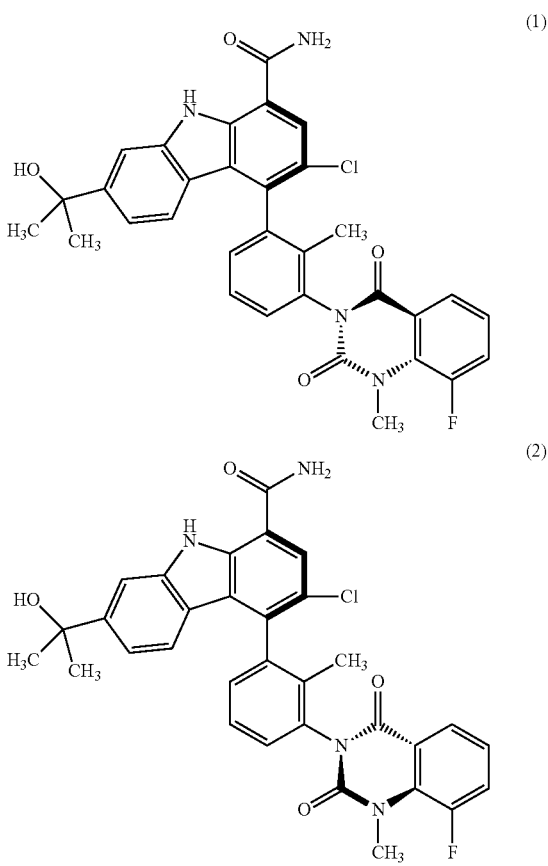

Preparation 1A: 3-Chloro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers)

A mixture of 4-bromo-3-chloro-7-(2-hydroxypropan-2-yl)-9H-carbazole-1-carboxamide [Intermediate 3] (100 mg, 0.262 mmol), 8-fluoro-1-methyl-3-(RS)-(2-methyl-3-(4,4,5,5-tetramethyl-1,3,2-dioxaborolan-2-yl)phenyl)quinazoline-2,4(1H,3H)-dione [Intermediate 2] (161 mg, 0.393 mmol), tetrakis(triphenylphosphine)palladium (15 mg, 0.013 mmol) and 2 M aqueous K$_3$PO$_4$ (0.26 mL, 0.524 mmol) in THF (2 mL) in a pressure reaction vial was heated at 90° C. for 2.5 h. The cooled mixture was concentrated, and the residue was purified by column chromatography on silica gel (40 g), eluting with DCM-MeOH—NH$_4$OH (gradient from 90:9:1-97:2.7:0.3). The resulting impure product was again purified by column chromatography on silica gel (40 g), eluting with EtOAc-hexanes (gradient from 50-100%), to give 3-chloro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as a white solid (110 mg, 68% yield). Mass spectrum m/z 567 (M+H-H$_2$O)$^+$. $^1$H NMR (400 MHz, chloroform-d) δ 10.46 (s, 1H), 8.17-8.10 (m, 1H), 7.76 (s, 1H), 7.69 (d, J=1.1 Hz, 1H), 7.59-7.53 (m, 1H), 7.48 (ddt, J=13.9, 8.1, 1.8 Hz, 1H), 7.39 (dd, J=12.4, 7.8 Hz, 2H), 7.28-7.19 (m, 2H), 6.97 (t, J=8.5 Hz, 1H), 3.87-3.93 (m, 3H), 1.87 (d, J=1.8 Hz, 3H), 1.65 (s, 3H), 1.65 (s, 3H).

Examples 1 and 2

A sample of the mixture of four atropisomers of 3-chloro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (90 mg) was separated by chiral super-critical fluid chromatography as follows: column: CHIRALPAK® AD-H (3×25 cm, 5 μm); Mobile Phase: CO$_2$-IPA (55:45) at 120 mL/min; sample preparation: 10 mg/mL; injection: 1 mL. The second peak eluting from the column provided 3-chloro-4-(R)-(3-(R)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide [Example 1] as a white solid. The isomeric purity was determined to be 97.7%. Mass spectrum m/z 567 (M+H-H$_2$O)$^+$. $^1$H NMR (400 MHz, chloroform-d) δ 10.46 (s, 1H), 8.15 (d, J=7.3 Hz, 1H), 7.75 (s, 1H), 7.69 (d, J=1.1 Hz, 1H), 7.59-7.54 (m, 1H), 7.49 (ddd, J=13.9, 8.0, 1.7 Hz, 1H), 7.43-7.36 (m, 2H), 7.28-7.19 (m, 2H), 6.97 (d, J=8.4 Hz, 1H), 3.89 (d, J=7.9 Hz, 3H), 1.88 (s, 3H), 1.65 (s, 6H).

The fourth peak eluting from the column provided 3-chloro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide [Example 2] as a white solid. The isomeric purity was determined to be 99.5%. Mass spectrum m/z 567 (M+H-H$_2$O)$^+$. $^1$H NMR (400 MHz, chloroform-d) δ 10.46 (s, 1H), 8.13 (d, J=7.3 Hz, 1H), 7.75 (s, 1H), 7.69 (d, J=1.3 Hz, 1H), 7.59-7.53 (m, 1H), 7.48 (ddd, J=13.9, 8.0, 1.7 Hz, 1H), 7.39 (dd, J=11.1, 7.8 Hz, 2H), 7.27-7.21 (m, 2H), 6.99 (d, J=8.4 Hz, 1H), 3.91 (d, J=7.9 Hz, 3H), 1.88 (s, 3H), 1.66 (s, 6H).

Figure 3:
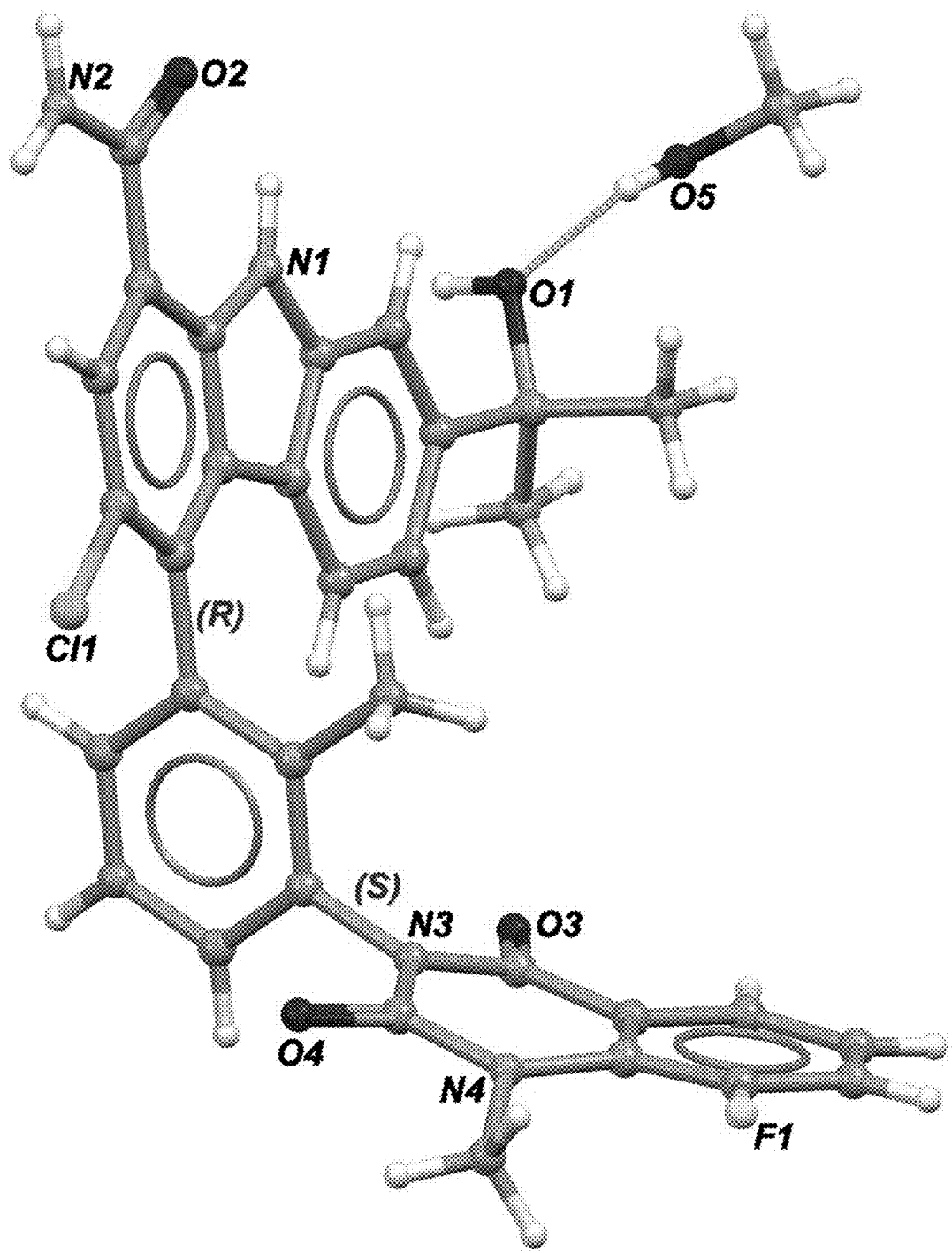
FIG. 3 shows the absolute stereochemistry of Example 2 methanolate, crystal Form M-1.

The absolute configuration of Example 2 was confirmed by single crystal x-ray analysis of crystals prepared by dissolving the compound in excess methanol and slowly evaporating the solvent at room temperature to provide a methanol solvate (crystalline form M-1). Unit cell dimensions: a=9.75 Å, b=14.21 Å, c=21.26 Å, α=90.0°, β=90.0°, γ=90.0°; Space group: P2$_1$2$_1$2$_1$; Molecules of Example 2/asymmetric unit: 1; Volume/Number of molecules in the unit cell=736 Å$^3$; Density (calculated)=1.391 g/cm$^3$. Fractional atomic coordinates at 203 K are given in Table 2, and a depiction of the structure is given in FIG. 3.

Example 3

3-Chloro-7-(2-hydroxypropan-2-yl)-4-(R)-(2-methyl-3-(1-methyl-2,4-dioxo-1,2-dihydroquinazolin-3(4H)-yl)phenyl)-9H-carbazole-1-carboxamide (single atropisomer)

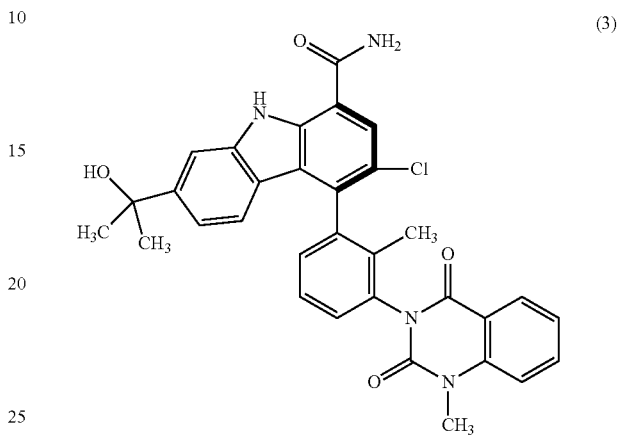

(3)

Preparation 3A: 3-Chloro-7-(2-hydroxypropan-2-yl)-4-(2-methyl-3-(1-methyl-2,4-dioxo-1,2-dihydroquinazolin-3(4H)-yl)phenyl)-9H-carbazole-1-carboxamide (mixture of four atropisomers)

A mixture of 4-bromo-3-chloro-7-(2-hydroxypropan-2-yl)-9H-carbazole-1-carboxamide [Intermediate 3] (100 mg, 0.262 mmol), 1-methyl-3-(RS)-(2-methyl-3-(4,4,5,5-tetramethyl-1,3,2-dioxaborolan-2-yl)phenyl)quinazoline-2,4(1H,3H)-dione [Intermediate 4] (154 mg, 0.393 mmol), 2 M aqueous K$_3$PO$_4$ (0.26 mL, 0.524 mmol) and tetrakis(triphenylphosphine)palladium (15 mg, 0.013 mmol) in THF (2 mL) in a pressure reaction vial was heated at 90° C. for 4 h. The cooled mixture was concentrated and the residue was purified by column chromatography on silica gel (40 g), eluting with DCM:MeOH:NH$_4$OH (gradient from 90:9:1-97:2.7:0.3). The resulting impure product was again purified by column chromatography on silica gel (40 g), eluting with EtOAc-hexanes (gradient from 50-100%), to give 3-chloro-7-(2-hydroxypropan-2-yl)-4-(2-methyl-3-(1-methyl-2,4-dioxo-1,2-dihydroquinazolin-3(4H)-yl)phenyl)-9H-carbazole-1-carboxamide (mixture of four atropisomers) as a white solid (105 mg, 68% yield). Mass spectrum m/z 549 (M+H-H$_2$O)$^+$. $^1$H NMR (400 MHz, chloroform-d) δ 10.46 (s, 1H), 8.33 (ddd, J=11.8, 7.9, 1.4 Hz, 1H), 7.80-7.74 (m, 2H), 7.69 (t, J=1.7 Hz, 1H), 7.58-7.52 (m, 1H), 7.41 (d, J=7.5 Hz, 1H), 7.38-7.30 (m, 3H), 7.24 (ddd, J=13.9, 8.4, 1.7 Hz, 1H), 6.98 (dd, J=12.8, 8.4 Hz, 1H), 3.67-3.76 (m, 3H), 1.88 (d, J=1.8 Hz, 3H), 1.65 (s, 3H), 1.65 (s, 3H).

Example 3

A sample of the mixture of four atropisomers of 3-chloro-7-(2-hydroxypropan-2-yl)-4-(2-methyl-3-(1-methyl-2,4-dioxo-1,2-dihydroquinazolin-3(4H)-yl)phenyl)-9H-carbazole-1-carboxamide was separated by chiral super-critical fluid chromatography as follows: column: CHIRALPAK® IB (2×25 cm, 5 μm); Mobile Phase: CO$_2$-MeOH (65:35) at 55 mL/min. The third peak eluting from the column provided a single atropisomer of 3-chloro-7-(2-hydroxypropan-2-yl)-4-(R)-(2-methyl-3-(1-methyl-2,4-dioxo-1,2-dihydroquinazolin-3(4H)-yl)phenyl)-9H-carbazole-1-carboxamide as a white solid. The chiral purity was determined to be 97.7%. Mass spectrum m/z 549 (M+H-H₂O)⁺. ¹H NMR (400 MHz, chloroform-d) δ 10.45 (s, 1H), 8.32 (dd, J=8.0, 1.7 Hz, 1H), 7.80-7.73 (m, 2H), 7.69 (d, J=1.1 Hz, 1H), 7.59-7.53 (m, 1H), 7.44-7.31 (m, 4H), 7.26 (dd, J=8.4, 1.5 Hz, 1H), 7.01 (d, J=8.4 Hz, 1H), 3.72 (s, 3H), 1.89 (s, 3H), 1.66 (s, 6H)

Example 4

3-Chloro-4-(R)-(3-(1,8-dimethyl-2,4-dioxo-1,2-dihydroquinazolin-3(4H)-yl)-2-methylphenyl)-7-(2-hydroxypropan-2-yl)-9H-carbazole-1-carboxamide (single atropisomer)

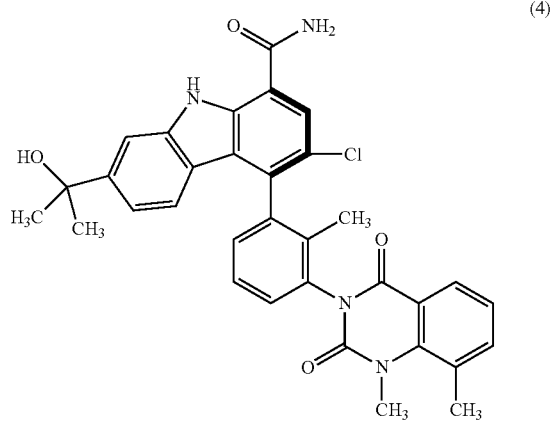

(4)

Preparation 4A: 3-Chloro-4-(3-(1,8-dimethyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers)

A mixture of 4-bromo-3-chloro-7-(2-hydroxypropan-2-yl)-9H-carbazole-1-carboxamide [Intermediate 3] (100 mg, 0.262 mmol), 1,8-dimethyl-3-(2-methyl-3-(4,4,5,5-tetramethyl-1,3,2-dioxaborolan-2-yl)phenyl)quinazoline-2,4(1H,3H)-dione [Intermediate 9] (138 mg, 0.341 mmol), Cs₂CO₃ (171 mg, 0.524 mmol) and PdCl₂(dppf) DCM adduct (10.7 mg, 0.013 mmol) in THF (2 mL) and water (500 µl) was heated at 60° C. for 18 h. The cooled mixture was concentrated, and the residue was purified by column chromatography on silica gel (40 g), eluting with EtOAc-hexanes (gradient from 30-100%), to give 3-chloro-4-(RS)-(3-(RS)-(1,8-dimethyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as a light yellow solid (97 mg, 57% yield). Mass spectrum m/z 563 (M+H-H₂O)⁺. ¹H NMR (400 MHz, chloroform-d) δ 10.45 (s, 1H), 8.21-8.15 (m, 1H), 7.75 (d, J=0.9 Hz, 1H), 7.69 (d, J=1.5 Hz, 1H), 7.59-7.51 (m, 2H), 7.44-7.40 (m, 1H), 7.36 (dd, J=7.7, 1.1 Hz, 1H), 7.26-7.19 (m, 2H), 6.98 (t, J=7.9 Hz, 1H), 3.80 (d, J=9.9 Hz, 3H), 2.70 (d, J=5.7 Hz, 3H), 1.88 (s, 3H), 1.64-1.66 (m, 6H).

Example 4

A sample of the mixture of four atropisomers of 3-chloro-4-(3-(1,8-dimethyl-2,4-dioxo-1,2-dihydroquinazolin-3(4H)-yl)-2-methylphenyl)-7-(2-hydroxypropan-2-yl)-9H-carbazole-1-carboxamide (90 mg) was separated by chiral supercritical fluid chromatography as follows: column: CHIRALPAK® AD-H (3×25 cm, 5 µm); Mobile Phase: CO₂-IPA (55:45) at 85 mL/min; sample preparation: 18 mg/mL in MeOH; injection: 2.5 mL. The fourth peak eluting from the column provided a single atropisomer of 3-chloro-4-(R)-(3-(1,8-dimethyl-2,4-dioxo-1,2-dihydroquinazolin-3(4H)-yl)-2-methylphenyl)-7-(2-hydroxypropan-2-yl)-9H-carbazole-1-carboxamide as a white solid (17 mg). The chiral purity was determined to be greater than 99%. Mass spectrum m/z 563 (M+H-H₂O)⁺. ¹H NMR (400 MHz, chloroform-d) δ 10.45 (s, 1H), 8.17 (dd, J=7.8, 1.2 Hz, 1H), 7.75 (s, 1H), 7.69 (d, J=1.1 Hz, 1H), 7.58-7.51 (m, 2H), 7.42 (dd, J=7.9, 1.1 Hz, 1H), 7.36 (dd, J=7.7, 1.1 Hz, 1H), 7.27-7.19 (m, 2H), 6.99 (d, J=8.4 Hz, 1H), 3.81 (s, 3H), 2.71 (s, 3H), 1.87 (s, 3H), 1.65 (s, 6H).

Examples 5 and 6

3-Chloro-7-(2-hydroxypropan-2-yl)-4-(R)-(3-(R)-(7-methoxy-1-methyl-2,4-dioxo-1,2-dihydroquinazolin-3(4H)-yl)-2-methylphenyl)-9H-carbazole-1-carboxamide, and 3-Chloro-7-(2-hydroxypropan-2-yl)-4-(R)-(3-(S)-(7-methoxy-1-methyl-2,4-dioxo-1,2-dihydroquinazolin-3(4H)-yl)-2-methylphenyl)-9H-carbazole-1-carboxamide (single atropisomers)

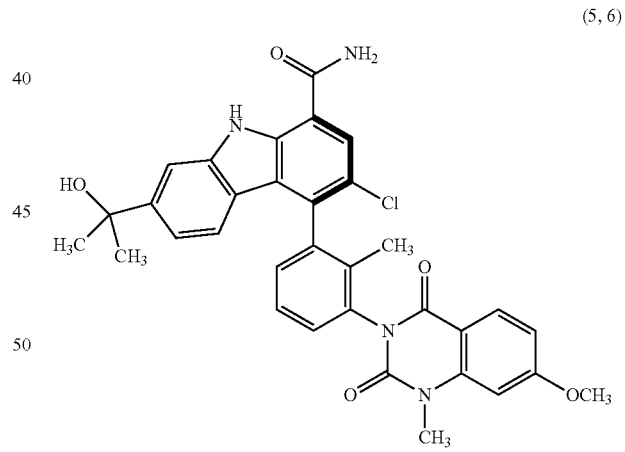

(5, 6)

A mixture of 4-bromo-3-chloro-7-(2-hydroxypropan-2-yl)-9H-carbazole-1-carboxamide [Intermediate 3] (200 mg, 0.524 mmol), 7-methoxy-1-methyl-3-(2-methyl-3-(4,4,5,5-tetramethyl-1,3,2-dioxaborolan-2-yl)phenyl)quinazoline-2,4(1H,3H)-dione [Intermediate 14] (221 mg, 0.524 mmol), Cs₂CO₃ (512 mg, 1.57 mmol) and PdCl₂(dppf) DCM adduct (21.4 mg, 0.026 mmol) in THF (3 mL) and water (0.50 mL) was heated at 60° C. overnight, then at 90° C. for 4 h. The cooled mixture was concentrated, and the residue was purified by column chromatography on silica gel (40 g), eluting with EtOAc-hexanes (gradient from 50-100%), to give 3-chloro-7-(2-hydroxypropan-2-yl)-4-(3-(7-methoxy-1- methyl-2,4-dioxo-1,2-dihydroquinazolin-3(4H)-yl)-2-methylphenyl)-9H-carbazole-1-carboxamide (mixture of four atropisomers) (164 mg, 92% yield). This material was separated by chiral super-critical fluid chromatography as follows: column: CHIRALPAK® AD-H (3×25 cm, 5 μm); Mobile Phase: CO$_2$-IPA (60:40) at 85 mL/min; sample preparation: 20.3 mg/mL in MeOH; injection: 0.75 mL.

The third peak eluting from the column provided a single atropisomer of 3-chloro-7-(2-hydroxypropan-2-yl)-4-(R)-(3-(7-methoxy-1-methyl-2,4-dioxo-1,2-dihydroquinazolin-3(4H)-yl)-2-methylphenyl)-9H-carbazole-1-carboxamide [Example 5] (14 mg). The chiral purity was determined to be greater than 99%. Mass spectrum m/z 579 (M+H-H$_2$O)$^+$. $^1$H NMR (400 MHz, chloroform-d) δ 10.43 (s, 1H), 8.24 (d, J=8.8 Hz, 1H), 7.73 (s, 1H), 7.65 (d, J=1.1 Hz, 1H), 7.55-7.49 (m, 1H), 7.44-7.34 (m, 1H), 7.35-7.31 (m, 1H), 7.19 (dd, J=8.5, 1.7 Hz, 1H), 6.94 (d, J=8.4 Hz, 1H), 6.85 (dd, J=8.8, 2.2 Hz, 1H), 6.69 (d, J=2.2 Hz, 1H), 3.95 (s, 3H), 3.63 (s, 3H), 1.85 (s, 3H), 1.62 (s, 6H).

The fourth peak eluting from the column provided the other single atropisomer 3-chloro-7-(2-hydroxypropan-2-yl)-4-(R)-(3-(7-methoxy-1-methyl-2,4-dioxo-1,2-dihydroquinazolin-3(4H)-yl)-2-methylphenyl)-9H-carbazole-1-carboxamide [Example 6] (28 mg). The chiral purity was determined to be greater than 99%. Mass spectrum m/z 579 (M+H-H$_2$O)$^+$. $^1$H NMR (400 MHz, chloroform-d) δ 10.41 (s, 1H), 8.21 (d, J=8.8 Hz, 1H), 7.71 (s, 1H), 7.66 (d, J=1.1 Hz, 1H), 7.55-7.49 (m, 1H), 7.41-7.36 (m, 1H), 7.35-7.31 (m, 1H), 7.22 (dd, J=8.4, 1.5 Hz, 1H), 6.97 (d, J=8.4 Hz, 1H), 6.84 (dd, J=9.0, 2.2 Hz, 1H), 6.70 (d, J=2.2 Hz, 1H), 3.95 (s, 3H), 3.65 (s, 3H), 1.85 (s, 3H), 1.63 (s, 6H).

Example 7

3-Chloro-7-(2-hydroxypropan-2-yl)-4-(R)-(3-(8-methoxy-1-methyl-2,4-dioxo-1,2-dihydroquinazolin-3(4H)-yl)-2-methylphenyl)-9H-carbazole-1-carboxamide (single atropisomer)

(7)

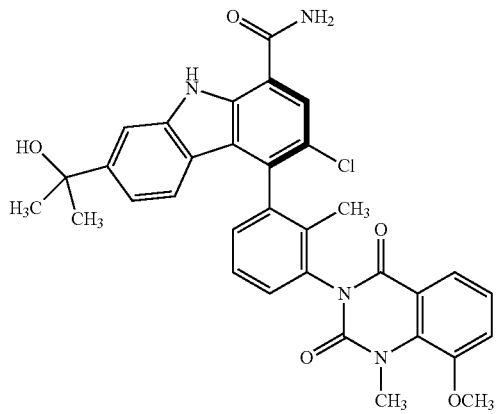

A mixture of 4-bromo-3-chloro-7-(2-hydroxypropan-2-yl)-9H-carbazole-1-carboxamide [Intermediate 3](200 mg, 0.524 mmol), 8-methoxy-1-methyl-3-(2-methyl-3-(4,4,5,5-tetramethyl-1,3,2-dioxaborolan-2-yl)phenyl)quinazoline-2,4(1H,3H)-dione [Intermediate 12] (221 mg, 0.524 mmol), Cs$_2$CO$_3$ (512 mg, 1.57 mmol) PdCl$_2$(dppf) DCM adduct (21.4 mg, 0.026 mmol) in THF (3 mL) and water (0.50 mL) in a pressure reaction vial was heated at 60° C. overnight, then at 90° C. for 4 hours. The cooled mixture was diluted with DCM and MeOH, and concentrated. The residue was purified by column chromatography on silica gel (24 g), eluting with EtOAc-hexanes (gradient from 20-55%), to give a mixture of four atropisomers of 3-chloro-7-(2-hydroxypropan-2-yl)-4-(3-(8-methoxy-1-methyl-2,4-dioxo-1,2-dihydroquinazolin-3(4H)-yl)-2-methylphenyl)-9H-carbazole-1-carboxamide (136 mg, 41% yield). This material was separated by chiral super-critical fluid chromatography as follows: column: CHIRALPAK® AD-H (3×25 cm, 5 μm); Mobile Phase: CO$_2$-IPA (55:45) at 85 mL/min; sample preparation: 17 mg/mL in MeOH; injection: 1.0 mL. The fourth peak eluting from the column provided a single atropisomer of 3-chloro-7-(2-hydroxypropan-2-yl)-4-(R)-(3-(8-methoxy-1-methyl-2,4-dioxo-1,2-dihydroquinazolin-3(4H)-yl)-2-methylphenyl)-9H-carbazole-1-carboxamide (26 mg, 20% yield). The chiral purity was determined to be greater than 99%. Mass spectrum m/z 579 (M+H-H$_2$O)$^+$. $^1$H NMR (400 MHz, chloroform-d) δ 10.42 (s, 1H), 7.90 (dd, J=7.2, 2.3 Hz, 1H), 7.71 (s, 1H), 7.66 (d, J=1.1 Hz, 1H), 7.55-7.49 (m, 1H), 7.40-7.36 (m, 1H), 7.35-7.31 (m, 1H), 7.25-7.19 (m, 3H), 6.97 (d, J=8.4 Hz, 1H), 3.94 (s, 3H), 3.91 (s, 3H), 1.85 (s, 3H), 1.63 (s, 6H).

Example 8

3-Chloro-4-(R)-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (single atropisomer)

(8)

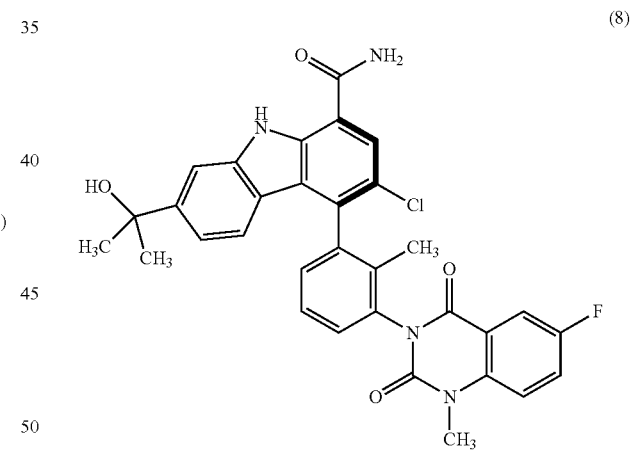

A mixture of 4-bromo-3-chloro-7-(2-hydroxypropan-2-yl)-9H-carbazole-1-carboxamide [Intermediate 3] (200 mg, 0.524 mmol), 6-fluoro-1-methyl-3-(2-methyl-3-(4,4,5,5-tetramethyl-1,3,2-dioxaborolan-2-yl)phenyl)quinazoline-2,4(1H,3H)-dione [Intermediate 13] (215 mg, 0.524 mmol), Cs$_2$CO$_3$ (512 mg, 1.57 mmol) and PdCl$_2$(dppf) DCM adduct (21.4 mg, 0.026 mmol) in THF (3 mL) and water (1 mL) was heated at 60° C. overnight, then at 90° C. for 4 h. The cooled mixture was concentrated and the residue was purified twice by column chromatography on silica gel (40 g), eluting with EtOAc-hexanes (gradient from 50-100%), to give a mixture of four atropisomers of 3-chloro-4-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (129 mg, 39% yield). This material was separated by chiral super-critical fluid chromatography as follows: column: CHIRALPAK® AD-H (3×25 cm, 5 μm); Mobile Phase: $CO_2$-MeOH-MeCN (65:17.5:17.5) at 85 mL/min; sample preparation: 15.4 mg/mL in MeOH; injection: 0.5 mL. The third peak eluting from the column provided a single atropisomer of 3-chloro-4-(R)-(3-(6-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (33 mg). The isomeric purity was determined to be greater than 98%. Mass spectrum m/z 567 $(M+H-H_2O)^+$. $^1$H NMR (400 MHz, chloroform-d) δ 10.44 (br. s., 1H), 8.29 (dd, J=8.1, 6.4 Hz, 1H), 7.73 (s, 1H), 7.66 (s, 1H), 7.56-7.49 (m, 1H), 7.36 (dd, J=15.2, 7.3 Hz, 2H), 7.22 (d, J=6.8 Hz, 1H), 7.04-6.92 (m, 3H), 3.65 (s, 3H), 1.84 (s, 3H), 1.63 (s, 6H).

Example 9

3-Chloro-4-(R)-(3-(7-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (single atropisomer)

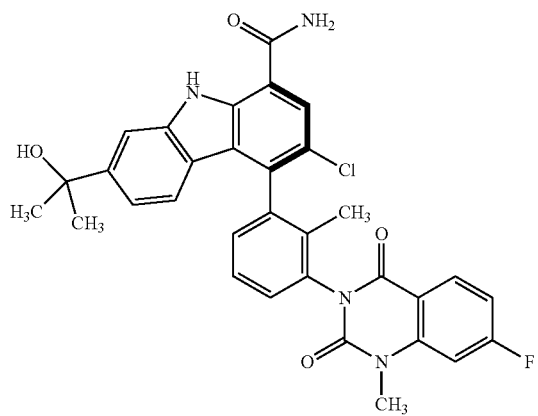

(9)

A mixture of 4-bromo-3-chloro-7-(2-hydroxypropan-2-yl)-9H-carbazole-1-carboxamide [Intermediate 3] (200 mg, 0.524 mmol), 7-fluoro-1-methyl-3-(2-methyl-3-(4,4,5,5-tetramethyl-1,3,2-dioxaborolan-2-yl)phenyl)quinazoline-2,4(1H,3H)-dione [Intermediate 15] (215 mg, 0.524 mmol), $Cs_2CO_3$ (512 mg, 1.57 mmol) and $PdCl_2$(dppf) DCM adduct (21.4 mg, 0.026 mmol) in THF (3 mL) and water (0.50 mL) was heated at 90° C. for 4 h. The cooled mixture was concentrated, and the residue was purified by column chromatography on silica gel (220 g), eluting with EtOAc-hexanes (gradient from 0-40%), to provide a mixture of four atropisomers of 3-chloro-4-(3-(7-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (164 mg, 53% yield). The material was separated by chiral super-critical fluid chromatography as follows: column: Lux Cel2 (3×25 cm, 5 μm); Mobile Phase: $CO_2$-MeOH-MeCN (62:19:19) at 85 mL/min; sample preparation: 30 mg/mL in MeOH; injection: 0.5 mL. The material isolated from the third peak eluting from the column was again separated by chiral super-critical fluid chromatography as follows: column: CHIRALPAK® AS (3×25 cm, 5 μm); Mobile Phase: $CO_2$-MeOH-MeCN (68:16:16) at 85 mL/min; sample preparation: 11.4 mg/mL in MeOH; injection: 3.5 mL. The first peak eluting from the column provided a single atropisomer of 3-chloro-4-(R)-(3-(7-fluoro-1-methyl-2,4-dioxo-1,2-dihydroquinazolin-3(4H)-yl)-2-methylphenyl)-7-(2-hydroxypropan-2-yl)-9H-carbazole-1-carboxamide as a white solid (25 mg, 15% yield). The isomeric purity was determined to be greater than 98%. Mass spectrum m/z 567 $(M+H-H_2O)^+$. $^1$H NMR (400 MHz, chloroform-d) δ 10.46 (s, 1H), 8.31 (dd, J=8.6, 6.2 Hz, 1H), 7.76 (s, 1H), 7.68 (d, J=1.1 Hz, 1H), 7.58-7.52 (m, 1H), 7.38 (ddd, J=14.1, 7.8, 1.0 Hz, 2H), 7.24 (dd, J=8.4, 1.5 Hz, 1H), 7.06-6.95 (m, 3H), 3.67 (s, 4H), 1.86 (s, 3H), 1.65 (s, 6H).

Example 10

3-Chloro-4-(RS)-(3-(RS)-(6,8-difluoro-2,4-dioxo-1,2-dihydroquinazolin-3(4H)-yl)-2-methylphenyl)-7-(2-hydroxypropan-2-yl)-9H-carbazole-1-carboxamide (mixture of four atropisomers)

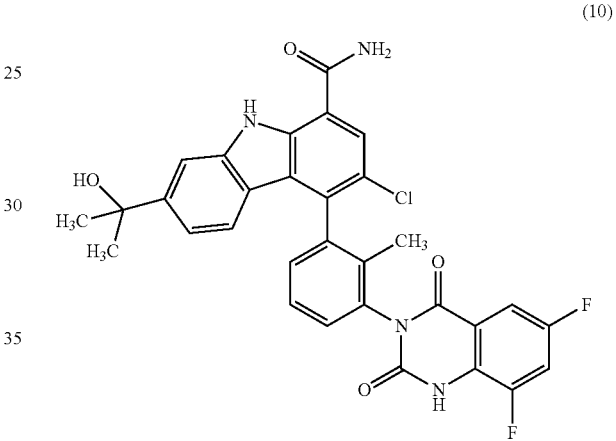

(10)

A mixture of 4-bromo-3-chloro-7-(2-hydroxypropan-2-yl)-9H-carbazole-1-carboxamide [Intermediate 3] (10 mg, 0.026 mmol), 6,8-difluoro-3-(2-methyl-3-(4,4,5,5-tetramethyl-1,3,2-dioxaborolan-2-yl)phenyl)quinazoline-2,4(1H, 3H)-dione [Intermediate 16] (14.1 mg, 0.034 mmol), 1,1'-bis(di-tert-butylphosphino)ferrocene palladium(II) chloride (12.8 mg, 0.020 mmol) and THF (2 mL) in a reaction vial was treated with 2 M aqueous $K_3PO_4$ (0.039 mL, 0.079 mmol). The vial was sealed and subjected to three evacuate-fill cycles with nitrogen. The mixture was stirred at room temperature overnight. The phases of the mixture were separated, the aqueous phase was extracted twice with EtOAc, and the combined organic phases were dried and concentrated. The residue was purified by column chromatography on silica gel (40 g), eluting with EtOAc-hexanes (gradient from 80-100%). The isolated material was triturated with MeOH to give a solid after filtration. The filtrate was concentrated and subjected to column chromatography on silica (40 g), eluting with DCM-MeOH—$NH_4OH$ (gradient from 90:9:1-97:2.7:0.3) to give additional solid. The two solids were combined to provide 3-chloro-4-(3-(6,8-difluoro-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as a pale yellow solid (164 mg, 71% yield). Mass spectrum m/z 571 $(M+H-H_2O)^+$. $^1$H NMR (500 MHz, MeOH-$d_4$) δ 8.04 (d, J=2.0 Hz, 1H), 7.70-7.68 (m, 1H), 7.65 (dd, J=7.2, 3.2 Hz, 1H), 7.57-7.52 (m, 1H), 7.43-7.34 (m, 3H), 7.18-7.07 (m, 1H), 6.90 (dd, J=8.4, 3.0 Hz, 1H), 1.84 (s, 3H), 1.62-1.56 (m, 6H).

Example 11

3-Chloro-4-(R)-(3-(S)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide (single atropisomer)

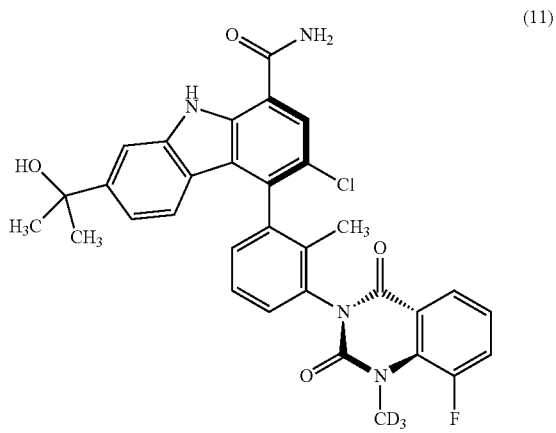

(11)

A solution of 4-bromo-3-chloro-7-(2-hydroxypropan-2-yl)-9H-carbazole-1-carboxamide [Intermediate 3] (3.08 g, 8.07 mmol) and 8-fluoro-1-methyl($d_3$)-3-(S)-(2-methyl-3-(4,4,5,5-tetramethyl-1,3,2-dioxaborolan-2-yl)phenyl)quinazoline-2,4(1H,3H)-dione [Intermediate 21] (4.00 g, 9.68 mmol) in THF (33 mL) was treated with 2 M aqueous $K_3PO_4$ (8.25 mL, 16.5 mmol). The mixture was bubbled with argon for ca. 4 min while agitating on an ultrasonic bath, then was treated with 1,1'-bis(di-tert-butylphosphino)ferrocene palladium(II) chloride (447 mg, 0.686 mmol). The reaction vessel was sealed and subjected to six evacuate-fill cycles with argon. The mixture was stirred at 50° C. for 16.5 h, then was cooled to room temperature. The mixture was diluted with EtOAc and washed with water. The aqueous phase was extracted twice with EtOAc and the combined organic phases were washed with brine, dried and concentrated. The residue was purified by column chromatography on silica gel (330 g), eluting with EtOAc-hexanes (gradient from 40-100%), to provide 3-chloro-4-(3-(S)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide (mixture of two diastereomers) as a light yellow-tan solid (3.877 g, 78% yield).

Material prepared by this method (5.01 g) was separated by chiral super-critical fluid chromatography as follows: column: CHIRALPAK® AS-H (3×25 cm, 5 µm); Mobile Phase: $CO_2$-MeOH (70:30) at 160 mL/min, 40° C.; sample preparation: 22.75 mg/mL in 2:1 MeOH-dichloromethane; injection: 1.4 mL. Pooled fractions containing the first peak eluting from the column were concentrated, and the residue was sonicated in a small amount of methanol. The precipitate was collected by filtration, rinsed with methanol and dried to provide 3-chloro-4-(R)-(3-(S)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide as a white solid (2.029 g). Mass spectrum m/z 570 $(M+H-H_2O)^+$, 610 $(M+Na)^+$. $^1H$ NMR (400 MHz, MeOH-$d_4$) δ 8.12-8.03 (m, 2H), 7.74 (d, J=1.1 Hz, 1H), 7.67-7.53 (m, 2H), 7.46 (dd, J=7.9, 1.1 Hz, 1H), 7.39-7.29 (m, 2H), 7.17 (dd, J=8.5, 1.7 Hz, 1H), 6.96-6.87 (m, 1H), 1.81 (s, 3H), 1.61 (d, J=1.3 Hz, 6H). $[α]_D$: +85.1° (c 2.38, $CHCl_3$). DSC melting point onset temperature=255.6° C. (heating rate=10° C./min.).

Figure 4:
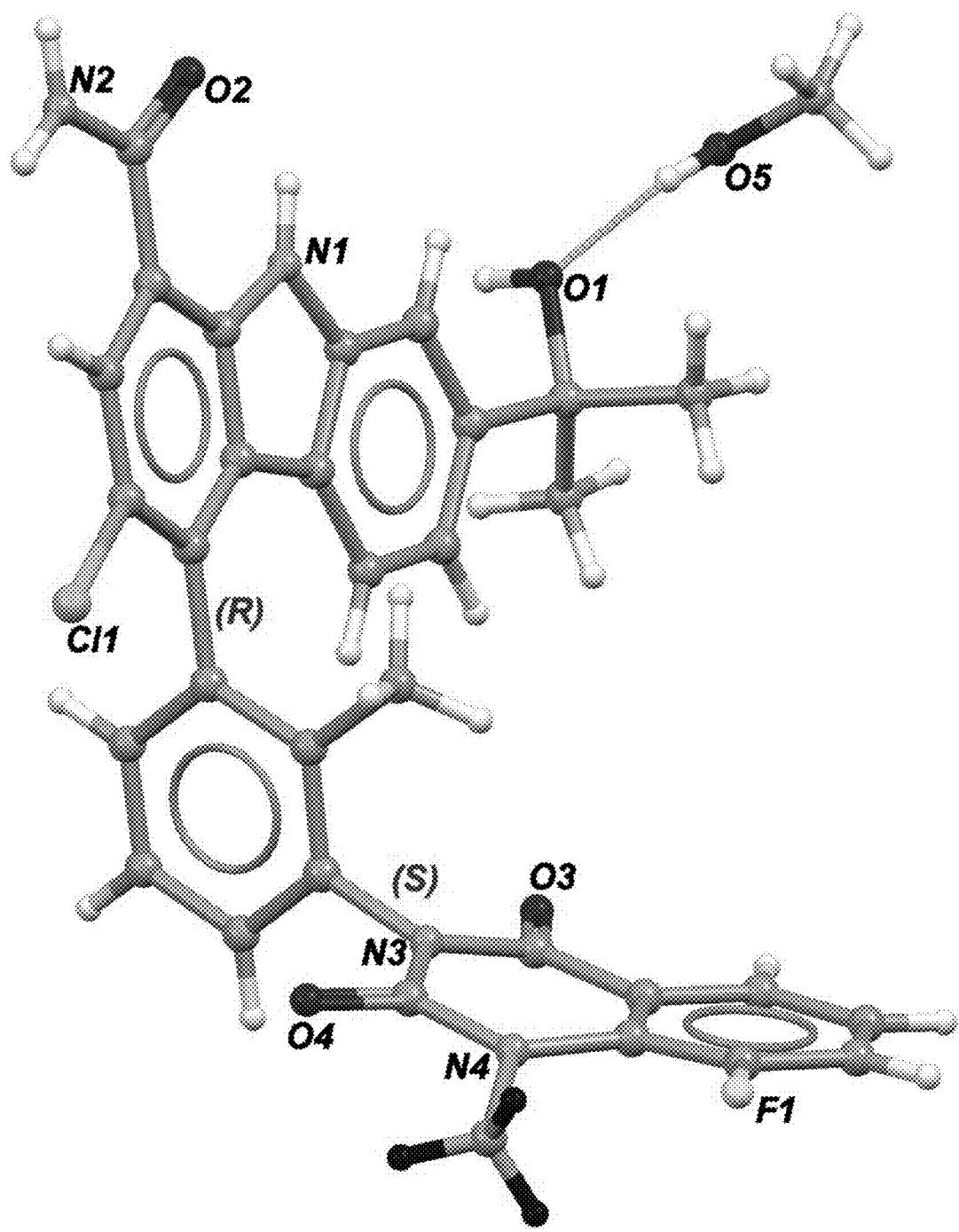
FIG. 4 shows the absolute stereochemistry of Example 11 methanolate, crystal Form M-1.

The absolute configuration of Example 11 was confirmed by single crystal x-ray analysis of crystals prepared by dissolving the compound in 1:1:1 methanol/acetonitrile/acetone and slowly evaporating the solvent at room temperature to provide a methanol solvate (crystalline form M-1). Unit cell dimensions: a=9.78 Å, b=14.26 Å, c=21.38 Å, α=90.0°, β=90.0°, γ=90.0°; Space group: $P2_12_12_1$; Molecules of Example 11/asymmetric unit: 1; Volume/Number of molecules in the unit cell=746 Å$^3$; Density (calculated)=1.381 g/cm$^3$. Fractional atomic coordinates at room temperature are given in Table 5, and a depiction of the structure is given in FIG. 4. The absolute configuration was further confirmed by single crystal x-ray analysis of crystals prepared by dissolving Example 11 in excess aqueous acetone and slowly evaporating the solvent at room temperature to provide a monohydrate (crystalline form H-1). Unit cell dimensions: a=9.41 Å, b=14.51 Å, c=21.12 Å, α=90.0°, β=90.0°, γ=90.0°; Space group: $P2_12_12_1$; Molecules of Example 11/asymmetric unit: 1; Volume/Number of molecules in the unit cell=721 Å$^3$; Density (calculated)=1.396 g/cm$^3$. Fractional atomic coordinates at room temperature are given in Table 3.

Example 12

3-Chloro-4-(R)-(3-(R)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide (single atropisomer)

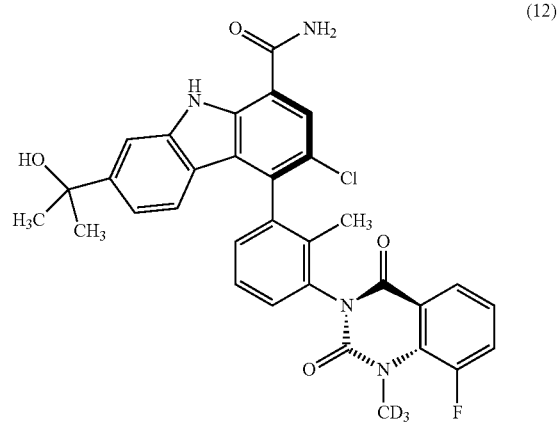

(12)

A mixture of 4-bromo-3-chloro-7-(2-hydroxypropan-2-yl)-9H-carbazole-1-carboxamide [Intermediate 3] (76 mg, 0.20 mmol), 8-fluoro-1-methyl($d_3$)-3-(R)-(2-methyl-3-(4,4,5,5-tetramethyl-1,3,2-dioxaborolan-2-yl)phenyl) quinazoline-2,4(1H,3H)-dione [Intermediate 22] (75 mg, 0.18 mmol), and $Cs_2CO_3$ (118 mg, 0.363 mmol) in THF (1.6 mL) and water (0.40 mL) in a vial was bubbled with argon for 1 min with sonication. The mixture was treated with $PdCl_2$(dppf) DCM adduct (7.4 mg, 0.009 mmol) and the vial was sealed and heated at 45° C. for 19 h. The cooled mixture was diluted with EtOAc and water. The layers were separated and the aqueous layer was extracted again with EtOAc. The combined organic layers were washed with brine, dried and concentrated. The residue was subjected to column chromatography on silica gel (12 g), eluting with EtOAc-hexanes (gradient from 60%-100%). The resulting impure product was purified by reverse phase HPLC (Luna Axia 5 $C_{18}$ 30×100 mm), eluting with MeCN-water containing 0.1% TFA (gradient from 10-100%, 30 mL/min). The appropriate fractions were treated with saturated aqueous $NaHCO_3$ and concentrated to an aqueous suspension. The precipitate was collected by filtration, washed with water and dried under vacuum to provide a mixture of two atropisomers of 3-chloro-4-(3-(R)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide as a white solid (60.9 mg, 57% yield). This material was separated by chiral super-critical fluid chromatography as follows: column: CHIRALPAK® AD-H (5×25 cm, 5 μm); Mobile Phase: $CO_2$-IPA (60:40) at 250 mL/min, 35° C.; sample preparation: 7.5 mg/mL in MeOH; injection: 2.5 mL. The residue obtained from concentration of the second peak eluting from the column was further purified by column chromatography on silica gel (4 g), eluting with EtOAc-hexanes (gradient from 40%-100%), to provide 3-chloro-4-(R)-(3-(R)-(8-fluoro-1-methyl($d_3$)-2,4-dioxo-1,2-dihydroquinazolin-3(4H)-yl)-2-methylphenyl)-7-(2-hydroxypropan-2-yl)-9H-carbazole-1-carboxamide as a white solid (19.7 mg, 68% yield). Mass spectrum m/z 570 $(M+H-H_2O)^+$, 610 $(M+Na)^+$. $^1$H NMR (400 MHz, MeOH-$d_4$) δ 8.11-8.04 (m, 2H), 7.74 (d, J=1.1 Hz, 1H), 7.66-7.53 (m, 2H), 7.46 (dd, J=7.9, 1.1 Hz, 1H), 7.38-7.28 (m, 2H), 7.14 (dd, J=8.5, 1.7 Hz, 1H), 6.90 (d, J=8.6 Hz, 1H), 1.80 (s, 3H), 1.60 (d, J=0.9 Hz, 6H).

Example 13

3-Chloro-4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of four atropisomers)

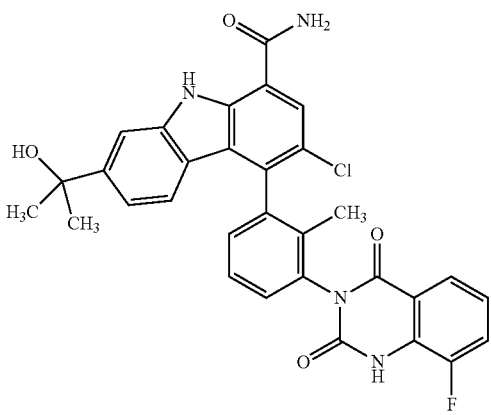

(13)

A mixture of 4-bromo-3-chloro-7-(2-hydroxypropan-2-yl)-9H-carbazole-1-carboxamide [Intermediate 3] (0.360 g, 0.943 mmol), 8-fluoro-3-(2-methyl-3-(4,4,5,5-tetramethyl-1,3,2-dioxaborolan-2-yl)phenyl)quinazoline-2,4(1H,3H)-dione [Intermediate 17] (0.392 g, 0.990 mmol), $PdCl_2$(dppf) DCM adduct (0.039 g, 0.047 mmol) and $Cs_2CO_3$ (0.615 g, 1.89 mmol) in dioxane (10 mL) and water (2.5 mL) was heated at 100° C. overnight. The cooled mixture was diluted with EtOAc and washed with water, dried and concentrated. The residue was purified by column chromatography on silica gel, eluting with EtOAc-hexanes (gradient from 0-50%, then to 70% containing 1% MeOH), to provide 3-chloro-4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as a white solid (0.361 g, 67% yield). Mass spectrum m/z 354 $(M+H-H_2O)^+$, 394 $(M+Na)^+$. $^1$H NMR (500 MHz, MeOH-$d_4$) δ 8.09 (d, J=1.1 Hz, 1H), 7.95 (d, J=8.0 Hz, 1H), 7.81-7.69 (m, 1H), 7.64-7.54 (m, 2H), 7.48 (dd, J=7.8, 1.1 Hz, 1H), 7.43-7.29 (m, 1H), 7.31-7.24 (m, 1H), 7.18 (dd, J=8.3, 1.7 Hz, 1H), 7.16-7.07 (m, 1H), 6.92 (dd, J=8.6, 5.3 Hz, 1H), 1.94-1.71 (m, 3H), 1.65-1.50 (m, 6H).

Example 14

3-Chloro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide (single atropisomer)

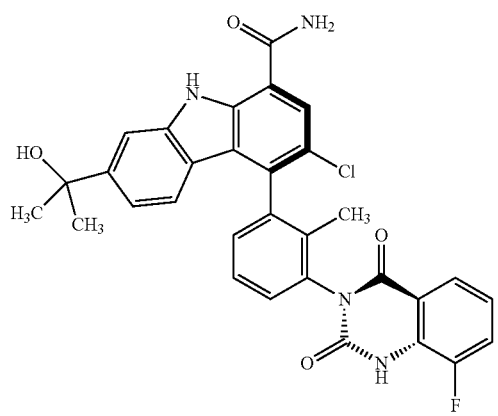

(14)

A sample of the mixture of four atropisomers of 3-chloro-4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 13] (250 mg) was separated by chiral super-critical fluid chromatography as follows: column: CHIRALPAK® AD-H (5×25 cm, 5 μm); Mobile Phase: $CO_2$-IPA (60:40) at 220 mL/min, 35° C., 100 bar; sample preparation: 21 mg/mL in MeOH; injection: 3.0 mL. The third peak eluting from the column provided 3-chloro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide (single atropisomer) as a white solid (24 mg). The chiral purity was determined to be greater than 95%. Mass spectrum m/z 553 $(M+H-H_2O)^+$, 593 $(M+Na)^+$. $^1$H NMR (400 MHz, MeOH-$d_4$) δ 8.09 (s, 1H), 7.95 (d, J=7.9 Hz, 1H), 7.74 (d, J=1.1 Hz, 1H), 7.60-7.54 (m, 2H), 7.54-7.43 (m, 1H), 7.37 (d, J=7.5 Hz, 1H), 7.28 (d, J=4.6 Hz, 1H), 7.11 (dd, J=8.6, 1.5 Hz, 1H), 6.91 (d, J=8.6 Hz, 1H), 2.00-1.76 (m, 3H), 1.69-1.52 (m, 6H).

Examples 15 and 16

3-Cyano-4-(S)-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (single atropisomers)

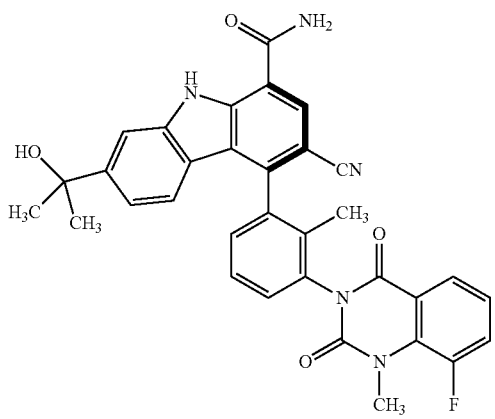

(15, 16)

Preparation 15A: 3-Cyano-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of 4 atropisomers)

A mixture of 4-bromo-3-cyano-7-(2-hydroxypropan-2-yl)-9H-carbazole-1-carboxamide [Intermediate 23] (0.400 g, 1.08 mmol), 8-fluoro-1-methyl-3-(2-methyl-3-(4,4,5,5-tetramethyl-1,3,2-dioxaborolan-2-yl)phenyl)quinazoline-2,4(1H,3H)-dione [Intermediate 2] (0.573 g, 1.40 mmol), $Cs_2CO_3$ (0.700 g, 2.15 mmol), and dioxane (5 mL) was subjected to 3 evacuate-fill cycles with nitrogen. The mixture was treated with $PdCl_2$(dppf) DCM adduct (0.053 g, 0.064 mmol) and subjected to 2 more evacuate-fill cycles with nitrogen. The mixture was heated at 88° C. for 2 days. The cooled mixture was diluted with EtOAc, washed sequentially with water and brine, and dried and concentrated. The residue was purified by column chromatography on silica gel, eluting with EtOAc-hexanes (sequentially 50%, 75%, 85% and 100%). The resulting impure product was purified by reverse-phase preparative HPLC to give 3-cyano-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as a white solid (0.200 g, 32% yield). Mass spectrum m/z 576 (M+H)$^+$. $^1$H NMR (400 MHz, DMSO-$d_6$) δ 11.96 (s, 1H), 8.45 (s, 1H), 8.35 (br. s., 1H), 8.00-7.94 (m, 1H), 7.92 (s, 1H), 7.77-7.68 (m, 2H), 7.60-7.52 (m, 2H), 7.41 (dd, J=6.6, 2.2 Hz, 1H), 7.38-7.29 (m, 1H), 7.13 (t, J=10.1 Hz, 1H), 6.85 (t, J=8.1 Hz, 1H), 5.05 (d, J=2.0 Hz, 1H), 3.74 (dd, J=8.1, 2.6 Hz, 3H), 1.73 (s, 3H), and 1.48-1.43 (m, 6H).

Examples 15 and 16

A sample of 3-cyano-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of 4 atropisomers) was separated by chiral super-critical fluid chromatography as follows: column: CHIRALPAK® AD-H (3×25 cm, 5 µm); Mobile Phase: $CO_2$-IPA (65:35) at 150 mL/min, 45° C. The second peak eluting from the column provided one single atropisomer of 3-cyano-4-(S)-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide [Example 15]. The chiral purity was determined to be greater than 94%. The fourth peak eluting from the column provided the other single atropisomer of 3-cyano-4-(S)-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide [Example 16]. The chiral purity was determined to be 99%. The mass spectrum of each single atropisomer was the same as that of the mixture of four atropisomers.

Example 17

3-Fluoro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers)

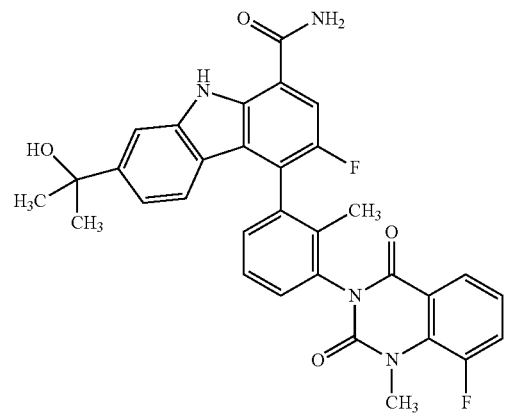

(17)

A mixture of 4-bromo-3-fluoro-7-(2-hydroxypropan-2-yl)-9H-carbazole-1-carboxamide [Intermediate 27] (0.080 g, 0.219 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 2] (0.094 g, 0.230 mmol), $PdCl_2$(dppf) DCM adduct (9.0 mg, 11.0 µmol) and $Cs_2CO_3$ (0.143 g, 0.438 mmol) in dioxane (8.0 mL) and water (2.0 mL) was heated at 100° C. overnight. The cooled mixture was diluted with EtOAc and filtered. The filtrate was washed with water, dried and concentrated. The residue was purified by reverse-phase preparative HPLC, followed by purification by column chromatography on silica gel, eluting with EtOAc-hexanes (gradient from 50%-100%), to give 3-fluoro-4-(3-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as an off-white solid (0.018 g, 15% yield). Mass spectrum m/z 551 (M+H-$H_2O$)$^+$. $^1$H NMR (500 MHz, MeOH-$d_4$) δ 7.66 (d, J=10.4 Hz, 1H), 7.51 (s, 1H), 7.47-7.34 (m, 3H), 7.29 (t, J=7.2 Hz, 2H), 7.22-7.11 (m, 1H), 7.09-6.97 (m, 1H), 6.90 (t, J=8.1 Hz, 1H), 3.81-3.63 (m, 3H), 2.06 (br. s., 3H), and 1.77-1.58 (m, 6H).

Example 18

3-Fluoro-4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two atropisomers)

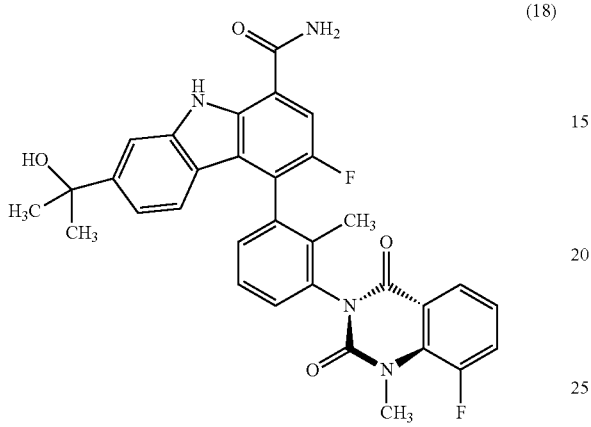

(18)

A mixture of 4-bromo-3-fluoro-7-(2-hydroxypropan-2-yl)-9H-carbazole-1-carboxamide [Intermediate 27] (0.100 g, 0.274 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 10] (0.146 g, 0.356 mmol), 2 M aqueous $K_3PO_4$ (0.41 mL, 0.821 mmol), and THF (2.0 mL) was subjected to 3 evacuate-fill cycles with nitrogen. The mixture was treated with 1,1'-bis(di-tert-butylphosphino)ferrocene palladium(II) chloride (8.9 mg, 0.014 mmol), and subjected to 2 more evacuate-fill cycles with nitrogen. The mixture was stirred at room temperature overnight. The mixture was diluted with EtOAc, washed sequentially with water and brine, and dried and concentrated. The residue was purified by column chromatography on silica gel, eluting with EtOAc-hexanes (sequentially 50%, 62%, 75% and 85%), to provide 3-fluoro-4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two atropisomers) as an off-white solid (0.084 g, 53% yield). Mass spectrum m/z 551 $(M+H-H_2O)^+$. $^1H$ NMR (500 MHz, DMSO-$d_6$) δ 11.39 (s, 1H), 8.21 (br. s., 1H), 7.99-7.92 (m, 3H), 7.84 (s, 1H), 7.73 (ddt, J=14.4, 8.0, 1.4 Hz, 1H), 7.59 (br. s., 1H), 7.54-7.47 (m, 3H), 7.40 (dd, J=7.2, 1.7 Hz, 1H), 7.34 (tt, J=7.9, 4.0 Hz, 1H), 7.04 (ddd, J=11.5, 8.6, 1.5 Hz, 1H), 6.88 (t, J=8.0 Hz, 1H), 4.99 (d, J=2.2 Hz, 1H), 3.74 (dd, J=8.2, 1.0 Hz, 3H), 1.77 (s, 3H), and 1.49-1.42 (m, 6H).

Alternative Synthesis of 3-Fluoro-4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two atropisomers)

A mixture of 4-bromo-3-fluoro-7-(2-hydroxypropan-2-yl)-9H-carbazole-1-carboxamide [Intermediate 27] (0.050 g, 0.137 mmol), 8-fluoro-1-methyl-3-(2-methyl-3-(4,4,5,5-tetramethyl-1,3,2-dioxaborolan-2-yl)phenyl)quinazoline-2,4(1H,3H)-dione [Intermediate 10] (0.073 g, 0.178 mmol), $Cs_2CO_3$ (0.089 g, 0.274 mmol), and dioxane (0.8 mL) was subjected to 3 evacuate-fill cycles with nitrogen. The mixture was treated with $PdCl_2$(dppf) DCM adduct (6.7 mg, 8.21 μmol), subjected to 2 more evacuate-fill cycles with nitrogen, and heated at 52° C. overnight. The cooled mixture was diluted with EtOAc, washed sequentially with water and brine, and dried and concentrated. The residue was purified by column chromatography on silica gel, eluting with EtOAc-hexanes (sequentially 50%, 62% and 75%), to give 3-fluoro-4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two atropisomers) as a white solid (0.034 g, 42% yield).

Example 19

3-Fluoro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (single atropisomer)

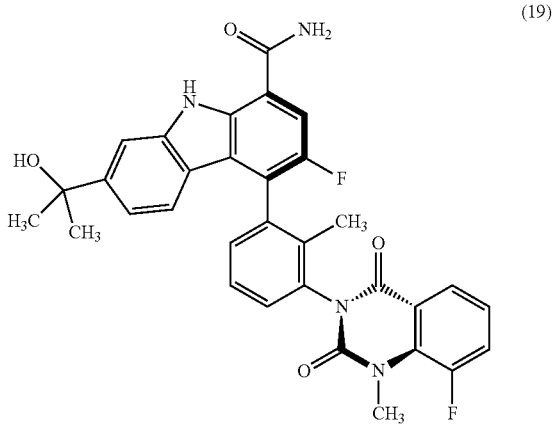

(19)

A sample of 3-fluoro-4-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide (mixture of two atropisomers) [Example 18] was separated by chiral super-critical fluid chromatography as follows: column: CHIRALPAK® AS-H (3×25 cm, 5 μm); Mobile Phase: $CO_2$-MeOH (70:30) at 120 mL/min, 40° C., 100 bar; sample preparation: 3.6 mg/mL in MeOH; injection: 2.0 mL. The first peak eluting from the column provided 3-fluoro-4-(R)-(3-(S)-(8-fluoro-1-methyl-2,4-dioxo-1,2-dihydroquinazolin-3(4H)-yl)-2-methylphenyl)-7-(2-hydroxypropan-2-yl)-9H-carbazole-1-carboxamide. The chiral purity was determined to be greater than 99.4%. Mass spectrum m/z 551 $(M+H-H_2O)^+$. $^1H$ NMR (500 MHz, DMSO-$d_6$) δ 11.39 (s, 1H), 8.21 (br. s., 1H), 8.00-7.92 (m, 2H), 7.84 (s, 1H), 7.73 (ddd, J=14.4, 8.0, 1.4 Hz, 1H), 7.59 (br. s., 1H), 7.55-7.47 (m, 2H), 7.40 (dd, J=7.2, 1.4 Hz, 1H), 7.33 (td, J=8.0, 4.0 Hz, 1H), 7.05 (dd, J=8.3, 1.4 Hz, 1H), 6.89 (d, J=8.3 Hz, 1H), 4.99 (s, 1H), 3.74 (d, J=8.0 Hz, 3H), 3.17 (d, J=5.3 Hz, 3H), 1.77 (s, 3H), and 1.46 (d, J=4.2 Hz, 6H).

Example 20

3-Fluoro-4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of 4 atropisomers)

Examples 21 and 22

3-Fluoro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide, and 3-Fluoro-4-(R)-(3-(S)-(8-fluoro-2,4-dioxo-1,2-dihydroquinazolin-3(4H)-yl)-2-methylphenyl)-7-(2-hydroxypropan-2-yl)-9H-carbazole-1-carboxamide (single atropisomers)

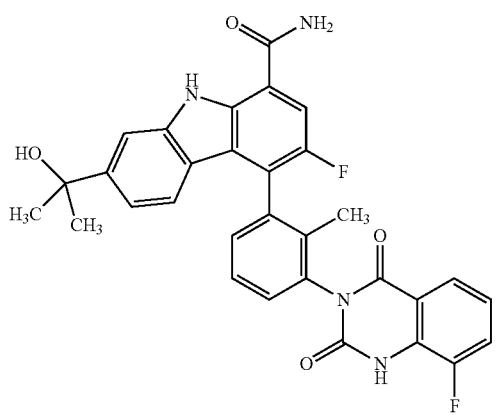

(20)

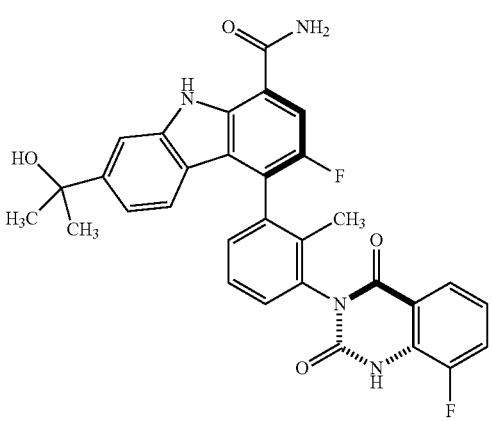

(21)

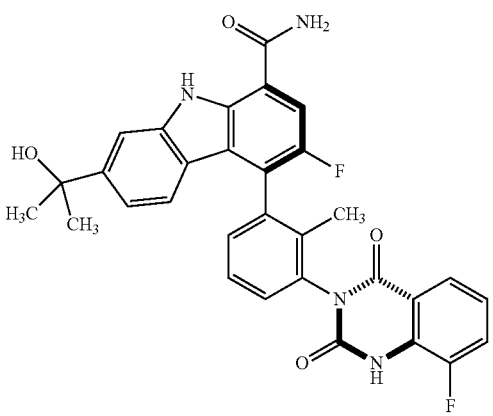

(22)

A mixture of 4-bromo-3-fluoro-7-(2-hydroxypropan-2-yl)-9H-carbazole-1-carboxamide [Intermediate 27] (0.104 g, 0.285 mmol), 8-fluoro-3-(2-methyl-3-(4,4,5,5-tetramethyl-1,3,2-dioxaborolan-2-yl)phenyl)quinazoline-2,4(1H,3H)-dione [Intermediate 17] (0.147 g, 0.370 mmol), Cs$_2$CO$_3$ (0.186 g, 0.570 mmol), and dioxane (1.6 mL) was subjected to 3 evacuate-fill cycles with nitrogen. The mixture was treated with PdCl$_2$(dppf) DCM adduct (14 mg, 0.017 mmol), and subjected to two more evacuate-fill cycles with nitrogen. The mixture was heated at 88° C. overnight. The cooled mixture was diluted with EtOAc, washed sequentially with water and brine, and dried and concentrated. The residue was purified by reverse phase preparative HPLC. The appropriate fractions were treated with saturated aqueous NaHCO$_3$ and concentrated to an aqueous residue which was extracted with EtOAc. The organic layer was washed with brine. The combined aqueous layers were extracted with EtOAc, and the combined organic layers were dried and concentrated. The residue was purified by column chromatography on silica gel, eluting with EtOAc-hexanes (sequentially 50%, 65% and 75%), to provide 3-fluoro-4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of four atropisomers) as a white solid (0.029 g, 18% yield). Mass spectrum m/z 537 (M+H-H$_2$O)$^+$. $^1$H NMR (500 MHz, DMSO-d$_6$) δ 11.81 (br. s., 1H), 11.39 (d, J=1.4 Hz, 1H), 8.21 (br. s., 1H), 7.95 (dd, J=10.7, 2.1 Hz, 1H), 7.86-7.80 (m, 2H), 7.64 (t, J=9.2 Hz, 1H), 7.59 (br. s., 1H), 7.53-7.50 (m, 2H), 7.42-7.38 (m, 1H), 7.26-7.20 (m, 1H), 7.07-6.99 (m, 1H), 6.97-6.88 (m, 1H), 4.98 (d, J=9.7 Hz, 1H), 1.81-1.75 (m, 3H), and 1.48-1.41 (m, 6H).

A sample of 3-fluoro-4-(3-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of 4 atropisomers) [Example 20] was separated by chiral supercritical fluid chromatography as follows: column: CHIRALPAK® AD-H (3×25 cm, 5 µm); Mobile Phase: CO$_2$-IPA (75:25) at 180 mL/min, 40° C., 100 bar. The third peak eluting from the column provided 3-fluoro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 21]. The chiral purity was determined to be 98%. Mass spectrum m/z 537 (M+H-H$_2$O)$^+$. $^1$H NMR (500 MHz, DMSO-d$_6$) δ 11.83 (br. s., 1H), 11.38 (s, 1H), 8.21 (br. s., 1H), 7.95 (d, J=10.8 Hz, 1H), 7.83 (d, J=1.1 Hz, 1H), 7.81 (d, J=8.0 Hz, 1H), 7.65-7.57 (m, 2H), 7.54-7.47 (m, 2H), 7.39 (dd, J=6.7, 1.9 Hz, 1H), 7.20 (br. s., 1H), 7.03-6.99 (m, 1H), 6.99-6.94 (m, 1H), 4.97 (s, 1H), 1.77 (s, 3H), and 1.44 (d, J=5.3 Hz, 6H).

The fourth peak eluting from the column provided 3-fluoro-4-(R)-(3-(S)-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 22]. The chiral purity was determined to be 95%. Mass spectrum m/z 537 (M+H-H$_2$O)$^+$. $^1$H NMR (500 MHz, DMSO-d$_6$) δ 11.80 (br. s., 1H), 11.39 (s, 1H), 8.21 (br. s., 1H), 7.95 (d, J=10.8 Hz, 1H), 7.85-7.78 (m, 2H), 7.59 (br. s., 2H), 7.54-7.46 (m, 2H), 7.38 (d, J=6.1 Hz, 1H), 7.19 (br. s., 1H), 7.05 (dd, J=8.5, 1.5 Hz, 1H), 6.90 (d, J=8.3 Hz, 1H), 4.99 (s, 1H), 1.77 (s, 3H), and 1.46 (d, J=4.7 Hz, 6H).

Alternative Procedure for the Preparation of 3-Fluoro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 21]

A mixture of 4-bromo-3-fluoro-7-(2-hydroxypropan-2-yl)-9H-carbazole-1-carboxamide [Intermediate 27] (0.118 g, 0.323 mmol), 8-fluoro-3-(R)-(2-methyl-3-(4,4,5,5-tetramethyl-1,3,2-dioxaborolan-2-yl)phenyl)quinazoline-2,4(1H,3H)-dione [Intermediate 18] (0.166 g, 0.420 mmol), 2 M aqueous K$_3$PO$_4$ (0.485 mL, 0.969 mmol) and THF (2.0 mL) was subjected to 3 evacuate-fill cycles with nitrogen. The mixture was treated with 1,1'-bis(di-tert-butylphosphino)ferrocene palladium(II) chloride (11 mg, 0.016 mmol) and subjected to 2 more evacuate-fill cycles with nitrogen. The mixture was stirred at room temperature overnight, diluted with EtOAc, washed sequentially with water and brine, and dried and concentrated. The residue was purified by column chromatography on silica gel, eluting with EtOAc-hexanes (sequentially 50%, 62%, 75% and 85%), to provide 3-fluoro-4-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of two atropisomers) as an off-white solid (0.117 g, 65% yield). A sample of this material was separated by chiral super-critical fluid chromatography as follows: column: CHIRALPAK® AD-H (3×25 cm, 5 μm); Mobile Phase: CO$_2$-MeOH (70:30) at 180 mL/min, 45° C.; sample preparation: 30 mg/mL; injection: 1.0 mL. The second peak eluting from the column provided 3-fluoro-4-(R)-(3-(R)-(8-fluoro-2,4-dioxo-1,2-dihydroquinazolin-3(4H)-yl)-2-methylphenyl)-7-(2-hydroxypropan-2-yl)-9H-carbazole-1-carboxamide. The chiral purity was determined to be greater than 99.9%. Mass spectrum m/z 537 (M+H-H$_2$O)$^+$. $^1$H NMR (500 MHz, DMSO-d$_6$) δ 11.83 (br. s., 1H), 11.38 (s, 1H), 8.21 (br. s., 1H), 7.95 (d, J=10.8 Hz, 1H), 7.83 (d, J=1.1 Hz, 1H), 7.81 (d, J=8.0 Hz, 1H), 7.65-7.57 (m, 2H), 7.54-7.47 (m, 2H), 7.39 (dd, J=6.7, 1.9 Hz, 1H), 7.20 (br. s., 1H), 7.03-6.99 (m, 1H), 6.99-6.94 (m, 1H), 4.97 (s, 1H), 1.77 (s, 3H), and 1.44 (d, J=5.3 Hz, 6H).

Alternative Procedure for the Preparation of 3-Fluoro-4-(R)-(3-(S)-(8-fluoro-2,4-dioxo-1,2-dihydroquinazolin-3(4H)-yl)-2-methylphenyl)-7-(2-hydroxypropan-2-yl)-9H-carbazole-1-carboxamide [Example 22]

Following the same procedure as that used for the alternative preparation of Example 21, 4-bromo-3-fluoro-7-(2-hydroxypropan-2-yl)-9H-carbazole-1-carboxamide [Intermediate 27] (0.118 g, 0.323 mmol) and 8-fluoro-3-(S)-(2-methyl-3-(4,4,5,5-tetramethyl-1,3,2-dioxaborolan-2-yl)phenyl)quinazoline-2,4(1H,3H)-dione [Intermediate 19] (0.166 g, 0.420 mmol) were converted to 3-fluoro-4-(3-(S)-(8-fluoro-2,4-dioxo-1,2-dihydroquinazolin-3(4H)-yl)-2-methylphenyl)-7-(2-hydroxypropan-2-yl)-9H-carbazole-1-carboxamide (mixture of two atropisomers) as an off-white solid (0.119 g, 66% yield). A sample of this material was separated by chiral super-critical fluid chromatography as follows: column: CHIRALPAK® AS-H (3×25 cm, 5 μm); Mobile Phase: CO$_2$-MeOH (75:25) at 180 mL/min, 45° C.; sample preparation: 10 mg/mL; injection: 1.0 mL. The second peak eluting from the column provided 3-fluoro-4-(R)-(3-(S)-(8-fluoro-2,4-dioxo-1,2-dihydroquinazolin-3(4H)-yl)-2-methylphenyl)-7-(2-hydroxypropan-2-yl)-9H-carbazole-1-carboxamide. The chiral purity was determined to be greater than 99.9%.

Example 23

3-Chloro-4-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (mixture of four atropisomers)

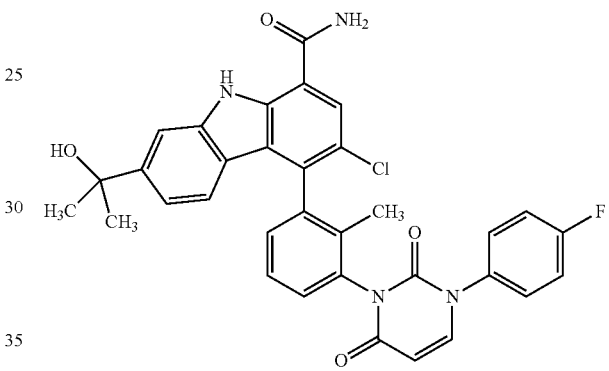

(23)

A mixture of 4-bromo-3-chloro-7-(2-hydroxypropan-2-yl)-9H-carbazole-1-carboxamide [Intermediate 3] (135 mg, 0.354 mmol), 1-(4-fluorophenyl)-3-(2-methyl-3-(4,4,5,5-tetramethyl-1,3,2-dioxaborolan-2-yl)phenyl)pyrimidine-2,4(1H,3H)-dione [Intermediate 44] (164 mg, 0.389 mmol), and tetrakis(triphenylphosphine)palladium (20 mg, 0.018 mmol) in toluene (5.3 mL) and ethanol (1.8 mL) was bubbled with argon for several min. The mixture was treated with 2 M aqueous Na$_2$CO$_3$ (354 μl, 0.707 mmol), bubbled again with argon, and heated at 90° C. for 16 h. The cooled mixture was partitioned between EtOAc and water. The organic phase was dried and concentrated. The residue was purified by column chromatography on silica gel (24 g), eluting with EtOAc-hexanes (gradient from 25-100%), to give 3-chloro-4-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (mixture of four atropisomers) as a white solid (103 mg, 49% yield). Mass spectrum m/z 579 (M+H-H$_2$O)$^+$. $^1$H NMR (500 MHz, DMSO-d$_6$) δ 11.52 (d, J=4.5 Hz, 1H), 8.29 (br. s., 1H), 8.13 (d, J=2.5 Hz, 1H), 7.91 (dd, J=7.9, 6.4 Hz, 1H), 7.85-7.80 (m, 1H), 7.64-7.54 (m, 3H), 7.53-7.45 (m, 2H), 7.36 (dt, J=11.9, 8.7 Hz, 2H), 7.25 (ddd, J=7.3, 4.3, 1.2 Hz, 1H), 7.03-6.83 (m, 1H), 6.73-6.47 (m, 1H), 5.97 (dd, J=7.9, 3.5 Hz, 1H), 5.04-4.92 (m, 1H), 1.75 (d, J=1.5 Hz, 3H), 1.47-1.33 (m, 6H).

Example 24

3-Chloro-4-(R)-(3-(3-(4-fluorophenyl)-2,6-dioxo-2,3-dihydropyrimidin-(6H)-yl)-2-methylphenyl)-7-(2-hydroxypropan-2-yl)-9H-carbazole-1-carboxamide (single atropisomer)

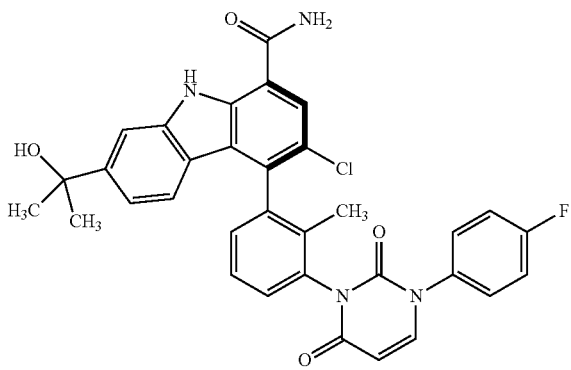

(24)

A sample of 3-chloro-4-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide (mixture of four atropisomers) [Example 23] (103 mg) was separated by chiral super-critical fluid chromatography as follows: column: CHIRALPAK® AD-H (3×25 cm, 5 μm); Mobile Phase: $CO_2$-IPA (60:40) at 85 mL/min; sample preparation: 6.1 mg/mL in 1:1 MeCN-MeOH; injection: 1.0 mL. The fourth peak eluting from the column was further purified by column chromatography on silica gel (4 g), eluting with EtOAc-hexanes (gradient from 60-80%), to give a single atropisomer of 3-chloro-4-(R)-(3-(3-(4-fluorophenyl)-2,6-dioxo-2,3-dihydropyrimidin-1(6H)-yl)-2-methylphenyl)-7-(2-hydroxypropan-2-yl)-9H-carbazole-1-carboxamide as an off-white solid (16 mg, 13% yield). Mass spectrum m/z 579 (M+H-$H_2O$)$^+$. $^1$H NMR (400 MHz, MeOH-$d_4$) δ 8.06 (s, 1H), 7.78 (d, J=7.9 Hz, 1H), 7.73 (d, J=1.1 Hz, 1H), 7.57-7.50 (m, 3H), 7.47-7.43 (m, 1H), 7.32 (dd, J=7.5, 1.1 Hz, 1H), 7.27 (t, J=8.7 Hz, 2H), 7.11 (dd, J=8.5, 1.7 Hz, 1H), 6.88 (d, J=8.4 Hz, 1H), 6.01 (d, J=7.9 Hz, 1H), 1.84 (s, 3H), 1.58 (d, J=3.1 Hz, 6H).

Example 25

6-Chloro-5-(3-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (mixture of four atropisomers)

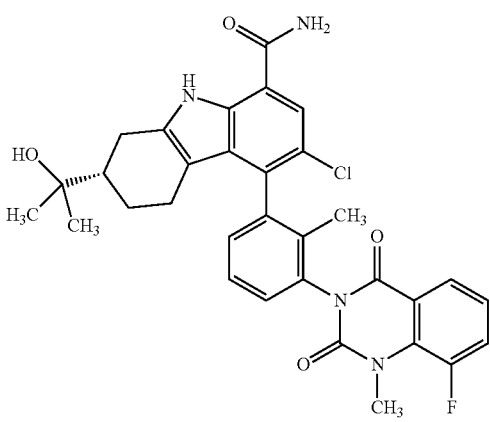

(25)

A mixture of (S)-5-bromo-6-chloro-2-(2-hydroxypropan-2-yl)-2,3,4,9-tetrahydro-1H-carbazole-8-carboxamide [Intermediate 31] (100 mg, 0.259 mmol), 8-fluoro-1-methyl-3-(2-methyl-3-(4,4,5,5-tetramethyl-1,3,2-dioxaborolan-2-yl)phenyl)quinazoline-2,4(1H,3H)-dione [Intermediate 2] (112 mg, 0.272 mmol), $Cs_2CO_3$ (169 mg, 0.519 mmol) and $PdCl_2$(dppf) DCM adduct (16.9 mg, 0.021 mmol) in THF (4.3 mL) and water (1.1 mL) was heated at 50° C. for 17.5 h. The cooled mixture was diluted with EtOAc, washed sequentially with water and brine, dried and concentrated. The residue was purified by column chromatography on silica gel (24 g), eluting with EtOAc-hexanes (gradient from 50-80%). The impure product was further purified by preparative HPLC to give 6-chloro-5-(3-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (mixture of four atropisomers) (76 mg, 50% yield). Mass spectrum m/z 589 (M+H)$^+$. $^1$H NMR (500 MHz, DMSO-$d_6$) δ 10.89 (s, 1H), 8.13 (br. s., 1H), 7.94 (d, J=7.9 Hz, 1H), 7.76-7.68 (m, 2H), 7.46 (br. s., 1H), 7.40-7.28 (m, 3H), 7.22-7.16 (m, 1H), 4.21-4.13 (m, 1H), 3.77-3.64 (m, 3H), 2.95-2.82 (m, 1H), 2.40 (d, J=16.3 Hz, 1H), 1.94-1.70 (m, 3H), 1.70-1.61 (m, 3H), 1.58-1.48 (m, 1H), 1.16-1.02 (m, 7H).

Example 26

6-Chloro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (single atropisomer)

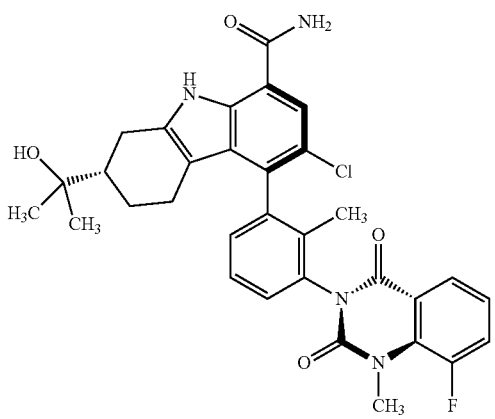

(26)

A sample of 6-chloro-5-(3-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (mixture of four atropisomers) [Example 25] (76 mg) was separated by chiral super-critical fluid chromatography as follows: column: CHIRALPAK® OD-H (3×25 cm, 5 μm); Mobile Phase: $CO_2$-MeOH (70:30) at 180 mL/min, 35° C., 100 bar; sample preparation: 8.35 mg/mL in MeOH-DCM (4:1); injection: 3.0 mL. The first peak eluting from the column was further purified by column chromatography on silica gel (4 g), eluting with EtOAc-hexanes (gradient from 50-80%), to give 6-chloro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide as a white solid (33.6 mg, 47% yield). Mass spectrum m/z 589 (M+H)$^+$. $^1$H NMR (400 MHz, MeOH-d$_4$) δ 8.06-7.99 (m, 1H), 7.69 (s, 1H), 7.60 (ddd, J=14.3, 8.1, 1.4 Hz, 1H), 7.40 (d, J=7.5 Hz, 1H), 7.34-7.27 (m, 2H), 7.24 (dd, J=7.5, 1.1 Hz, 1H), 3.85 (d, J=7.9 Hz, 3H), 2.90 (dd, J=16.5, 5.1 Hz, 1H), 2.56 (dd, J=16.4, 12.0 Hz, 1H), 2.10-2.02 (m, 1H), 2.00-1.84 (m, 2H), 1.77 (s, 3H), 1.75-1.68 (m, 1H), 1.28 (d, J=3.1 Hz, 1H), 1.22 (d, J=2.2 Hz, 6H).

Example 27

6-Fluoro-5-(R)-(3-(S)-(8-fluoro-1-methyl-2,4-dioxo-1,2-dihydroquinazolin-3(4H)-yl)-2-methylphenyl)-2-(R)-(2-hydroxypropan-2-yl)-2,3,4,9-tetrahydro-1H-carbazole-8-carboxamide (single atropisomer)

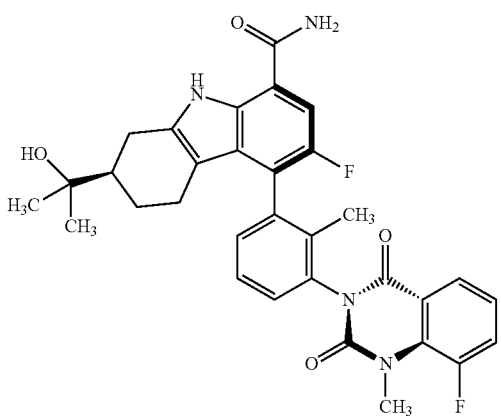

(27)

Preparation 27A: 6-Fluoro-5-(3-(S)-(8-fluoro-1-methyl-2,4-dioxo-1,2-dihydroquinazolin-3(4H)-yl)-2-methylphenyl)-2-(R)-(2-hydroxypropan-2-yl)-2,3,4,9-tetrahydro-1H-carbazole-8-carboxamide (mixture of 2 atropisomers)

A mixture of (R)-5-bromo-6-fluoro-2-(2-hydroxypropan-2-yl)-2,3,4,9-tetrahydro-1H-carbazole-8-carboxamide (single enantiomer) [Intermediate 25] (5.00 g, 13.5 mmol), 8-fluoro-1-methyl-3-(S)-(2-methyl-3-(4,4,5,5-tetramethyl-1,3,2-dioxaborolan-2-yl)phenyl) quinazoline-2,4(1H,3H)-dione [Intermediate 10] (6.94 g, 16.9 mmol), 2 M aqueous K$_3$PO$_4$ (20.3 mL, 40.6 mmol) and THF (60 mL) was subjected to three evacuate-fill cycles with nitrogen. The mixture was treated with 1,1'-bis(di-tert-butylphosphino)ferrocene palladium(II) chloride (441 mg, 677 µmol) and subjected to two more evacuate-fill cycles with nitrogen. The mixture was stirred at room temperature overnight. The mixture was diluted with EtOAc, washed sequentially with water and brine, and dried and concentrated. The residue was purified by column chromatography on silica gel, eluting with EtOAc-hexanes (sequentially 50%, 62%, 75% and 85%), to give 6-fluoro-5-(3-(S)-(8-fluoro-1-methyl-2,4-dioxo-1,2-dihydroquinazolin-3(4H)-yl)-2-methylphenyl)-2-(R)-(2-hydroxypropan-2-yl)-2,3,4,9-tetrahydro-1H-carbazole-8-carboxamide (mixture of two atropisomers) as an off-white solid (6.77 g, 87% yield). Mass spectrum m/z 573 (M+H)$^+$. $^1$H NMR (500 MHz, DMSO-d$_6$) δ 10.79-10.74 (m, 1H), 8.05 (br. s., 1H), 7.98-7.93 (m, 1H), 7.76-7.69 (m, 1H), 7.57-7.51 (m, 1H), 7.43 (br. s., 1H), 7.40-7.26 (m, 4H), 4.19-4.13 (m, 1H), 3.74-3.68 (m, 3H), 2.94-2.84 (m, 1H), 2.49-2.35 (m, 2H), 1.92-1.80 (m, 3H), 1.76-1.68 (m, 3H), 1.62-1.52 (m, 1H), and 1.12-1.06 (m, 6H).

Example 27

A sample of 6-fluoro-5-(3-(S)-(8-fluoro-1-methyl-2,4-dioxo-1,2-dihydroquinazolin-3(4H)-yl)-2-methylphenyl)-2-(R)-(2-hydroxypropan-2-yl)-2,3,4,9-tetrahydro-1H-carbazole-8-carboxamide (mixture of two atropisomers) was separated by chiral super-critical fluid chromatography as follows: column: CHIRALPAK® AS-H (3×25 cm, 5 µm); Mobile Phase: CO$_2$-MeOH (70:30) at 120 mL/min, 35° C., 100 bar; sample preparation: 9 mg/mL in MeOH; injection: 1.7 mL. The first peak eluting from the column provided 6-fluoro-5-(R)-(3-(S)-(8-fluoro-1-methyl-2,4-dioxo-1,2-dihydroquinazolin-3(4H)-yl)-2-methylphenyl)-2-(R)-(2-hydroxypropan-2-yl)-2,3,4,9-tetrahydro-1H-carbazole-8-carboxamide. The chiral purity was determined to be greater than 99.5%. Mass spectrum m/z 573 (M+H)$^+$. $^1$H NMR (500 MHz, DMSO-d$_6$) δ 10.76 (s, 1H), 8.05 (br. s., 1H), 7.96 (d, J=7.8 Hz, 1H), 7.72 (ddd, J=14.3, 8.0, 1.2 Hz, 1H), 7.55 (d, J=10.8 Hz, 1H), 7.44 (br. s., 1H), 7.40-7.36 (m, 1H), 7.35-7.28 (m, 3H), 4.18 (s, 1H), 3.72 (d, J=8.0 Hz, 3H), 2.89 (dd, J=16.9, 4.4 Hz, 1H), 2.45-2.37 (m, 1H), 2.02-1.93 (m, 1H), 1.91-1.82 (m, 2H), 1.57 (td, J=11.7, 3.6 Hz, 1H), and 1.15-1.11 (m, 1H).

Example 28

6-Fluoro-5-(R)-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (single atropisomer)

(28)

Following the procedure used to prepare Example 27, (S)-5-bromo-6-fluoro-2-(2-hydroxypropan-2-yl)-2,3,4,9-tetrahydro-1H-carbazole-8-carboxamide (single enantiomer) [Intermediate 26] (0.045 g, 0.122 mmol) and 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 10] (0.065 g, 0.158 mmol) were converted into 6-fluoro-5-(3-(S)-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide (mixture of two atropisomers) as a yellow solid (0.035 g, 49% yield). Separation of a sample of this material by chiral super-critical fluid chromatography, using the conditions used to separate Example 27, provided (as the first peak to elute from the column) 6-fluoro-5-(R)-(3-(S)-(8-fluoro-1-methyl-2,4-dioxo-1,2-dihydroquinazolin-3 (4H)-yl)-2-methylphenyl)-2-(S)-(2-hydroxypropan-2-yl)-2, 3,4,9-tetrahydro-1H-carbazole-8-carboxamide. The chiral purity was determined to be greater than 99.5%. The relative and absolute configurations were determined by x-ray crystallography. Mass spectrum m/z 573 (M+H)$^+$. $^1$H NMR (500 MHz, DMSO-d$_6$) δ 10.77 (s, 1H), 8.05 (br. s., 1H), 7.94 (dd, J=7.9, 1.2 Hz, 1H), 7.56-7.52 (m, 1H), 7.43 (br. s., 1H), 7.40-7.36 (m, 1H), 7.35-7.30 (m, 2H), 7.28 (dd, J=7.5, 1.4 Hz, 1H), 4.15 (s, 1H), 3.75-3.70 (m, 3H), 2.90 (dd, J=16.8, 4.6 Hz, 1H), 2.47-2.39 (m, 1H), 1.93-1.82 (m, 3H), 1.74 (s, 3H), 1.57 (td, J=11.7, 4.2 Hz, 1H), 1.16-1.11 (m, 1H), and 1.10 (d, J=1.9 Hz, 6H). [α]$_D$: +63.8° (c 2.1, CHCl$_3$). DSC melting point onset temperature=202.9° C. (heating rate=10° C./min.).

Figure 5:
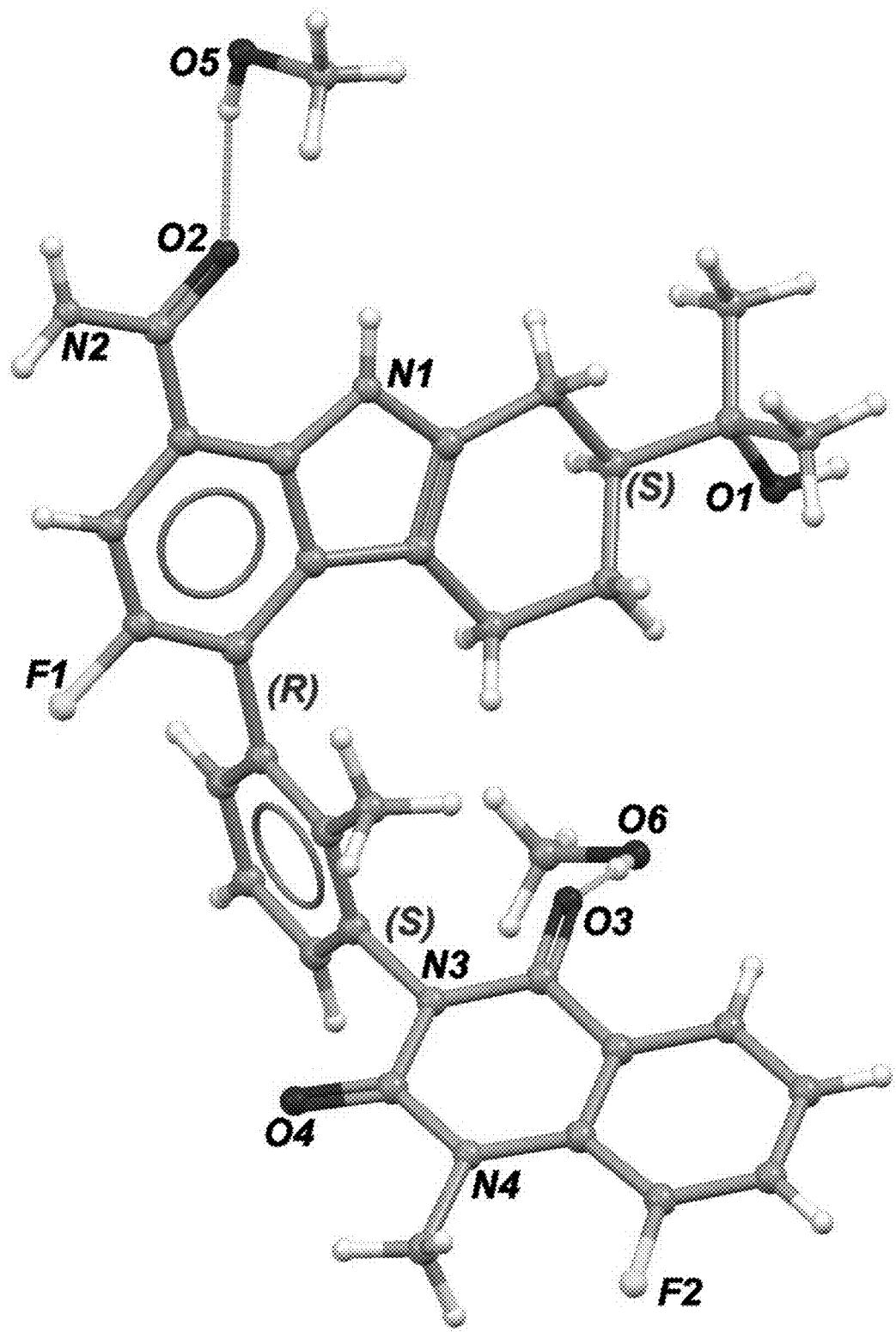
FIG. 5 shows the absolute stereochemistry of Example 28 dimethanolate, crystal Form M2-1.

The absolute configuration of Example 28 was confirmed by single crystal x-ray analysis of crystals prepared by dissolving the compound in excess methanol and slowly evaporating the solvent at room temperature to provide a di-methanol solvate (crystalline form M2-1). Unit cell dimensions: a=9.24 Å, b=7.97 Å, c=22.12 Å, α=90.0°, β=94.1°, γ=90.0°; Space group: P2$_1$; Molecules of Example 28/asymmetric unit: 1; Volume/Number of molecules in the unit cell=813 Å$^3$; Density (calculated)=1.301 g/cm$^3$. Fractional atomic coordinates at 173 K are given in Table 6, and a depiction of the structure is given in FIG. 5.

Alternative Synthesis of Example 28:

A mixture of (S)-5-bromo-6-fluoro-2-(2-hydroxypropan-2-yl)-2,3,4,9-tetrahydro-1H-carbazole-8-carboxamide [Intermediate 11] (5.00 g, 13.54 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 10] (6.67 g, 16.25 mmol), tripotassium phosphate (2 M in water) (20.31 mL, 40.6 mmol), and tetrahydrofuran (25 mL) was subjected to 3 evacuate-fill cycles with nitrogen. The mixture was treated with 1,1'-bis(di-tert-butylphosphino)ferrocene palladium dichloride (0.441 g, 0.677 mmol) and the mixture was subjected to 2 more evacuate-fill cycles with nitrogen. The mixture was stirred at room temperature overnight, then was diluted with EtOAc, washed sequentially with water and brine, and dried and concentrated. The residue was purified by column chromatography on silica gel, eluting with EtOAc-hexanes (sequentially 50%, 62%, 75% and 85%), to provide 6-fluoro-5-(3-(8-fluoro-1-methyl-2,4-dioxo-1,2-dihydroquinazolin-3-(S)-3(4H)-yl)-2-methylphenyl)-2-(S)-(2-hydroxypropan-2-yl)-2,3,4,9-tetrahydro-1H-carbazole-8-carboxamide as a white solid (6.58 g, 85% yield).

Material prepared by this method (40.03 g, 69.9 mmol) was separated by chiral super-critical fluid chromatography to give (2S, 5R)-6-fluoro-5-(3-(8-fluoro-1-methyl-2,4-dioxo-1,2-dihydroquinazolin-3(4H)-yl)-2-methylphenyl)-2-(S)-(2-hydroxypropan-2-yl)-2,3,4,9-tetrahydro-1H-carbazole-8-carboxamide. Further purification was achieved by suspending this material in methanol, sonicating for 5 min, collection of the solid by filtration, rinsing the collected solid with methanol and drying at room temperature under reduced pressure to give a white solid (22.0 g, 90% yield).

Example 29

4-(R)-(3-(S)-(8-Fluoro-1-methyl-2,4-dioxo-1,2-dihydroquinazolin-3(4H)-yl)-2-methylphenyl)-7-(2-hydroxypropan-2-yl)-3-methyl-9H-carbazole-1-carboxamide (single atropisomer)

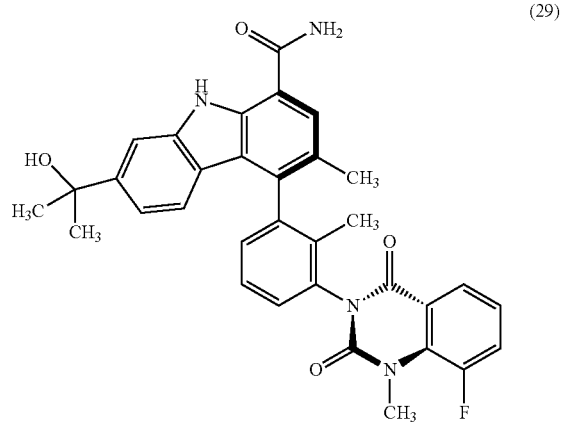

(29)

A mixture of 4-bromo-7-(2-hydroxypropan-2-yl)-3-methyl-9H-carbazole-1-carboxamide [Intermediate 28] (0.091 g, 0.252 mmol), 8-fluoro-1-methyl-3-(S)-(2-methyl-3-(4,4,5,5-tetramethyl-1,3,2-dioxaborolan-2-yl)phenyl)quinazoline-2,4(1H,3H)-dione [Intermediate 10] (0.134 g, 0.327 mmol), 2 M aqueous K$_3$PO$_4$ (0.378 mL, 0.756 mmol), and THF (2.0 mL) was subjected to three evacuate-fill cycles with nitrogen. The mixture was treated with 1,1'-bis(di-tert-butylphosphino)ferrocene palladium(II) chloride (8.2 mg, 0.013 mmol) and subjected to two additional evacuate-fill cycles with nitrogen. The mixture was stirred at room temperature overnight, then was diluted with EtOAc, washed sequentially with water and brine, and dried and concentrated. The residue was purified by column chromatography on silica gel, eluting with EtOAc-hexanes (sequentially 50%, 62%, 75% and 85%) to give 4-(3-(S)-(8-fluoro-1-methyl-2,4-dioxo-1,2-dihydroquinazolin-3(4H)-yl)-2-methylphenyl)-7-(2-hydroxypropan-2-yl)-3-methyl-9H-carbazole-1-carboxamide (mixture of two atropisomers) as pale yellow solid (0.087 g, 59% yield). Mass spectrum m/z 547 (M+H-H$_2$O)$^+$. $^1$H NMR (500 MHz, DMSO-d$_6$) δ 11.20 (s, 1H), 8.10 (br. s., 1H), 7.97 (ddd, J=7.9, 7.2, 1.0 Hz, 1H), 7.90 (s, 1H), 7.78 (s, 1H), 7.76-7.68 (m, 1H), 7.53-7.48 (m, 1H), 7.44 (dd, J=7.9, 1.2 Hz, 1H), 7.40 (br. s., 1H), 7.36-7.30 (m, 1H), 7.23 (dd, J=7.4, 1.2 Hz, 1H), 6.98 (ddd, J=12.0, 8.4, 1.5 Hz, 1H), 6.68 (t, J=7.9 Hz, 1H), 4.94 (d, J=3.1 Hz, 1H), 3.73 (dd, J=8.2, 3.5 Hz, 3H), 2.17 (s, 3H), 1.66 (s, 3H), and 1.48-1.41 (m, 6H).

A sample of this material was separated by chiral super-critical fluid chromatography as follows: column: CHIRALPAK® AD-H (3×25 cm, 5 µm); Mobile Phase: CO$_2$-MeOH (65:35) at 150 mL/min, 40° C.; sample preparation: 15 mg/mL in MeOH; injection: 1.5 mL. The second peak eluting from the column provided 4-(R)-(3-(S)-(8-fluoro-1-methyl-2,4-dioxo-1,2-dihydroquinazolin-3(4H)-yl)-2-methylphenyl)-7-(2-hydroxypropan-2-yl)-3-methyl-9H-carbazole-1-carboxamide. The chiral purity was determined to be greater than 99%. Mass spectrum m/z 547 (M+H-H$_2$O)$^+$. $^1$H NMR (500 MHz, DMSO-d$_6$) δ 11.19 (s, 1H), 8.10 (br. s., 1H), 7.97 (dd, J=7.9, 1.0 Hz, 1H), 7.90 (s, 1H), 7.78 (d, J=1.1 Hz, 1H), 7.72 (ddd, J=14.3, 8.0, 1.5 Hz, 1H), 7.53-7.48 (m, 1H), 7.44 (dd, J=7.8, 1.1 Hz, 1H), 7.40 (br. s., 1H), 7.33 (td, J=8.0, 4.2 Hz, 1H), 7.23 (dd, J=7.5, 1.1 Hz, 1H), 6.99 (dd, J=8.5, 1.5 Hz, 1H), 6.69 (d, J=8.6 Hz, 1H), 4.94 (s, 1H), 2.20-2.14 (m, 3H), 1.66 (s, 3H), and 1.45 (d, J=3.6 Hz, 6H).

Examples 30 and 31

4-(R)-(3-(5-Chloro-1,3-dioxo-1H-pyrido[1,2-c]pyrimidin-2(3H)-yl)-2-methylphenyl)-3-fluoro-7-(2-hydroxypropan-2-yl)-9H-carbazole-1-carboxamide (single atropisomers)

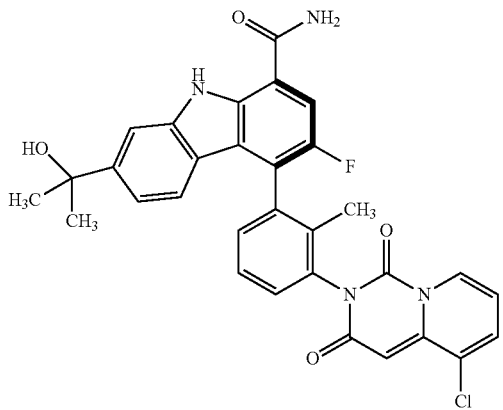

(30, 31)

Preparation 30A: 4-(3-(5-Chloro-1,3-dioxo-1H-pyrido[1,2-c]pyrimidin-2(3H)-yl)-2-methylphenyl)-3-fluoro-7-(2-hydroxypropan-2-yl)-9H-carbazole-1-carboxamide (mixture of four atropisomers)

A mixture of 4-bromo-3-fluoro-7-(2-hydroxypropan-2-yl)-9H-carbazole-1-carboxamide [Intermediate 27] (0.098 g, 0.268 mmol), 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 33] (0.144 g, 0.349 mmol), $Cs_2CO_3$ (0.175 g, 0.537 mmol), and dioxane (1.6 mL) was subjected to three evacuate-fill cycles with nitrogen. The mixture was treated with $PdCl_2$(dppf) DCM adduct (0.013 g, 0.016 mmol) and subjected to two more evacuate-fill cycles with nitrogen. The mixture was heated at 52° C. overnight. The cooled mixture was diluted with EtOAc, washed sequentially with water and brine, and dried and concentrated. The residue was purified by reverse-phase preparative HPLC. The appropriate fractions were treated with saturated aqueous $NaHCO_3$ and concentrated. The residue was partitioned between EtOAc and water, and the organic layer was washed with brine. The aqueous layers were extracted with EtOAc, and the combined organic layers were dried and concentrated. The residue was purified twice by column chromatography on silica gel, eluting with EtOAc-hexanes (sequentially 50%, 65% and 75%) to give 4-(3-(5-chloro-1,3-dioxo-1H-pyrido[1,2-c]pyrimidin-2 (3H)-yl)-2-methylphenyl)-3-fluoro-7-(2-hydroxypropan-2-yl)-9H-carbazole-1-carboxamide (mixture of four atropisomers) as a yellow solid (0.013 g, 8% yield). Mass spectrum m/z 571, 573 (M+H)$^+$. $^1$H NMR (500 MHz, DMSO-d$_6$) δ 11.39 (d, J=5.3 Hz, 1H), 8.30-8.24 (m, 1H), 8.21 (br. s., 1H), 7.95 (dd, J=10.5, 1.7 Hz, 1H), 7.84 (s, 1H), 7.60 (d, J=7.2 Hz, 2H), 7.55-7.47 (m, 2H), 7.42-7.39 (m, 1H), 7.04-6.99 (m, 1H), 6.93 (d, J=8.6 Hz, 0.6H), 6.84 (d, J=8.6 Hz, 0.4H), 6.57 (td, J=7.3, 3.5 Hz, 1H), 6.00 (d, J=8.6 Hz, 1H), 4.98 (s, 1H), 1.78 (d, J=1.9 Hz, 3H), and 1.45 (d, J=3.9 Hz, 6H).

Examples 30 and 31

A sample of 4-(3-(5-chloro-1,3-dioxo-1H-pyrido[1,2-c]pyrimidin-2(3H)-yl)-2-methylphenyl)-3-fluoro-7-(2-hydroxypropan-2-yl)-9H-carbazole-1-carboxamide (mixture of 4 atropisomers) was separated by chiral super-critical fluid chromatography as follows: column: CHIRALPAK® AD-H (3×25 cm, 5 μm); Mobile Phase: $CO_2$-IPA (55:45) at 120 mL/min, 45° C., 100 bar; sample preparation: 5.6 mg/mL in MeOH; injection: 1.7 mL. The second peak eluting from the column provided one single atropisomer of 4-(R)-(3-(5-chloro-1,3-dioxo-1H-pyrido[1,2-c]pyrimidin-2(3H)-yl)-2-methylphenyl)-3-fluoro-7-(2-hydroxypropan-2-yl)-9H-carbazole-1-carboxamide [Example 30]. The chiral purity was determined to be greater than 97.5%. Mass spectrum m/z 571 (M+H)$^+$. The fourth peak eluting from the column provided the other single atropisomer of 4-(R)-(3-(5-chloro-1,3-dioxo-1H-pyrido[1,2-c]pyrimidin-2(3H)-yl)-2-methylphenyl)-3-fluoro-7-(2-hydroxypropan-2-yl)-9H-carbazole-1-carboxamide [Example 31]. The chiral purity was determined to be greater than 99.5%. Mass spectrum m/z 553 (M+H-$H_2O$)$^+$.

Examples 32 and 33

3-Chloro-4-(R)-(3-(R)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (32), and 3-Chloro-4-(R)-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (33) (single atropisomers)

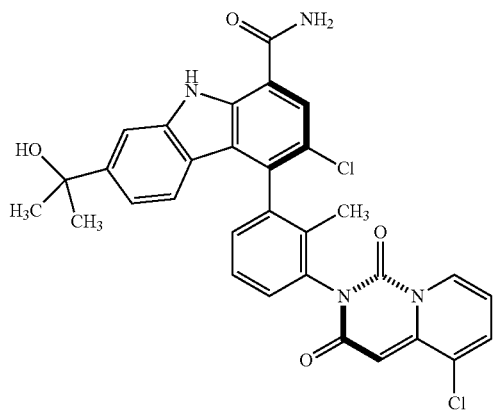

(32)

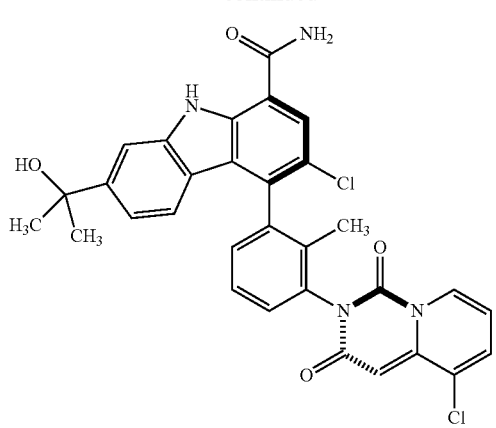

(33)

A mixture of 4-bromo-3-chloro-7-(2-hydroxypropan-2-yl)-9H-carbazole-1-carboxamide [Intermediate 3] (1.11 g, 2.91 mmol), 5-chloro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 33] (1.00 g, 2.42 mmol) and $Cs_2CO_3$ (1.58 g, 4.85 mmol) in THF (8 mL) and water (2 mL) was bubbled with argon for three min. The mixture was treated with $PdCl_2$(dppf) DCM adduct (0.099 g, 0.121 mmol) and heated at 60° C. overnight. The cooled mixture was diluted with EtOAc and washed sequentially with water and brine. The combined aqueous layers were extracted with DCM containing a small amount of MeOH. The combined organic layers were dried and concentrated until a tan precipitate formed, which was removed by filtration. The filtrate was concentrated and purified by column chromatography on silica gel (120 g), eluting with EtOAc-DCM (sequentially 70%, 80%, and 100%), to give 3-chloro-4-(3-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four atropisomers) as a yellow solid (993 mg, 69% yield). The material was separated by chiral super-critical fluid chromatography as follows: column: CHIRALPAK® AD-H (3×25 cm, 5 µm); Mobile Phase: $CO_2$-IPA (50:50) at 150 mL/min, 45° C., 100 bar; sample preparation: 5.6 mg/mL in MeOH-DCM (1:1); injection: 3 mL. The second peak eluting from the column provided 3-chloro-4-(R)-(3-(R)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 32]. Mass spectrum m/z 587 $(M+H)^+$. $^1$H NMR (400 MHz, DMSO-$d_6$) δ 11.50 (s, 1H), 8.27 (s, 2H), 8.14 (s, 1H), 7.84 (d, J=1.1 Hz, 1H), 7.59 (d, J=6.8 Hz, 1H), 7.56-7.46 (m, 2H), 7.29 (dd, J=7.4, 1.2 Hz, 1H), 7.01 (dd, J=8.4, 1.5 Hz, 1H), 6.64 (d, J=8.6 Hz, 1H), 6.55 (t, J=7.3 Hz, 1H), 5.98 (s, 1H), 5.75 (s, 1H), 4.98 (s, 1H), 1.71 (s, 3H), 1.46-1.42 (m, 6H).

The fourth peak eluting from the column provided 3-chloro-4-(R)-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 33]. Mass spectrum m/z 569 $(M+H-H_2O)^+$. $^1$H NMR (400 MHz, DMSO-$d_6$) δ 11.49 (s, 1H), 8.34-8.24 (m, 2H), 8.14 (s, 1H), 7.84 (d, J=1.1 Hz, 1H), 7.60 (d, J=6.6 Hz, 1H), 7.56-7.46 (m, 2H), 7.28 (dd, J=7.4, 1.4 Hz, 1H), 6.99 (dd, J=8.5, 1.7 Hz, 1H), 6.72 (d, J=8.4 Hz, 1H), 6.57 (t, J=7.3 Hz, 1H), 5.99 (s, 1H), 5.75 (s, 1H), 4.98 (s, 1H), 1.71 (s, 3H), 1.45-1.42 (m, 6H). $[α]_D$: +332.34° (c 2.0, $CHCl_3$).

Alternative Preparation of Example 33

A mixture of 4-bromo-3-chloro-7-(2-hydroxypropan-2-yl)-9H-carbazole-1-carboxamide [Intermediate 3] (50.5 g, 132 mmol), 5-chloro-2-(S)-(2-methyl-3-(4,4,5,5-tetramethyl-1,3,2-dioxaborolan-2-yl)phenyl)-1H-pyrido[1,2-c]pyrimidine-1,3(2H)-dione [Intermediate 35] (60.1 g, 146 mmol) and $Cs_2CO_3$ (86 g, 265 mmol) in THF (342 mL) and water (85 mL) was bubbled with nitrogen for 5 min, then was treated with $PdCl_2$(dppf) DCM adduct (11.9 g, 14.57 mmol). Bubbling with nitrogen was continued for 5 min more, then the mixture was heated at 62° C. under nitrogen for 20 h. The mixture was cooled to room temperature, MeOH (300 mL) was added with stirring followed 15 min later by the addition of water (2 L) to give a rusty brown colored gum. The supernatant was removed, the gummy residue was washed twice with water and then suspended in EtOAc (2 L) with stirring for one h. The mixture was filtered, the filtrate was concentrated to about 1-1.5 L and treated with heptane (3 L). The mixture was stirred for two days, the precipitate was collected by filtration, washed with heptane and dried under vacuum to give a yellow solid (104 g). The solid was dissolved in THF, absorbed on CELITE®, dried under vacuum, placed on a silica gel plug and eluted with heptane/EtOAc (10:90) to give an orange-yellow oil (74.87 g). The material was subjected to column chromatography on silica gel (3 kg), eluting with EtOAc-hexanes (gradient from 40-90%), to give 3-chloro-4-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of two atropisomers) as a yellow foam (44 g, 51% yield). To remove residual palladium, the residue was dissolved in EtOAc (about 300 mL) and stirred with a 10% aqueous solution of N-acetyl-L-cysteine (500 mL) overnight. The organic layer was treated again with a 10% solution of N-acetyl-L-cysteine (500 mL) for six h, then was washed sequentially with 5% $NH_4OH$ (twice) and brine, dried and concentrated to a yellow foam (43 g). The material was separated by chiral super-critical fluid chromatography as follows: column: CHIRALPAK® AS-H (2×50 cm, 10 µm); Mobile Phase: $CO_2$-MeOH (55:45) at 140 mL/min, 40° C., 100 bar; sample preparation: 56 mg/mL in MeOH-DCM (1:1); injection: 3.33 mL. The first peak eluting from the column provided 3-chloro-4-(R)-(3-(S)-(5-chloro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 33] as a yellow solid (18.3 g, 24% yield).

Figure 6:
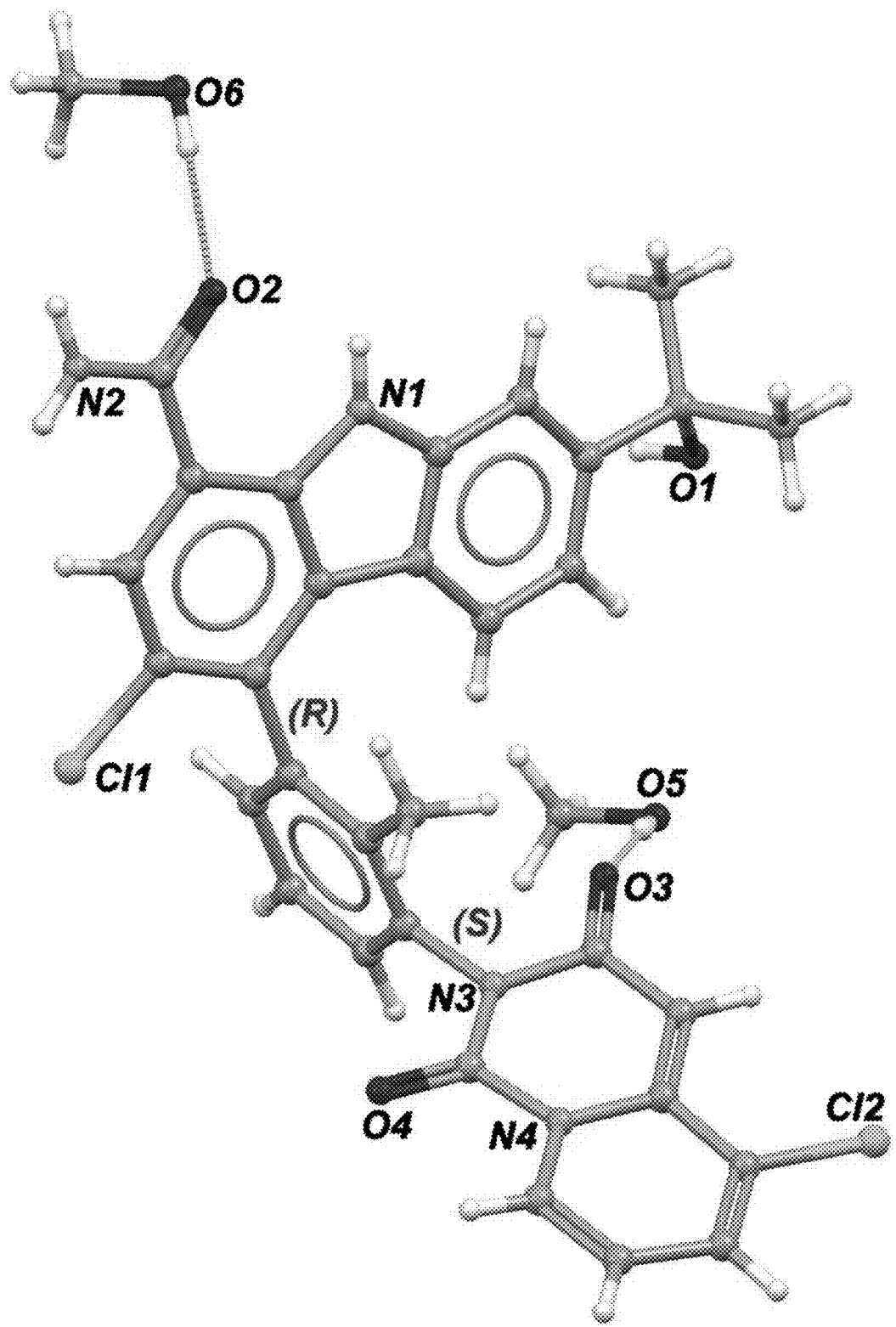
FIG. 6 shows the absolute stereochemistry of Example 33 dimethanolate, crystal Form M2-1.

The absolute configuration of Example 33 was confirmed by single crystal x-ray analysis of crystals prepared by dissolving the compound in excess methanol and slowly evaporating the solvent at room temperature to provide a di-methanol solvate (crystalline form M2-1). Unit cell dimensions: a=7.41 Å, b=9.74 Å, c=44.55 Å, α=90.0°, β=90.0°, γ=90.0°; Space group: $P2_12_12_1$; Molecules of Example 33/asymmetric unit: 1; Volume/Number of molecules in the unit cell=3214 Å$^3$; Density (calculated)=1.346 g/cm$^3$. Fractional atomic coordinates at 173 K are given in Table 7, and a depiction of the structure is given in FIG. 6.

Example 34

3-Chloro-4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four atropisomers)

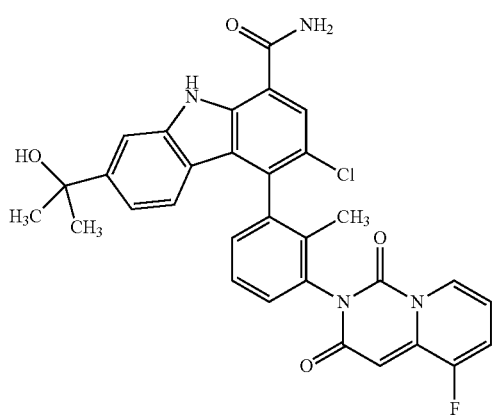

(34)

A mixture of 4-bromo-3-chloro-7-(2-hydroxypropan-2-yl)-9H-carbazole-1-carboxamide [Intermediate 3] (0.076 g, 0.200 mmol), 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 37] (0.072 g, 0.182 mmol) and Cs₂CO₃ (0.118 g, 0.363 mmol) in THF (3 mL) and water (0.75 mL) was bubbled with nitrogen for 2 min, then was treated with PdCl₂(dppf) DCM adduct (7.4 mg, 9.09 μmol). Bubbling with nitrogen was continued for 30 sec and the reaction vessel was sealed. The mixture was stirred at room temperature overnight, then was diluted with EtOAc and washed sequentially with water and brine. The combined aqueous layers were extracted with DCM. The combined organic layers were dried and concentrated. The residue was purified by column chromatography on silica gel, eluting with EtOAc-hexanes, to give 3-chloro-4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four atropisomers) as a yellow solid (0.049 g, 43% yield). Mass spectrum m/z 571 (M+H)⁺. ¹H NMR (400 MHz, DMSO-d₆) δ 11.52-11.48 (m, 1H), 8.27 (br. s., 1H), 8.15-8.09 (m, 2H), 7.84 (s, 1H), 7.59 (br. s., 1H), 7.56-7.46 (m, 2H), 7.30-7.26 (m, 1H), 7.03-6.97 (m, 1H), 6.72 (d, J=8.4 Hz, 1H), 6.60-6.51 (m, 2H), 5.85 (s, 1H), 4.98 (s, 1H), 1.71 (s, 3H), 1.46-1.42 (m, 6H).

Examples 35 and 36

3-Chloro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (single atropisomers)

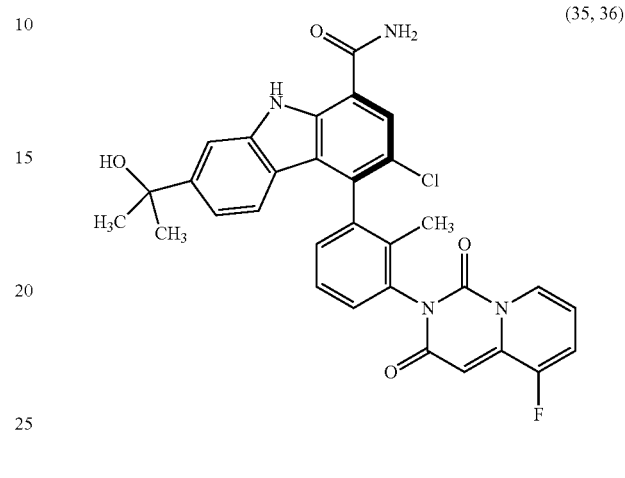

(35, 36)

A sample of 3-chloro-4-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of four atropisomers) [Example 34] (690 mg) was separated by chiral super-critical fluid chromatography as follows: column: CHIRALPAK® IB (2×25 cm, 5 μm); Mobile Phase: CO₂-MeOH (63:37) at 50 mL/min, 45° C., 100 bar. The first peak eluting from the column provided one single atropisomer of 3-chloro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 35]. Mass spectrum m/z 571 (M+H)⁺. ¹H NMR (400 MHz, DMSO-d₆) δ 11.50 (s, 1H), 8.27 (br. s., 1H), 8.14 (s, 1H), 8.11 (d, J=7.5 Hz, 1H), 7.84 (d, J=1.1 Hz, 1H), 7.59 (br. s., 1H), 7.56-7.51 (m, 1H), 7.49-7.46 (m, 1H), 7.29 (dd, J=7.5, 1.3 Hz, 1H), 7.23 (dd, J=10.3, 7.5 Hz, 1H), 7.01 (dd, J=8.4, 1.5 Hz, 1H), 6.65 (d, J=8.6 Hz, 1H), 6.54 (td, J=7.4, 5.2 Hz, 1H), 5.85 (s, 1H), 4.98 (s, 1H), 1.71 (s, 3H), 1.48-1.41 (m, 6H).

The third peak eluting from the column provided the other single atropisomer of 3-chloro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 36]. Mass spectrum m/z 553 (M+H-H₂O)⁺. ¹H NMR (400 MHz, DMSO-d₆) δ 11.49 (s, 1H), 8.27 (br. s., 1H), 8.14 (s, 1H), 8.10 (d, J=7.7 Hz, 1H), 7.83 (s, 1H), 7.59 (br. s., 1H), 7.56-7.45 (m, 2H), 7.30-7.20 (m, 2H), 6.99 (d, J=8.6 Hz, 1H), 6.72 (d, J=8.6 Hz, 1H), 6.56 (td, J=7.5, 5.3 Hz, 1H), 5.85 (s, 1H), 4.98 (s, 1H), 1.71 (s, 3H), 1.45-1.42 (m, 6H).

Example 37

3-Chloro-7-(2-hydroxypropan-2-yl)-4-(3-(5-methoxy-1,3-dioxo-1H-pyrido[1,2-c]pyrimidin-2(3H)-yl)-2-methylphenyl)-9H-carbazole-1-carboxamide (mixture of four atropisomers) (37)

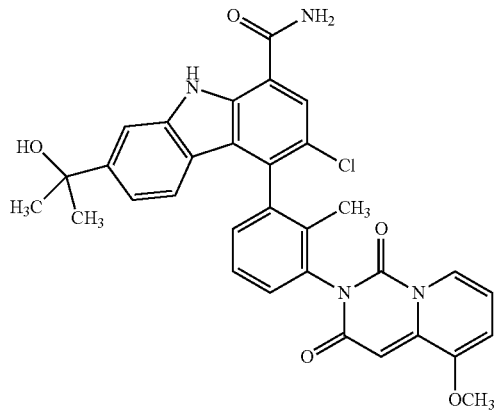

A mixture of 4-bromo-3-chloro-7-(2-hydroxypropan-2-yl)-9H-carbazole-1-carboxamide [Intermediate 3] (0.051 g, 0.135 mmol), 5-methoxy-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 32] (0.050 g, 0.122 mmol) and $Cs_2CO_3$ (0.080 g, 0.245 mmol) in THF (2 mL) and water (0.5 mL) was bubbled with nitrogen for 2 min, then was treated with $PdCl_2$(dppf) DCM adduct (5.0 mg, 6.12 μmol). Bubbling with nitrogen was continued for 30 sec and the reaction vessel was sealed. The mixture was heated at 60° C. overnight. The cooled mixture was diluted with DCM and MeOH, dried and concentrated. The residue was purified by column chromatography on silica gel, eluting with EtOAc-hexanes, to give 3-chloro-7-(2-hydroxypropan-2-yl)-4-(3-(5-methoxy-1,3-dioxo-1H-pyrido [1,2-c]pyrimidin-2(3H)-yl)-2-methylphenyl)-9H-carbazole-1-carboxamide (mixture of four atropisomers) as a yellow solid (32.8 mg, 44% yield). Mass spectrum m/z 583 $(M+H)^+$. $^1H$ NMR (400 MHz, DMSO-$d_6$) δ 11.51-11.47 (m, 1H), 8.27 (br. s., 1H), 8.14 (d, J=1.5 Hz, 1H), 7.93 (d, J=7.5 Hz, 1H), 7.83 (s, 1H), 7.59 (br. s., 1H), 7.55-7.45 (m, 3H), 7.30-7.25 (m, 1H), 7.03-6.97 (m, 1H), 6.71 (d, J=8.1 Hz, 1H), 6.56 (q, J=7.6 Hz, 1H), 5.90 (s, 1H), 4.98 (s, 1H), 3.91 (s, 3H), 1.69 (s, 3H), 1.45-1.42 (m, 6H).

Examples 38 and 39

3-Chloro-4-(R)-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide (single atropisomers) (38, 39)

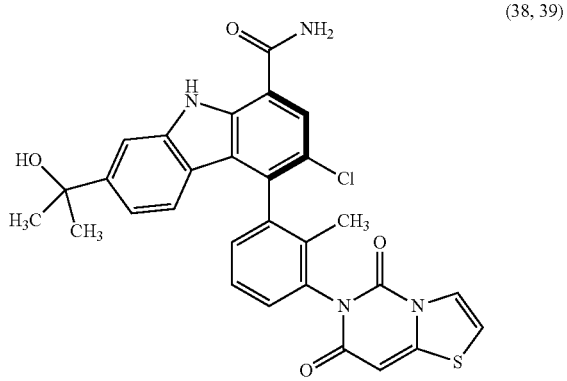

A mixture of 4-bromo-3-chloro-7-(2-hydroxypropan-2-yl)-9H-carbazole-1-carboxamide [Intermediate 3] (0.139 g, 0.364 mmol), 6-(2-methyl-3-(4,4,5,5-tetramethyl-1,3,2-dioxaborolan-2-yl)phenyl)-5H-thiazolo[3,2-c]pyrimidine-5,7(6H)-dione [Intermediate 36] (0.127 g, 0.331 mmol) and $Cs_2CO_3$ (0.215 g, 0.661 mmol) in THF (3.0 mL) and water (0.75 mL) was bubbled with argon for 3 min, then was treated with $PdCl_2$(dppf) DCM adduct (0.013 g, 0.017 mmol). The mixture was bubbled with argon for 30 sec more and the reaction vessel was sealed. The mixture was stirred at 50° C. for 5 h. The cooled mixture was diluted with EtOAc and washed sequentially with water and brine. The combined aqueous layers was extracted with EtOAc, and the combined organic layers were dried and concentrated. The residue was purified by column chromatography on silica gel (80 g), eluting with EtOAc-hexanes (90%, then 100%), to give 3-chloro-4-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide (mixture of four atropisomers) as a tan solid (62.7 mg, 32% yield). This material was separated by chiral super-critical fluid chromatography as follows: column: CHIRALPAK® AD-H (3×25 cm, 5 μm); Mobile Phase: $CO_2$-MeOH (60:40) at 85 mL/min; sample preparation: 9 mg/mL in MeOH-DMSO; injection: 2 mL. The third peak eluted from the column provided one single atropisomer of 3-chloro-4-(R)-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide [Example 38]. Mass spectrum m/z 559 $(M+H)^+$. $^1H$ NMR (400 MHz, DMSO-$d_6$) δ 11.50 (s, 1H), 8.27 (br. s., 1H), 8.14 (s, 1H), 7.83 (d, J=0.9 Hz, 1H), 7.69 (dd, J=4.6, 0.7 Hz, 1H), 7.59 (br. s., 1H), 7.54-7.49 (m, 1H), 7.47-7.43 (m, 1H), 7.26 (dd, J=7.4, 1.2 Hz, 1H), 7.03 (d, J=4.6 Hz, 1H), 6.99 (dd, J=8.6, 1.5 Hz, 1H), 6.62 (d, J=8.4 Hz, 1H), 6.28 (s, 1H), 4.98 (s, 1H), 1.70 (s, 3H), 1.45-1.42 (m, 6H).

The fourth peak eluted from the column provided the other single atropisomer of 3-chloro-4-(R)-(3-(5,7-dioxo-5H-thiazolo[3,2-c]pyrimidin-6(7H)-yl)-2-methylphenyl)-7-(2-hydroxypropan-2-yl)-9H-carbazole-1-carboxamide [Example 39]. Mass spectrum m/z 541 $(M+H-H_2O)^+$. $^1H$ NMR (400 MHz, DMSO-$d_6$) δ 11.49 (s, 1H), 8.27 (br. s., 1H), 8.13 (s, 1H), 7.83 (d, J=0.9 Hz, 1H), 7.73-7.65 (m, 2H), 7.59 (br. s., 1H), 7.54-7.43 (m, 2H), 7.26 (dd, J=7.5, 1.3 Hz, 1H), 7.05 (d, J=4.6 Hz, 1H), 6.98 (dd, J=8.5, 1.7 Hz, 1H), 6.71 (d, J=8.6 Hz, 1H), 6.28 (s, 1H), 1.70 (s, 3H), 1.43 (d, J=2.9 Hz, 6H).

Examples 40 and 41

3-Fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (single atropisomers) (40, 41)

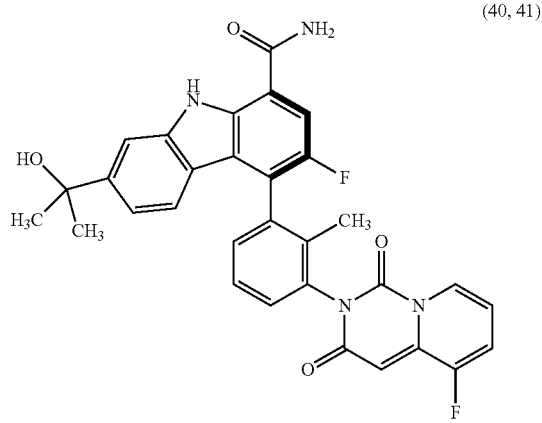

Preparation 40A: 3-Fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (mixture of two atropisomers)

A mixture of 4-bromo-3-fluoro-7-(2-hydroxypropan-2-yl)-9H-carbazole-1-carboxamide [Intermediate 27] (0.200 g, 0.548 mmol), 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione [Intermediate 37] (0.260 g, 0.657 mmol) and $Cs_2CO_3$ (0.357 g, 1.10 mmol) in dioxane (4 mL) and water (1 mL) was bubbled with nitrogen for 2 min, then was treated with $PdCl_2$(dppf) DCM adduct (0.022 g, 0.027 mmol). Bubbling with nitrogen was continued for 30 sec and the reaction vessel was sealed. The mixture was heated at 60° C. overnight. The cooled mixture was diluted with EtOAc and washed sequentially with water and brine. The combined aqueous layers were extracted with DCM, and combined organic layers were dried and concentrated. The residue was purified by column chromatography on silica gel, eluting with EtOAc-hexanes, to give 3-fluoro-4-(3-(5-fluoro-1,3-dioxo-1H-pyrido [1,2-c]pyrimidin-2(3H)-yl)-2-methylphenyl)-7-(2-hydroxypropan-2-yl)-9H-carbazole-1-carboxamide (mixture of four atropisomers) as a yellow solid (0.194 g, 63% yield).

Examples 40 and 41

A sample of 3-fluoro-4-(3-(5-fluoro-1,3-dioxo-1H-pyrido [1,2-c]pyrimidin-2(3H)-yl)-2-methylphenyl)-7-(2-hydroxypropan-2-yl)-9H-carbazole-1-carboxamide (mixture of four atropisomers) was separated by chiral super-critical fluid chromatography as follows: column: CHIRALPAK® OD-H (5×25 cm, 5 μm); Mobile Phase: $CO_2$-IPA (55:45) at 120 mL/min, 50° C., 100 bar; sample preparation: 6.8 mg/mL in MeOH—$CHCl_3$ (1:1); injection: 1 mL. The first peak eluting from the column provided one single atropisomer of 3-fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 40]. Mass spectrum m/z 555 (M+H)$^+$. $^1$H NMR (400 MHz, DMSO-$d_6$) δ 11.40 (s, 1H), 8.21 (br. s., 1H), 8.12 (d, J=7.5 Hz, 1H), 7.95 (d, J=10.8 Hz, 1H), 7.84 (d, J=1.1 Hz, 1H), 7.60 (br. s., 1H), 7.56-7.46 (m, 2H), 7.41 (dd, J=7.4, 1.4 Hz, 1H), 7.23 (dd, J=10.2, 7.4 Hz, 1H), 7.02 (dd, J=8.6, 1.5 Hz, 1H), 6.88-6.82 (m, 1H), 6.56 (td, J=7.4, 5.2 Hz, 1H), 5.86 (s, 1H), 4.98 (s, 1H), 1.77 (s, 3H), 1.47-1.42 (m, 6H).

The third peak eluting from the column provided the other single atropisomer of 3-fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 41]. Mass spectrum m/z 537 (M+H-$H_2O$)$^+$. $^1$H NMR (400 MHz, DMSO-$d_6$) δ 11.41 (s, 1H), 8.29-8.17 (m, 1H), 8.13 (d, J=7.3 Hz, 1H), 7.96 (d, J=10.8 Hz, 1H), 7.85 (d, J=1.1 Hz, 1H), 7.65-7.57 (m, 1H), 7.57-7.47 (m, 2H), 7.43 (d, J=1.5 Hz, 1H), 7.28-7.21 (m, 1H), 7.02 (d, J=1.5 Hz, 1H), 6.90-6.83 (m, 1H), 6.64-6.53 (m, 1H), 5.87 (s, 1H), 4.99 (s, 1H), 1.78 (s, 3H), 1.48-1.44 (m, 6H).

Alternative Preparation of 3-Fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide (single atropisomer) [Example 41]

A mixture of 4-bromo-3-fluoro-7-(2-hydroxypropan-2-yl)-9H-carbazole-1-carboxamide [Intermediate 27] (6.00 g, 16.4 mmol), 5-fluoro-2-(2-methyl-3-(4,4,5,5-tetramethyl-1,3,2-dioxaborolan-2-yl)phenyl)-1H-pyrido[1,2-c]pyrimidine-1,3(2H)-dione (single enantiomer) [Intermediate 38] (7.81 g, 19.7 mmol), 2 M aqueous $K_3PO_4$ (24.6 mL, 49.3 mmol), and THF (70 mL) was subjected to three evacuate-fill cycles with nitrogen. The mixture was treated with 1,1'-bis(di-tert-butylphosphino)ferrocene palladium(II) chloride (0.535 g, 0.821 mmol), and subjected to two more evacuate-fill cycles with nitrogen. The mixture was stirred at room temperature overnight. The mixture was diluted with EtOAc, washed sequentially with water and brine, and dried. The aqueous layer was filtered and the collected solid was added to the organic layer. The organic layer was concentrated, and the residue was purified by column chromatography on silica gel, eluting with EtOAc-hexanes (sequentially 50%, 62%, 75%, 85% and 100%), to provide 3-fluoro-4-(3-(5-fluoro-1,3-dioxo-1H-pyrido [1,2-c]pyrimidin-2 (3H)-yl)-2-methylphenyl)-7-(2-hydroxypropan-2-yl)-9H-carbazole-1-carboxamide (mixture of two atropisomers) as a yellow solid (8.55 g, 94% yield). A sample of this material (combined with other batches of the same material) was separated by chiral super-critical fluid chromatography as follows: column: CHIRALPAK® IC (3×25 cm, 5 μm); Mobile Phase: $CO_2$-MeOH (50:50) at 165 mL/min, 45° C., 100 bar; sample preparation: 55 mg/mL in MeOH-THF-DMSO (2:1:1); injection: 3 mL. The first peak eluting from the column provided a single atropisomer of 3-fluoro-4-(R)-(3-(5-fluoro-1,3-dioxo-1H-pyrido[1,2-c]pyrimidin-2(3H)-yl)-2-methylphenyl)-7-(2-hydroxypropan-2-yl)-9H-carbazole-1-carboxamide [Example 41].

Example 42

3-Chloro-4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (mixture of four atropisomers)

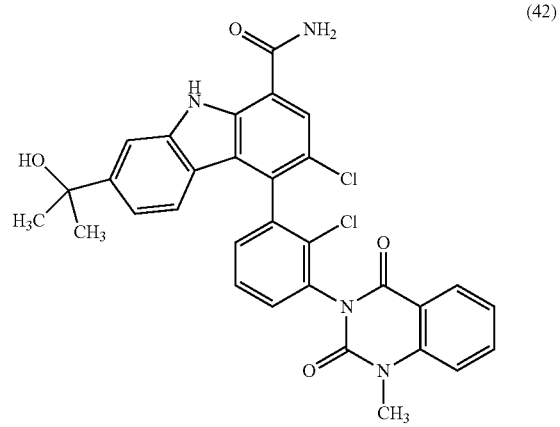 [SMILES: Cn1c(=O)n(-c2cccc(-c3c(Cl)cc(C(N)=O)c4[nH]c5cc(C(C)(C)O)ccc5c34)c2Cl)c(=O)c2ccccc21]

(42)

A mixture of 4-bromo-3-chloro-7-(2-hydroxypropan-2-yl)-9H-carbazole-1-carboxamide [Intermediate 3] (36 mg, 0.094 mmol), (Z)-4-((2-chloro-3-(4,4,5,5-tetramethyl-1,3,2-dioxaborolan-2-yl)phenyl)imino)-1-methyl-1H-benzo[d][1,3]oxazin-2(4H)-one [Intermediate 40] (42.8 mg, 0.104 mmol), EtOH (1 mL), toluene (1 mL) and 2 M aqueous $Na_2CO_3$ (0.16 mL, 0.311 mmol) was bubbled with nitrogen for 5 min. The mixture was treated with tetrakis(triphenylphosphine)palladium (8.7 mg, 7.55 μmol), and the reaction vessel was sealed and heated at 90° C. for 16 h. The cooled mixture was partitioned between EtOAc and water, and the organic phase was dried and concentrated. The residue was purified by column chromatography on silica gel (4 g), eluting with MeOH-DCM containing 1% TEA (gradient from 0-5%). The resulting material was further purified using preparative HPLC (PHENOMENEX® Axia $C_{18}$ 30×100 mm), eluting with MeCN-water containing 0.1% TFA (gradient from 20-100%, 30 mL/min). The appropriate fractions were treated with saturated aqueous NaHCO$_3$ and concentrated. The residue was partitioned between EtOAc and water, and the organic phase was washed with brine, dried and concentrated to give 3-chloro-4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (mixture of four atropisomers) as a white solid (2.5 mg, 4% yield). Mass spectrum m/z 569 (M+H-H$_2$O)$^+$. $^1$H NMR (400 MHz, chloroform-d) δ 8.38-8.23 (m, 1H), 7.73 (d, J=1.5 Hz, 2H), 7.70-7.66 (m, 1H), 7.64 (s, 1H), 7.60-7.55 (m, 1H), 7.51-7.45 (m, 1H), 7.37-7.28 (m, 2H), 7.26-7.20 (m, 1H), 7.10-6.78 (m, 1H), 3.70 (s, 2H), 3.67 (s, 1H), 1.65 (s, 4H), 1.64 (s, 2H).

Example 43

3-Chloro-4-(R)-(2-chloro-3-(1-methyl-2,4-dioxo-1, 2-dihydroquinazolin-3(4H)-yl) phenyl)-7-(2-hydroxypropan-2-yl)-9H-carbazole-1-carboxamide (single atropisomer)

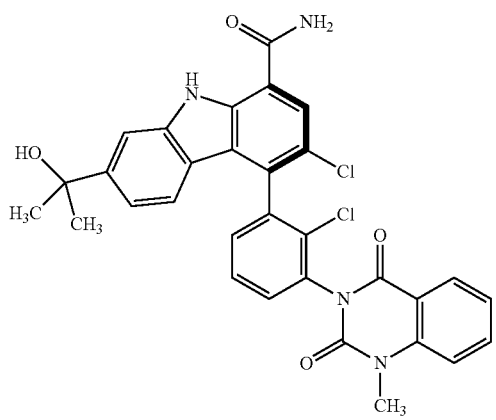

(43)

A sample of 3-chloro-4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (mixture of four atropisomers) [Example 42] (110 mg) was separated by chiral super-critical fluid chromatography as follows: column: Lux Cel-4 (3×25 cm, 5 µm); Mobile Phase: CO$_2$-MeOH (60:40) at 85 mL/min; sample preparation: 6.7 mg/mL in MeOH-acetone (9:1); injection: 3.0 mL. The fourth peak eluting from the column provided a single atropisomer of 3-chloro-4-(R)-(2-chloro-3-(1-methyl-2,4-dioxo-1,2-dihydroquinazolin-3(4H)-yl)phenyl)-7-(2-hydroxypropan-2-yl)-9H-carbazole-1-carboxamide as a yellow solid (20 mg, 18% yield). Mass spectrum m/z 569 (M+H-H$_2$O)$^+$. $^1$H NMR (400 MHz, chloroform-d) δ 10.44 (s, 1H), 8.41-8.17 (m, 1H), 7.78-7.72 (m, 2H), 7.68 (s, 1H), 7.65-7.60 (m, 1H), 7.59-7.54 (m, 1H), 7.46 (d, J=7.5 Hz, 1H), 7.34-7.28 (m, 2H), 7.25 (s, 1H), 7.01 (d, J=8.6 Hz, 1H), 3.70 (s, 3H), 1.64 (s, 6H).

Example 44

3-Chloro-4-(2-chloro-3-(8-fluoro-1-methyl-2,4-dioxo-1,2-dihydroquinazolin-3(4H)-yl) phenyl)-7-(2-hydroxypropan-2-yl)-9H-carbazole-1-carboxamide (mixture of four atropisomers)

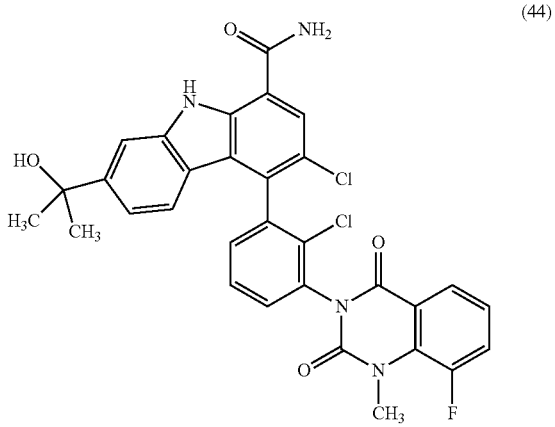 [SMILES: Cn1c(=O)n(-c2cccc(-c3c(Cl)cc(C(N)=O)c4[nH]c5cc(C(C)(C)O)ccc5c34)c2Cl)c(=O)c2cccc(F)c21]

(44)

A mixture of 4-bromo-3-chloro-7-(2-hydroxypropan-2-yl)-9H-carbazole-1-carboxamide [Intermediate 3] (30 mg, 0.079 mmol), 3-(2-chloro-3-(4,4,5,5-tetramethyl-1,3,2-dioxaborolan-2-yl)phenyl)-8-fluoro-1-methylquinazoline-2,4 (1H,3H)-dione [Intermediate 41] (40.6 mg, 0.094 mmol), EtOH (1 mL), toluene (1 mL) and 2 M aqueous Na$_2$CO$_3$ (0.13 mL, 0.26 mmol) was bubbled with nitrogen for 5 min. The mixture was treated with tetrakis(triphenylphosphine) palladium (7.3 mg, 6.29 µmol), and the reaction vessel was sealed and heated at 90° C. for 16 h. The cooled mixture was partitioned between EtOAc and water, and the organic phase was dried and concentrated. The residue was purified by column chromatography on silica gel (12 g), eluting with MeOH-DCM containing 1% TEA (gradient from 0-5%). The resulting material was further purified using preparative HPLC (PHENOMENEX® Axia C$_{18}$ 30×100 mm), eluting with MeCN-water containing 0.1% TFA (gradient from 20-100%, 10 min, 30 mL/min). The appropriate fractions were treated with saturated aqueous NaHCO$_3$ and concentrated. The residue was partitioned between EtOAc and water, and the organic phase was washed with brine, dried and concentrated to provide 3-chloro-4-(2-chloro-3-(8-fluoro-1-methyl-2,4-dioxo-1,2-dihydroquinazolin-3(4H)-yl) phenyl)-7-(2-hydroxypropan-2-yl)-9H-carbazole-1-carboxamide (mixture of four atropisomers) as a white solid (6 mg, 11% yield). Mass spectrum m/z 587 (M+H-H$_2$O)$^+$. $^1$H NMR (400 MHz, chloroform-d) ☐δ 10.46 (s, 1H), 7.74 (s, 1H), 7.68 (s, 1H), 7.66-7.61 (m, 1H), 7.59-7.54 (m, 1H), 7.51-7.46 (m, 2H), 7.27-7.17 (m, 2H), 7.06-6.88 (m, 1H), 3.88 (dd, J=11.6, 8.0 Hz, 3H), 1.64 (s, 6H). $^{19}$F NMR (400 MHz, chloroform-d) δ −121.34.

Example 45

3-Chloro-4-(R)-(2-chloro-3-(8-fluoro-1-methyl-2,4-dioxo-1,2-dihydroquinazolin-3(4H)-yl)phenyl)-7-(2-hydroxypropan-2-yl)-9H-carbazole-1-carboxamide (single atropisomer)

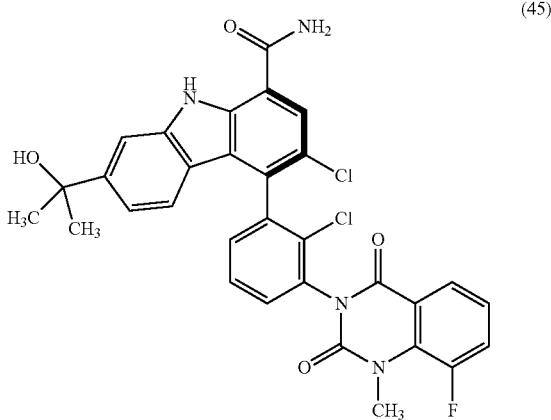

(45)

A sample of 3-chloro-4-(2-chloro-3-(1-methyl-2,4-dioxo-1,2-dihydroquinazolin-3(4H)-yl)phenyl)-7-(2-hydroxypropan-2-yl)-9H-carbazole-1-carboxamide (mixture of four atropisomers) [Example 44] (100 mg) was separated by chiral super-critical fluid chromatography as follows: column: Lux Cel-4 (3×25 cm, 5 μm); Mobile Phase: $CO_2$-MeOH (60:40) at 85 mL/min, 50° C., 100 bar; sample preparation: 6.7 mg/mL in MeOH-acetone (1:1); injection: 3.0 mL. The fourth peak eluting from the column provided a single atropisomer of 3-chloro-4-(R)-(2-chloro-3-(1-methyl-2,4-dioxo-1,2-dihydroquinazolin-3(4H)-yl)phenyl)-7-(2-hydroxypropan-2-yl)-9H-carbazole-1-carboxamide as a yellow solid (9.3 mg). Mass spectrum m/z 569 (M+H-$H_2O$)+. $^1$H NMR (400 MHz, chloroform-d) δ 10.45 (s, 1H), 8.11 (d, J=7.3 Hz, 1H), 7.73 (s, 1H), 7.72 (d, J=9.0 Hz, 1H), 7.68 (d, J=1.1 Hz, 1H), 7.67-7.61 (m, 1H), 7.56 (dd, J=7.9, 1.8 Hz, 1H), 7.54-7.52 (m, 1H), 7.51-7.42 (m, 2H), 7.26-7.19 (m, 2H), 7.00 (d, J=8.6 Hz, 1H), 3.90 (d, J=8.1 Hz, 3H), 1.64 (s, 6H). $^{19}$F NMR (376 MHz, chloroform-d) δ -121.33.

Example 46

4-(2-Chloro-3-(8-fluoro-1-methyl-2,4-dioxo-1,2-dihydroquinazolin-3(4H)-yl)phenyl)-3-fluoro-7-(2-hydroxypropan-2-yl)-9H-carbazole-1-carboxamide (mixture of four atropisomers)

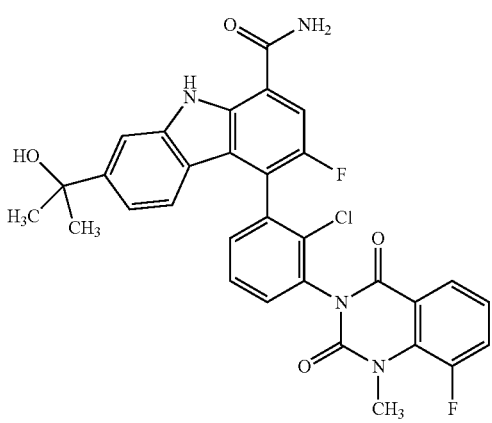

(46)

A mixture of 4-bromo-3-fluoro-7-(2-hydroxypropan-2-yl)-9H-carbazole-1-carboxamide [Intermediate 27] (40 mg, 0.110 mmol), 3-(2-chloro-3-(4,4,5,5-tetramethyl-1,3,2-dioxaborolan-2-yl)phenyl)-8-fluoro-1-methylquinazoline-2,4(1H,3H)-dione [Intermediate 41] (47 mg, 0.110 mmol), $Cs_2CO_3$ (107 mg, 0.329 mmol), dioxane (8 mL) and water (2 mL) was bubbled with nitrogen for 10 min. The mixture was treated with $PdCl_2$(dppf) DCM adduct (7.2 mg, 8.76 μmol), and heated at 60° C. overnight. The cooled mixture was partitioned between EtOAc and water. The organic phase was dried and concentrated. The residue was purified by column chromatography on silica gel, eluting with MeOH-DCM (gradient from 0-5%), to give 4-(2-chloro-3-(8-fluoro-1-methyl-2,4-dioxo-1,2-dihydroquinazolin-3(4H)-yl)phenyl)-3-fluoro-7-(2-hydroxypropan-2-yl)-9H-carbazole-1-carboxamide (mixture of four atropisomers) as a white solid (20 mg, 31% yield). Mass spectrum m/z 569 (M+H-$H_2O$)+. $^1$H NMR (400 MHz, chloroform-d) δ 10.46 (s, 1H), 7.74 (s, 1H), 7.68 (s, 1H), 7.66-7.61 (m, 1H), 7.59-7.54 (m, 1H), 7.51-7.46 (m, 2H), 7.27-7.17 (m, 2H), 7.06-6.88 (m, 1H), 3.88 (dd, J=11.6, 8.0 Hz, 3H), 1.64 (s, 6H). $^{19}$F NMR (400 MHz, chloroform-d) δ -121.34, -127.34.

Example 47

3-Chloro-4-(R)-(2-chloro-3-(8-fluoro-2,4-dioxo-1,2-dihydroquinazolin-3(4H)-yl)phenyl)-7-(2-hydroxypropan-2-yl)-9H-carbazole-1-carboxamide (single atropisomer)

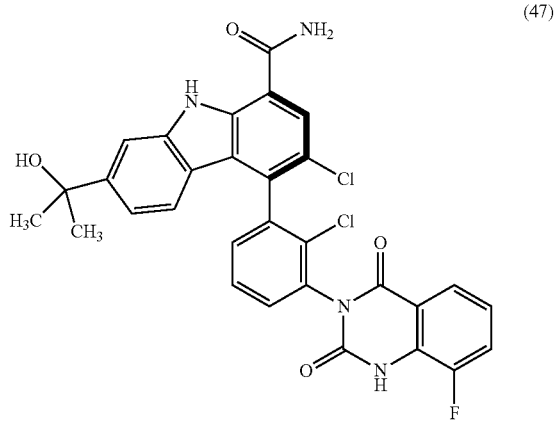

(47)

A mixture of 4-bromo-3-chloro-7-(2-hydroxypropan-2-yl)-9H-carbazole-1-carboxamide [Intermediate 3] (103 mg, 0.269 mmol), 3-(2-chloro-3-(4,4,5,5-tetramethyl-1,3,2-dioxaborolan-2-yl)phenyl)-8-fluoroquinazoline-2,4(1H,3H)-dione [Intermediate 42] (140 mg, 0.336 mmol), THF (5 mL), 2 M aqueous $K_3PO_4$ (0.504 mL, 1.01 mmol) was bubbled with nitrogen for 15 min. The mixture was treated with 1,1'-bis(di-tert-butylphosphino)ferrocene palladium(II) chloride (17.5 mg, 0.027 mmol) and was stirred at room temperature overnight. The mixture was concentrated, and the residue was partitioned between EtOAc and water. The organic phase was dried and concentrated. The residue was purified by preparative HPLC. The appropriate fractions were treated with saturated aqueous $NaHCO_3$ and concentrated. The aqueous residue was extracted with EtOAc. The organic phase was washed sequentially with water and brine, and dried and concentrated to give 3-chloro-4-(2-chloro-3-(8-fluoro-2,4-dioxo-1,2-dihydroquinazolin-3(4H)-yl)phenyl)-7-(2-hydroxypropan-2-yl)-9H-carbazole-1-carboxamide (mixture of four atropisomers) (30 mg, 15% yield). This material was separated by chiral super-critical fluid chromatography as follows: column: CHIRALCEL® OJ-H (3×25 cm, 5 µm); Mobile Phase: $CO_2$-MeOH-MeCN (65:17.5:17.5) at 85 mL/min; sample preparation: 6.8 mg/mL in MeOH—$CHCl_3$ (1:1); injection: 3.0 mL. The first peak eluting from the column provided a single atropisomer of 3-chloro-4-(R)-(2-chloro-3-(8-fluoro-2,4-dioxo-1,2-dihydroquinazolin-3(4H)-yl)phenyl)-7-(2-hydroxypropan-2-yl)-9H-carbazole-1-carboxamide. Mass spectrum m/z 573 $(M+H-H_2O)^+$. $^1H$ NMR (500 MHz, DMSO-$d_6$) δ 11.63-11.48 (m, 1H), 8.39-8.25 (m, 1H), 8.17-8.12 (m, 1H), 7.99-7.92 (m, 1H), 7.88-7.85 (m, 1H), 7.85-7.81 (m, 1H), 7.81-7.76 (m, 1H), 7.76-7.70 (m, 1H), 7.70-7.62 (m, 2H), 7.57-7.46 (m, 1H), 7.32-7.20 (m, 1H), 7.13-6.99 (m, 1H), 6.77-6.63 (m, 1H), 5.10-4.98 (m, 1H), 1.47-1.45 (m, 6H). $^{19}F$ NMR (400 MHz, chloroform-d) δ −129.63.

The compounds in Table 10 were prepared by procedures analogous to those described above, using Intermediates described or prepared by methods similar to those described.

TABLE 10

| Ex. | Structure | Description | Formula weight | Mass spectrum |
|---|---|---|---|---|
| 48 | 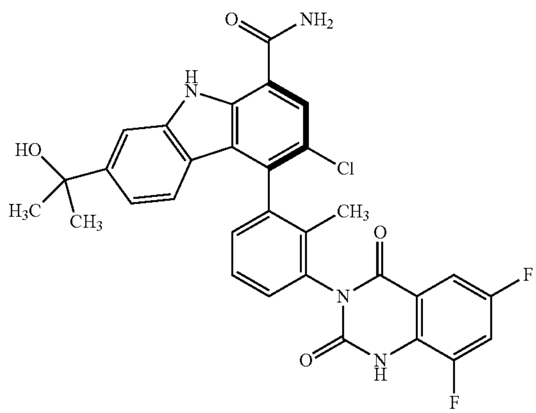 | Single atropisomer Peak 4 | 589.00 | 571 $(M + H—H_2O)^+$ |
| 49 | 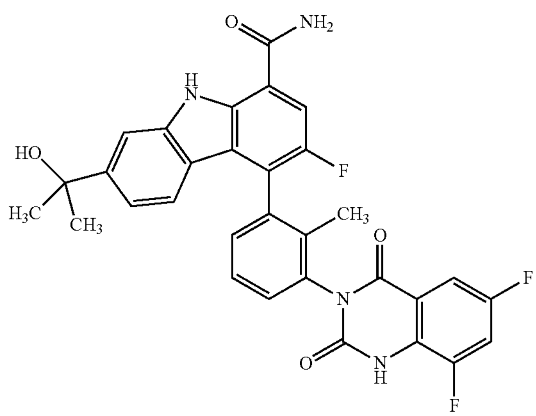 [SMILES: Cc1c(-c2c(F)cc(C(N)=O)c3[nH]c4cc(C(C)(C)O)ccc4c23)cccc1-n1c(=O)[nH]c2c(F)cc(F)cc2c1=O] | Mixture of four atropisomer | 572.54 | 555 $(M + H—H_2O)^+$ |
| 50 | 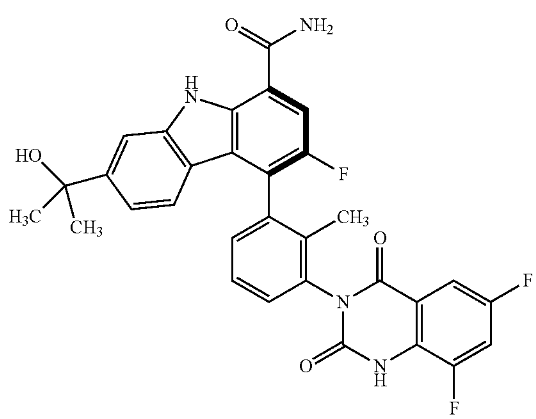 | Single atropisomer Peak 2 | 572.54 | 555 $(M + H—H_2O)^+$ |

TABLE 10-continued

| Ex. | Structure | Description | Formula weight | Mass spectrum |
|---|---|---|---|---|
| 51 | 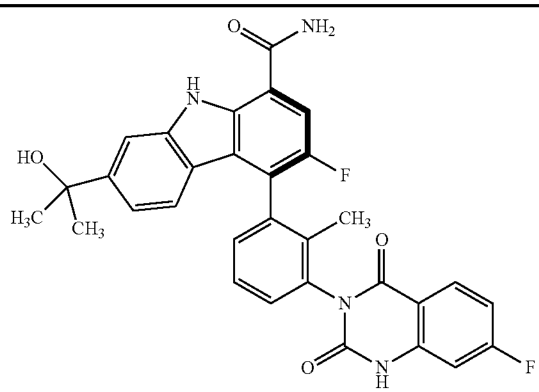 | Single atropisomer Peak 3 | 554.55 | 537 (M + H—H$_2$O)$^+$ |
| 52 | 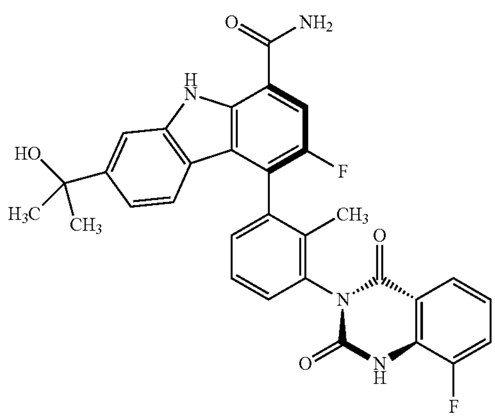 | Single atropisomer Peak 2 | 571.60 | 554 (M + H—H$_2$O)$^+$ |
| 53 | 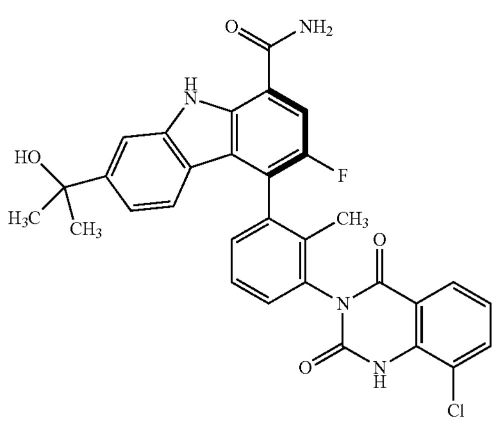 | Single atropisomer Peak 3 | 571.01 | 553 (M + H—H$_2$O)$^+$ |

TABLE 10-continued
| Ex. | Structure | Description | Formula weight | Mass spectrum |
|---|---|---|---|---|
| 54 | 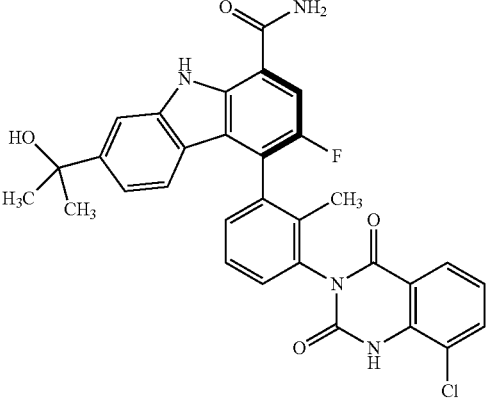 | Single atropisomer Peak 4 | 571.01 | 553 (M + H—H$_2$O)$^+$ |
| 55 | 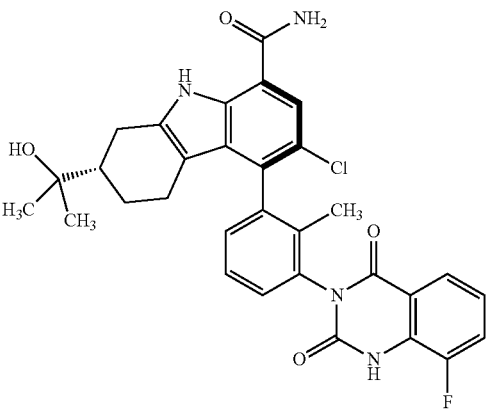 | Single atropisomer Peak 2 | 575.04 | 575 (M + H)$^+$ |
| 56 | 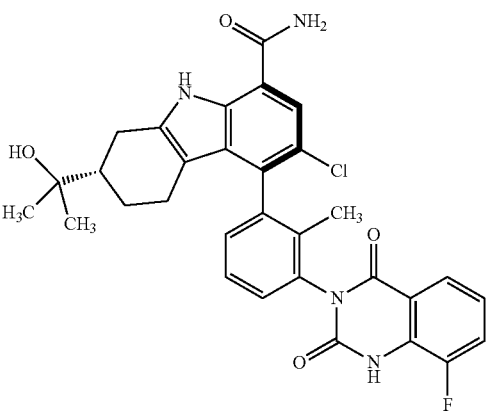 | Single atropisomer Peak 4 | 575.04 | 575 (M + H)$^+$ |

TABLE 10-continued

| Ex. | Structure | Description | Formula weight | Mass spectrum |
|---|---|---|---|---|
| 57 | 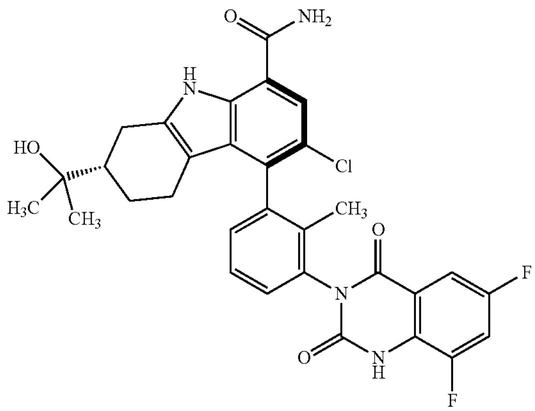 | Single atropisomer Peak 1 | 593.03 | 593 (M + H)+ |
| 58 | 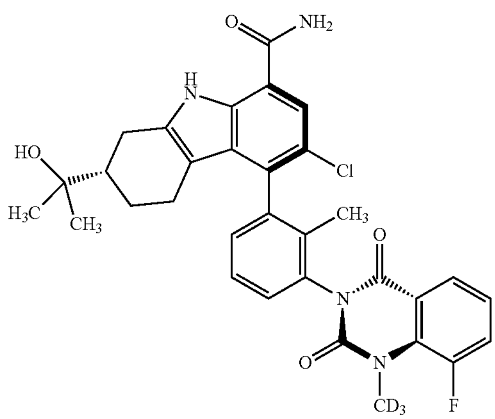 | Single atropisomer Peak 2 | 592.08 | 592 (M + H)+ |
| 59 | 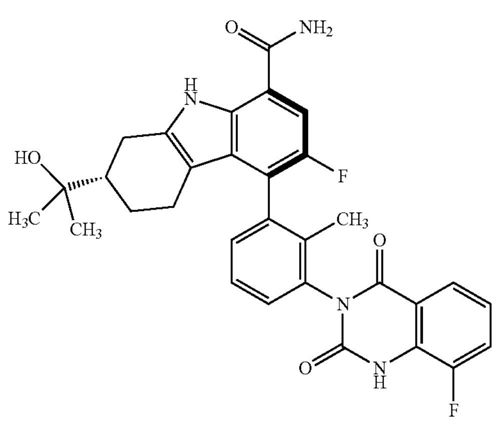 | Single atropisomer Peak 2 | 558.58 | 559 (M + H)+ |

TABLE 10-continued
| Ex. | Structure | Description | Formula weight | Mass spectrum |
|---|---|---|---|---|
| 60 | 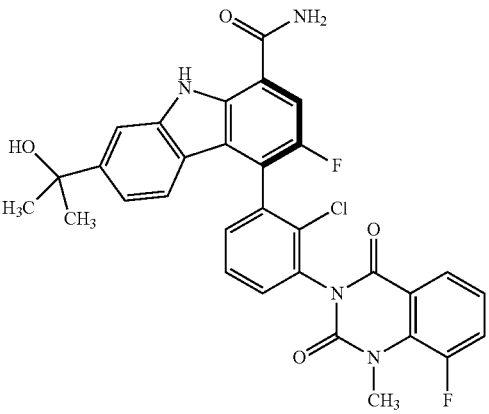 | Single atropisomer Peak 4 | 589.00 | 569 $(M + H - H_2O)^+$ |
| 61 | 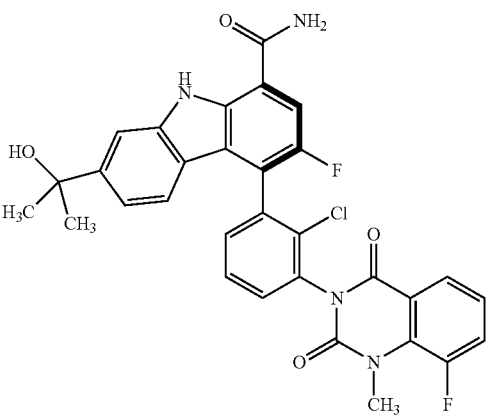 | Single atropisomer Peak 2 | 589.00 | 569 $(M + H - H_2O)^+$ |
| 62 | 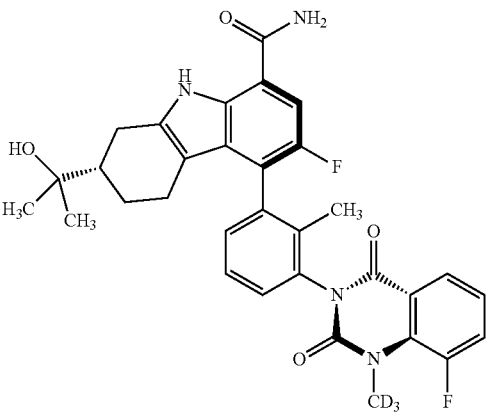 | Single atropisomer Peak 2 | 575.63 | 576 $(M + H)^+$ |

TABLE 10-continued
| Ex. | Structure | Description | Formula weight | Mass spectrum |
|---|---|---|---|---|
| 63 | 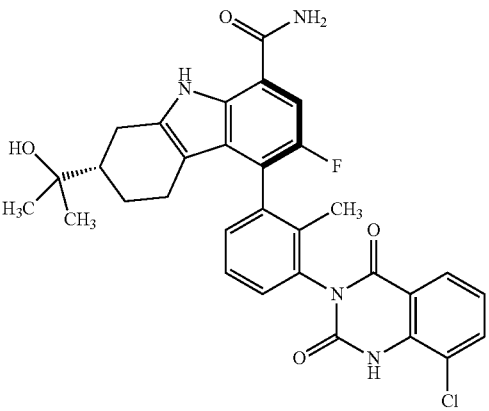 | Single atropisomer Peak 3 | 575.04 | 575 (M + H)+ |
| 64 | 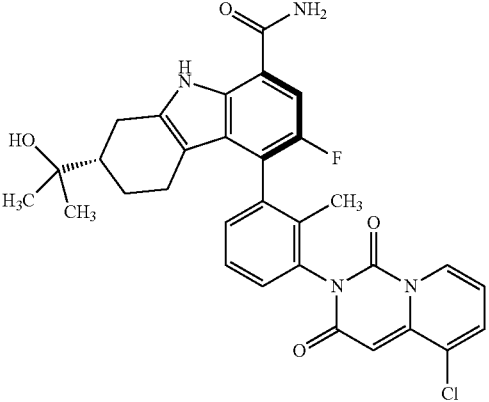 | Single atropisomer Peak 2 | 575.04 | 575 (M + H)+ |
| 65 | 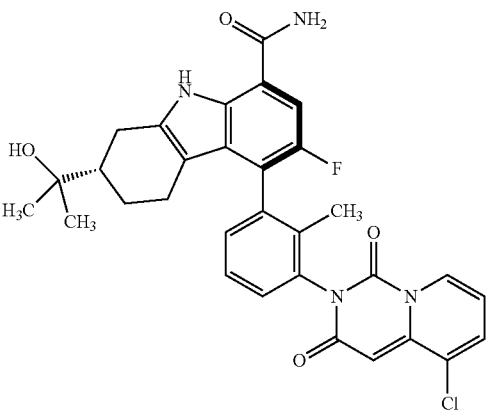 | Single atropisomer Peak 4 | 575.04 | 575 (M + H)+ |

TABLE 10-continued
| Ex. | Structure | Description | Formula weight | Mass spectrum |
|---|---|---|---|---|
| 66 | 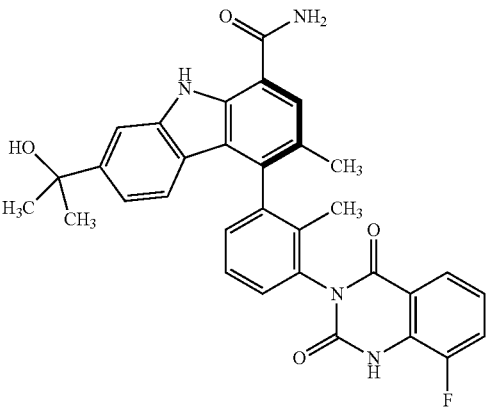 | Single atropisomer Peak 1 | 550.59 | 533 (M + H—H$_2$O)$^+$ |
| 67 | 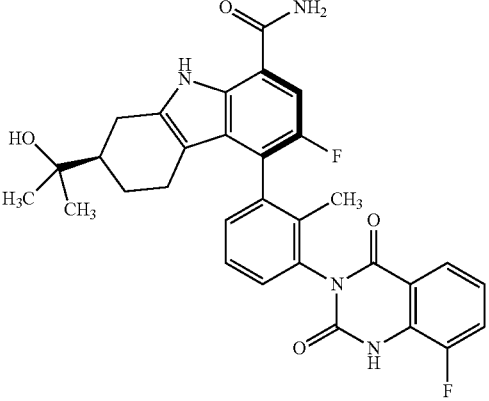 | Single atropisomer Peak 1 | 558.58 | 559 (M + H)$^+$ |
| 68 | 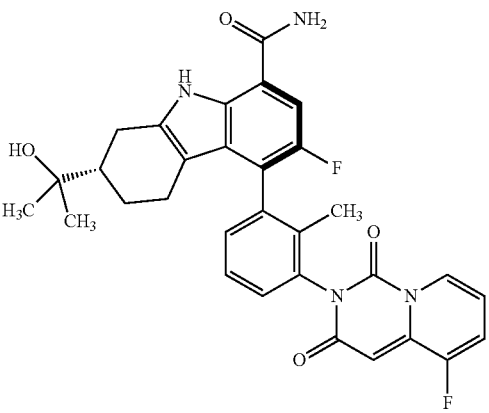 | Single atropisomer Peak 2 | 558.58 | 559 (M + H)$^+$ |

TABLE 10-continued

| Ex. | Structure | Description | Formula weight | Mass spectrum |
|---|---|---|---|---|
| 69 | 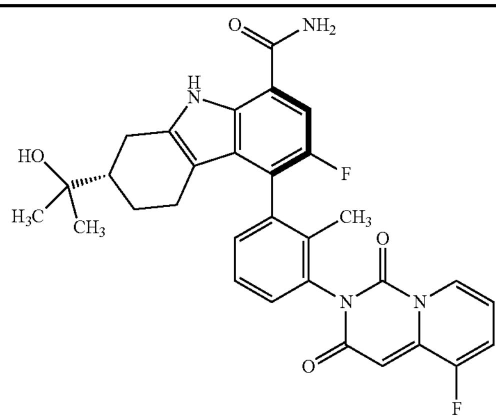 | Single atropisomer Peak 1 | 558.58 | 559 (M + H)+ |
| 70 | 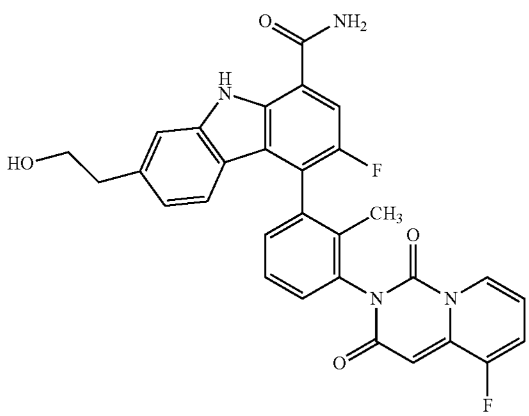 [SMILES: Cc1c(-c2c(F)cc(C(N)=O)c3[nH]c4cc(CCO)ccc4c23)cccc1-n1c(=O)cc2c(F)cccn2c1=O] | Mixture of four atropisomers | 540.52 | 541 (M + H)+ |
| 71 | 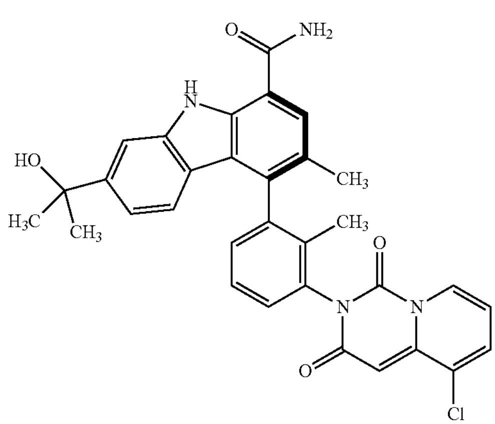 | Single atropisomer Peak 2 | 567.04 | 549 (M + H—H$_2$O)+ |

TABLE 10-continued

| Ex. | Structure | Description | Formula weight | Mass spectrum |
|---|---|---|---|---|
| 72 | 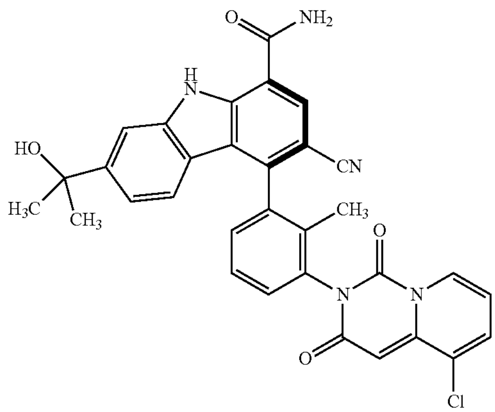 | Single atropisomer Peak 2 | 578.03 | 560 (M + H—H$_2$O)$^+$ |
| 73 | 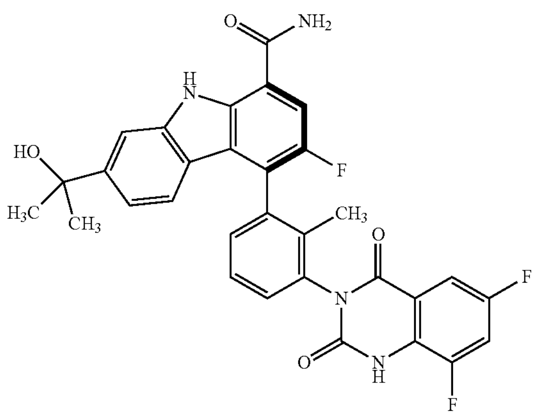 | Single atropisomer Peak 1 | 572.54 | 555 (M + H—H$_2$O)$^+$ |
| 74 | 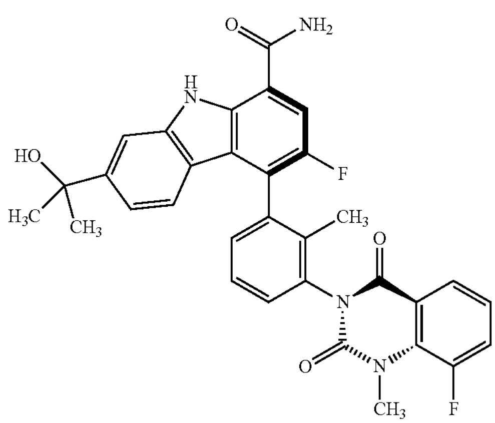 | Single atropisomer Peak 2 | 568.58 | 551 (M + H—H$_2$O)$^+$ |

Comparative Example 75

7-(2-Hydroxypropan-2-yl)-4-(2-methyl-3-(4-oxoquinazolin-3(4H)-yl)phenyl)-9H-carbazole-1-carboxamide

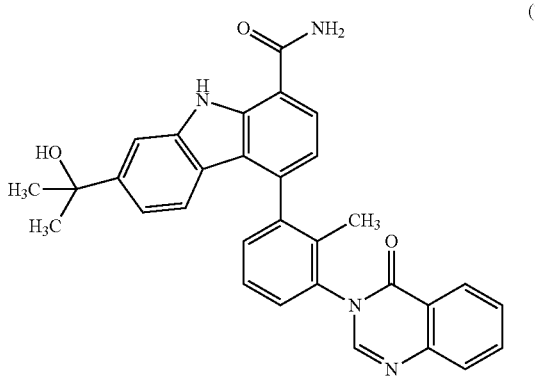

(75)

Comparative Example 75 was disclosed in U.S. Pat. No. 8,084,620 as Example 76-15 and was prepared according to the procedure described therein.

Comparative Example 76

7-(2-Hydroxypropan-2-yl)-3-methyl-4-(2-methyl-3-(4-oxoquinazolin-3(4H)-yl)phenyl)-9H-pyrido[3,4-b]indole-1-carboxamide

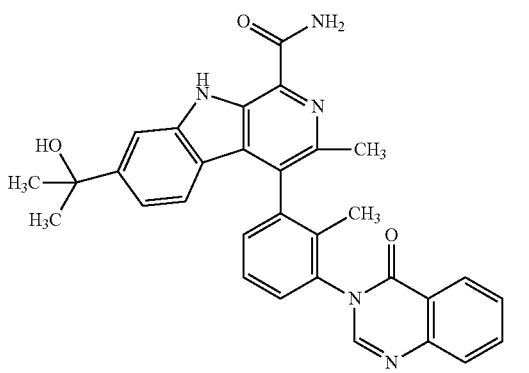

(76)

Comparative Example 76 was disclosed in WO 2011/159857 as Example 38 and was prepared according to the procedure described therein.

Biological Assays

The pharmacological properties of the compounds of this invention may be confirmed by a number of biological assays. The exemplified biological assays, which follow, have been carried out with compounds of the invention.

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM $MgCl_2$, 0.015% Brij 35 surfactant and 4 mM DTT in 1.6% DMSO), with a final volume of 30 µL. After incubating at room temperature for 60 min, the reaction was terminated by adding 45 µL of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required for inhibiting 50% of kinase activity ($IC_{50}$). Compounds were dissolved at 10 mM in DMSO and evaluated at eleven concentrations.

Ramos FLIPR Assay

Ramos RA1 B cells (ATCC CRL-1596) at a density of $2 \times 10^6$ cells/mL in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, room temperature, 5 min) and resuspended at room temperature in RPMI minus phenol red with 50 mM HEPES and 10% FBS to a density of $1 \times 10^6$ cells/mL. 150 L aliquots (150,000 cells/well) were plated into 96 well poly-D-lysine coated assay plates (BD 35 4640) and briefly centrifuged (Beckmann GS-CKR 800 rpm, 5 min, without brake). Next, 50 µL compound dilutions in 0.4% DMSO/RPMI minus phenol red+50 mM HEPES+10% FBS were added to the wells and the plate was incubated at room temperature in the dark for 1 hour. The assay plate was briefly centrifuged as above prior to measuring calcium levels.

Using the FLIPR1 (Molecular Devices), cells were stimulated by adding goat anti-human IgM (Invitrogen AHI0601) to 2.5 µg/mL. Changes in intracellular calcium concentrations were measured for 180 seconds and percent inhibition was determined relative to peak calcium levels seen in the presence of stimulation only.

Jak2 Tyrosine Kinase Assay

Compounds with activity against Jak2 tyrosine kinase have been observed to cause thrombocytopenia, anemia and neutropenia in human patients in clinical trials (see, for example, Pardanani, A., *Leukemia*, 26:1449-1451 (2012)). Jak2 signaling occurs thru EPO and TPO, which control erythrocyte and platelet proliferation, respectively. Thus, inhibition of Jak2 tyrosine kinase can potentially lead to side-effects in the clinic. Btk inhibitors with improved selectivity over Jak2 tyrosine kinase are desired in order to minimize off target side-effects related to the inhibition of Jak2 tyrosine kinase.

The assays were performed in V-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerolphosphate, 0.015% Brij 35 surfactant and 4 mM DTT). The reaction was initiated by the combination of Jak2 tyrosine kinase with substrates and test compounds. The reaction mixture was incubated at room temperature for 60 minutes and terminated by adding 45 µL of 35 mM EDTA to each sample. The reaction mixture was analyzed on the Caliper LABCHIP® 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 μM; Jak2 fluorescent peptide, 1.5 μM; Jak2, 1 nM; and DMSO, 1.6%. Dose response curves were generated to determine the concentration required inhibiting 50% of kinase activity ($IC_{50}$). Compounds were dissolved at 10 mM in DMSO and evaluated at eleven concentrations, each in duplicate. $IC_{50}$ values were derived by non-linear regression analysis.

Whole Blood Assay of BCR-Stimulated CD69 Expression on B Cells

The efficacy of Btk inhibitor compounds in suppressing CD69 expression on B cells human in whole blood assays is useful for predicting efficacious doses in the clinic and minimizing potential side-effects. Btk inhibitor compounds having higher activity in the whole blood CD69 expression assay are expected to require lower doses than compounds having lower activity, and are expected to cause fewer unwanted side-effects. (Uetrecht, *Chem. Res. Toxicol.,* 12:387-395 (1999); Nakayama, *Drug Metabolism and Disposition*, 37(9):1970-1977 (2009); Sakatis, *Chem. Res. Toxicol.* (2012)).

To measure BCR-stimulated B cells, ACD-A human whole blood was treated with various concentrations of test compound and stimulated with 30 μg/mL AffiniPure F(ab')2 fragment goat anti human IgM (Jackson 109-006-1299-endotoxin cleared) and 10 ng/mL human IL-4 (PeproTech 200-04) for 18 h at 37° C. with agitation. The cells were blocked with human gamma globulin (Jackson 009-000-002) and stained with FITC-conjugated mouse anti-human CD20 (BD Pharmingen 555622) and PE-conjugated mouse anti-human CD69 monoclonal antibody (BD Pharmingen 555531), lysed and fixed, then washed. The amount of CD69 expression was quantitated by the median fluorescence intensity (MFI) after gating on the CD20-positive B cell population as measured by FACS analysis.

In the whole blood assay of BCR-Stimulated CD69 expression on B cells, increased efficacy of a Btk inhibitor compound is indicated by a lower CD69 $IC_{50}$ value.

TABLE 11

| Example | Btk $IC_{50}$ value (nM) | Jak2 $IC_{50}$ value (nM) | Ratio of Jak2/Btk $IC_{50}$ values | CD69 $IC_{50}$ values (nM) |
|---|---|---|---|---|
| 1 | 2.1 | >2000 | >950 | 190 |
| 2 | 1.1 | 2000 | 1800 | 90 |
| 3 | 1.0 | 2000 | 2000 | 130 |
| 4 | 1.3 | 350 | 270 | 180 |
| 5 | 2.1 | >2000 | >950 | 170 |
| 6 | 1.1 | 1500 | 1400 | 100 |
| 7 | 0.81 | 1600 | 2000 | 130 |
| 8 | 0.65 | >2000 | >3100 | 75 |
| 9 | 0.62 | >2000 | >3200 | 76 |
| 10 | 0.83 | >2000 | >2400 | 110 |
| 11 | 0.40 | 910 | 2300 | 65 |
| 12 | 1.8 | 1900 | 1100 | 190 |
| 13 | 2.9 | 570 | 200 | 140 |
| 14 | 1.2 | 300 | 250 | 20 |
| 15 | 1.0 | 2400 | 2400 | 170 |
| 16 | 0.27 | 1900 | 7000 | 120 |
| 17 | 0.59 | 170 | 290 | 120 |
| 18 | 0.65 | 2200 | 3400 | 56 |
| 19 | 0.45 | 2000 | 4400 | 91 |
| 20 | 0.46 | 1200 | 2600 | 16 |
| 21 | 0.48 | 760 | 1600 | 17 |
| 22 | 0.33 | 1700 | 5200 | 120 |
| 23 | 0.44 | 440 | 1000 | 98 |
| 24 | 0.33 | 1800 | 5500 | 21 |
| 25 | 0.90 | >2000 | >2200 | 200 |
| 26 | 1.2 | 7500 | 6300 | 160 |
| 27 | 2.2 | >2000 | >910 | 150 |

TABLE 11-continued

| Example | Btk $IC_{50}$ value (nM) | Jak2 $IC_{50}$ value (nM) | Ratio of Jak2/Btk $IC_{50}$ values | CD69 $IC_{50}$ values (nM) |
|---|---|---|---|---|
| 28 | 0.54 | 32000 | 59000 | 90 |
| 29 | 0.66 | 790 | 1200 | 240 |
| 30 | 0.22 | 1300 | 5900 | 64 |
| 31 | 0.19 | 1300 | 6800 | 37 |
| 32 | 0.55 | 1400 | 2500 | 160 |
| 33 | 0.26 | 970 | 3700 | 24 |
| 34 | 0.85 | 370 | 440 | 98 |
| 35 | 0.25 | 800 | 3200 | 31 |
| 36 | 0.28 | 450 | 1600 | 28 |
| 37 | 0.91 | 630 | 690 | 200 |
| 38 | 0.34 | 300 | 880 | 53 |
| 39 | 0.31 | 370 | 1200 | 130 |
| 40 | 0.46 | 830 | 1800 | 19 |
| 41 | 0.20 | 800 | 4000 | 22 |
| 42 | 2.0 | 1200 | 600 | 210 |
| 43 | 0.47 | 2000 | 4300 | 71 |
| 44 | 4.7 | 710 | 150 | 160 |
| 45 | 0.45 | 3700 | 8200 | 68 |
| 46 | 1.5 | 2000 | 1300 | 88 |
| 47 | 0.35 | 1800 | 5100 | 27 |
| 48 | 0.33 | 1100 | 3300 | 25 |
| 49 | 0.77 | >2000 | >2600 | 17 |
| 50 | 0.32 | 1200 | 3800 | 120 |
| 51 | 0.30 | >2000 | >6700 | 190 |
| 52 | 0.48 | 1100 | 2300 | 25 |
| 53 | 1.1 | 2200 | 2000 | 110 |
| 54 | 0.35 | 1200 | 3400 | 10 |
| 55 | 0.26 | 9000 | 35000 | 44 |
| 56 | 0.62 | >2000 | >3200 | 140 |
| 57 | 0.25 | 270 | 1100 | 54 |
| 58 | 0.84 | 13000 | 15000 | 240 |
| 59 | 0.90 | >2000 | >2200 | 260 |
| 60 | 0.18 | 270 | 1500 | 57 |
| 61 | 1.4 | 1900 | 1400 | 93 |
| 62 | 0.41 | >2000 | >4900 | 74 |
| 63 | 0.45 | 11000 | 24000 | 190 |
| 64 | 0.34 | >2000 | >5900 | 88 |
| 65 | 0.46 | >2000 | >4300 | 110 |
| 66 | 0.34 | 290 | 850 | 89 |
| 67 | 0.49 | 16000 | 33000 | 160 |
| 68 | 0.56 | 350 | 630 | 75 |
| 69 | 0.84 | 9500 | 11000 | 150 |
| 70 | 0.59 | 550 | 930 | 66 |
| 71 | 0.41 | 800 | 2000 | 240 |
| 72 | 0.49 | 770 | 1600 | 200 |
| 73 | 0.26 | 580 | 2200 | 21 |
| 74 | 0.79 | 4300 | 5400 | 180 |
| Comparative Example 75 | 2.6 | 240 | 92 | 650 |
| Comparative Example 76 | 6.9 | 200 | 29 | — |

The compounds of the present invention, as exemplified by Examples 1 to 74, have been compared to Comparative Examples 75 and 76, disclosed in U.S. Pat. No. 8,084,620 and WO 2011/159857, respectively, and have been found to be advantageous. The compounds of the present invention have the surprising advantage of the combination of Btk inhibition activity and improved kinase selectivity of Btk inhibition activity over Jak2 inhibition activity. As shown in Table 11, in the reported tests, Examples 1 to 74 show the surprising advantage of the combination of efficacy of Btk inhibition activity and improved kinase selectivity of Btk inhibition activity over Jak2 inhibition activity, as characterized by the ratio of Jak2/Btk $IC_{50}$ values. Increased selectivity for Btk kinase over Jak2 kinase is indicated by a larger value for the ratio of the Jak2/Btk $IC_{50}$ values. Examples 1 to 74 had Btk $IC_{50}$ values of less than 5 nM and ratios of Jak2/Btk $IC_{50}$ values of 150 and greater. In contrast, Comparative Examples 75 and 76 had Btk $IC_{50}$ values of 2.6 and 6.9 nM and ratios of Jak2/Btk $IC_{50}$ values of 92 and 29, respectively.

Additionally, the compounds of the present invention, as exemplified by Examples 1 to 74, also have improved potency in the whole blood BCR-stimulated CD69 expression assay, compared to Comparative Example 75. As shown in Table 11, in the reported tests, Examples 1 to 74 show the surprising advantage of the combination of efficacy of Btk inhibition activity, improved kinase selectivity of Btk inhibition activity over Jak2 inhibition activity, and improved potency in the whole blood BCR-stimulated CD69 expression assay. Examples 1 to 74 had Btk $IC_{50}$ values of less than 5 nM, ratios of Jak2/Btk $IC_{50}$ values of 150 and greater, and CD69 $IC_{50}$ values of 260 nM and less. In contrast, Comparative Example 75 had a Btk $IC_{50}$ value of 2.6 nM, a ratio of Jak2/Btk $IC_{50}$ value of 92, and a CD69 $IC_{50}$ values of 650 nM.

What is claimed is:

1. A compound having the structure:

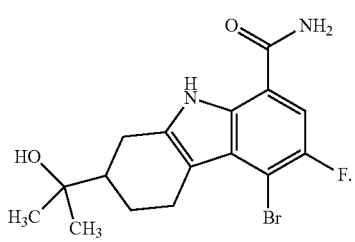

(I-24)

2. The compound according to claim 1 having the structure:

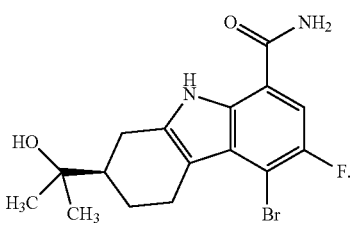

(I-25)

3. The compound according to claim 1 having the structure:

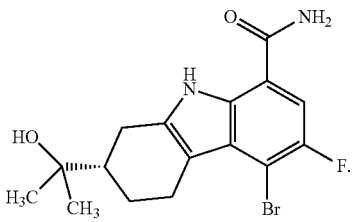

(I-26)

* * * * *